US009241989B2

(12) United States Patent
Otto et al.

(10) Patent No.: US 9,241,989 B2
(45) Date of Patent: Jan. 26, 2016

(54) NEUTRALIZING PROLACTIN RECEPTOR ANTIBODIES AND THEIR THERAPEUTIC USE

(75) Inventors: Christiane Otto, Berlin (DE); Siegmund Wolf, Berlin (DE); Christoph Freiberg, Wuppertal (DE); Axel Harrenga, Wuppertal (DE); Simone Greven, Dormagen (DE); Mark Trautwein, Wülfrath (DE); Sandra Bruder, Leverkusen (DE); Andrea Eicker, Mönchengladbach (DE); Andreas Wilmen, Köln (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 3 days.

(21) Appl. No.: 13/514,996

(22) PCT Filed: Nov. 18, 2010

(86) PCT No.: PCT/EP2010/067747
§ 371 (c)(1),
(2), (4) Date: Jan. 3, 2013

(87) PCT Pub. No.: WO2011/069799
PCT Pub. Date: Jun. 16, 2011

(65) Prior Publication Data
US 2013/0129739 A1    May 23, 2013

(30) Foreign Application Priority Data
Dec. 10, 2009    (EP) .................................... 09075546

(51) Int. Cl.
*A61K 39/395*  (2006.01)
*C07K 16/28*   (2006.01)
*A61K 45/06*   (2006.01)
*A61K 39/00*   (2006.01)

(52) U.S. Cl.
CPC ............. *A61K 39/3955* (2013.01); *A61K 45/06* (2013.01); *C07K 16/28* (2013.01); *C07K 16/2866* (2013.01); *C07K 16/2869* (2013.01); *A61K 2039/505* (2013.01); *C07K 2316/96* (2013.01); *C07K 2317/56* (2013.01); *C07K 2317/565* (2013.01); *C07K 2317/73* (2013.01)

(58) Field of Classification Search
None
See application file for complete search history.

(56) References Cited

U.S. PATENT DOCUMENTS

| 4,399,216 A | 8/1983 | Axel et al. |
| 4,510,245 A | 4/1985 | Cousens et al. |
| 4,634,665 A | 1/1987 | Axel et al. |
| 4,816,567 A | 3/1989 | Cabilly et al. |
| 4,986,615 A | 1/1991 | Hieb et al. |
| 5,168,062 A | 12/1992 | Stinski |
| 5,179,017 A | 1/1993 | Axel et al. |
| 5,766,886 A | 6/1998 | Studnicka et al. |
| 6,300,064 B1 | 10/2001 | Knappik et al. |
| 6,989,250 B2 | 1/2006 | Soderlind et al. |
| 7,422,899 B2 * | 9/2008 | Elenbaas et al. ............. 435/346 |
| 7,867,493 B2 * | 1/2011 | Damiano et al. ........... 424/133.1 |
| 2005/0250689 A1 * | 11/2005 | Brooks et al. .................. 514/12 |

FOREIGN PATENT DOCUMENTS

| EP | 2025683 A1 | 2/2009 |
| WO | WO 9216562 A1 * | 10/1992 |
| WO | 2008022295 A2 | 2/2008 |
| WO | WO2008022295 A2 * | 2/2008 |

OTHER PUBLICATIONS

Gorman et al., Semin Immunol. Nov. 1990;2(6):457-66.*
Luisa Bermejo Martinez, Manuel Zamarripa Leyva, and Ivone Castro Romero, "Prolactin receptor in human endometriotic tissues," Acta Obstet Gynecol Scand, vol. 81, No. 1, pp. 5-10 (Jan. 1, 2002).
H.G. Bohnet, R.P.C. Shiu, D. Grinwich, and H.G. Friesen, "In Vivo Effects of Antisera to Prolactin Receptors in Female Rats," Endocrinology, vol. 102, No. 6, pp. 1657-1661 (Jun. 1, 1978).
Janice F. Sissom, PhD, Marsha L. Eigenbrodt, MD, and John C. Porter, PhD, "Anti-Growth Action on Mouse Mammary and Prostate Glands of a Monoclonal Antibody to Prolactin Receptor," American Journal of Pathology, vol. 133, No. 3, pp. 589-595 (Dec. 1, 1988).
English Language Abstract of Kerstin Foitzik, "New Findings in the Treatment of Alopecia: The Influence of Prolactin, Retinoids and Transforming Growth Factor-β on Hair Growth," Akt Dermatol, vol. 31, No. 3, pp. 109-116 (Mar. 1, 2005).
European Search Report and Search Opinion for EP App. No. 09075546 (Oct. 26, 2010).
Gerlo et al., "Prolactin in Man: a Tale of Two Promoters," BioEssays, 2006, 28(10):1051-1055.
Bole-Feysot et al., "Prolactin (PRL) and Its Receptor: Actions, Signal Transduction Pathways and Phenotypes Observed in PRL Receptor Knockout Mice," Endocrine Reviews, Jun. 1998, 19(3):225-268.
Goffin et al., "Drug Insight: prolactin-receptor antagonists, a novel approach to treatment of unresolved systemic and local hyperprolactinemia?," Nature Clinical Practice Endocrinology & Metabolism, Oct. 2006, 2(10):571-581.

(Continued)

*Primary Examiner* — Michael Szperka
(74) *Attorney, Agent, or Firm* — Karen B. King; Yonggang Ji

(57) ABSTRACT

The present invention is directed to the neutralizing prolactin receptor antibody 005-C04, as well as maturated forms thereof, and antigen binding fragments, pharmaceutical compositions containing them and their use in the treatment or prevention of benign disorders and indications mediated by the prolactin receptor such as endometriosis, adenomyosis, non-hormonal female contraception, benign breast disease and mastalgia, lactation inhibition, benign prostate hyperplasia, fibroids, hyper- and normoprolactinemic hair loss, and cotreatment in combined hormone therapy to inhibit mammary epithelial cell proliferation. The antibodies of the invention block prolactin receptor-mediated signaling.

16 Claims, 26 Drawing Sheets

(56) References Cited

OTHER PUBLICATIONS

Manni et al., "Endocrine effects of combined somatostatin analog and bromocriptine therapy in women with advanced breast cancer," Breast Cancer Research and Treatment, 1989, 14:289-298.

Bogorad et al, "Identification of a gain-of-function mutation of the prolactin receptor in women with benign breast tumors," PNAS, Sep. 23, 2008, 105(38):14533-14538.

J Alvarez-Nemegyei, et al., "Bromocriptine in systemic lupus erythematosus: a double-blind, randomized, palcebo-controlled study," 1998, 7:414-419.

Goffin et al., "PROLACTIN: The New Biology of an Old Hormone," Annual Review Physiol, 2002, 64:47-67.

S. Kumar et al., "Prediction of Response to Endocrine Therapy in Pronounced Cyclical Mastalgia Using Dynamic Tests of Prolactin Release," Clin Endocrinol 23: 699-704, 1985.

Sissom et al., "Anti-growth Action on Mouse Mammary and Prostate Glands of a Monoclonal Antibody to Prolactin Receptor," American Journal of Pathology, 1988, 133(3): 589-595.

Martinez et al, "Prolactin Receptor in Human Endometriotic Tissues," Acta Obstet Gynecol Scand, 2002; 81: 5-10.

Bohnet et al, "In Vivo Effects of Antisera to prolactin Receptors in Female Rats," Endocrinology, 1978; 102(6): 1657-1661.

Courtillot et al, "Characterization of Two Constitutively Active Prolactin Receptor Variants in a Cohort of 95 Women with Multiple Breast Fibroadenomas," J Clin Endocrinol Metab, 2010; 95(1):271-279.

K. Foitzik, "New Findings in the Treatment of Alopecia: The Influence of Prolactin, Retinoids and Transforming Growth Factor-B on Hair Growth," Akt Dermatol 2005; 31: 109-116.

Perks et al., "Prolactin Acts as a: Potent Survival Factor Against C2-ceramide-induced Apoptosis in Human Granulosa Cells," Human Reprod. 18: 2672-2677, 2003.

Nevalainen et al., "Prolactin and Prolactin Receptors are Expressed and Functioning in Human Prostate," J. Clin. Invest. 99: 618 pp, 1997.

* cited by examiner

Figure 1: Expression of prolactin in eutopic endometrium from patients and healthy controls and in endometriotic lesions
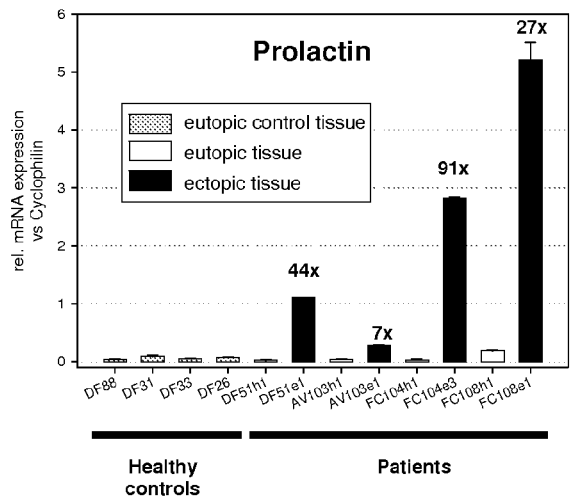
Figure 2: Expression of the prolactin receptor in eutopic endometrium from patients and healthy controls and in endometriotic lesions
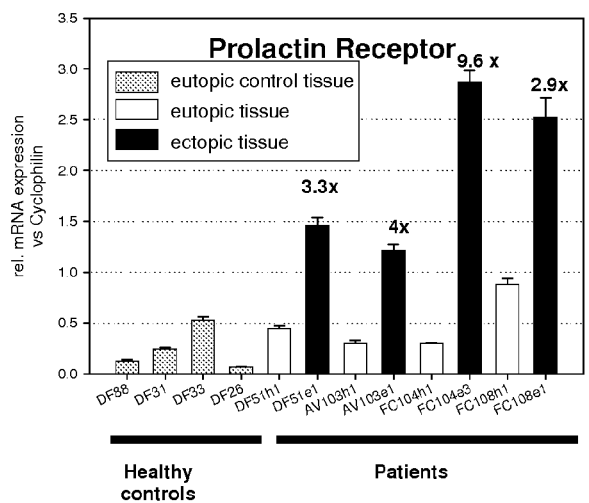

Figure 3: Analysis of prolactin receptor mRNA expression in rat tissues by Northern blot

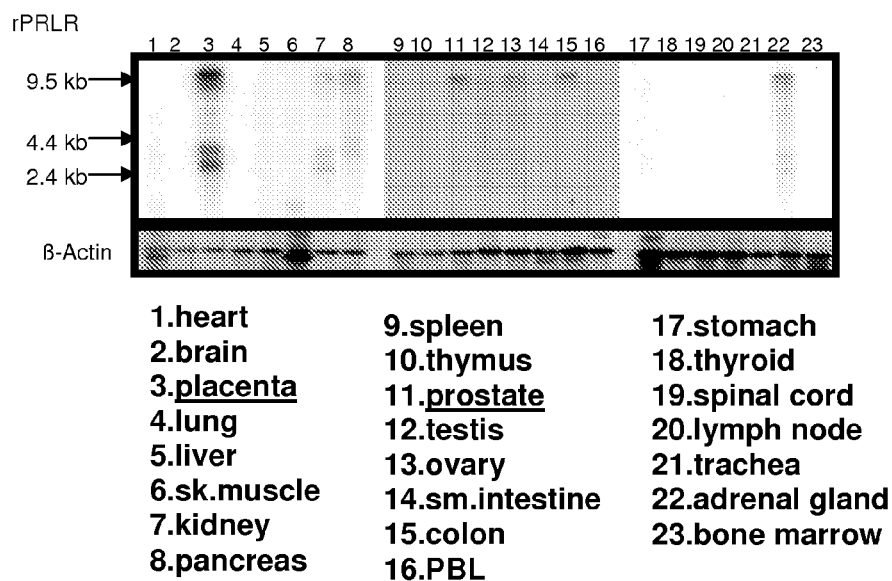

1. heart
2. brain
3. placenta
4. lung
5. liver
6. sk.muscle
7. kidney
8. pancreas
9. spleen
10. thymus
11. prostate
12. testis
13. ovary
14. sm.intestine
15. colon
16. PBL
17. stomach
18. thyroid
19. spinal cord
20. lymph node
21. trachea
22. adrenal gland
23. bone marrow Figure 4: Analysis of prolactin receptor protein expression in rat prostate from castrated animals (gdx) and from intact animals treated with vehicle (intact), dihydrotestosterone (DHT) or estradiol (E2)

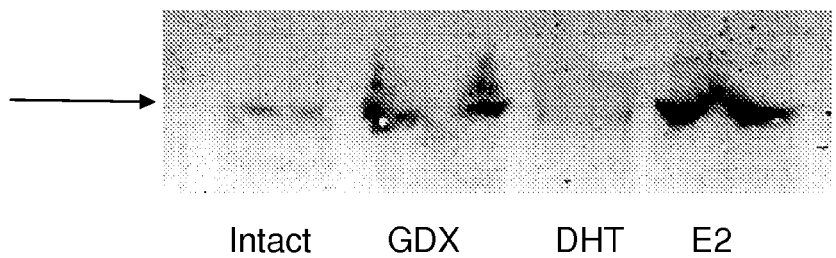

Intact    GDX    DHT    E2

Figure 5: Inhibition of Baf cell proliferation (cells stably transfected with hPRLR) by different neutralising PRLR antibodies
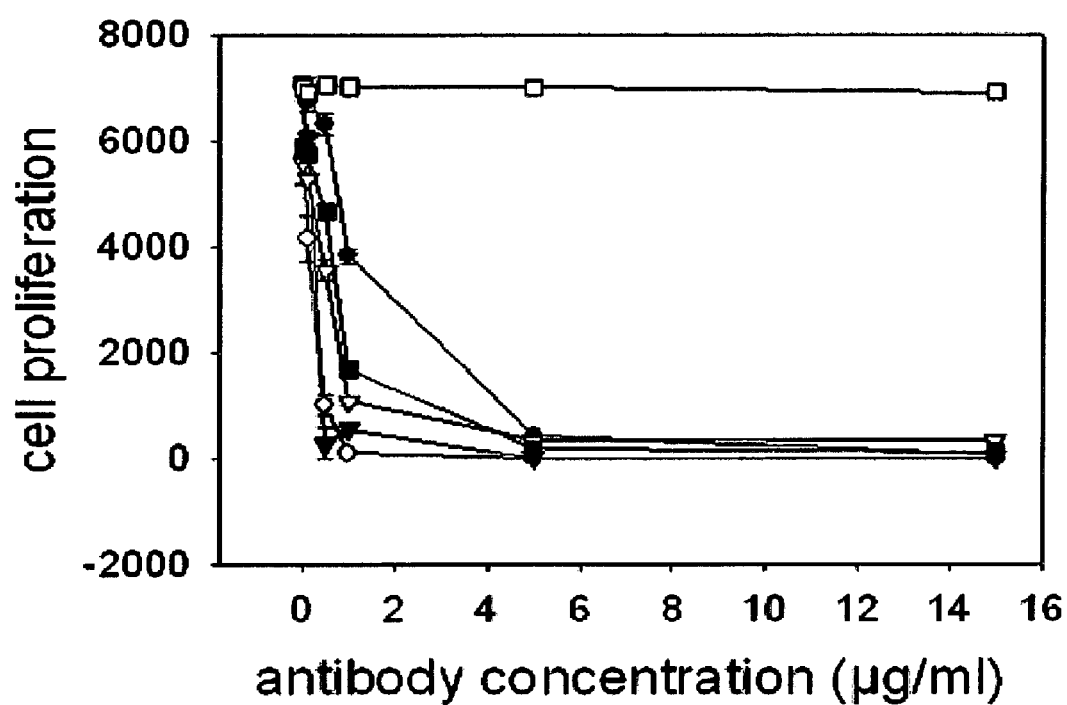

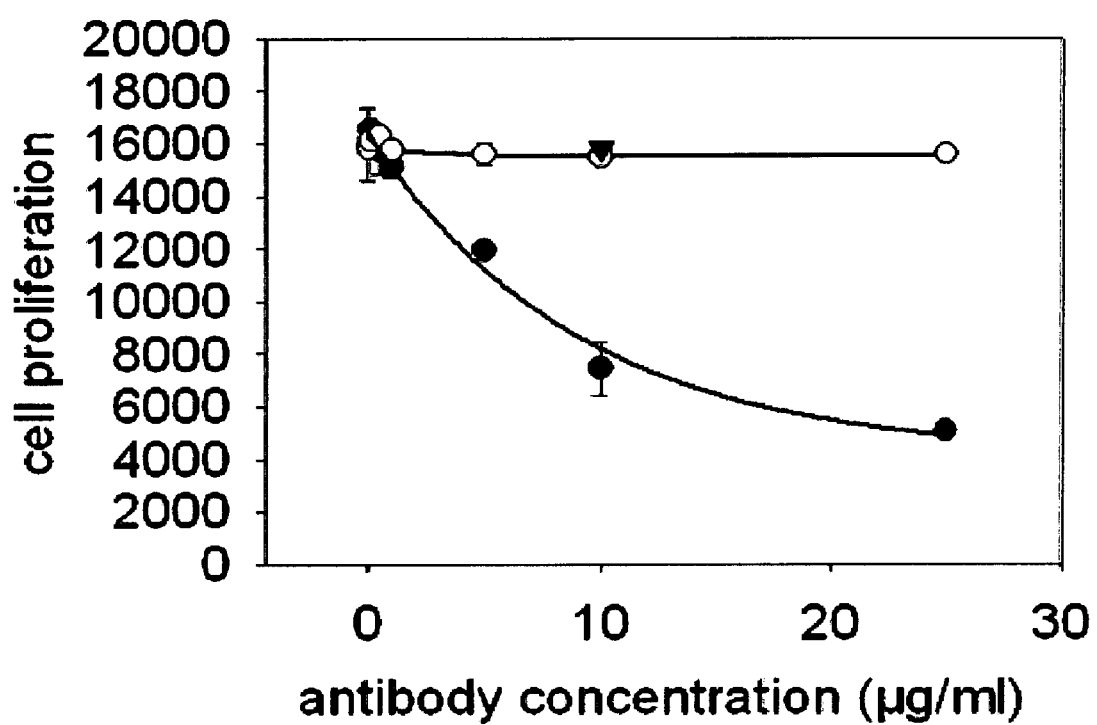
Figure 6: Inhibition of prolactin-induced rat lymphoma cell proliferation (NB2 cells) by neutralising prolactin receptor antibodies Figure 7: Inhibition of prolactin-induced STAT5 phosphorylation in T47D cells by neutralizing prolactin receptor antibodies and unspecific control antibody

XHA06.642

Prolactin  0  +     +     +    +    +
Antibody   0  0  0.01 0.1  1    3   µg/ml

pSTAT5

β-tubulin

FITC
Prolactin  0  +     +     +    +    +
Antibody   0  0  0.01 0.1  1    3   µg/ml

pSTAT5

β-tubulin

IgG1 005_C04
Prolactin  0  +     +     +    +    +    +
Antibody   0  0  0.01 0.1  1    3   10 µg/ml

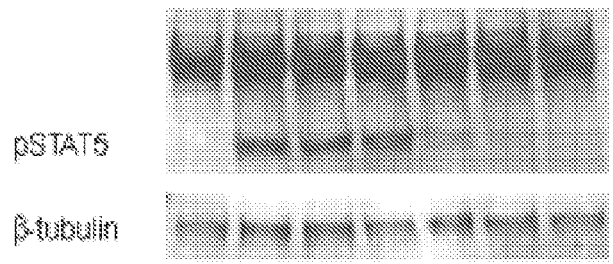

pSTAT5

β-tubulin

IgG1 006_H08
Prolactin  0  +     +     +    +    +    +
Antibody   0  0  0.01 0.1  1    3   10 µg/ml

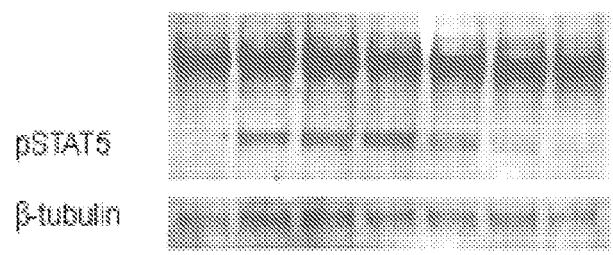

pSTAT5

β-tubulin

Figure 8: Luciferase assay in HEK293 cells stably transfected with hPRLR and transiently transfected with luciferase under the control of LHRE's. Inhibition of luciferase activity by specific and unspecific antibodies.
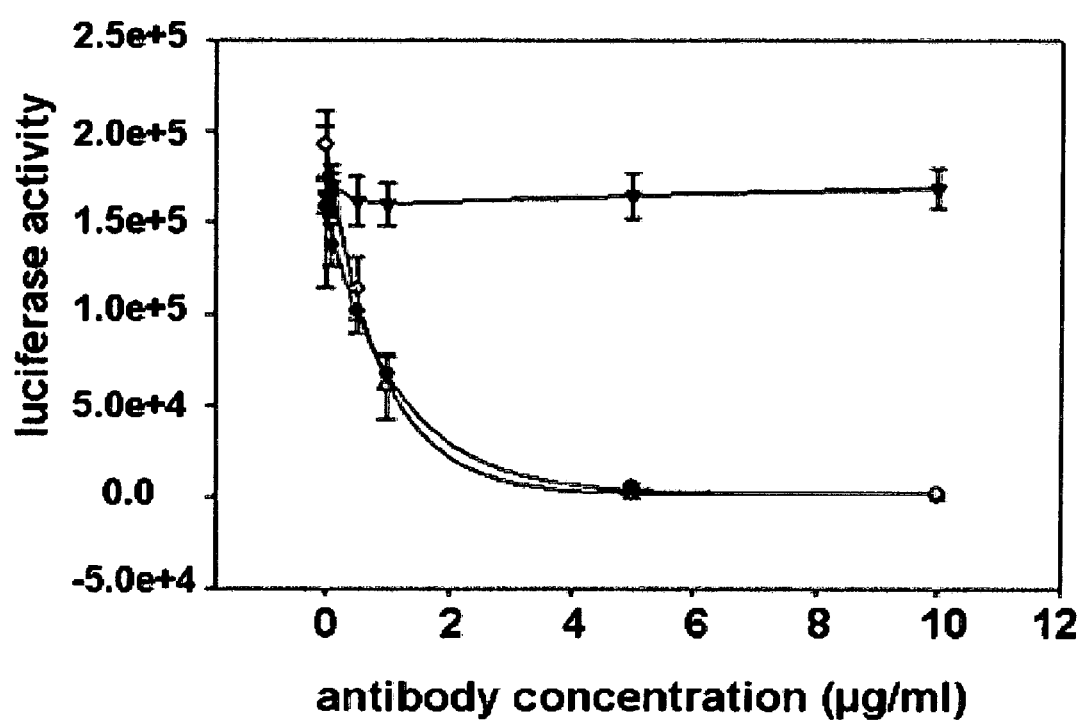

Figure 9: Luciferase assay in Hek293 cells stably transfected with murine PRLR and transiently transfected with luciferase under the control of LHREs – analysis of inhibition of luciferase activity by specific and unspecific antibodies
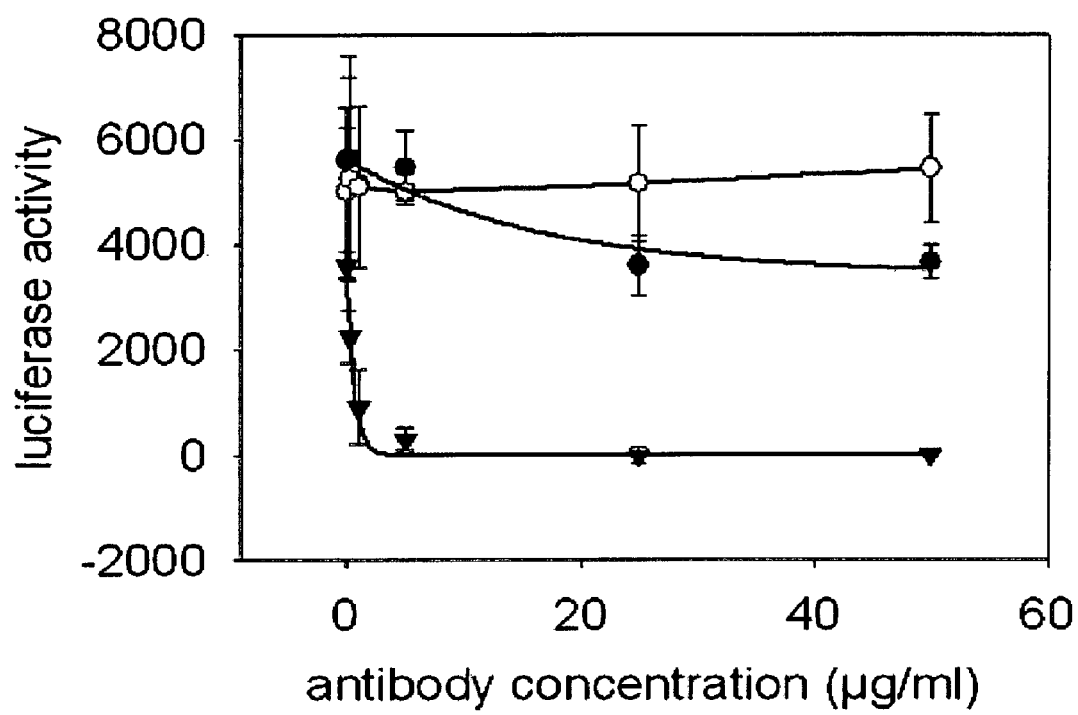

Figure 10: Inhibition of Baf cell proliferation (cells stably transfected with murine PRLR) by different neutralizing PRLR antibodies
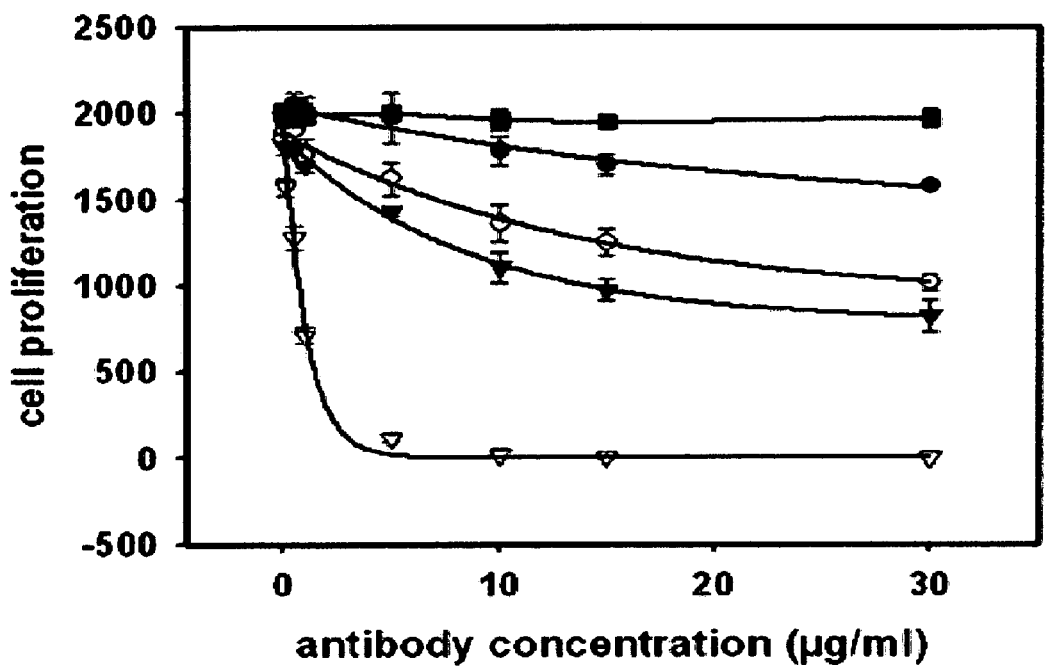

Figure 11: Contraceptive effect of neutralizing PRLR antibodies in mice
A    Pregnancy rates
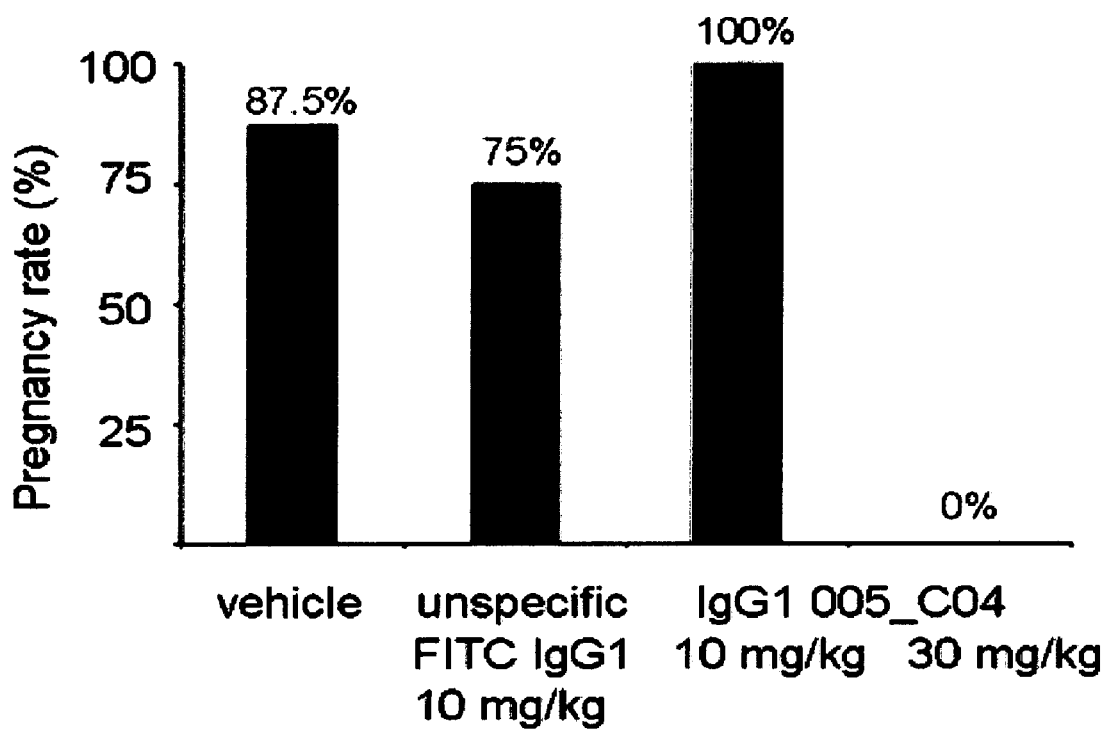

Figure 11: Contraceptive effect of neutralizing PRLR antibodies in mice
B    Litter size
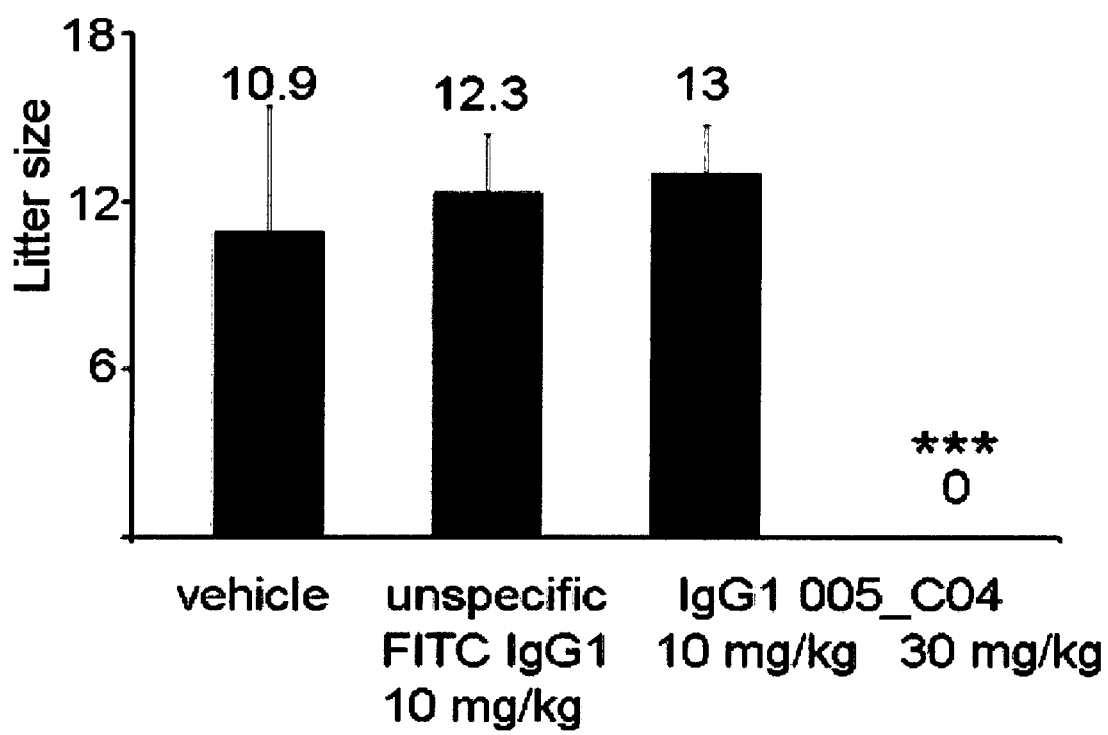

Figure 12: Kabat Numbering of framework amino acid positions according to Johnson and Wu (Nucleic Acids Res. 2000, 28, 214-218)

VL chain:

| Kabat No. | L1 | L2 | L3 | L4 | L5 | L6 | L7 | L8 | L9 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|
| LFR1 | Q/D | S/I | V | L | T | Q | P | P | S | A | S | G | T | P | G | Q | R | V | T | I | S | C |

| Kabat No. | L24 – L34 |
|---|---|
| LCDR1 | (X)n |

| Kabat No. | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|
| LFR2 | W | Y | Q | Q | L | P | G | T | A | P | K | L | L | I | Y |

| Kabat No. | L50 – L56 |
|---|---|
| LCDR2 | (X)n |

| Kabat No. | L57 | L58 | L59 | L60 | L61 | L62 | L63 | L64 | L65 | L66 | L67 | L68 | L69 | L70 | L71 | L72 | L73 | L74 | L75 | L76 | L77 | L78 |
|---|---|---|---|---|---|---|---|---|---|---|---|---|---|---|---|---|---|---|---|---|---|---|
| LFR3 | G | V | P | D | R | F | S | G | S | K | S | G | T | S | A | S | L | A | I | S | G | L |

| Kabat No. | L79 | L80 | L81 | L82 | L83 | L84 | L85 | L86 | L87 |
|---|---|---|---|---|---|---|---|---|---|
| LFR3 | R | S | E | D | E | A | D | Y | Y |

| Kabat No. | L88 – L97 |
|---|---|
| LCDR3 | (X)n |

| Kabat No. | L98 | L99 | L100 | L101 | L102 | L103 | L104 | L105 | L106 | L107 | L108 | L109 |
|---|---|---|---|---|---|---|---|---|---|---|---|---|
| LFR4 | F | G | G | G | T | K | L | T | V | L | G | Q |

VH chain:

| Kabat No. | H1 | H2 | H3 | H4 | H5 | H6 | H7 | H8 | H9 | H10 | H11 | H12 | H13 | H14 | H15 | H16 | H17 | H18 | H19 | H20 | H21 | H22 |
|---|---|---|---|---|---|---|---|---|---|---|---|---|---|---|---|---|---|---|---|---|---|---|
| HFR1 | E/Q | V | Q/E | L | L | E | S | G | G | G | L | V | Q | P | G | G | S | L | R | L | S | C |

| Kabat No. | H23 | H24 | H25 | H26 | H27 | H28 |
|---|---|---|---|---|---|---|
| HFR1 | A | A | S | G | F | T |

| Kabat No. | H29 – H36 |
|---|---|
| HCDR1 | (X)n |

| Kabat No. | H37 | H38 | H39 | H40 | H41 | H42 | H43 | H44 | H45 | H46 | H47 |
|---|---|---|---|---|---|---|---|---|---|---|---|
| HFR2 | V | R | Q | A | P | G | K | G | L | E | W |

| Kabat No. | H48 – H66 |
|---|---|
| HCDR2 | (X)n |

| Kabat No. | H67 | H68 | H69 | H70 | H71 | H72 | H73 | H74 | H75 | H76 | H77 | H78 | H79 | H80 | H81 | H82 | H82A | H82B | H82C | H83 | H84 | H85 |
|---|---|---|---|---|---|---|---|---|---|---|---|---|---|---|---|---|---|---|---|---|---|---|
| HFR3 | F | T | I | S | R | D | N | S | K | N | T | L | Y | L | Q | M | N | S | L | R | A | E |

| Kabat No. | H86 | H87 | H88 | H89 | H90 | H91 | H92 |
|---|---|---|---|---|---|---|---|
| HFR3 | D | T | A | V | Y | Y | C |

| Kabat No. | H93 – H102 |
|---|---|
| HCDR3 | (X)n |

| Kabat No. | H103 | H104 | H105 | H106 | H107 | H108 | H109 | H110 | H111 | H112 | H113 |
|---|---|---|---|---|---|---|---|---|---|---|---|
| HFR4 | W | G | Q | G | T | L | V | T | V | S | S |

Figure 14: Effect of neutralizing PRLR antibodies on lactation in mice
A  Percentage of daily litter weight gain if compared to litter weight on day 1 post partum
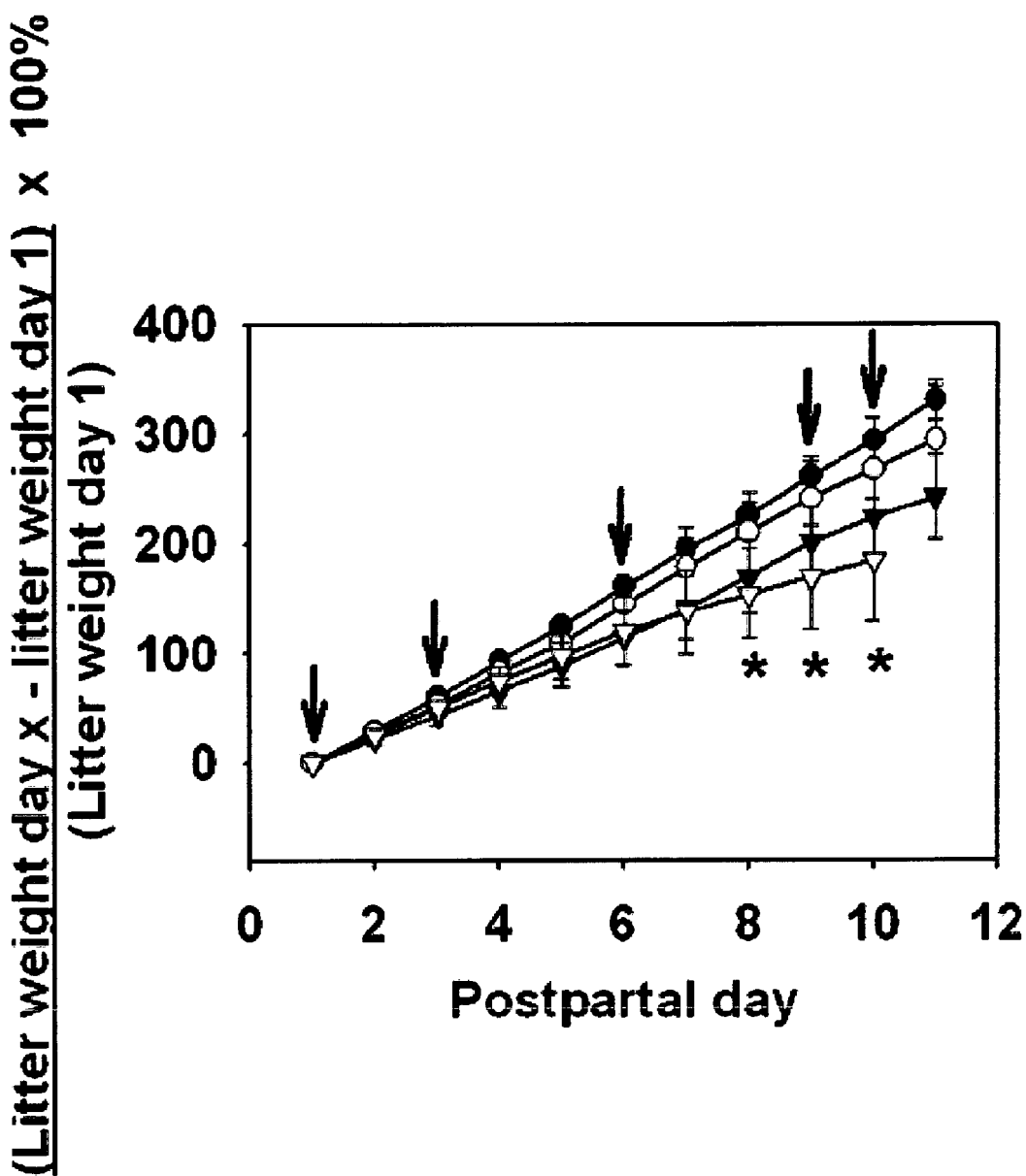

Figure 14: Effect of neutralizing PRLR antibodies on lactation in mice
B  Litter weight gain from day to day expressed as percentage of litter weight on postpartal day 1
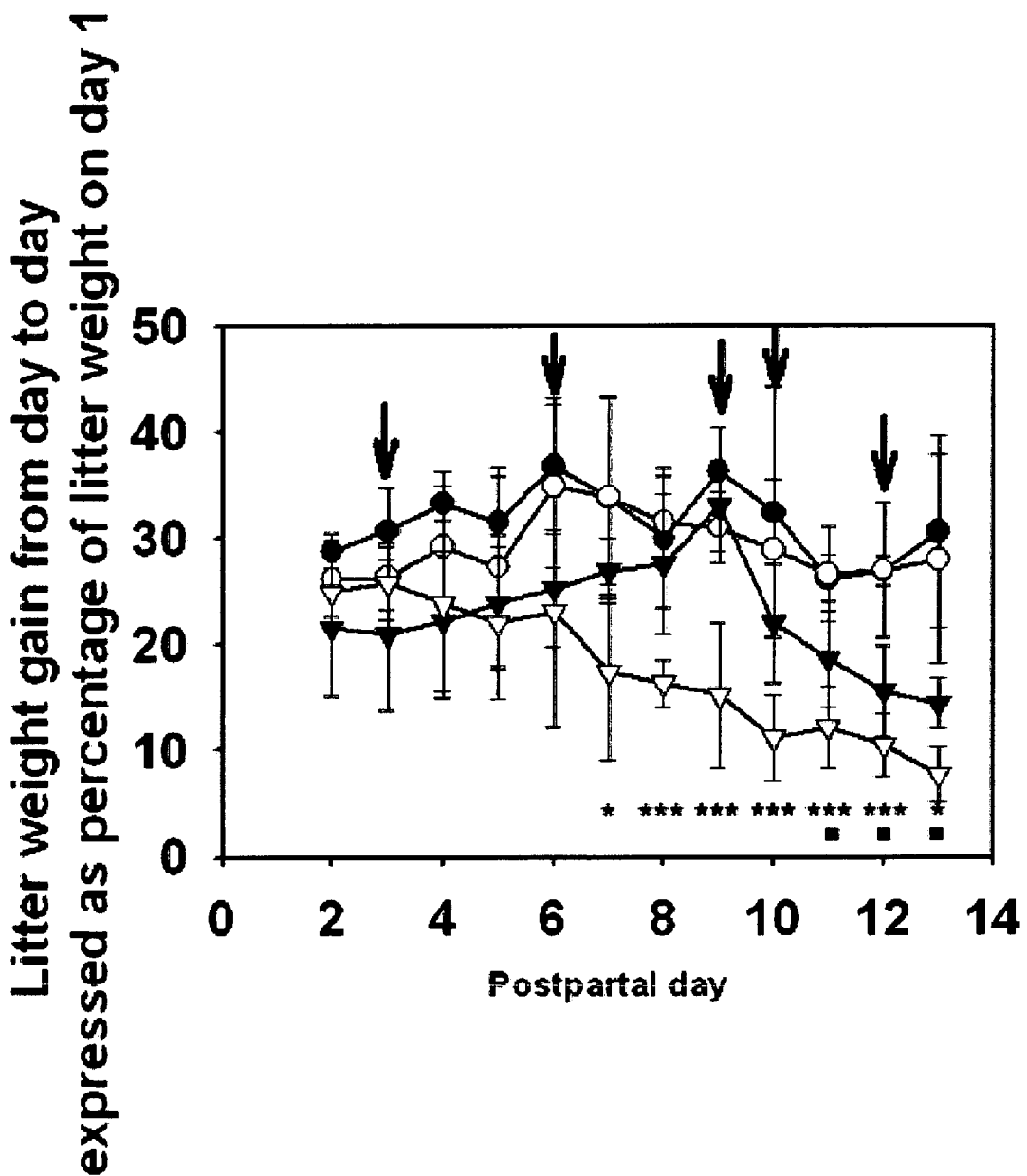

Figure 14: Effect of neutralizing PRLR antibodies on lactation in mice
C  Involution of mammary glands in lactating mice treated with neutralizing PRLR antibodies
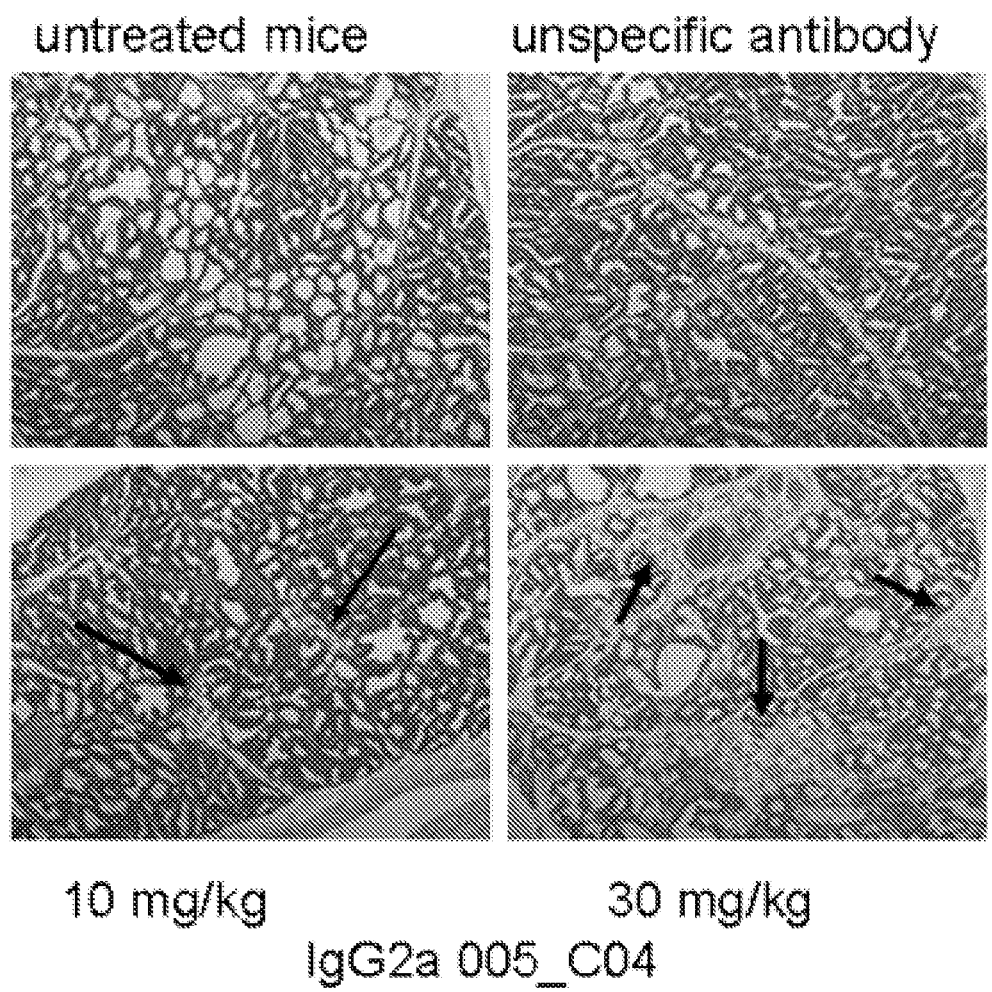

Figure 14: Effect of neutralizing PRLR antibodies on lactation in mice
D    Expression of the milk proteins whey acidic protein (WAP), IGF1 and beta-casein (Csn2) is severely reduced in mammary glands from lactating mice treated with neutralizing PRLR antibodies
Beta-casein (snCsn2) expression:
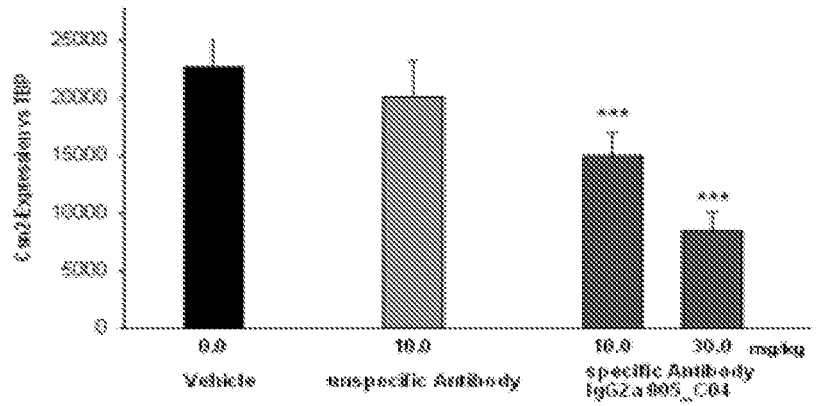
WAP expression
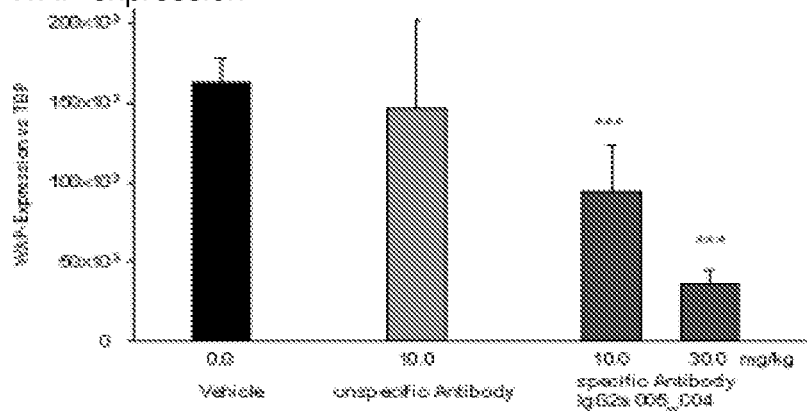
IGF-1 expression
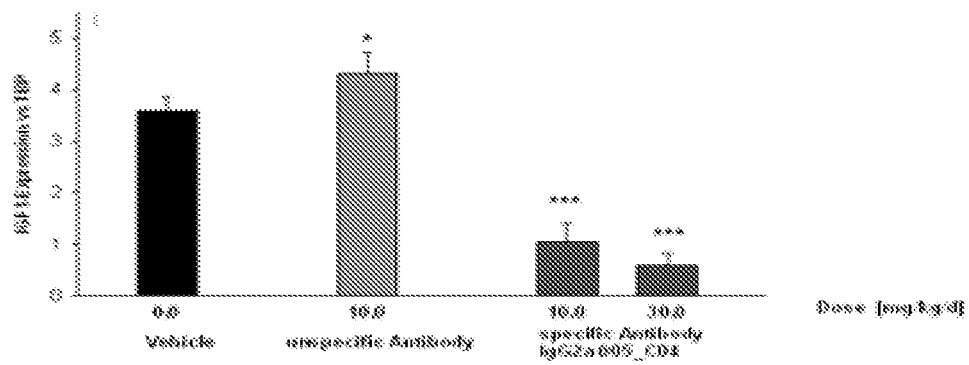

Figure 15: Effect of neutralizing PRLR antibodies on mammary gland epithelial cell proliferation and hyperplasia in a hyperprolactinemic model of benign breast disease
A        Inhibition of side-branching in the mammary gland by neutralizing PRLR antibodies
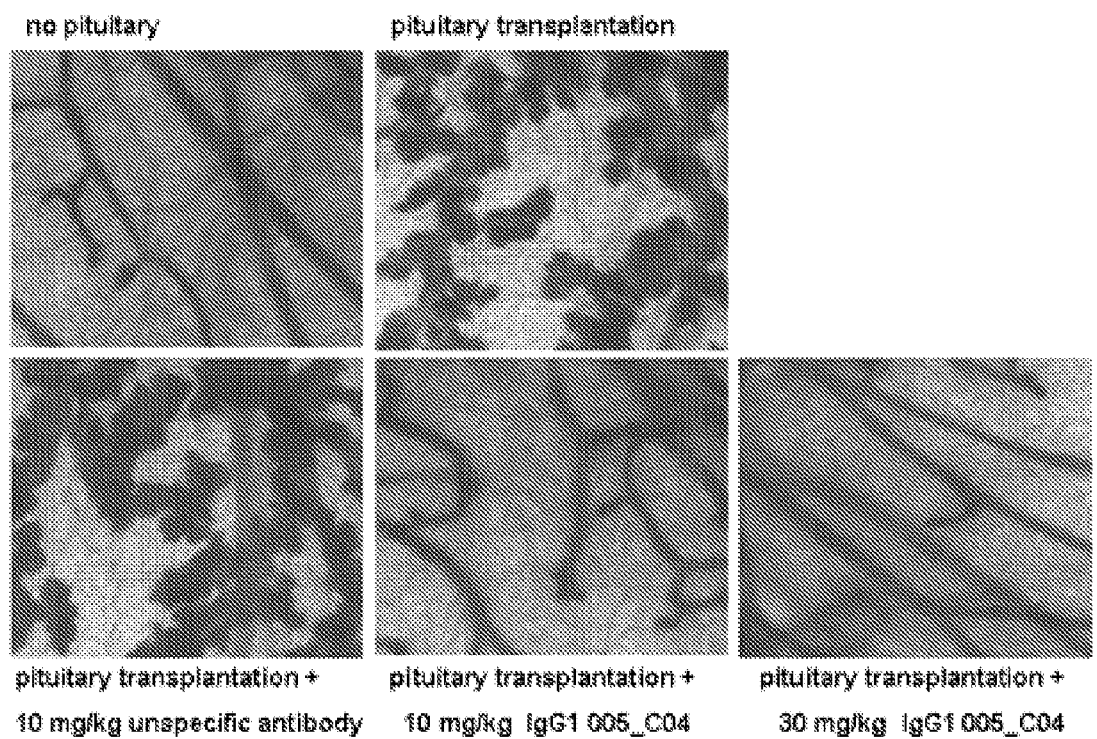

Figure 15: Effect of neutralizing PRLR antibodies on mammary gland epithelial cell proliferation and hyperplasia in a hyperprolactinemic model of benign breast disease
B       Inhibition of mammary epithelial cell proliferation by using neutralising PRLR antibodies
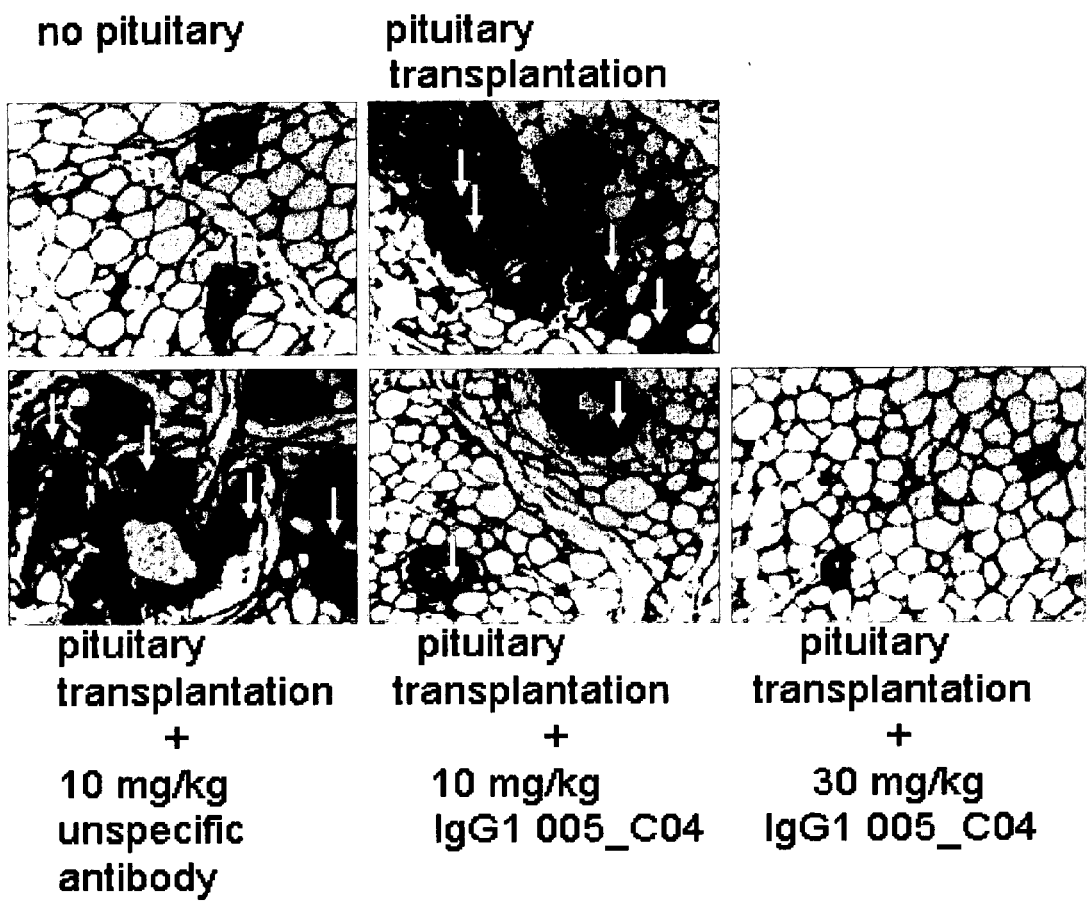

Figure 15: Effect of neutralising PRLR antibodies on mammary gland epithelial cell proliferation and hyperplasia in a hyperprolactinemic model of benign breast disease
C    Inhibition of STAT5 phosphorylation in mammay epithelial cells by application of neutralising PRLR antibodies
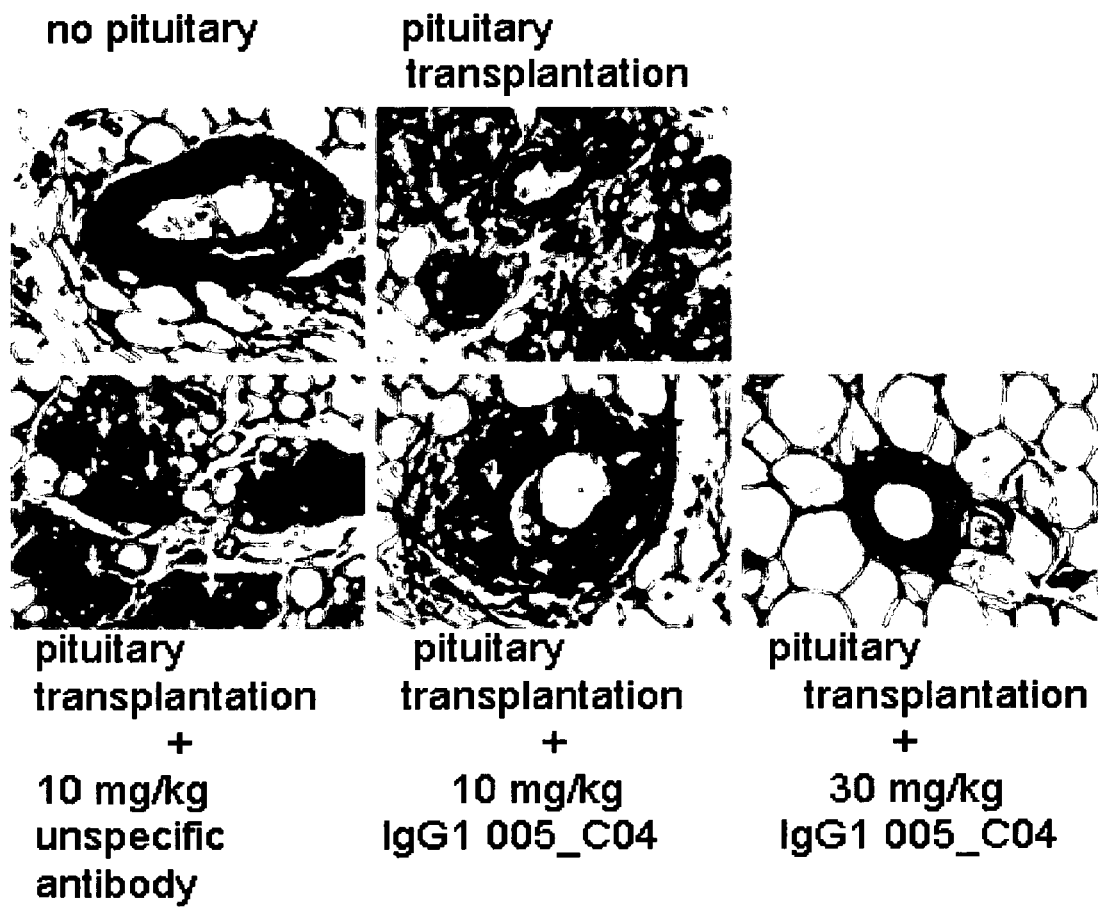

Figure 16: Effect of neutralising PRLR on inhibition of prostate hyperplasia
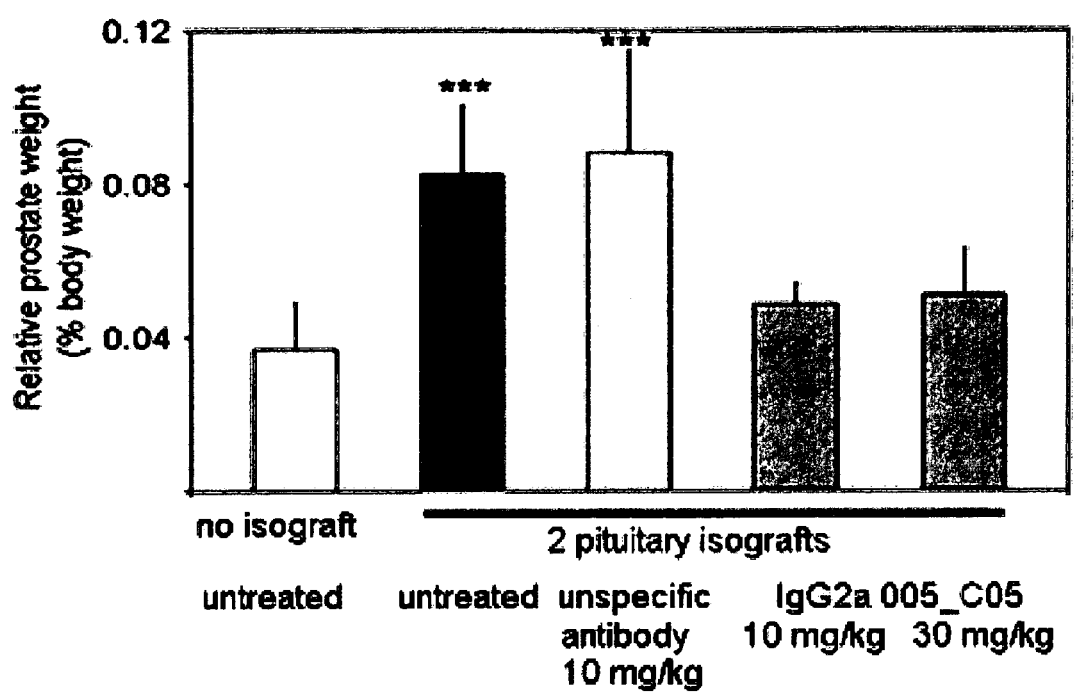

Figure 17: Effect of neutralizing PRLR antibodies on hair growth in the presence of hyperprolactinemia

Figure 18: Effect of neutralizing PRLR antibodies on hair regrowth in male and female mice under normo- and hyperprolactinemic conditions.
5    A        Analysis of female mice
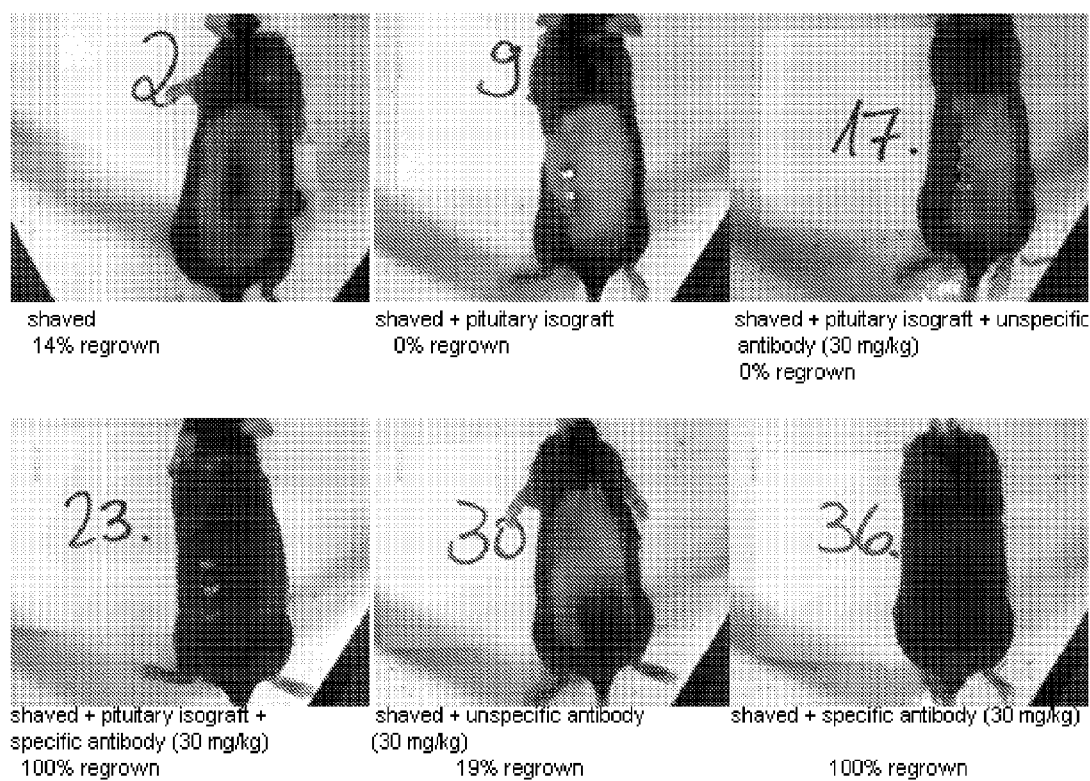

Figure 18: Effect of neutralizing PRLR antibodies stimulateon hair regrowth in male and female mice under normo- and hyperprolactinemic conditions.
5  B   Analysis of male mice
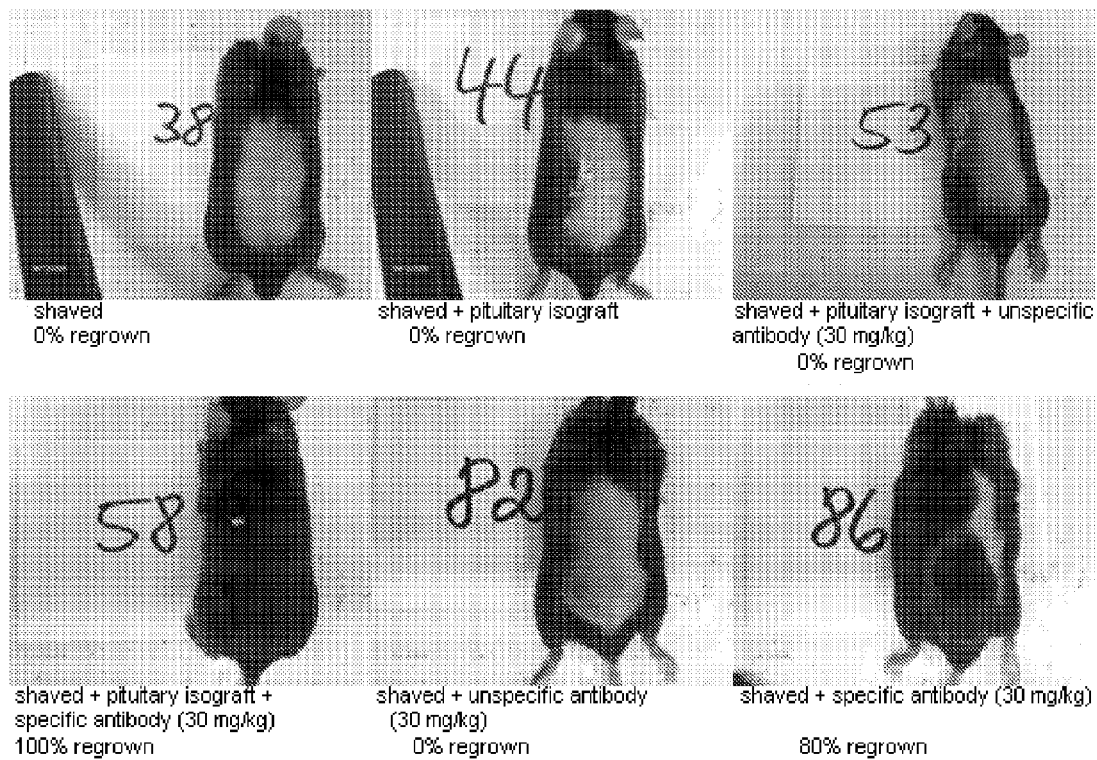

Figure 19: Effect of neutralizing PRLR antibodies on epithelial cell proliferation in the mammary gland under combined estrogen plus progestin hormone therapy

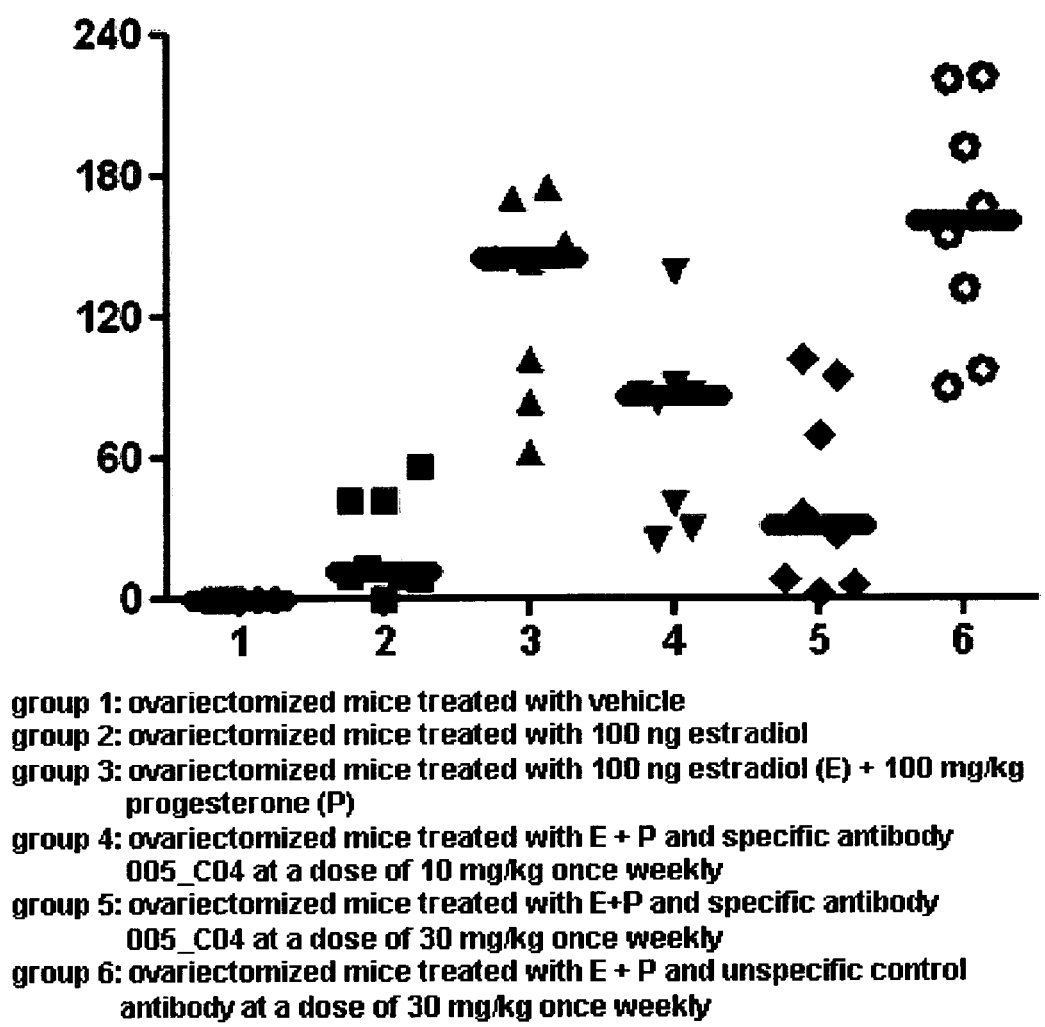

group 1: ovariectomized mice treated with vehicle
group 2: ovariectomized mice treated with 100 ng estradiol
group 3: ovariectomized mice treated with 100 ng estradiol (E) + 100 mg/kg progesterone (P)
group 4: ovariectomized mice treated with E + P and specific antibody 005_C04 at a dose of 10 mg/kg once weekly
group 5: ovariectomized mice treated with E+P and specific antibody 005_C04 at a dose of 30 mg/kg once weekly
group 6: ovariectomized mice treated with E + P and unspecific control antibody at a dose of 30 mg/kg once weekly Figure 20: Effect of neutralizing PRLR antibodies on endometriosis interna (adenomyosis uteri)

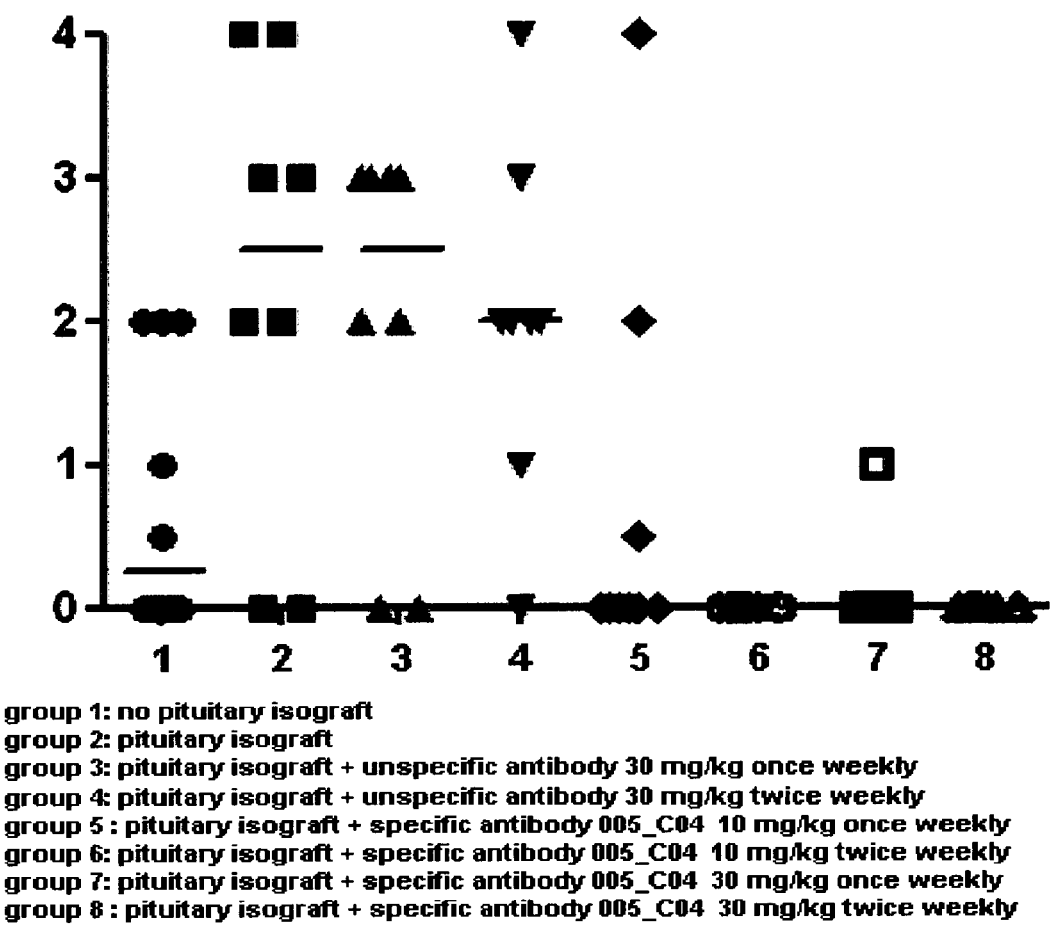

group 1: no pituitary isograft
group 2: pituitary isograft
group 3: pituitary isograft + unspecific antibody 30 mg/kg once weekly
group 4: pituitary isograft + unspecific antibody 30 mg/kg twice weekly
group 5 : pituitary isograft + specific antibody 005_C04 10 mg/kg once weekly
group 6: pituitary isograft + specific antibody 005_C04 10 mg/kg twice weekly
group 7: pituitary isograft + specific antibody 005_C04 30 mg/kg once weekly
group 8 : pituitary isograft + specific antibody 005_C04 30 mg/kg twice weekly

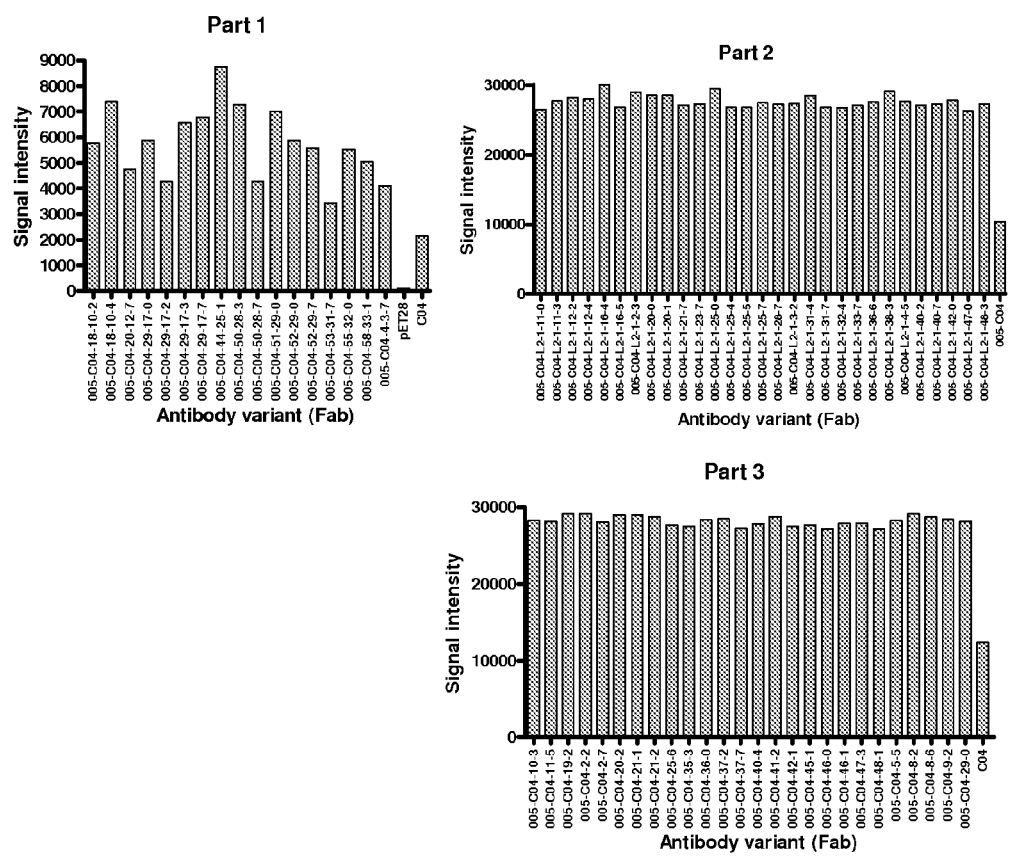
Figure 21. ELISA-based binding tests of maturated 005-C04 Fab variants in E. coli supernatants with the extracellular domain of the human PRLR.

NEUTRALIZING PROLACTIN RECEPTOR ANTIBODIES AND THEIR THERAPEUTIC USE

The present invention is directed towards the prolactin receptor antibody 005-C04 and provides recombinant antigen-binding regions and antibodies and functional fragments containing such antigen-binding regions, that specifically bind and neutralize the prolactin receptor, nucleic acid sequences encoding the foregoing antibodies, vectors containing the same, pharmaceutical compositions containing them and their use in the treatment or prevention of benign diseases and indications which benefit from inhibition of prolactin receptor mediated signaling such as endometriosis, adenomyosis, non-hormonal female contraception, benign breast disease, mastalgia, lactation inhibition, benign prostate hyperplasia, fibroids as well as hyper- and normoprolactinemic hair loss, and cotreatment in combined hormone therapy to inhibit mammary epithelial cell proliferation.

There is an unmet medical need for the treatment of various benign diseases and indications such as endometriosis, adenomyosis, non-hormonal female contraception, benign breast disease, mastalgia, lactation inhibition, benign prostate hyperplasia, fibroids, hyper- and normoprolactinemic hair loss, and prevention of mammary epithelial cell proliferation in combined (i.e. estrogen plus progestin) hormone therapy.

Prolactin (PRL) is a polypeptide hormone composed of 199 amino acids. PRL belongs to the growth hormone (GH), placental lactogen (PL) family of polypeptide hormones and is synthesized in lactotroph cells of the pituitary and in several extrapituitary tissues such as lymphocytes, mammary epithelial cells, the myometrium, and the prostate. Two different promoters regulate pituitary and extrapituitary PRL synthesis (BioEssays 28:1051-1055, 2006).

PRL binds to the PRL receptor (PRLR), a single transmembrane receptor belonging to the class 1 cytokine receptor superfamily (Endocrine Reviews 19:225-268, 1998). The PRLR exists in three different isoforms, the short, the long, and the intermediate form that can be distinguished by the length of their cytoplasmic tails. Upon ligand binding, a sequential process leads to PRLR activation. PRL interacts via its binding site 1 with one PRLR molecule and then attracts via its binding site 2 a second receptor molecule leading to an active dimer of PRLRs. PRLR dimerization leads to the predominant activation of the JAK/STAT (Janus Kinase/Signal transducers and activators of transcription) pathway. Upon receptor dimerization, JAKs (predominantly JAK2) associated with the receptor, transphosphorylate and activate each other. In addition the PRLR is also phosphorylated and can bind to SH2-domain containing proteins such as STATs. Receptor bound STATs are subsequently phosphorylated, dissociate from the receptor and translocate to the nucleus where they stimulate transcription of target genes. In addition, activation of the Ras-Raf-MAPK pathway and activation of the cytoplasmic src kinase by PRLRs have been described (for review Endocrine Reviews 19: 225-268, 1998).

PRLR-mediated signaling plays a role in a variety of processes such as mammary gland development, lactation, reproduction, mammary and prostate tumor growth, autoimmune diseases, general growth and metabolism, and immunomodulation (Endocrine Reviews 19: 225-268, 1998; Annu. Rev. Physiol. 64: 47-67, 2002).

Currently, complete interference with PRLR-mediated signaling is not possible. The only way to interfere with PRLR-mediated signaling is the inhibition of pituitary PRL secretion by use of bromocriptine and other dopamine receptor 2 agonists (Nature Clinical Practice Endocrinology and Metabolism 2(10): 571-581, 2006). These agents however, do not suppress extrapituitary PRL synthesis that can compensate successfully for the inhibition of pituitary PRL synthesis leading to almost unimpaired PRLR-mediated signaling (Endocrine Reviews 19:225-268, 1998). Therefore it is not surprising that dopamine type 2 receptor agonists were not beneficial in patients suffering from breast cancer or autoimmune diseases such as systemic lupus or rheumatoid arthritis (Breast Cancer Res. Treat. 14:289-29, 1989; Lupus 7:414-419, 1998) although prolactin has been implicated in these diseases. Local prolactin synthesis in breast cancer cells or lymphocytes which plays a pivotal role in mammary carcinoma or autoimmune diseases, respectively, was not blocked by dopamine receptor agonists.

Despite the above-mentioned attempts to provide means for treatment or prevention of benign diseases and indications such as endometriosis, adenomyosis, non-hormonal female contraception, benign breast disease and mastalgia, lactation inhibition, benign prostate hyperplasia, fibroids, hyper- and normoprolactinemic hair loss, and cotreatment in combined hormone therapy for the prevention of mammary epithelial cell proliferation no compounds are available yet to meet that need. It is therefore an object of the present invention, to solve that problem by providing compounds that are therapeutics for these benign diseases and indications.

Now novel antibodies have been identified that are specific to and have a high affinity for PRLR and this way neutralize the PRLR-mediated signaling and that can deliver a therapeutic benefit to the subject.

Blockade of PRLR activation by neutralizing PRLR antibodies leads to a complete inhibition of PRLR-mediated signaling. In contrast, dopamine receptor agonists can only interfere with enhanced PRLR-mediated signaling in response to elevated pituitary prolactin secretion, but not with enhanced PRLR-mediated signaling due to an activating PRLR mutation or due to locally elevated prolactin production.

Therefore the problem is solved by provision of the antibody 005-C04, and antigen-binding fragments thereof, or variants thereof for the treatment of the afore mentioned benign diseases and indications, that bind to PRLR with high affinity, efficiently neutralize the PRLR-mediated signaling, and that are preferably cross-reactive to PRLR from other species such as *Macacca mulatta* and *Macacca fascicularis*, *Mus musculus* or *Rattus norvegicus*.

Some PRLR antibodies have already been described in the application WO2008/022295 (Novartis) and in the U.S. Pat. No. 7,422,899 (Biogen). The present invention is based on the discovery of novel antibodies that are specific to and have a high affinity for PRLR and this way neutralize the PRLR-mediated signaling and that can deliver a therapeutic benefit to the subject (sequences of novel antibodies are as in SEQ ID NO: 34, 40, 46, and 52). The antibodies of the invention, which may be human or humanized or chimeric or human engineered, can be used in many contexts which are more fully described herein.

Therefore an object of the present invention is an antibody or antigen-binding fragment, whereby said antibody antagonizes prolactin receptor-mediated signaling.

The novel antibodies '002-H06', '002-H08', '006-H07', '001-E06', '006-H08' are subject matter of corresponding applications.

The antibodies were characterized in several cellular systems to determine their species specificity and their potency as well as efficacy in different readout paradigms addressing the inactivation of PRLR-mediated signaling (see Examples 5-10). Proliferation assays were performed with rat Nb2-11 cells (Example 6, FIG. 6) or Ba/F cells either stably transfected with the human PRLR (Example 5, FIG. 5) or the murine PRLR (Example 10, FIG. 10). Whereas Novartis antibody XHA 06.983 did not show activity on the rat and murine PRLR, Novartis antibody XHA06.642 showed activity on the rat PRLR but not on the murine PRLR. XHA 06.642 inhibited human PRLR-mediated signaling (Example 5, 7, 8). The novel antibody of a corresponding application 006-H08 showed the highest potency with regard to proliferation inhibition of Ba/F cells stably transfected with the human PRLR (Example 5, FIG. 5). The novel antibody 005-C04 of a present invention was the only antibody showing crossreactivity on the murine (Example 10, 9) and human PRLR (Examples 5, 7, 8). In contrast to the Novartis antibody XHA06.642 the novel antibody 005-C04 is therefore suitable for testing the inhibition of PRLR-mediated signaling in murine models. All other antibodies described in this application or in the corresponding applications are specific for the human PRLR. In addition to cellular proliferation assays (Examples 5, 6, 10), luciferase reporter assays were performed using HEK293 cells stably transfected with either the human (Example 8) or murine (Example 9) PRLR and transiently transfected with a luciferase reporter gene under the control of LHRE's (lactogenic hormone response elements). Using these systems the inability of the Novartis antibody XHA06.642 to efficiently block murine PRLR-mediated signaling became evident again (Example 9). In contrast, the novel antibody 005-C04 blocked luciferase reporter gene activation by the murine PRLR (Example 9). STAT5 phosphorylation in human T47D cells was used as additional readout to analyze the inhibitory activity of the antibodies on the human PRLR (Example 7, FIG. 7). As expected, unspecific antibodies were inactive in all experimental paradigms analyzed.

The present invention relates to methods to inhibit growth of PRLR-positive cells and the progression of the afore mentioned benign diseases and indications by providing anti-PRLR antibodies. Provided are human monoclonal antibodies, antigen-binding fragments thereof, and variants of the antibodies and fragments, that specifically bind to the extracellular domain (ECD) of PRLR (SEQ ID NO: 70) or human polymorphic variants of SEQ ID No: 70 such as the I146L and I76V variants being described in PNAS 105 (38), 14533, 2008, and J. Clin. Endocrinol. Metab. 95 (1), 271, 2010.

Another object of the present invention is an antibody which binds to epitopes of the extracellular domain of the prolactin receptor and human polymorphic variants thereof, whereby the amino acid sequence of the extracellular domain of the prolactin receptor corresponds to SEQ ID NO: 70, and the nucleic acid sequence corresponds to SEQ ID NO: 71.

The antibodies, antigen-binding fragments, and variants of the antibodies and fragments of the invention are comprised of a light chain variable region and a heavy chain variable region. Variants of the antibodies or antigen-binding fragments contemplated in the invention are molecules in which the binding activity of the antibody or antigen-binding antibody fragment for PRLR is maintained (for sequences see table 5).

Therefore an object of the present invention is an antibody or antigen-binding fragment, whereby the antibody or the antigen-binding fragment competes to the antibody 005-C04 or defined maturated variants thereof. The sequences of the antibodies and its maturate variants are depicted in table 5.

Also an object of the present invention are an antibody or antigen-binding fragment a. whereby the amino acid sequences of the variable heavy and light regions are at least 60%, more preferred 70%, more preferred 80%, or 90%, or even more preferred 95% identical to SEQ ID NO: 39 for the variable heavy chain domain and, identical to SEQ ID NO: 45 for the variable light chain domain, or b. whereby for the maturated forms of antibody 005-C04 the amino acid sequences of the variable heavy chain and light chain domain are at least 60%, more preferred 70%, more preferred 80%, or 90%, or even more preferred 95% identical thereto, or c. whereby the amino acid sequences of the CDRs are at least 60%, more preferred 70%, more preferred 80%, more preferred 90%, or even more preferred 95% identical to SEQ ID NO: 6, 12 and 17 for the heavy chain domain, and to SEQ ID NO: 23, 28, and 33 for the variable light chain domain.

In one embodiment an antibody or antigen-binding fragment comprising the CDRs of the antibody as described above, whereby a. the variable heavy chain contains the CDR sequences corresponding to SEQ ID NO: 6, 12 and 17 and the variable light chain contains the CDR sequences corresponding to SEQ ID NO: 23, 28, and 33, or b. the variable heavy chain contains the CDR sequences corresponding to SEQ ID NO: 103, 104, 17, and the variable light chain contains the CDR sequences corresponding to SEQ ID NO: 136, 140, 33; or c. the variable heavy chain contains the CDR sequences corresponding to SEQ ID NO: 103, 105, 17, and the variable light chain contains the CDR sequences corresponding to SEQ ID NO: 136, 139, 33; or d. the variable heavy chain contains the CDR sequences corresponding to SEQ ID NO: 6, 12, 17, and the variable light chain contains the CDR sequences corresponding to SEQ ID NO: 23, 139, 33; or e. the variable heavy chain contains the CDR sequences corresponding to SEQ ID NO: 6, 12, 17, and the variable light chain contains the CDR sequences corresponding to SEQ ID NO: 23, 141, 33; or f. the variable heavy chain contains the CDR sequences corresponding to SEQ ID NO: 102, 106, 17, and the variable light chain contains the CDR sequences corresponding to SEQ ID NO: 136, 138, 33; or g. the variable heavy chain contains the CDR sequences corresponding to SEQ ID NO: 102, 106, 17, and the variable light chain contains the CDR sequences corresponding to SEQ ID NO: 136, 140, 33; or h. the variable heavy chain contains the CDR sequences corresponding to SEQ ID NO: 103, 108, 17, and the variable light chain contains the CDR sequences corresponding to SEQ ID NO: 137, 28, 33; or i. the variable heavy chain contains the CDR sequences corresponding to SEQ ID NO: 6, 12, 17, and the variable light chain contains the CDR sequences corresponding to SEQ ID NO: 23, 138, 33; or j. the variable heavy chain contains the CDR sequences corresponding to SEQ ID NO: 102, 114, 17, and the variable light chain contains the CDR sequences corresponding to SEQ ID NO: 136, 28, 33; or k. the variable heavy chain contains the CDR sequences corresponding to SEQ ID NO: 102, 104, 17, and the variable light chain contains the CDR sequences corresponding to SEQ ID NO: 136, 140, 33; or l. the variable heavy chain contains the CDR sequences corresponding to SEQ ID NO: 102, 111, 17, and the variable light chain contains the CDR sequences corresponding to SEQ ID NO: 136, 139, 33; or m. the variable heavy chain contains the CDR sequences corresponding to SEQ ID NO: 103, 116, 17, and the variable light chain contains the CDR sequences corresponding to SEQ ID NO: 136, 140, 33; or
n. the variable heavy chain contains the CDR sequences corresponding to SEQ ID NO: 102, 118, 17, and the variable light chain contains the CDR sequences corresponding to SEQ ID NO: 136, 138, 33; or
o. the variable heavy chain contains the CDR sequences corresponding to SEQ ID NO: 6, 12, 17, and the variable light chain contains the CDR sequences corresponding to SEQ ID NO: 23, 28, 143; or
p. the variable heavy chain contains the CDR sequences corresponding to SEQ ID NO: 6, 12, 17, and the variable light chain contains the CDR sequences corresponding to SEQ ID NO: 23, 28, 145; or
q. the variable heavy chain contains the CDR sequences corresponding to SEQ ID NO: 6, 12, 17, and the variable light chain contains the CDR sequences corresponding to SEQ ID NO: 23, 28, 144; or
r. the variable heavy chain contains the CDR sequences corresponding to SEQ ID NO: 6, 12, 17, and the variable light chain contains the CDR sequences corresponding to SEQ ID NO: 23, 28, 146; or
s. the variable heavy chain contains the CDR sequences corresponding to SEQ ID NO: 103, 110, 17, and the variable light chain contains the CDR sequences corresponding to SEQ ID NO: 136, 140, 33; or
t. the variable heavy chain contains the CDR sequences corresponding to SEQ ID NO: 103, 110, 17, and the variable light chain contains the CDR sequences corresponding to SEQ ID NO: 136, 139, 33; or
u. the variable heavy chain contains the CDR sequences corresponding to SEQ ID NO: 103, 127, 17, and the variable light chain contains the CDR sequences corresponding to SEQ ID NO: 136, 141, 33; or
v. the variable heavy chain contains the CDR sequences corresponding to SEQ ID NO: 103, 127, 17, and the variable light chain contains the CDR sequences corresponding to SEQ ID NO: 136, 141, 33; or
w. the variable heavy chain contains the CDR sequences corresponding to SEQ ID NO: 6, 12, 17, and the variable light chain contains the CDR sequences corresponding to SEQ ID NO: 136, 28, 33; or
x. the variable heavy chain contains the CDR sequences corresponding to SEQ ID NO: 102, 117, 17, and the variable light chain contains the CDR sequences corresponding to SEQ ID NO: 136, 140, 33; or
y. the variable heavy chain contains the CDR sequences corresponding to SEQ ID NO: 102, 119, 17, and the variable light chain contains the CDR sequences corresponding to SEQ ID NO: 136, 28, 33; or
z. the variable heavy chain contains the CDR sequences corresponding to SEQ ID NO: 102, 115, 17, and the variable light chain contains the CDR sequences corresponding to SEQ ID NO: 136, 138, 33; or
aa. the variable heavy chain contains the CDR sequences corresponding to SEQ ID NO: 102, 12, 17, and the variable light chain contains the CDR sequences corresponding to SEQ ID NO: 23, 28, 33; or
bb. the variable heavy chain contains the CDR sequences corresponding to SEQ ID NO: 102, 119, 17, and the variable light chain contains the CDR sequences corresponding to SEQ ID NO: 136, 139, 33; or
cc. the variable heavy chain contains the CDR sequences corresponding to SEQ ID NO: 102, 116, 17, and the variable light chain contains the CDR sequences corresponding to SEQ ID NO: 136, 140, 33; or
dd. the variable heavy chain contains the CDR sequences corresponding to SEQ ID NO: 102, 107, 17, and the variable light chain contains the CDR sequences corresponding to SEQ ID NO: 136, 140, 33; or
ee. the variable heavy chain contains the CDR sequences corresponding to SEQ ID NO: 103, 108, 17, and the variable light chain contains the CDR sequences corresponding to SEQ ID NO: 136, 28, 33; or
ff. the variable heavy chain contains the CDR sequences corresponding to SEQ ID NO: 102, 119, 17, and the variable light chain contains the CDR sequences corresponding to SEQ ID NO: 136, 28, 33; or
gg. the variable heavy chain contains the CDR sequences corresponding to SEQ ID NO: 102, 133, 17, and the variable light chain contains the CDR sequences corresponding to SEQ ID NO: 136, 138, 33; or
hh. the variable heavy chain contains the CDR sequences corresponding to SEQ ID NO: 6, 123, 17, and the variable light chain contains the CDR sequences corresponding to SEQ ID NO: 23, 28, 33; or
ii. the variable heavy chain contains the CDR sequences corresponding to SEQ ID NO: 6, 120, 17, and the variable light chain contains the CDR sequences corresponding to SEQ ID NO: 23, 28, 33; or
jj. the variable heavy chain contains the CDR sequences corresponding to SEQ ID NO: 6, 125, 17, and the variable light chain contains the CDR sequences corresponding to SEQ ID NO: 23, 28, 33; or
kk. the variable heavy chain contains the CDR sequences corresponding to SEQ ID NO: 6, 134, 17, and the variable light chain contains the CDR sequences corresponding to SEQ ID NO: 23, 28, 33; or
ll. the variable heavy chain contains the CDR sequences corresponding to SEQ ID NO: 6, 119, 17, and the variable light chain contains the CDR sequences corresponding to SEQ ID NO: 23, 28, 33; or
mm. the variable heavy chain contains the CDR sequences corresponding to SEQ ID NO: 6, 128, 17, and the variable light chain contains the CDR sequences corresponding to SEQ ID NO: 23, 28, 33; or
nn. the variable heavy chain contains the CDR sequences corresponding to SEQ ID NO: 6, 122, 17, and the variable light chain contains the CDR sequences corresponding to SEQ ID NO: 23, 28, 33; or
oo. the variable heavy chain contains the CDR sequences corresponding to SEQ ID NO: 6, 124, 17, and the variable light chain contains the CDR sequences corresponding to SEQ ID NO: 23, 28, 33; or
pp. the variable heavy chain contains the CDR sequences corresponding to SEQ ID NO: 102, 106, 17, and the variable light chain contains the CDR sequences corresponding to SEQ ID NO: 136, 28, 33; or
qq. the variable heavy chain contains the CDR sequences corresponding to SEQ ID NO: 103, 118, 17, and the variable light chain contains the CDR sequences corresponding to SEQ ID NO: 135, 28, 33; or
rr. the variable heavy chain contains the CDR sequences corresponding to SEQ ID NO: 103, 120, 17, and the variable light chain contains the CDR sequences corresponding to SEQ ID NO: 136, 142, 33; or
ss. the variable heavy chain contains the CDR sequences corresponding to SEQ ID NO: 103, 117, 17, and the variable light chain contains the CDR sequences corresponding to SEQ ID NO: 23, 140, 33; or
tt. the variable heavy chain contains the CDR sequences corresponding to SEQ ID NO: 102, 130, 17, and the variable light chain contains the CDR sequences corresponding to SEQ ID NO: 23, 139, 33; or
uu. the variable heavy chain contains the CDR sequences corresponding to SEQ ID NO: 102, 111, 17, and the variable light chain contains the CDR sequences corresponding to SEQ ID NO: 23, 140, 33; or
vv. the variable heavy chain contains the CDR sequences corresponding to SEQ ID NO: 102, 114, 17, and the variable light chain contains the CDR sequences corresponding to SEQ ID NO: 23, 141, 33; or
ww. the variable heavy chain contains the CDR sequences corresponding to SEQ ID NO: 102, 116, 17, and the variable light chain contains the CDR sequences corresponding to SEQ ID NO: 23, 141, 33; or
xx. the variable heavy chain contains the CDR sequences corresponding to SEQ ID NO: 103, 119, 17, and the variable light chain contains the CDR sequences corresponding to SEQ ID NO: 23, 140, 33; or
yy. the variable heavy chain contains the CDR sequences corresponding to SEQ ID NO: 102, 112, 17, and the variable light chain contains the CDR sequences corresponding to SEQ ID NO: 23, 141, 33; or
zz. the variable heavy chain contains the CDR sequences corresponding to SEQ ID NO: 103, 116, 17, and the variable light chain contains the CDR sequences corresponding to SEQ ID NO: 23, 140, 33; or
aaa. the variable heavy chain contains the CDR sequences corresponding to SEQ ID NO: 103, 120, 17, and the variable light chain contains the CDR sequences corresponding to SEQ ID NO: 136, 141, 33; or
bbb. the variable heavy chain contains the CDR sequences corresponding to SEQ ID NO: 103, 116, 17, and the variable light chain contains the CDR sequences corresponding to SEQ ID NO: 23, 138, 33; or
ccc. the variable heavy chain contains the CDR sequences corresponding to SEQ ID NO: 102, 109, 17, and the variable light chain contains the CDR sequences corresponding to SEQ ID NO: 23, 141, 33; or
ddd. the variable heavy chain contains the CDR sequences corresponding to SEQ ID NO: 103, 120, 17, and the variable light chain contains the CDR sequences corresponding to SEQ ID NO: 23, 141, 33; or
eee. the variable heavy chain contains the CDR sequences corresponding to SEQ ID NO: 102, 105, 17, and the variable light chain contains the CDR sequences corresponding to SEQ ID NO: 23, 138, 33; or
fff. the variable heavy chain contains the CDR sequences corresponding to SEQ ID NO: 102, 132, 17, and the variable light chain contains the CDR sequences corresponding to SEQ ID NO: 23, 138, 33; or
ggg. the variable heavy chain contains the CDR sequences corresponding to SEQ ID NO: 103, 120, 17, and the variable light chain contains the CDR sequences corresponding to SEQ ID NO: 136, 141, 33; or
hhh. the variable heavy chain contains the CDR sequences corresponding to SEQ ID NO: 102, 129, 17, and the variable light chain contains the CDR sequences corresponding to SEQ ID NO: 23, 140, 33; or
iii. the variable heavy chain contains the CDR sequences corresponding to SEQ ID NO: 102, 117, 17, and the variable light chain contains the CDR sequences corresponding to SEQ ID NO: 23, 140, 33; or
jjj. the variable heavy chain contains the CDR sequences corresponding to SEQ ID NO: 102, 129, 17, and the variable light chain contains the CDR sequences corresponding to SEQ ID NO: 23, 142, 33; or
kkk. the variable heavy chain contains the CDR sequences corresponding to SEQ ID NO: 103, 104, 17, and the variable light chain contains the CDR sequences corresponding to SEQ ID NO: 23, 142, 33; or
lll. the variable heavy chain contains the CDR sequences corresponding to SEQ ID NO: 102, 107, 17, and the variable light chain contains the CDR sequences corresponding to SEQ ID NO: 23, 142, 33; or
mmm. the variable heavy chain contains the CDR sequences corresponding to SEQ ID NO: 102, 113, 17, and the variable light chain contains the CDR sequences corresponding to SEQ ID NO: 23, 140, 33; or
nnn. the variable heavy chain contains the CDR sequences corresponding to SEQ ID NO: 102, 131, 17, and the variable light chain contains the CDR sequences corresponding to SEQ ID NO: 23, 142, 33; or
ooo. the variable heavy chain contains the CDR sequences corresponding to SEQ ID NO: 102, 115, 17, and the variable light chain contains the CDR sequences corresponding to SEQ ID NO: 136, 141, 33; or
ppp. the variable heavy chain contains the CDR sequences corresponding to SEQ ID NO: 103, 119, 17, and the variable light chain contains the CDR sequences corresponding to SEQ ID NO: 136, 141, 33; or
qqq. the variable heavy chain contains the CDR sequences corresponding to SEQ ID NO: 102, 109, 17, and the variable light chain contains the CDR sequences corresponding to SEQ ID NO: 23, 138, 33; or
rrr. the variable heavy chain contains the CDR sequences corresponding to SEQ ID NO: 102, 121, 17, and the variable light chain contains the CDR sequences corresponding to SEQ ID NO: 23, 142, 33; or
sss. the variable heavy chain contains the CDR sequences corresponding to SEQ ID NO: 102, 126, 17, and the variable light chain contains the CDR sequences corresponding to SEQ ID NO: 23, 142, 33; or
ttt. the variable heavy chain contains the CDR sequences corresponding to SEQ ID NO: 102, 105, 17, and the variable light chain contains the CDR sequences corresponding to SEQ ID NO: 23, 141, 33; or
uuu. the variable heavy chain contains the CDR sequences corresponding to SEQ ID NO: 102, 108, 17, and the variable light chain contains the CDR sequences corresponding to SEQ ID NO: 23, 138, 33.

In one embodiment human antibody 005-C04, or maturated form thereof or chimeric antibody or antigen-binding fragment thereof are disclosed, whereby the antibody
  a. 005-C04 comprises a variable heavy chain domain corresponding to a nucleic acid sequence according to SEQ ID NO: 46, and an amino acid sequence according to SEQ ID NO: 34, and a variable light chain domain with a nucleic acid sequence according to SEQ ID NO: 52, and an amino acid sequence according to SEQ ID NO: 40.
  b. 005-C04-10-3 comprises a variable heavy chain domain corresponding to a nucleic acid sequence according to SEQ ID NO: 375, and an amino acid sequence according to SEQ ID NO: 447, and a variable light chain domain with a nucleic acid sequence according to SEQ ID NO: 259, and an amino acid sequence according to SEQ ID NO: 187,
  c. 005-C04-11-5 comprises a variable heavy chain domain corresponding to a nucleic acid sequence according to SEQ ID NO: 376, and an amino acid sequence according to SEQ ID NO: 448, and a variable light chain domain with a nucleic acid sequence according to SEQ ID NO: 260, and an amino acid sequence according to SEQ ID NO: 188, d. 005-C04-18-10-2 comprises a variable heavy chain domain corresponding to a nucleic acid sequence according to SEQ ID NO: 377, and an amino acid sequence according to SEQ ID NO: 449, and a variable light chain domain with a nucleic acid sequence according to SEQ ID NO: 261, and an amino acid sequence according to SEQ ID NO: 189, e. 005-C04-18-10-4 comprises a variable heavy chain domain corresponding to a nucleic acid sequence according to SEQ ID NO: 378, and an amino acid sequence according to SEQ ID NO: 450, and a variable light chain domain with a nucleic acid sequence according to SEQ ID NO: 262, and an amino acid sequence according to SEQ ID NO: 190, f. 005-C04-19-2 comprises a variable heavy chain domain corresponding to a nucleic acid sequence according to SEQ ID NO: 379, and an amino acid sequence according to SEQ ID NO: 451, and a variable light chain domain with a nucleic acid sequence according to SEQ ID NO: 263, and an amino acid sequence according to SEQ ID NO: 191, g. 005-C04-2-2 comprises a variable heavy chain domain corresponding to a nucleic acid sequence according to SEQ ID NO: 380, and an amino acid sequence according to SEQ ID NO: 452, and a variable light chain domain with a nucleic acid sequence according to SEQ ID NO: 264, and an amino acid sequence according to SEQ ID NO: 192, h. 005-C04-2-7 comprises a variable heavy chain domain corresponding to a nucleic acid sequence according to SEQ ID NO: 381, and an amino acid sequence according to SEQ ID NO: 453, and a variable light chain domain with a nucleic acid sequence according to SEQ ID NO: 265, and an amino acid sequence according to SEQ ID NO: 193, i. 005-C04-20-12-7 comprises a variable heavy chain domain corresponding to a nucleic acid sequence according to SEQ ID NO: 382, and an amino acid sequence according to SEQ ID NO: 454, and a variable light chain domain with a nucleic acid sequence according to SEQ ID NO: 266, and an amino acid sequence according to SEQ ID NO: 194, j. 005-C04-20-2 comprises a variable heavy chain domain corresponding to a nucleic acid sequence according to SEQ ID NO: 383, and an amino acid sequence according to SEQ ID NO: 455, and a variable light chain domain with a nucleic acid sequence according to SEQ ID NO: 267, and an amino acid sequence according to SEQ ID NO: 195, k. 005-C04-21-1 comprises a variable heavy chain domain corresponding to a nucleic acid sequence according to SEQ ID NO: 384, and an amino acid sequence according to SEQ ID NO: 456, and a variable light chain domain with a nucleic acid sequence according to SEQ ID NO: 268, and an amino acid sequence according to SEQ ID NO: 196, l. 005-C04-21-2 comprises a variable heavy chain domain corresponding to a nucleic acid sequence according to SEQ ID NO: 385, and an amino acid sequence according to SEQ ID NO: 457, and a variable light chain domain with a nucleic acid sequence according to SEQ ID NO: 269, and an amino acid sequence according to SEQ ID NO: 197, m. 005-C04-25-6 comprises a variable heavy chain domain corresponding to a nucleic acid sequence according to SEQ ID NO: 386, and an amino acid sequence according to SEQ ID NO: 458, and a variable light chain domain with a nucleic acid sequence according to SEQ ID NO: 270, and an amino acid sequence according to SEQ ID NO: 198, n. 005-C04-29-0 comprises a variable heavy chain domain corresponding to a nucleic acid sequence according to SEQ ID NO: 387, and an amino acid sequence according to SEQ ID NO: 459, and a variable light chain domain with a nucleic acid sequence according to SEQ ID NO: 271, and an amino acid sequence according to SEQ ID NO: 199, o. 005-C04-29-17-0 comprises a variable heavy chain domain corresponding to a nucleic acid sequence according to SEQ ID NO: 388, and an amino acid sequence according to SEQ ID NO: 460, and a variable light chain domain with a nucleic acid sequence according to SEQ ID NO: 272, and an amino acid sequence according to SEQ ID NO: 200, p. 005-C04-29-17-2 comprises a variable heavy chain domain corresponding to a nucleic acid sequence according to SEQ ID NO: 389, and an amino acid sequence according to SEQ ID NO: 461, and a variable light chain domain with a nucleic acid sequence according to SEQ ID NO: 273, and an amino acid sequence according to SEQ ID NO: 201, q. 005-C04-29-17-3 comprises a variable heavy chain domain corresponding to a nucleic acid sequence according to SEQ ID NO: 390, and an amino acid sequence according to SEQ ID NO: 462, and a variable light chain domain with a nucleic acid sequence according to SEQ ID NO: 274, and an amino acid sequence according to SEQ ID NO: 202, r. 005-C04-29-17-7 comprises a variable heavy chain domain corresponding to a nucleic acid sequence according to SEQ ID NO: 391, and an amino acid sequence according to SEQ ID NO: 463, and a variable light chain domain with a nucleic acid sequence according to SEQ ID NO: 275, and an amino acid sequence according to SEQ ID NO: 203, s. 005-C04-35-3 comprises a variable heavy chain domain corresponding to a nucleic acid sequence according to SEQ ID NO: 392, and an amino acid sequence according to SEQ ID NO: 464, and a variable light chain domain with a nucleic acid sequence according to SEQ ID NO: 276, and an amino acid sequence according to SEQ ID NO: 204, t. 005-C04-36-0 comprises a variable heavy chain domain corresponding to a nucleic acid sequence according to SEQ ID NO: 393, and an amino acid sequence according to SEQ ID NO: 465, and a variable light chain domain with a nucleic acid sequence according to SEQ ID NO: 277, and an amino acid sequence according to SEQ ID NO: 205, u. 005-C04-37-2 comprises a variable heavy chain domain corresponding to a nucleic acid sequence according to SEQ ID NO: 394, and an amino acid sequence according to SEQ ID NO: 466, and a variable light chain domain with a nucleic acid sequence according to SEQ ID NO: 278, and an amino acid sequence according to SEQ ID NO: 206, v. 005-C04-37-7 comprises a variable heavy chain domain corresponding to a nucleic acid sequence according to SEQ ID NO: 395, and an amino acid sequence according to SEQ ID NO: 467, and a variable light chain domain with a nucleic acid sequence according to SEQ ID NO: 279, and an amino acid sequence according to SEQ ID NO: 207, w. 005-C04-4-3-7 comprises a variable heavy chain domain corresponding to a nucleic acid sequence according to SEQ ID NO: 396, and an amino acid sequence according to SEQ ID NO: 468, and a variable light chain domain with a nucleic acid sequence according to SEQ ID NO: 280, and an amino acid sequence according to SEQ ID NO: 208, x. 005-C04-40-4 comprises a variable heavy chain domain corresponding to a nucleic acid sequence according to SEQ ID NO: 397, and an amino acid sequence according to SEQ ID NO: 469, and a variable light chain domain with a nucleic acid sequence according to SEQ ID NO: 281, and an amino acid sequence according to SEQ ID NO: 209, y. 005-C04-41-2 comprises a variable heavy chain domain corresponding to a nucleic acid sequence according to SEQ ID NO: 398, and an amino acid sequence according to SEQ ID NO: 470, and a variable light chain domain with a nucleic acid sequence according to SEQ ID NO: 282, and an amino acid sequence according to SEQ ID NO: 210, z. 005-C04-42-1 comprises a variable heavy chain domain corresponding to a nucleic acid sequence according to SEQ ID NO: 399, and an amino acid sequence according to SEQ ID NO: 471, and a variable light chain domain with a nucleic acid sequence according to SEQ ID NO: 283, and an amino acid sequence according to SEQ ID NO: 211, aa. 005-C04-44-25-1 comprises a variable heavy chain domain corresponding to a nucleic acid sequence according to SEQ ID NO: 400, and an amino acid sequence according to SEQ ID NO: 472, and a variable light chain domain with a nucleic acid sequence according to SEQ ID NO: 284, and an amino acid sequence according to SEQ ID NO: 212, bb. 005-C04-45-1 comprises a variable heavy chain domain corresponding to a nucleic acid sequence according to SEQ ID NO: 401, and an amino acid sequence according to SEQ ID NO: 473, and a variable light chain domain with a nucleic acid sequence according to SEQ ID NO: 285, and an amino acid sequence according to SEQ ID NO: 213, cc. 005-C04-46-0 comprises a variable heavy chain domain corresponding to a nucleic acid sequence according to SEQ ID NO: 402, and an amino acid sequence according to SEQ ID NO: 474, and a variable light chain domain with a nucleic acid sequence according to SEQ ID NO: 286, and an amino acid sequence according to SEQ ID NO: 214, dd. 005-C04-46-1 comprises a variable heavy chain domain corresponding to a nucleic acid sequence according to SEQ ID NO: 403, and an amino acid sequence according to SEQ ID NO: 475, and a variable light chain domain with a nucleic acid sequence according to SEQ ID NO: 287, and an amino acid sequence according to SEQ ID NO: 215, ee. 005-C04-47-3 comprises a variable heavy chain domain corresponding to a nucleic acid sequence according to SEQ ID NO: 404, and an amino acid sequence according to SEQ ID NO: 476, and a variable light chain domain with a nucleic acid sequence according to SEQ ID NO: 288, and an amino acid sequence according to SEQ ID NO: 216, ff. 005-C04-48-1 comprises a variable heavy chain domain corresponding to a nucleic acid sequence according to SEQ ID NO: 405, and an amino acid sequence according to SEQ ID NO: 477, and a variable light chain domain with a nucleic acid sequence according to SEQ ID NO: 289, and an amino acid sequence according to SEQ ID NO: 217, gg. 005-C04-5-5 comprises a variable heavy chain domain corresponding to a nucleic acid sequence according to SEQ ID NO: 406, and an amino acid sequence according to SEQ ID NO: 478, and a variable light chain domain with a nucleic acid sequence according to SEQ ID NO: 290, and an amino acid sequence according to SEQ ID NO: 218, hh. 005-C04-50-28-3 comprises a variable heavy chain domain corresponding to a nucleic acid sequence according to SEQ ID NO: 407, and an amino acid sequence according to SEQ ID NO: 479, and a variable light chain domain with a nucleic acid sequence according to SEQ ID NO: 291, and an amino acid sequence according to SEQ ID NO: 219, ii. 005-C04-50-28-7 comprises a variable heavy chain domain corresponding to a nucleic acid sequence according to SEQ ID NO: 408, and an amino acid sequence according to SEQ ID NO: 480, and a variable light chain domain with a nucleic acid sequence according to SEQ ID NO: 292, and an amino acid sequence according to SEQ ID NO: 220, jj. 005-C04-51-29-0 comprises a variable heavy chain domain corresponding to a nucleic acid sequence according to SEQ ID NO: 409, and an amino acid sequence according to SEQ ID NO: 481, and a variable light chain domain with a nucleic acid sequence according to SEQ ID NO: 293, and an amino acid sequence according to SEQ ID NO: 221, kk. 005-C04-52-29-0 comprises a variable heavy chain domain corresponding to a nucleic acid sequence according to SEQ ID NO: 410, and an amino acid sequence according to SEQ ID NO: 482, and a variable light chain domain with a nucleic acid sequence according to SEQ ID NO: 294, and an amino acid sequence according to SEQ ID NO: 222, ll. 005-C04-52-29-7 comprises a variable heavy chain domain corresponding to a nucleic acid sequence according to SEQ ID NO: 411, and an amino acid sequence according to SEQ ID NO: 483, and a variable light chain domain with a nucleic acid sequence according to SEQ ID NO: 295, and an amino acid sequence according to SEQ ID NO: 223, mm. 005-C04-53-31-7 comprises a variable heavy chain domain corresponding to a nucleic acid sequence according to SEQ ID NO: 412, and an amino acid sequence according to SEQ ID NO: 484, and a variable light chain domain with a nucleic acid sequence according to SEQ ID NO: 296, and an amino acid sequence according to SEQ ID NO: 224, nn. 005-C04-55-32-0 comprises a variable heavy chain domain corresponding to a nucleic acid sequence according to SEQ ID NO: 413, and an amino acid sequence according to SEQ ID NO: 485, and a variable light chain domain with a nucleic acid sequence according to SEQ ID NO: 297, and an amino acid sequence according to SEQ ID NO: 225, oo. 005-C04-58-33-1 comprises a variable heavy chain domain corresponding to a nucleic acid sequence according to SEQ ID NO: 414, and an amino acid sequence according to SEQ ID NO: 486, and a variable light chain domain with a nucleic acid sequence according to SEQ ID NO: 298, and an amino acid sequence according to SEQ ID NO: 226,
pp. 005-C04-8-2 comprises a variable heavy chain domain corresponding to a nucleic acid sequence according to SEQ ID NO: 415, and an amino acid sequence according to SEQ ID NO: 487, and a variable light chain domain with a nucleic acid sequence according to SEQ ID NO: 299, and an amino acid sequence according to SEQ ID NO: 227,
qq. 005-C04-8-6 comprises a variable heavy chain domain corresponding to a nucleic acid sequence according to SEQ ID NO: 416, and an amino acid sequence according to SEQ ID NO: 488, and a variable light chain domain with a nucleic acid sequence according to SEQ ID NO: 300, and an amino acid sequence according to SEQ ID NO: 228,
rr. 005-C04-9-2 comprises a variable heavy chain domain corresponding to a nucleic acid sequence according to SEQ ID NO: 417, and an amino acid sequence according to SEQ ID NO: 489, and a variable light chain domain with a nucleic acid sequence according to SEQ ID NO: 301, and an amino acid sequence according to SEQ ID NO: 229,
ss. 005-C04-L2-1-11-0 comprises a variable heavy chain domain corresponding to a nucleic acid sequence according to SEQ ID NO: 418, and an amino acid sequence according to SEQ ID NO: 490, and a variable light chain domain with a nucleic acid sequence according to SEQ ID NO: 302, and an amino acid sequence according to SEQ ID NO: 230,
tt. 005-C04-L2-1-11-3 comprises a variable heavy chain domain corresponding to a nucleic acid sequence according to SEQ ID NO: 419, and an amino acid sequence according to SEQ ID NO: 491, and a variable light chain domain with a nucleic acid sequence according to SEQ ID NO: 303, and an amino acid sequence according to SEQ ID NO: 231,
uu. 005-C04-L2-1-12-2 comprises a variable heavy chain domain corresponding to a nucleic acid sequence according to SEQ ID NO: 420, and an amino acid sequence according to SEQ ID NO: 492, and a variable light chain domain with a nucleic acid sequence according to SEQ ID NO: 304, and an amino acid sequence according to SEQ ID NO: 232,
vv. 005-C04-L2-1-12-4 comprises a variable heavy chain domain corresponding to a nucleic acid sequence according to SEQ ID NO: 421, and an amino acid sequence according to SEQ ID NO: 493, and a variable light chain domain with a nucleic acid sequence according to SEQ ID NO: 305, and an amino acid sequence according to SEQ ID NO: 233,
ww. 005-C04-L2-1-16-4 comprises a variable heavy chain domain corresponding to a nucleic acid sequence according to SEQ ID NO: 422, and an amino acid sequence according to SEQ ID NO: 494, and a variable light chain domain with a nucleic acid sequence according to SEQ ID NO: 306, and an amino acid sequence according to SEQ ID NO: 234,
xx. 005-C04-L2-1-16-5 comprises a variable heavy chain domain corresponding to a nucleic acid sequence according to SEQ ID NO: 423, and an amino acid sequence according to SEQ ID NO: 495, and a variable light chain domain with a nucleic acid sequence according to SEQ ID NO: 307, and an amino acid sequence according to SEQ ID NO: 235,
yy. 005-C04-L2-1-2-3 comprises a variable heavy chain domain corresponding to a nucleic acid sequence according to SEQ ID NO: 424, and an amino acid sequence according to SEQ ID NO: 496, and a variable light chain domain with a nucleic acid sequence according to SEQ ID NO: 308, and an amino acid sequence according to SEQ ID NO: 236,
zz. 005-C04-L2-1-20-0 comprises a variable heavy chain domain corresponding to a nucleic acid sequence according to SEQ ID NO: 425, and an amino acid sequence according to SEQ ID NO: 497, and a variable light chain domain with a nucleic acid sequence according to SEQ ID NO: 309, and an amino acid sequence according to SEQ ID NO: 237,
aaa. 005-C04-L2-1-20-1 comprises a variable heavy chain domain corresponding to a nucleic acid sequence according to SEQ ID NO: 426, and an amino acid sequence according to SEQ ID NO: 498, and a variable light chain domain with a nucleic acid sequence according to SEQ ID NO: 310, and an amino acid sequence according to SEQ ID NO: 238,
bbb. 005-C04-L2-1-21-7 comprises a variable heavy chain domain corresponding to a nucleic acid sequence according to SEQ ID NO: 427, and an amino acid sequence according to SEQ ID NO: 499, and a variable light chain domain with a nucleic acid sequence according to SEQ ID NO: 311, and an amino acid sequence according to SEQ ID NO: 239,
ccc. 005-C04-L2-1-23-7 comprises a variable heavy chain domain corresponding to a nucleic acid sequence according to SEQ ID NO: 428, and an amino acid sequence according to SEQ ID NO: 500, and a variable light chain domain with a nucleic acid sequence according to SEQ ID NO: 312, and an amino acid sequence according to SEQ ID NO: 240,
ddd. 005-C04-L2-1-25-0 comprises a variable heavy chain domain corresponding to a nucleic acid sequence according to SEQ ID NO: 429, and an amino acid sequence according to SEQ ID NO: 501, and a variable light chain domain with a nucleic acid sequence according to SEQ ID NO: 313, and an amino acid sequence according to SEQ ID NO: 241,
eee. 005-C04-L2-1-25-4 comprises a variable heavy chain domain corresponding to a nucleic acid sequence according to SEQ ID NO: 430, and an amino acid sequence according to SEQ ID NO: 502, and a variable light chain domain with a nucleic acid sequence according to SEQ ID NO: 314, and an amino acid sequence according to SEQ ID NO: 242,
fff. 005-C04-L2-1-25-5 comprises a variable heavy chain domain corresponding to a nucleic acid sequence according to SEQ ID NO: 431, and an amino acid sequence according to SEQ ID NO: 503, and a variable light chain domain with a nucleic acid sequence according to SEQ ID NO: 315, and an amino acid sequence according to SEQ ID NO: 243,
ggg. 005-C04-L2-1-25-7 comprises a variable heavy chain domain corresponding to a nucleic acid sequence according to SEQ ID NO: 432, and an amino acid sequence according to SEQ ID NO: 504, and a variable light chain domain with a nucleic acid sequence according to SEQ ID NO: 316, and an amino acid sequence according to SEQ ID NO: 244,
hhh. 005-C04-L2-1-28-7 comprises a variable heavy chain domain corresponding to a nucleic acid sequence according to SEQ ID NO: 433, and an amino acid sequence according to SEQ ID NO: 505, and a variable light chain domain with a nucleic acid sequence according to SEQ ID NO: 317, and an amino acid sequence according to SEQ ID NO: 245, iii. 005-C04-L2-1-3-2 comprises a variable heavy chain domain corresponding to a nucleic acid sequence according to SEQ ID NO: 434, and an amino acid sequence according to SEQ ID NO: 506, and a variable light chain domain with a nucleic acid sequence according to SEQ ID NO: 318, and an amino acid sequence according to SEQ ID NO: 246, jjj. 005-C04-L2-1-31-4 comprises a variable heavy chain domain corresponding to a nucleic acid sequence according to SEQ ID NO: 435, and an amino acid sequence according to SEQ ID NO: 507, and a variable light chain domain with a nucleic acid sequence according to SEQ ID NO: 319, and an amino acid sequence according to SEQ ID NO: 247, kkk. 005-C04-L2-1-31-7 comprises a variable heavy chain domain corresponding to a nucleic acid sequence according to SEQ ID NO: 436, and an amino acid sequence according to SEQ ID NO: 508, and a variable light chain domain with a nucleic acid sequence according to SEQ ID NO: 320, and an amino acid sequence according to SEQ ID NO: 248, lll. 005-C04-L2-1-32-4 comprises a variable heavy chain domain corresponding to a nucleic acid sequence according to SEQ ID NO: 437, and an amino acid sequence according to SEQ ID NO: 509, and a variable light chain domain with a nucleic acid sequence according to SEQ ID NO: 321, and an amino acid sequence according to SEQ ID NO: 249.

mmm. 005-C04-L2-1-33-7 comprises a variable heavy chain domain corresponding to a nucleic acid sequence according to SEQ ID NO: 438, and an amino acid sequence according to SEQ ID NO: 510, and a variable light chain domain with a nucleic acid sequence according to SEQ ID NO: 322, and an amino acid sequence according to SEQ ID NO: 250, nnn. 005-C04-L2-1-36-6 comprises a variable heavy chain domain corresponding to a nucleic acid sequence according to SEQ ID NO: 439, and an amino acid sequence according to SEQ ID NO: 511, and a variable light chain domain with a nucleic acid sequence according to SEQ ID NO: 323, and an amino acid sequence according to SEQ ID NO: 251, ooo. 005-C04-L2-1-38-3 comprises a variable heavy chain domain corresponding to a nucleic acid sequence according to SEQ ID NO: 440, and an amino acid sequence according to SEQ ID NO: 512, and a variable light chain domain with a nucleic acid sequence according to SEQ ID NO: 324, and an amino acid sequence according to SEQ ID NO: 252, ppp. 005-C04-L2-1-4-5 comprises a variable heavy chain domain corresponding to a nucleic acid sequence according to SEQ ID NO: 441, and an amino acid sequence according to SEQ ID NO: 513, and a variable light chain domain with a nucleic acid sequence according to SEQ ID NO: 325, and an amino acid sequence according to SEQ ID NO: 253, qqq. 005-C04-L2-1-40-2 comprises a variable heavy chain domain corresponding to a nucleic acid sequence according to SEQ ID NO: 442, and an amino acid sequence according to SEQ ID NO: 514, and a variable light chain domain with a nucleic acid sequence according to SEQ ID NO: 326, and an amino acid sequence according to SEQ ID NO: 254, rrr. 005-C04-L2-1-40-7 comprises a variable heavy chain domain corresponding to a nucleic acid sequence according to SEQ ID NO: 443, and an amino acid sequence according to SEQ ID NO: 515, and a variable light chain domain with a nucleic acid sequence according to SEQ ID NO: 327, and an amino acid sequence according to SEQ ID NO: 255, sss. 005-C04-L2-1-42-0 comprises a variable heavy chain domain corresponding to a nucleic acid sequence according to SEQ ID NO: 444, and an amino acid sequence according to SEQ ID NO: 516, and a variable light chain domain with a nucleic acid sequence according to SEQ ID NO: 328, and an amino acid sequence according to SEQ ID NO: 256, ttt. 005-C04-L2-1-47-0 comprises a variable heavy chain domain corresponding to a nucleic acid sequence according to SEQ ID NO: 445, and an amino acid sequence according to SEQ ID NO: 517, and a variable light chain domain with a nucleic acid sequence according to SEQ ID NO: 329, and an amino acid sequence according to SEQ ID NO: 257, uuu. 005-C04-L2-1-48-3 comprises a variable heavy chain domain corresponding to a nucleic acid sequence according to SEQ ID NO: 446, and an amino acid sequence according to SEQ ID NO: 518, and a variable light chain domain with a nucleic acid sequence according to SEQ ID NO: 330, and an amino acid sequence according to SEQ ID NO: 258.

In another embodiment an antibody or antigen-binding fragment of the afore mentioned antibodies are disclosed, whereby a. the antibody contains one, two, three, four, five or six of the CDRs corresponding to SEQ ID NO: 6, 12, 17, 23, 28, 33; or b. the antibody contains one, two, three, four, five or six of the CDRs corresponding to SEQ ID NO: 103, 104, 17, 136, 140, 33; or c. the antibody contains one, two, three, four, five or six of the CDRs corresponding to SEQ ID NO: 103, 105, 17, 136, 139, 33; or d. the antibody contains one, two, three, four, five or six of the CDRs corresponding to SEQ ID NO: 6, 12, 17, 23, 139, 33; or e. the antibody contains one, two, three, four, five or six of the CDRs corresponding to SEQ ID NO: 6, 12, 17, 23, 141, 33; or f. the antibody contains one, two, three, four, five or six of the CDRs corresponding to SEQ ID NO: 102, 106, 17, 136, 138, 33; or g. the antibody contains one, two, three, four, five or six of the CDRs corresponding to SEQ ID NO: 102, 106, 17, 136, 140, 33; or h. the antibody contains one, two, three, four, five or six of the CDRs corresponding to SEQ ID NO: 103, 108, 17, 137, 28, 33; or i. the antibody contains one, two, three, four, five or six of the CDRs corresponding to SEQ ID NO: 6, 12, 17, 23, 138, 33; or j. the antibody contains one, two, three, four, five or six of the CDRs corresponding to SEQ ID NO: 102, 114, 17, 136, 28, 33; or k. the antibody contains one, two, three, four, five or six of the CDRs corresponding to SEQ ID NO: 102, 104, 17, 136, 140, 33; or l. the antibody contains one, two, three, four, five or six of the CDRs corresponding to SEQ ID NO: 102, 111, 17, 136, 139, 33; or m. the antibody contains one, two, three, four, five or six of the CDRs corresponding to SEQ ID NO: 103, 116, 17, 136, 140, 33; or
n. the antibody contains one, two, three, four, five or six of the CDRs corresponding to SEQ ID NO: 102, 118, 17, 136, 138, 33; or
o. the antibody contains one, two, three, four, five or six of the CDRs corresponding to SEQ ID NO: 6, 12, 17, 23, 28, 143; or
p. the antibody contains one, two, three, four, five or six of the CDRs corresponding to SEQ ID NO: 6, 12, 17, 23, 28, 145; or
q. the antibody contains one, two, three, four, five or six of the CDRs corresponding to SEQ ID NO: 6, 12, 17, 23, 28, 144; or
r. the antibody contains one, two, three, four, five or six of the CDRs corresponding to SEQ ID NO: 6, 12, 17, 23, 28, 146; or
s. the antibody contains one, two, three, four, five or six of the CDRs corresponding to SEQ ID NO: 103, 110, 17, 136, 140, 33; or
t. the antibody contains one, two, three, four, five or six of the CDRs corresponding to SEQ ID NO: 103, 110, 17, 136, 139, 33; or
u. the antibody contains one, two, three, four, five or six of the CDRs corresponding to SEQ ID NO: 103, 127, 17, 136, 141, 33; or
v. the antibody contains one, two, three, four, five or six of the CDRs corresponding to SEQ ID NO: 103, 127, 17, 136, 141, 33; or
w. the antibody contains one, two, three, four, five or six of the CDRs corresponding to SEQ ID NO: 6, 12, 17, 136, 28, 33; or
x. the antibody contains one, two, three, four, five or six of the CDRs corresponding to SEQ ID NO: 102, 117, 17, 136, 140, 33; or
y. the antibody contains one, two, three, four, five or six of the CDRs corresponding to SEQ ID NO: 102, 119, 17, 136, 28, 33; or
z. the antibody contains one, two, three, four, five or six of the CDRs corresponding to SEQ ID NO: 102, 115, 17, 136, 138, 33; or
aa. the antibody contains one, two, three, four, five or six of the CDRs corresponding to SEQ ID NO: 102, 12, 17, 23, 28, 33; or
bb. the antibody contains one, two, three, four, five or six of the CDRs corresponding to SEQ ID NO: 102, 119, 17, 136, 139, 33; or
cc. the antibody contains one, two, three, four, five or six of the CDRs corresponding to SEQ ID NO: 102, 116, 17, 136, 140, 33; or
dd. the antibody contains one, two, three, four, five or six of the CDRs corresponding to SEQ ID NO: 102, 107, 17, 136, 140, 33; or
ee. the antibody contains one, two, three, four, five or six of the CDRs corresponding to SEQ ID NO: 103, 108, 17, 136, 28, 33; or
ff. the antibody contains one, two, three, four, five or six of the CDRs corresponding to SEQ ID NO: 102, 119, 17, 136, 28, 33; or
gg. the antibody contains one, two, three, four, five or six of the CDRs corresponding to SEQ ID NO: 102, 133, 17, 136, 138, 33; or
hh. the antibody contains one, two, three, four, five or six of the CDRs corresponding to SEQ ID NO: 6, 123, 17, 23, 28, 33; or
ii. the antibody contains one, two, three, four, five or six of the CDRs corresponding to SEQ ID NO: 6, 120, 17, 23, 28, 33; or
jj. the antibody contains one, two, three, four, five or six of the CDRs corresponding to SEQ ID NO: 6, 125, 17, 23, 28, 33; or
kk. the antibody contains one, two, three, four, five or six of the CDRs corresponding to SEQ ID NO: 6, 134, 17, 23, 28, 33; or
ll. the antibody contains one, two, three, four, five or six of the CDRs corresponding to SEQ ID NO: 6, 119, 17, 23, 28, 33; or
mm. the antibody contains one, two, three, four, five or six of the CDRs corresponding to SEQ ID NO: 6, 128, 17, 23, 28, 33; or
nn. the antibody contains one, two, three, four, five or six of the CDRs corresponding to SEQ ID NO: 6, 122, 17, 23, 28, 33; or
oo. the antibody contains one, two, three, four, five or six of the CDRs corresponding to SEQ ID NO: 6, 124, 17, 23, 28, 33; or
pp. the antibody contains one, two, three, four, five or six of the CDRs corresponding to SEQ ID NO: 102, 106, 17, 136, 28, 33; or
qq. the antibody contains one, two, three, four, five or six of the CDRs corresponding to SEQ ID NO: 103, 118, 17, 135, 28, 33; or
rr. the antibody contains one, two, three, four, five or six of the CDRs corresponding to SEQ ID NO: 103, 120, 17, 136, 142, 33; or
ss. the antibody contains one, two, three, four, five or six of the CDRs corresponding to SEQ ID NO: 103, 117, 17, 23, 140, 33; or
tt. the antibody contains one, two, three, four, five or six of the CDRs corresponding to SEQ ID NO: 102, 130, 17, 23, 139, 33; or
uu. the antibody contains one, two, three, four, five or six of the CDRs corresponding to SEQ ID NO: 102, 111, 17, 23, 140, 33; or
vv. the antibody contains one, two, three, four, five or six of the CDRs corresponding to SEQ ID NO: 102, 114, 17, 23, 141, 33; or
ww. the antibody contains one, two, three, four, five or six of the CDRs corresponding to SEQ ID NO: 102, 116, 17, 23, 141, 33; or
xx. the antibody contains one, two, three, four, five or six of the CDRs corresponding to SEQ ID NO: 103, 119, 17, 23, 140, 33; or
yy. the antibody contains one, two, three, four, five or six of the CDRs corresponding to SEQ ID NO: 102, 112, 17, 23, 141, 33; or
zz. the antibody contains one, two, three, four, five or six of the CDRs corresponding to SEQ ID NO: 103, 116, 17, 23, 140, 33; or
aaa. the antibody contains one, two, three, four, five or six of the CDRs corresponding to SEQ ID NO: 103, 120, 17, 136, 141, 33; or
bbb. the antibody contains one, two, three, four, five or six of the CDRs corresponding to SEQ ID NO: 103, 116, 17, 23, 138, 33; or
ccc. the antibody contains one, two, three, four, five or six of the CDRs corresponding to SEQ ID NO: 102, 109, 17, 23, 141, 33; or
ddd. the antibody contains one, two, three, four, five or six of the CDRs corresponding to SEQ ID NO: 103, 120, 17, 23, 141, 33; or eee. the antibody contains one, two, three, four, five or six of the CDRs corresponding to SEQ ID NO: 102, 105, 17, 23, 138, 33; or fff. the antibody contains one, two, three, four, five or six of the CDRs corresponding to SEQ ID NO: 102, 132, 17, 23, 138, 33; or ggg. the antibody contains one, two, three, four, five or six of the CDRs corresponding to SEQ ID NO: 103, 120, 17, 136, 141, 33; or hhh. the antibody contains one, two, three, four, five or six of the CDRs corresponding to SEQ ID NO: 102, 129, 17, 23, 140, 33; or iii. the antibody contains one, two, three, four, five or six of the CDRs corresponding to SEQ ID NO: 102, 117, 17, 23, 140, 33; or jjj. the antibody contains one, two, three, four, five or six of the CDRs corresponding to SEQ ID NO: 102, 129, 17, 23, 142, 33; or kkk. the antibody contains one, two, three, four, five or six of the CDRs corresponding to SEQ ID NO: 103, 104, 17, 23, 142, 33; or lll. the antibody contains one, two, three, four, five or six of the CDRs corresponding to SEQ ID NO: 102, 107, 17, 23, 142, 33; or mmm. the antibody contains one, two, three, four, five or six of the CDRs corresponding to SEQ ID NO: 102, 113, 17, 23, 140, 33; or nnn. the antibody contains one, two, three, four, five or six of the CDRs corresponding to SEQ ID NO: 102, 131, 17, 23, 142, 33; or ooo. the antibody contains one, two, three, four, five or six of the CDRs corresponding to SEQ ID NO: 102, 115, 17, 136, 141, 33; or ppp. the antibody contains one, two, three, four, five or six of the CDRs corresponding to SEQ ID NO: 103, 119, 17, 136, 141, 33; or qqq. the antibody contains one, two, three, four, five or six of the CDRs corresponding to SEQ ID NO: 102, 109, 17, 23, 138, 33; or rrr. the antibody contains one, two, three, four, five or six of the CDRs corresponding to SEQ ID NO: 102, 121, 17, 23, 142, 33; or sss. the antibody contains one, two, three, four, five or six of the CDRs corresponding to SEQ ID NO: 102, 126, 17, 23, 142, 33; or ttt. the antibody contains one, two, three, four, five or six of the CDRs corresponding to SEQ ID NO: 102, 105, 17, 23, 141, 33; or uuu. the antibody contains one, two, three, four, five or six of the CDRs corresponding to SEQ ID NO: 102, 108, 17, 23, 138, 33.

In another embodiment of the present invention the antibody 005-C04 consists of an antigen-binding region that binds specifically to or has a high affinity of for one or more regions of PRLR, whose amino acid sequence is depicted by SEQ ID NO: 70, amino acid position 1 to 210, whereby the affinity is at least 100 nM, preferably less than about 100 nM, more preferably less than about 30 nM, even more preferred with an affinity of less than about 10 nM or even more preferred with an affinity less than 1 nM, or even more preferred with an affinity of less than 30 pM.

Also object of the present invention is the afore mentioned antibody 005-C04, wherein the heavy constant is a modified or unmodified IgG1, IgG2, IgG3 or IgG4.

Table 1 provides a summary of dissociation constants and dissociation rates of representative antibodies of the invention, as determined by surface plasmon resonance (Biacore) with monomeric extracellular domains of PRLR (SEQ ID NO: 70) on directly immobilized antibodies.

TABLE 1

Monovalent dissociation constants and dissociation rates of the extracellular domain of human PRLR expressed in HEK293 cells determined for anti-PRLR human IgG1 molecules by surface plasmon resonance

| Antibody | $K_D$ [M] | kd [1/s] |
|---|---|---|
| 006-H08 | $0.7 \times 10^{-9}$ | $2.4 \times 10^{-4}$ |
| 002-H06 | $2.7 \times 10^{-9}$ | $5.4 \times 10^{-4}$ |
| 002-H08 | $1.8 \times 10^{-9}$ | $2.0 \times 10^{-4}$ |
| 006-H07 | $2.0 \times 10^{-9}$ | $1.3 \times 10^{-3}$ |
| 001-E06 | $15.8 \times 10^{-9}$ | $4.8 \times 10^{-3}$ |
| 005-C04 | $12.2 \times 10^{-9}$ | $9.3 \times 10^{-3}$ |
| HE06.642 | $0.3 \times 10^{-9}$ | $3.2 \times 10^{-4}$ |
| XHA06.642 | $1.2 \times 10^{-9}$ | $1.3 \times 10^{-4}$ |
| XHA06.983 | $0.2 \times 10^{-9}$ | $1.7 \times 10^{-4}$ |

The IgG1 format was used for the cell-based affinity determination, determined by fluorescence-activated cell sorting (FACS) combined with Scatchard analysis.

Table 2 denotes the binding strength of representative IgG antibodies on the human breast cancer cell line T47D and rat lymphoma cell line Nb2.

TABLE 2

Cell-based binding potency of anti-PRLR antibodies as determined by FACS on the human breast cancer cell line T47D and rat lymphoma cell line Nb2

| | $EC_{50}$ [M] | |
|---|---|---|
| Antibody | T47D | Nb2 |
| 006-H08 | $1.3 \times 10^{-9}$ | No binding |
| 006-H07 | $0.4 \times 10^{-9}$ | No binding |
| 001-E06 | $1.8 \times 10^{-9}$ | $1.2 \times 10^{-3}$ |
| 005-C04 | $1.9 \times 10^{-9}$ | $0.5 \times 10^{-9}$ |
| HE06.642 | $1.8 \times 10^{-9}$ | $0.9 \times 10^{-9}$ |
| XHA06.642 | $1.5 \times 10^{-9}$ | $1.1 \times 10^{-9}$ |
| XHA06.983 | $0.3 \times 10^{-9}$ | No binding |

Antibody Generation

To isolate a panel of antibodies able to functionally block the human and murine PRLR, two formats of the synthetic human antibody phage display library called n-CoDeR® from Bioinvent (Söderlind et al. 2000, Nature BioTechnology. 18, 852-856.), expressing scFv and Fab fragments, respectively, were investigated in parallel. The targets used for scFv or Fab selection were the soluble ECD of human PRLR (amino acid positions 1 to 210 of SEQ ID NO. 70) and mouse PRLR (amino acid positions 1 to 210 of SEQ ID NO: 72), applied as biotinylated (NHS-LC biotin, Pierce) and as non-biotinylated variant as well as the human breast cancer cell line T47D expressing PRLR.

A combination of various approaches in phage-display technology (PDT) was used to isolate high affinity, PRLR-specific, human monoclonal antibodies, by a combination of protein and whole cell pannings and through the development of specific tools. The panning tools and screening methods include the ECD of the human and mouse PRLR recombinantly expressed in fusion with an Fc domain (R&D Systems, catalogue no. 1167-PR and 1309-PR, respectively; pos. 1-216 of SEQ ID NO: 70 and 72, respectively, each fused to the human IgG1 Fc domain, pos. 100 to 330 of human IgG1), the extracellular domain of the human PRLR recombinantly expressed in fusion with a six-histidine tag (SEQ ID NO: 70), the HEK293 and the murine lymphoma cell line Ba/F each stably transfected with human and murine PRLR, respectively, and the breast cancer cell line T47D and the rat lymphoma cell Nb2 each naturally expressing PRLR as well as the development of panning procedures and screening assays capable of identifying neutralizing antibodies that preferentially bind to PRLR displayed on the cell surface and that are cross-reactive to PRLR from mouse and rat (see example 6 and 10).

Screening was performed by first identifying binders for human PRLR and eventually mouse PRLR in ELISA tests using recombinantly expressed antigens. Then, cell binding of the Fab and scFv fragments on T47D cells was examined by FACS analyses followed by testing the neutralizing activity of these agents on intracellular signaling. For this purpose, inhibition of phosphorylation of PRLR, of STAT5 and of ERK1/2 in T47D cells was determined (see example 14). The best function blocking scFvs and Fabs were converted into full IgG1 molecules and tested for monovalent affinities to the ECD of PRLR and for inhibitory activity in luciferase reporter gene assays as well as in proliferation assays with cells growing in dependence of prolactin. The combination of these specific methods allowed the isolation of the novel antibody '005-C04' which is subject matter of the present invention, as well as of the antibodies '002-H06', '002-H08', '006-H07', '001-E06', '006-H08' which are subject matter of corresponding applications.

Peptide Variants

Antibodies of the invention are not limited to the specific peptide sequences provided herein. Rather, the invention also embodies variants of these polypeptides. With reference to the instant disclosure and conventionally available technologies and references, the skilled worker will be able to prepare, test and utilize functional variants of the antibodies disclosed herein, while appreciating that variants having the ability to bind and to functionally block PRLR fall within the scope of the present invention.

A variant can include, for example, an antibody that has at least one altered complementarity determining region (CDR) (hyper-variable) and/or framework (FR) (variable) domain/position, vis-à-vis a peptide sequence disclosed herein. To better illustrate this concept, a brief description of antibody structure follows.

An antibody is composed of two peptide chains, each containing one (light chain) or three (heavy chain) constant domains and a variable region (VL, VH), the latter of which is in each case made up of four FR regions (VH: HFR1, HFR2, HFR3, HFR4; VL: LFR1, LFR2, LFR3, LFR4) and three interspaced CDRs (VL: LCDR1, LCDR2, LCDR3; VH: HCDR1, HCDR2, HCDR3). The antigen-binding site is formed by one or more CDRs, yet the FR regions provide the structural framework for the CDRs and, hence, play an important role in antigen binding. By altering one or more amino acid residues in a CDR or FR region, the skilled worker routinely can generate mutated or diversified antibody sequences, which can be screened against the antigen, for new or improved properties, for example.

FIG. 12 provides the schemes for numbering each amino acid position in the variable domains VL and VH. Tables 3 (VH) and 4 (VL) delineate the CDR regions for certain antibodies of the invention and compare amino acids at a given position to each other and to a corresponding consensus or "master gene" sequence, in which the CDR regions are marked with 'X'. Table 5 and 6 help to assign the SEQ ID Numbers to the antibodies, antibody fragments and PRLR variants provided in this invention.

TABLE 3

VH Sequences

```
                                                         |-HCDR1--|                    |
001-E06 VH    QVELLESGGG  LVQPGGSLRL  SCAASGFTFS  S.YWMSWVRQ  APGKGLEWVS
002-H06 VH    QVELLESGGG  LVQPGGSLRL  SCAASGFTFA  N.YGLTWVRQ  APGKGLEWVA
002-H08 VH    QVELLESGGG  LVQPGGSLRL  SCAASGFTFS  S.YGMHWVRQ  APGKGLEWVS
005-C04 VH    EVQLLESGGG  LVQPGGSLRL  SCAASGFTFS  S.YWMHWVRQ  APGKGLEWVS
006-H07 VH    QVELLESGGG  LVQPGGSLRL  SCAASGFTFE  D.HGMSWVRQ  APGKGLEWVS
006-H08 VH    QVELLESGGG  LVQPGGSLRL  SCAASGFTFD  D.YGMSWVRQ  APGKGLEWVA
Consensus     EVQLLESGGG  LVQPGGSLRL  SCAASGFTXX  XXXXXXXVRQ  APGKGLEWVX ----HCDR2----------|                                                |-
001-E06 VH    SVSDT.GTDT  HYADSVKGRF  TISRDNSKNT  LYLQMNSLRA  EDTAVYYCAK
002-H06 VH    VISFN.GDKK  YYADSVKGRF  TISRDNSKNT  LYLQMNSLRA  EDTAVYYCAS
002-H08 VH    GVSWN.GSRT  HYADSVKGRL  TISRDNSKNT  LYLQMNSLRA  EDTAVYYCAR
005-C04 VH    DISSA.SSYT  NYADSVKGRF  TISRDNSKNT  LYLQMNSLRA  EDTAVYYCAR
006-H07 VH    LISWDDGSNK  YYADSVKGRF  TISRDNSKNT  LYLQMNSLRA  EDTAVYYCAT
006-H08 VH    VISYD.GSNK  YYADSVKGRF  TISRDNSQNT  LYLQMNSLRA  EDTAVYYCAS
Consensus     XXXXXXXXXX  XXXXXXXXXF  TISRDNSKNT  LYLQMNSLRA  EDTAVYYCXX --HCDR3-------|
001-E06 VH    TPLAYSSGWY  YFDYWGQGTL  VTVSS
002-H06 VH    PLES....PV  AFDIWGQGTL  VTVSS
002-H08 VH    G........G  DFDYWGQGTL  VTVSS
005-C04 VH    GLDA.....R  RMDYWGQGTL  VTVSS
006-H07 VH    SLR.....AT  AFDTWGQGTL  VTVSS
006-H08 VH    PLES....PV  AFDIWGQGTM  VIVSS
Consensus     XXXXXXXXXX  XXXXWGQGTL  VTVSS
```

TABLE 4

VL Sequences

```
                         |---LCDR1-----|
001-E06 VH   DIVLTQPPSA  SGTPGQRVTI  SCSGSSSNIG  S.NTVNWYQQ  LPGTAPKLLI
002-H06 VH   QSVLTQPPSA  SGTPGQRVTI  SCSGSYSNIG  G.NPVNWYQQ  LPGTAPKLLI
002-H08 VH   QSVLTQPPSA  SGTPGQRVTI  SCSGSSSNIG  S.NDVYWYQQ  LPGTAPKLLI
005-C04 VH   QSVLTQPPSA  SGTPGQRVTI  SCTGSSSNIG  AGYVVHWYQQ  LPGTAPKLLI
006-H07 VH   QSVLTQPPSA  SGTPGQRVTI  SCSGSSSNIG  N.NAVNWYQQ  LPGTAPKLLI
006-H08 VH   DIVLTQPPSA  SGTPGQRVTI  SCSGSNSNIG  S.NPVNWYQQ  LPGTAPKLLI
Consensus    QSVLTQPPSA  SGTPGQRVTI  SCXXXXXXXX  XXXXXWYQQ   LPGTAPKLLI
             |LCDR2|                                        |----LCDR3--
001-E06 VH   YRNYQRPSGV  PDRFSGSKSG  TSASLAISGL  RSEDEADYYC  QSYDSSLSG.
002-H06 VH   YGNSNRPSGV  PDRFSGSKSG  TSASLAISGL  RSEDEADYYC  QSYDSSLSG.
002-H08 VH   YDNNKRPSGV  PDRFSGSKSG  TSASLAISGL  RSEDEADYYC  QSYDSSLSGS
005-C04 VH   YRNNQRPSGV  PDRFSGSKSG  TSASLAISGL  RSEDEADYYC  AAWDDSLNG.
006-H07 VH   YSNNQRPSGV  PDRFSGSKSG  TSASLAISGL  RSEDEADYYC  AAWDDSLSG.
006-H08 VH   YDNNKRPSGV  PDRFSGSKSG  TSASLAISGL  RSEDEADYYC  QSYDTGLSG.
Consensus    YXXXXXXXGV  PDRFSGSKSG  TSASLAISGL  RSEDEADYYX  XXXXXXXXXX
             -|
001-E06 VH   SVFGGGTKLT  VLGQ
002-H06 VH   SVFGGGTKLT  VLGQ
002-H08 VH   WVFGGGTKLT  VLGQ
005-C04 VH   WLFGGGTKLT  VLGQ
006-H07 VH   WVFGGGTKLT  VLGQ
006-H08 VH   WVFGGGTKLT  VLGQ
Consensus    XXFGGGTKLT  VLGQ
```

TABLE 5

Sequences of the antibodies

| Antibody | HCDR1 SEQ ID | HCDR2 SEQ ID | HCDR3 SEQ ID | LCDR1 SEQ ID | LCDR2 SEQ ID | LCDR3 SEQ ID | VH Protein SEQ ID | VL Protein SEQ ID | VH Nucleotide SEQ ID | VL Nucleotide SEQ ID |
|---|---|---|---|---|---|---|---|---|---|---|
| 006-H08 | 1 | 7 | 13 | 18 | 24 | 29 | 34 | 40 | 46 | 52 |
| 002-H06 | 2 | 8 | 13 | 19 | 25 | 30 | 35 | 41 | 47 | 53 |
| 002-H08 | 3 | 9 | 14 | 20 | 24 | 31 | 36 | 42 | 48 | 54 |
| 006-H07 | 4 | 10 | 15 | 21 | 26 | 32 | 37 | 43 | 49 | 55 |
| 001-E06 | 5 | 11 | 16 | 22 | 27 | 30 | 38 | 44 | 50 | 56 |
| 005-C04 | 6 | 12 | 17 | 23 | 28 | 33 | 39 | 45 | 51 | 57 |
| HE06.642 | — | — | — | — | — | — | 58 | 61 | 64 | 67 |
| XHA06.642 | — | — | — | — | — | — | 59 | 62 | 65 | 68 |
| XHA06.983 | — | — | — | — | — | — | 60 | 63 | 66 | 69 |
| 005-C04-10-3 | 103 | 104 | 17 | 136 | 140 | 33 | 187 | 259 | 375 | 447 |
| 005-C04-11-5 | 103 | 105 | 17 | 136 | 139 | 33 | 188 | 260 | 376 | 448 |
| 005-C04-18-10-2 | 6 | 12 | 17 | 23 | 139 | 33 | 189 | 261 | 377 | 449 |
| 005-C04-18-10-4 | 6 | 12 | 17 | 23 | 141 | 33 | 190 | 262 | 378 | 450 |
| 005-C04-19-2 | 102 | 106 | 17 | 136 | 138 | 33 | 191 | 263 | 379 | 451 |
| 005-C04-2-2 | 102 | 106 | 17 | 136 | 140 | 33 | 192 | 264 | 380 | 452 |
| 005-C04-2-7 | 103 | 108 | 17 | 137 | 28 | 33 | 193 | 265 | 381 | 453 |
| 005-C04-20-12-7 | 6 | 12 | 17 | 23 | 138 | 33 | 194 | 266 | 382 | 454 |
| 005-C04-20-2 | 102 | 114 | 17 | 136 | 28 | 33 | 195 | 267 | 383 | 455 |
| 005-C04-21-1 | 102 | 104 | 17 | 136 | 140 | 33 | 196 | 268 | 384 | 456 |
| 005-C04-21-2 | 102 | 111 | 17 | 136 | 139 | 33 | 197 | 269 | 385 | 457 |
| 005-C04-25-6 | 103 | 116 | 17 | 136 | 140 | 33 | 198 | 270 | 386 | 458 |
| 005-C04-29-0 | 102 | 118 | 17 | 136 | 138 | 33 | 199 | 271 | 387 | 459 |
| 005-C04-29-17-0 | 6 | 12 | 17 | 23 | 28 | 143 | 200 | 272 | 388 | 460 |
| 005-C04-29-17-2 | 6 | 12 | 17 | 23 | 28 | 145 | 201 | 273 | 389 | 461 |
| 005-C04-29-17-3 | 6 | 12 | 17 | 23 | 28 | 144 | 202 | 274 | 390 | 462 |
| 005-C04-29-17-7 | 6 | 12 | 17 | 23 | 28 | 146 | 203 | 275 | 391 | 463 |

TABLE 5-continued

Sequences of the antibodies

| Antibody | HCDR1 SEQ ID | HCDR2 SEQ ID | HCDR3 SEQ ID | LCDR1 SEQ ID | LCDR2 SEQ ID | LCDR3 SEQ ID | VH Protein SEQ ID | VL Protein SEQ ID | VH Nucleotide SEQ ID | VL Nucleotide SEQ ID |
|---|---|---|---|---|---|---|---|---|---|---|
| 005-C04-35-3 | 103 | 110 | 17 | 136 | 140 | 33 | 204 | 276 | 392 | 464 |
| 005-C04-36-0 | 103 | 110 | 17 | 136 | 139 | 33 | 205 | 277 | 393 | 465 |
| 005-C04-37-2 | 103 | 127 | 17 | 136 | 141 | 33 | 206 | 278 | 394 | 466 |
| 005-C04-37-7 | 103 | 127 | 17 | 136 | 141 | 33 | 207 | 279 | 395 | 467 |
| 005-C04-4-3-7 | 6 | 12 | 17 | 136 | 28 | 33 | 208 | 280 | 396 | 468 |
| 005-C04-40-4 | 102 | 117 | 17 | 136 | 140 | 33 | 209 | 281 | 397 | 469 |
| 005-C04-41-2 | 102 | 119 | 17 | 136 | 28 | 33 | 210 | 282 | 398 | 470 |
| 005-C04-42-1 | 102 | 115 | 17 | 136 | 138 | 33 | 211 | 283 | 399 | 471 |
| 005-C04-44-25-1 | 102 | 12 | 17 | 23 | 28 | 33 | 212 | 284 | 400 | 472 |
| 005-C04-45-1 | 102 | 119 | 17 | 136 | 139 | 33 | 213 | 285 | 401 | 473 |
| 005-C04-46-0 | 102 | 116 | 17 | 136 | 140 | 33 | 214 | 286 | 402 | 474 |
| 005-C04-46-1 | 102 | 107 | 17 | 136 | 140 | 33 | 215 | 287 | 403 | 475 |
| 005-C04-47-3 | 103 | 108 | 17 | 136 | 28 | 33 | 216 | 288 | 404 | 476 |
| 005-C04-48-1 | 102 | 119 | 17 | 136 | 28 | 33 | 217 | 289 | 405 | 477 |
| 005-C04-5-5 | 102 | 133 | 17 | 136 | 138 | 33 | 218 | 290 | 406 | 478 |
| 005-C04-50-28-3 | 6 | 123 | 17 | 23 | 28 | 33 | 219 | 291 | 407 | 479 |
| 005-C04-50-28-7 | 6 | 120 | 17 | 23 | 28 | 33 | 220 | 292 | 408 | 480 |
| 005-C04-51-29-0 | 6 | 125 | 17 | 23 | 28 | 33 | 221 | 293 | 409 | 481 |
| 005-C04-52-29-0 | 6 | 134 | 17 | 23 | 28 | 33 | 222 | 294 | 410 | 482 |
| 005-C04-52-29-7 | 6 | 119 | 17 | 23 | 28 | 33 | 223 | 295 | 411 | 483 |
| 005-C04-53-31-7 | 6 | 128 | 17 | 23 | 28 | 33 | 224 | 296 | 412 | 484 |
| 005-C04-55-32-0 | 6 | 122 | 17 | 23 | 28 | 33 | 225 | 297 | 413 | 485 |
| 005-C04-58-33-1 | 6 | 124 | 17 | 23 | 28 | 33 | 226 | 298 | 414 | 486 |
| 005-C04-8-2 | 102 | 106 | 17 | 136 | 28 | 33 | 227 | 299 | 415 | 487 |
| 005-C04-8-6 | 103 | 118 | 17 | 135 | 28 | 33 | 228 | 300 | 416 | 488 |
| 005-C04-9-2 | 103 | 120 | 17 | 136 | 142 | 33 | 229 | 301 | 417 | 489 |
| 005-C04-L2-1-11-0 | 103 | 117 | 17 | 23 | 140 | 33 | 230 | 302 | 418 | 490 |
| 005-C04-L2-1-11-3 | 102 | 130 | 17 | 23 | 139 | 33 | 231 | 303 | 419 | 491 |
| 005-C04-L2-1-12-2 | 102 | 111 | 17 | 23 | 140 | 33 | 232 | 304 | 420 | 492 |
| 005-C04-L2-1-12-4 | 102 | 114 | 17 | 23 | 141 | 33 | 233 | 305 | 421 | 493 |
| 005-C04-L2-1-16-4 | 102 | 116 | 17 | 23 | 141 | 33 | 234 | 306 | 422 | 494 |
| 005-C04-L2-1-16-5 | 103 | 119 | 17 | 23 | 140 | 33 | 235 | 307 | 423 | 495 |
| 005-C04-L2-1-2-3 | 102 | 112 | 17 | 23 | 141 | 33 | 236 | 308 | 424 | 496 |
| 005-C04-L2-1-20-0 | 103 | 116 | 17 | 23 | 140 | 33 | 237 | 309 | 425 | 497 |
| 005-C04-L2-1-20-1 | 103 | 120 | 17 | 136 | 141 | 33 | 238 | 310 | 426 | 498 |
| 005-C04-L2-1-21-7 | 103 | 116 | 17 | 23 | 138 | 33 | 239 | 311 | 427 | 499 |
| 005-C04-L2-1-23-7 | 102 | 109 | 17 | 23 | 141 | 33 | 240 | 312 | 428 | 500 |

TABLE 5-continued

Sequences of the antibodies

| Antibody | HCDR1 SEQ ID | HCDR2 SEQ ID | HCDR3 SEQ ID | LCDR1 SEQ ID | LCDR2 SEQ ID | LCDR3 SEQ ID | VH Protein SEQ ID | VL Protein SEQ ID | VH Nucleotide SEQ ID | VL Nucleotide SEQ ID |
|---|---|---|---|---|---|---|---|---|---|---|
| 005-C04-L2-1-25-0 | 103 | 120 | 17 | 23 | 141 | 33 | 241 | 313 | 429 | 501 |
| 005-C04-L2-1-25-4 | 102 | 105 | 17 | 23 | 138 | 33 | 242 | 314 | 430 | 502 |
| 005-C04-L2-1-25-5 | 102 | 132 | 17 | 23 | 138 | 33 | 243 | 315 | 431 | 503 |
| 005-C04-L2-1-25-7 | 103 | 120 | 17 | 136 | 141 | 33 | 244 | 316 | 432 | 504 |
| 005-C04-L2-1-28-7 | 102 | 129 | 17 | 23 | 140 | 33 | 245 | 317 | 433 | 505 |
| 005-C04-L2-1-3-2 | 102 | 117 | 17 | 23 | 140 | 33 | 246 | 318 | 434 | 506 |
| 005-C04-L2-1-31-4 | 102 | 129 | 17 | 23 | 142 | 33 | 247 | 319 | 435 | 507 |
| 005-C04-L2-1-31-7 | 103 | 104 | 17 | 23 | 142 | 33 | 248 | 320 | 436 | 508 |
| 005-C04-L2-1-32-4 | 102 | 107 | 17 | 23 | 142 | 33 | 249 | 321 | 437 | 509 |
| 005-C04-L2-1-33-7 | 102 | 113 | 17 | 23 | 140 | 33 | 250 | 322 | 438 | 510 |
| 005-C04-L2-1-36-6 | 102 | 131 | 17 | 23 | 142 | 33 | 251 | 323 | 439 | 511 |
| 005-C04-L2-1-38-3 | 102 | 115 | 17 | 136 | 141 | 33 | 252 | 324 | 440 | 512 |
| 005-C04-L2-1-4-5 | 103 | 119 | 17 | 136 | 141 | 33 | 253 | 325 | 441 | 513 |
| 005-C04-L2-1-40-2 | 102 | 109 | 17 | 23 | 138 | 33 | 254 | 326 | 442 | 514 |
| 005-C04-L2-1-40-7 | 102 | 121 | 17 | 23 | 142 | 33 | 255 | 327 | 443 | 515 |
| 005-C04-L2-1-42-0 | 102 | 126 | 17 | 23 | 142 | 33 | 256 | 328 | 444 | 516 |
| 005-C04-L2-1-47-0 | 102 | 105 | 17 | 23 | 141 | 33 | 257 | 329 | 445 | 517 |
| 005-C04-L2-1-48-3 | 102 | 108 | 17 | 23 | 138 | 33 | 258 | 330 | 446 | 518 |

TABLE 6

Sequences of PRLR variants

| Antibody | SEQ ID |
|---|---|
| Human ECD PRLR (Protein) | 70 |
| Human ECD PRLR (Nucleotide) | 71 |
| Murine ECD PRLR (Protein) | 72 |
| Murine ECD PRLR (Nucleotide) | 73 |

The skilled worker can use the data in Tables 3, 4 and 5 to design peptide variants that are within the scope of the present invention. It is preferred that variants are constructed by changing amino acids within one or more CDR regions; a variant might also have one or more altered framework regions (FR). For example, a peptide FR domain might be altered where there is a deviation in a residue compared to a germline sequence. With reference to a comparison of the novel antibodies to the corresponding consensus or "master gene" sequence, which are listed in FIG. 12, candidate residues that can be changed include e.g. the following ones:
- residue lysine (K) at position 75 to glutamine (Q) in VH 006-H08 (SEQ ID 34)
- residue leucine (L) at position 108 to methionine (M) in VH 006-H08 (SEQ ID 34)
- residue threonine (T) at position 110 to isoleucine (I) in VH 006-H08 (SEQ ID 34)
- residue phenylalanine (F) at position 67 to leucine (L) in VH 002-H08 (SEQ ID 36).

Furthermore, variants may be obtained by maturation, i.e. by using one antibody as starting point for optimization by diversifying one or more amino acid residues in the antibody, preferably amino acid residues in one or more CDRs, and by screening the resulting collection of antibody variants for variants with improved properties. Particularly preferred is diversification of one or more amino acid residues in LCDR3 of VL, HCDR3 of VH, LCDR1 of VL and/or HCDR2 of VH. Diversification can be done by synthesizing a collection of DNA molecules using trinucleotide mutagenesis (TRIM) technology [Virnekäs, B., Ge, L., Plückthun, A., Schneider, K. C., Wellnhofer, G., and Moroney S. E. (1994) Trinucleotide phosphoramidites: ideal reagents for the synthesis of mixed oligonucleotides for random mutagenesis. Nucl. Acids Res. 22, 5600].

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

As used herein, "sequence identity" between two polypeptide sequences, indicates the percentage of amino acids that are identical between the sequences. "Sequence homology" indicates the percentage of amino acids that either are identical or that represent conservative amino acid substitutions. Preferred polypeptide sequences of the invention have a sequence identity in the CDR regions of at least 60%, more preferably, at least 70% or 80%, still more preferably at least 90% and most preferably at least 95%. Preferred antibodies also have a sequence homology in the CDR regions of at least 80%, more preferably 90% and most preferably 95%.

DNA Molecules of the Invention

The present invention also relates to the DNA molecules that encode an antibody of the invention. These sequences include, but are not limited to, those DNA molecules set forth in SEQ ID NOs 46 and 52, and 375 to 815.

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 [Sambrook, J., Fritsch, E. F. and Maniatis, T. (1989) Molecular Cloning: A laboratory manual, Cold Spring Harbor Laboratory Press, Cold Spring Harbor, USA)] and Ausubel et al., 1995 [Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons].

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where $T_m$ is the melting temperature of a nucleic acid duplex):

a. $T_m = 69.3 + 0.41(G+C)/\%$
b. The $T_m$ of a duplex DNA decreases by 1° C. with every increase of 1% in the number of mismatched base pairs.
c. $(T_m)_{\mu2} - (T_m)_{\mu1} = 18.5 \log_{10} \mu2/\mu1$
where μ1 and μ2 are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5×Denhardt's solution and 100 μg of nonspecific carrier DNA [see Ausubel et al., section 2.9, supplement 27 (1994)]. Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

Accordingly, subject of the present invention is an isolated nucleic acid sequence that encodes the antibody and antigen-binding fragments of the present invention.

Another embodiment of the present invention is the afore mentioned isolated nucleic acid sequence, which encodes the antibodies of the present invention, whereby the nucleic acid sequences are as given in table 5.

Accordingly, the present invention includes nucleic acid molecules that hybridize to the molecules of set forth in Table 5 under high stringency binding and washing conditions, where such nucleic molecules encode an antibody or functional fragment thereof having properties as described herein. Preferred molecules (from an mRNA perspective) are those that have at least 75% or 80% (preferably at least 85%, more preferably at least 90% and most preferably at least 95%) sequence identity with one of the DNA molecules described herein. The molecules block prolactin receptor mediated signaling.

Functionally Equivalent Variants

Yet another class of DNA variants within the scope of the invention may be described with reference to the product they encode. These functionally equivalent genes are characterized by the fact that they encode the same peptide sequences found in SEQ ID No: 34-45 due to the degeneracy of the genetic code.

It is recognized that variants of DNA molecules provided herein can be constructed in several different ways. For example, they may be constructed as completely synthetic DNAs. Methods of efficiently synthesizing oligonucleotides in the range of 20 to about 150 nucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides recombinant DNA constructs comprising one or more of the nucleotide sequences of the present invention. The recombinant constructs of the present invention are used in connection with a vector, such as a plasmid, phagemid, phage or viral vector, into which a DNA molecule encoding an antibody of the invention is inserted.

The encoded gene may be produced by techniques described in Sambrook et al., 1989, and Ausubel et al., 1989. Alternatively, the DNA sequences may be chemically synthesized using, for example, synthesizers. See, for example, the techniques described in OLIGONUCLEOTIDE SYNTHESIS (1984, Gait, ed., IRL Press, Oxford), which is incorporated by reference herein in its entirety. The expert in the field is able to fuse DNA encoding the variable domains with gene fragments encoding constant regions of various human IgG isotypes or derivatives thereof, either mutated or non-mutated. He is able to apply recombinant DNA technology in order to fuse both variable domains in a single chain format using linkers such as a fifteen-amino acid stretch containing three times glycine-glycine-glycine-glycine-serine. Recombinant constructs of the invention are comprised with expression vectors that are capable of expressing the RNA and/or protein products of the encoded DNA(s). The vector may further comprise regulatory sequences, including a promoter operably linked to the open reading frame (ORF). The vector may further comprise a selectable marker sequence. Specific initiation and bacterial secretory signals also may be required for efficient translation of inserted target gene coding sequences.

The present invention further provides host cells containing at least one of the DNAs of the present invention. The host cell can be virtually any cell for which expression vectors are available. It may be, for example, a higher eukaryotic host cell, such as a mammalian cell, a lower eukaryotic host cell, such as a yeast cell, and may be a prokaryotic cell, such as a bacterial cell. Introduction of the recombinant construct into the host cell can be effected by calcium phosphate transfection, DEAE, dextran mediated transfection, electroporation or phage infection.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and bacterial origin of replication derived from commercially available plasmids typically containing elements of the well known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therefore an object of the present invention is an expression vector comprising a nucleic acid sequence encoding for the novel antibodies of the present invention.

Mammalian Expression & Purification

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al. The recombinant expression vectors can also include origins of replication and selectable markers (see e.g., U.S. Pat. Nos. 4,399,216, 4,634,665 and U.S. Pat. No. 5,179,017, by Axel et al.). Suitable selectable markers include genes that confer resistance to drugs such as G418, hygromycin or methotrexate, on a host cell into which the vector has been introduced. For example, the dihydrofolate reductase (DHFR) gene confers resistance to methotrexate and the neo gene confers resistance to G418.

Transfection of the expression vector into a host cell can be carried out using standard techniques such as electroporation, calcium-phosphate precipitation, and DEAE-dextran transfection.

Suitable mammalian host cells for expressing the antibodies, antigen binding portions, or derivatives thereof provided herein include Chinese Hamster Ovary (CHO cells) [including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621]], NSO myeloma cells, COS cells and SP2 cells. In some embodiments, the expression vector is designed such that the expressed protein is secreted into the culture medium in which the host cells are grown. The antibodies, antigen binding portions, or derivatives thereof can be recovered from the culture medium using standard protein purification methods.

Antibodies of the invention or an antigen-binding fragment thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention or antigen-binding fragment thereof include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20.

Therefore an object of the present invention are also host cells comprising the vector or a nucleic acid molecule, whereby the host cell can be a higher eukaryotic host cell, such as a mammalian cell, a lower eukaryotic host cell, such as a yeast cell, and may be a prokaryotic cell, such as a bacterial cell.

Another object of the present invention is a method of using the host cell to produce an antibody and antigen binding fragments, comprising culturing the host cell under suitable conditions and recovering said antibody.

Therefore another object of the present invention is the antibody as described in the present invention produced with the host cells of the present invention and purified to at least 95% homogeneity by weight.

Endometriosis and Adenomyosis (Endometriosis Interna)

Endometriosis is a benign, estrogen-dependent, gynecological disorder that is characterized by the presence of endometrial tissue (glands and stroma) outside the uterine cavity. Endometriotic lesions are mainly found on the pelvic peritoneum, in the ovaries and the rectovaginal septum (Obstet. Gynecol. Clin. North. Am. 24:235-238, 1997). Endometriosis is often associated with infertility and pain symptoms such as dysmenorrhoea. In addition, many patients suffer from autoimmune diseases (Hum. Reprod. 17(19): 2715-2724, 2002). Adenomyosis uteri also known as endometriosis interna describes a subform of endometriosis which is restricted to the uterus. In case of adenomyosis uteri, endometrial glands invade the myometrium and the uterine wall. According to the transplantation theory, endometrial fragments are flushed by retrograde menstruation into the peritoneal cavity in both, patients and healthy women (Obstet. Gynecol. 64:151-154, 1984). Four main factors seem to be critically involved in the successful establishment of endometriotic lesions in the pelvic cavity of patients:

a) In the late secretory phase of the menstrual cycle, endometrial cells in healthy women become apoptotic. In patients, the extent of apoptosis in endometrial cells is clearly reduced (Fertil. Steril. 69:1042-1047, 1998). Therefore, in patients there is a higher probability than in healthy women, that endometrial fragments that have been flushed into the peritoneal cavity by retrograde menstruation do not die and implant successfully.

b) For successful implantation in the peritoneum and long-term survival of the ectopic endometrial fragments, new blood vessels have to form (British Journal of Pharmacology, 149:133-135, 2006).

c) Many patients suffer from autoimmune disease and thus have a compromised immune system (Hum. Reprod. 17(19): 2002, 2715-2724, 2002). This may lead to the conclusion that an intact immune response—as it is present in healthy women—may play a role for the prevention of the establishment of endometriotic lesions.

d) Lesions have to grow and thus depend on the presence of mitogenic stimuli and growth factors.

For the treatment of endometriosis, the following approaches exist currently:

a) Gonadotropin-releasing hormone (GnRH) analogues: lead to suppression of ovarian estradiol synthesis and induce atrophy of ectopic endometriotic implants that depend critically on the presence of estradiol for growth.

b) Aromatase inhibitors: inhibit the local production of estradiol by endometriotic implants, induce apoptosis and inhibit proliferation of ectopic endometriotic fragments.

c) Selective estrogen receptor modulators: have estrogen receptor antagonistic activity in normal endometrial and ectopic implants and thus lead to atrophy of implanted ectopic endometriotic tissue.

d) Progesterone receptor agonists: inhibit proliferation of normal and ectopic endometrial cells, induce differentiation and apoptosis.

e) Combined oral contraceptives: maintain the status quo, prevent progression of the disease, and induce atrophy of the ectopic and eutopic endometrium.

f) Surgical excision of lesions.

GnRH analogues, SERMs, and aromatase inhibitors have severe side effects and lead to hot flushes and bone loss in young women suffering from endometriosis. Treatment with progesterone receptor agonists leads to ovulation inhibition, irregular menstrual bleeding followed by amenorrhoea, body weight gain and depression. Due to increased risk for venous thrombembolism, combined oral contraceptives are not indicated in women older than 35 years, smokers and individuals suffering from overweight. Surgical excision of lesions is prone to high recurrence rates.

The antibodies of the present invention interfere with PRLR-mediated signaling stimulated by pituitary- and locally-produced prolactin or due to activating PRLR mutations and are therefore more effective than dopamine-2-receptor agonists which interfere only with pituitary prolactin secretion.

Therefore an object of the present invention is the antibody or antigen-binding fragments as described in the present invention as a medicament.

PRL and the PRLR are expressed in the uterus and play a role in normal uterine physiology; PRL can act as a potent mitogen and has an immunomodulatory role. In the present invention it is shown that alterations in the PRL/PRLR system play a role in human endometriosis. An analysis of the expression of PRL and the PRLR in endometrium of healthy women and in endometrium and lesions of patients (see Example 2) by quantitative Taqman PCR is shown in FIGS. 1 and 2.

As demonstrated in FIG. 1 (PRL expression) and FIG. 2 (PRLR expression), both PRL and its receptor are strongly upregulated in endometriotic lesions. This discovery generates for the first time experimental evidence that autocrine PRL signaling may play a fundamental role in the establishment, growth, and maintenance of endometriotic lesions.

The PRLR antibodies were successfully tested in an animal model for endometriosis interna, i.e. adenomyosis uteri in mice (see Example 20). Adenomyosis is characterized by infiltrative growth of endometrial glands in the myometrial layer of the endometrium. It resembles an endometriosis form restricted to the uterus—the only form of endometriosis non-menstruating species can develop. Danazol which is effective in the clinical treatment of patients suffering from endometriosis is also effective in the treatment of adenomyosis uteri (Life Sciences 51:1119-1125, 1992). However danazol is an androgenic progestin and leads to severe androgenic side-effects in young women, which limits its use.

The antibodies of the present invention solve the problem for providing new treatments or prevention for endometriosis and exhibit lesser side effects than current standard therapies.

Therefore a further aspect of the present invention is to employ neutralizing PRLR antibodies and antigen binding fragments for the treatment or prevention of endometriosis and adenomyosis (endometriosis interna).

Another aspect of the present invention is the use of the antibody and antigen binding fragments as described in the present invention for the treatment or prevention of endometriosis and adenomyosis (endometriosis interna).

Non-Hormonal Female Contraception

Current approaches for female contraception are the following:
  a) Combined oral contraceptives containing estrogens and progestins.
    The progestogenic component mediates the contraceptive effect via negative feedback on the hypothalamic-pituitary-gonadal axis. The estrogenic component guarantees a good bleeding control and potentiates the gestagenic action via induction of the progesterone receptor in target cells.
  b) Intrauterine devices containing progestins only.
    The locally released progestin renders the endometrium in an implantation-resistant state. In addition, the cervical mucos becomes almost impermeable for sperm cells.
  c) Progestin only pills and implants.
    The progestin inhibits ovulation via negative feedback on the hypothalamic-pituitary-gonadal axis. In addition the permeability of the cervical mucos for sperm cells is reduced.
  d) Vaginal rings containing ethinylestradiol plus progestins The main side-effect of combined oral contraceptives is the elevated risk for venous thromboembolism (VTE). Moreover, overweight or smoking women, as well as women suffering from autoimmune diseases such as lupus and women older than 35 years cannot use oral combined contraceptives.

Intrauterine devices and implants containing progestins only can lead to dysfunctional uterine bleeding.

Progestin only pills can cause irregular bleeding patterns, spotting, amenorrhea. The risk for ectopic pregnancies increases. Weight gain and reductions in bone mass density are further side effects.

Vaginal rings can lead to vaginitis, leukorrhea or expulsion.

PRLR-deficient mice have been generated a few years ago (Genes Dev 11:167-178, 1997). Interestingly, PRLR-deficient females, but not male mice, are completely sterile. $PRLR^{-/-}$ females exhibited an arrest of egg development immediately after fertilization, i.e. they showed an arrest of preimplantation development. Only very few oocytes reached the blastocyst stage and were unable to implant in mutant females but developed to normal embryos in wildtype foster mothers after transplantation. The infertility phenotype of PRLR-deficient mice could be rescued until midterm pregnancy by progesterone supplementation. Obviously, PRLR-mediated signaling plays an important role in the maintenance and function of the corpus luteum producing progesterone that is necessary to allow and maintain pregnancy. In addition PRLR-deficient females, but not males, exhibited a reduction in body weight associated with a reduction in abdominal fat mass and leptin levels.

So far, no inactivating human PRLR mutation is known, therefore the precise role of PRLR-mediated signaling in human fertility is still unknown. However, there is increasing evidence that also in humans, a minimal prolactin level is required to allow for successful pregnancy. Patients suffering from primary infertility due to hyperprolactinemic corpus luteum insufficiency were treated with bromocriptin. In some cases, prolactin levels were oversuppressed and shortened luteal phases reappeared again (Bohnet H G et al. in Lisuride and other dopamine agonists edited by D. B. Calne et al, Raven Press, New York, 1983). From these data it was concluded that hyper- and hypoprolactinemic states interfere negatively with female fertility. This can be explained by the interaction of PRL with its receptor. In case of low prolactin levels, there is no sufficient receptor activation, whereas in case of hyperprolactinemia, there is also no sufficient receptor activation, since all receptors are blocked by one prolactin molecule and cannot dimerize anymore. In other words, the dose response for prolactin is bell-shaped and optimal receptor activation is achieved only in a certain concentration range. There is evidence from a second study that lack of endometrial prolactin expression in patients leads to early implantation failure (Human Reprod. 19:1911-1916, 2004). Moreover, it has been shown that ex vivo, prolactin can prevent apoptosis of cultured human granulosa cells and thus maintains early corpus luteum function as it has been demonstrated in PRLR-deficient mice (Human Reprod. 18: 2672-2677, 2003).

To test the contraceptive efficacy of neutralizing PRLR antibodies, mice were injected with specific and unspecific PRLR antibodies and mated with males as described in example 11. Readouts were litter number per treatment group and litter size per animal. The experiment presented in FIG. 11 demonstrates that the treatment with the neutralizing antibody of the present invention completely prevented pregnancy in mice when tested at 30 mg/kg body weight.

Compared to the afore mentioned standard approaches, female contraception with neutralizing PRLR antibodies has several advantages:
  the antibodies can be used in smoking, overweight, and older women as well as in women suffering from lupus erythematodes (PRLR antibodies might even be beneficial for the treatment of lupus and the reduction of abdominal fat, i.e. PRLR-deficient mice had less abdominal fat).
  the PRLR antibodies do not elevate the VTE (venous thrombembolic) risk
  in contrast to estrogens and progestins used in combined oral contraception, neutralization of PRLR-mediated signaling leads to inhibition of breast epithelial proliferation and in contrast to hormonal approaches for fertility control might even protect users from breast cancer.

Another object of the present invention is the use of PRLR-neutralizing PRLR antibodies and antigen binding fragments for female contraception with reduced side effects compared to standard treatments.

Another aspect of the present invention is the use of the antibody and antigen binding fragments as described in the present invention for female contraception with reduced side effects compared to standard treatments.

Benign Breast Disease and Mastalgia

Benign breast disease encompasses a variety of symptoms, such as fibrocystic breast disease, fibroadenoma, mastalgia, and macrocysts. 30-50% of premenopausal women suffer from fibrocystic breast disease (Epidemiol Rev 19:310-327, 1997). Depending on the women's age, benign breast disease can present with distinct phenotypes (J Mammary Gland Biol Neoplasia 10: 325-335, 2005): during the early reproductive phases (15-25 years) when lobular development in the normal breast takes place, benign breast disease results in fibroadenomas. Single giant fibroadenomas as well as multiple adenomas are observed. These fibroadenomas are composed of stromal as well as epithelial cells and arise from lobules. In the mature reproductive phase (25-40 years) the breast is subject to cyclical changes during each menstrual cycle. Diseased women present with cyclical mastalgia and several nodules in their breast. Later (35-55 years of age), the normal breast involutes whereas in the diseased breast macrocysts and epithelial hyperplasia with and without atypia can be observed. Those forms of benign breast disease that are accompanied by enhanced epithelial cell proliferation have a higher risk for developing mammary carcinomas. This risk can be up to 11% if cellular atypias are present in the proliferating cell fraction (Zentralbl Gynäkol 119: 54-58, 1997). 25% of women aged 60-80 years also suffer from benign breast disease, often estrogen replacement therapy or adiposity are the reasons for persisting benign breast disease after menopause (Am J Obstet Gynecol 154: 161-179, 1986).

The pathophysiology of fibrocystic breast disease is determined by estrogen predominance and progesterone deficiency that results in hyperproliferation of connective tissues (fibrosis) which is followed by facultative epithelial cell proliferation. As already mentioned, the risk of breast cancer is elevated in patients exhibiting enhanced epithelial cell proliferation within the fibrocystic foci. Clinically fibrocystic breast disease presents with breast pain and breast tenderness. 70% of the patients with fibrocystic breast disease suffer from either corpus luteum insufficiency or anovulation (Am J Obstet 154: 161-179, 1986). Corpus luteum insufficiency results in reduced progesterone levels and estrogen predominance.

Mastalgia (breast pain) affects about 70% of women at some time in their reproductive lifespan. Breast pain may or may not be associated with other criteria of the premenstrual syndrome. It has been demonstrated that women suffering from mastalgia respond with an excess prolactin release after stimulation of the hypothalamic pituitary axis (Clin Endocrinol 23: 699-704, 1985).

Standard therapies of benign breast disease and mastalgia are:
1) Bromocriptine

Bromocriptine as a dopamin agonist blocks only pituitary prolactin synthesis, but not local synthesis of prolactin in the mammary epithelial cells. It is therefore only effective in those forms of mastalgia and benign breast disease that rely on elevated systemic prolactin levels. Major side effects of bromocriptine are:

Nausea, vomiting, edema, hypotension, dizziness, hair loss, headache, and halluzinations
2) Danazol Danazol is an androgenic progestin that via its antigonadotrophic activity counteracts the estrogen predominance observed in benign breast disease. Major side effects are:

Menstrual irregularities, depression, acne, hirsutism, voice deepening, and hot flushes as well as weight gain.
3) Tamoxifen Tamoxifen is a selective estrogen receptor modulator with antiestrogenic activity in the breast and estrogenic activity in the uterus. Major side effects are:

postmenopausal symptoms such as bone loss and hot flushes, ovarial cysts, and endometrial carcinoma.
4) Progestins Progestins inhibit benign breast disease via suppression of the pituitary gonadal axis, ovulation inhibition and estrogen depletion. Estrogen depletion leads to menopausal symptoms such as bone loss and hot flushes.
5) Low Dose Combined Oral Contraceptives This treatment is not indicated in women older than 35 years of age, smoking as well as diabetic and overweight patients.

In general, prolactin levels have been found to be increased in one third of women with benign breast disease. Since estrogens enhance pituitary prolactin secretion, the increase in serum prolactin levels has been thought to be a consequence of the predominance of estrogens in this disease. It has been reported that an activating PRLR mutation is often present in women suffering from multiple breast adenomas—resembling a subtype of fibrocystic breast disease (Paul Kelly, Breast Congress Turin, 2007 and Proc Natl Acad Sci 105: 14533-14538; 2008).

Benign breast disease, mastalgia and premenstrual breast tension rely on one common pathophysiological mechanism: enhanced prolactin signaling. Elevated prolactin signaling can be the consequence of:

systemic hyperprolactinemia (due to pituitary adenoma)
local hyperprolactinemia (due to prolactin synthesis in proliferating mammary gland epithelial cells). Local hyperprolactinemia does not translate into elevated prolactin levels in the blood.
constitutively active PRLR signaling in the presence of normal prolactin levels (due to an activating PRLR mutation).

Given that certain forms of benign breast disease can give rise to breast cancer there is a medical need for the treatment of this disease.

To demonstrate the efficacy of neutralizing PRLR antibodies in a preclinical model of benign breast disease, a mouse model based on systemic hyperprolactinemia was employed. Adult Balb/c mice were transplanted with pituitary isografts under the kidney capsule as described in Example 16 (In: Methods in Mammary gland Biology and Breast Cancer Research, 101-107, 2000). Systemic hyperprolactinemia caused enhanced epithelial cell proliferation in the mammary gland, and stimulated sidebranching and lobuloalveolar development in comparison to untreated virgin control mice. The most severe forms of human fibrocystic breast diseases that bear an enhanced risk of cancerous development are characterized by increased epithelial cell proliferation. As described in Example 16, the neutralizing PRLR antibodies were tested in this Balb/c mouse model in comparison to unspecific antibodies with regard to their ability to:

block sidebranching and lobuloalveolar development
inhibit mammary epithelial cell proliferation
inhibit phosphorylation of STAT5, a transcription factor that is normally activated and phosphorylated after PRLR activation.

As demonstrated in FIG. 15A-C neutralizing PRLR antibodies block all the above mentioned readout paradigms in a dose-dependent manner.

Another object of the present invention is the use of neutralizing PRLR antibodies and antigen binding fragments for treatment of benign breast disease and mastalgia in pre- and postmenopausal women.

Another aspect of the present invention is the use of the antibody and antigen binding fragments as described in the present invention for treatment of benign breast disease and mastalgia in pre- and postmenopausal women.

Lactation Inhibition

Prolactin is the main hormone involved in lactation after child birth. This is evidenced by the phenotype of PRLR-deficient mice. Even heterozygous mice have severe lactational problems and are completely unable to nurse their offspring (Frontiers in Neuroendocrinology 22: 140-145, 2001).

For many reasons, women have to stop breast feeding, i.e. maternal intake of drugs potentially dangerous to the infant, serious infections (mastitis, nephritis), profuse postpartum hemorrhage, and severe maternal diseases such as diabetes, carcinoma, and debility or diseases of the newborn. Currently, dopamine receptor agonists such as bromocriptine and lisuride are used to inhibit lactation after child birth. However, these compounds can provoke severe side effects such as nausea, vomiting, edema, hypotension, dizziness, hair loss, headache, and halluzinations. In addition dopamine receptor agonists are not indicated in women suffering from cardiovascular disease and hypertension. A further disadvantage of bromocriptine is its short half life time requiring drug intake 4-6 times daily over a period of 14 days.

To test the efficacy of the neutralizing prolactin receptor antibodies in mice, NMRI mice were mated with males. After birth, littersize was adjusted to 8 animals, and females were treated with specific and unspecific antibodies directed against the PRLR as described in example 15. As a measure for maternal lactation capacity, weight of the offspring was monitored daily. Readouts are described in detail in example 15 and results are depicted in FIG. 14A-D. Neutralizing PRLR antibodies show a dose-dependent inhibition of lactation and lead to mammary gland involution and reduced milk protein production.

Another object of the present invention is the use of neutralizing PRLR antibodies for inhibition of lactation.

Another object of the present invention is the use of the antibody and antigen binding fragments as described in the present invention for inhibition of lactation.

Benign Prostate Hyperplasia

Benign prostate hyperplasia (BPH) is the fourth most prevalent healthcare condition in older men. Prostate enlargement is an age-dependent progressive condition that affects more than 50% of men aged ≥50 years of age. BPH is characterized by hyperplasia of prostatic stromal and epithelial cells, resulting in the formation of large discrete nodules in the periurethral region of the prostate which compresses the urethral canal. Thus, impairment of urine flow is one major consequence of BPH.

Standard therapies for BPH encompass:
a) α1-adrenergic receptor antagonists (e.g. tamsulosin, alfuzosin, terazosin, doxazosin) relief the BPH symptoms in the lower urinary tract. They decrease bladder outlet obstruction by blocking alpha-receptor-mediated stimulation of prostate smooth muscle. Major side-effects are vasodilatory adverse events, dizziness and ejaculation failure.
b) 5α-reductase inhibitors (e.g. finasteride)
5α-reductase inhibitors prevent the formation of dihydrotestosterone, the active form of testosterone in the prostate, which is responsible for the enlargement of the prostate. Major side-effects are sexual dysfunction, such as erectile disorders and decreased libido.
c) Transurethral resection of the prostate (TURP)
This surgical treatment is associated with high morbidity. Side-effects are bleeding, incontinence, stricture formation, loss of ejaculation, and bladder perforation.
d) Prostate stenting
A stent is inserted into the prostatic part of the urethra to guarantee proper urine flow. Major side-effects are encrustation, urinary tract infection, and migration of the stent. Moreover, stents have to be removed before any transurethral manipulation.

As described for the mammary gland, PRL and the PRLR act in an autocrine/paracrine way (J. Clin. Invest. 99: 618 pp, 1997) within the prostate.

Clinical studies indicate that hyperprolactinemia (and agromegaly) is associated with prostatic enlargement and stromal accumulation of inflammatory cells. Human growth hormone can bind to the human PRLR in the presence of zinc which might explain why acromegaly can lead to benign prostate hyperplasia. PRL serum levels are often elevated in patients with BPH.

Transgenic animals overexpressing the PRL gene ubiquitously, develop severe stromal prostate hyperplasia, indicating PRL as an important pathophysiological factor for the development of prostate hyperplasia (Endocrinology 138: 4410 pp, 1997). Furthermore, local overexpression of PRL in transgenic mice under the prostate specific probasin promoter results in stromal expansion, accumulation of inflammatory cells and focal epithelial dysplasia which are basic characteristics of human BPH (Endocrinology 144: 2269 pp, 2003).

The PRLR is highly expressed in the prostate gland (Example 3, FIG. 3). Variation of PRLR protein expression was observed in rat prostate tissue after hormonal depletion and treatment (Example 4, FIG. 4). In addition to the PRLR, the prostate cells express also prolactin.

As described in Example 17, male Balb/c mice received pituitary isografts under the kidney capsule and developed benign prostate hyperplasia. The effect of neutralizing prolactin receptor antibodies and unspecific antibodies on benign prostate hyperplasia was tested in this model. Readout paradigms are described in Example 17. As depicted in FIG. 16, neutralizing PRLR antibodies inhibit benign prostate growth and are therefore suitable for the treatment of benign prostate hyperplasia.

Another object of the present invention is the use of neutralizing PRLR antibodies and antigen binding fragments for treatment of benign prostate hyperplasia.

Another aspect of the present invention is the use of the antibody and antigen binding fragments as described in the present invention for treatment of benign prostate hyperplasia.

Hyperprolactinemic Hair Loss

Treatment of hair loss is still an unmet need. Scalp hair growth in cycles: the anagen phase is characterized by active hair growth, the catagen phase shows involution and is followed by the telogen phase (resting). The exogen phase (the release of the dead hair) coincides with the end of the telogen phase. Hair loss can be the consequence of disturbed hair growth in any phase.

Telogen hair loss can have many triggers (physiological and emotional stress, medical conditions, iron and zinc deficiency), importantly androgenic alopecia in its early stages shows telogen hair shedding (Cleveland clinic journal of medicine 2009; 76: 361-367). Anagen hair loss is often the consequence of radiation or chemotherapy.

Minoxidil and Finasteride are used for the treatment of androgenetic hair loss, whereas glucocorticoids are used for alopecia areata. In general, all of these treatments have side-effects (finasteride: libido loss and impotence in men, glucocorticoids: diabetes, weight gain, osteoporosis), and the problem of treating hair loss has not been completely solved.

In rodents, shaving experiments in adult animals were used to analyze the effect of compounds on hair loss by using hair regrowth in the shaved area as readout paradigm (British Journal of Dermatology 2008; 159: 300-305). Shaving of adult animals (hair mostly in telogen phase) induces the anagen phase that is charactzerized by hair growth.

In the experiments as described in Example 17 (benign prostate hyperplasia), animals receiving pituitary isografts, were shaved. In the course of these experiments, it was unexpectedly discovered that animals which received pituitary isografts showed a severe impairment of hair regrowth in the shaved area. Treatment with neutralizing PRLR antibodies but not with unspecific antibodies stimulated hair growth (FIG. 17). This observation demonstrates that elevated prolactin receptor-mediated signaling is involved in hair loss. To analyze this in more detail, further shaving experiments in close analogy to previously described experiments were performed (British Journal of Dermatology 2008; 159: 300-305). These additional shaving experiments are described in Example 18. The experiments demonstrate that neutralising PRLR antibodies stimulate hair growth in hyper- and normoprolactinemic male and female mice.

The antibodies of the present invention solve the problem for providing new treatments for hyper- and normoprolactinemic hair loss in women and men.

Therefore a further aspect of the present invention is to employ neutralizing PRLR antibodies and antigen binding fragments for the treatment or prevention of hyper- and normoprolactinemic hair loss.

Another aspect of the present invention is the use of the antibody and antigen binding fragments as described in the present invention for treatment or prevention of hyperprolactinemic hair loss.

Combined Hormone Therapy

For the treatment of hot flushes in postmenopausal women still having a uterus, combinations of estrogen (estradiol, or conjugated equine estrogens=CEE) and progestins (for example medroxyprogesterone acetate (MPA), progesterone, drospirenone, levonorgestrel) were used. Progestins have to be added to inhibit estradiol-activated uterine epithelial cell proliferation. However, addition of progestins increases mammary epithelial cell proliferation. Since both, normal as well as cancerous mammary epithelial cells respond with proliferation towards combined estrogen plus progestin treatment, the relative risk of breast cancer was found to be increased after CEE plus MPA treatment (JAMA 233: 321-333; 2002).

Neutralizing PRLR antibodies when administered every month or every second month to women under combined hormone therapy will inhibit enhanced breast epithelial cell proliferation.

As described in Example 19, a previously developed mouse model for the quantitative analysis of progestin effects in the uterus and the breast was employed (Endocrinology 149: 3952-3959, 2008). Mice were ovariectomized and were treated 14 days after ovariectomy for three weeks with vehicle or 100 ng estradiol plus 100 mg/kg progesterone to mimic hormone replacement therapy. Animals were treated once weekly with specific PRLR (10 mg/kg or 30 mg/kg) or unspecific antibodies (30 mg/kg). The effects of neutralizing PRLR antibodies on proliferative activity in the breast under combined hormone therapy were analyzed.

The antibodies of the present invention solve the problem for treating enhanced breast epithelial cell proliferation observed under combined hormone therapy.

Another object of the present invention is the use of neutralizing PRLR antibodies and antigen binding fragments in combined hormone therapy (i.e. estrogen+progestin therapy) to inhibit mammary epithelial cell proliferation.

Another aspect of the present invention is the use of the antibody and antigen binding fragments as described in the present invention in combined hormone therapy (i.e. estrogen+progestin therapy) to inhibit mammary epithelial cell proliferation.

DEFINITIONS

The target antigen human "PRLR" as used herein refers to a human polypeptide having substantially the same amino acid sequence in its extracellular domain as the amino acid positions 1 to 210 of SEQ ID NO. 70 and naturally occurring allelic and/or splice variants thereof. "ECD of PRLR" as used herein refers to the extracellular portion of PRLR represented by the afore mentioned amino acids. In addition the target human PRLR also encompasses mutated versions of the receptor, such as the activating mutation I146L described by Paul Kelly (Proc Natl Acad Sci USA. 105 (38): 14533-14538, 2008; and oral communication Turin, 2007).

As used herein, the phrase "therapeutically effective amount" is meant to refer to an amount of therapeutic or prophylactic antibody that would be appropriate to elicit the desired therapeutic or prophylactic effect or response, including alleviating some or all of such symptoms of disease or reducing the predisposition to the disease, when administered in accordance with the desired treatment regimen.

As used herein, an antibody "binds specifically to," is "specific to/for" or "specifically recognizes" an antigen (here, PRLR) if such an antibody is able to discriminate between such antigen and one or more reference antigen(s), since binding specificity is not an absolute, but a relative property. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. However, "specific binding" also may refer to the ability of an antibody to discriminate between the target antigen and one or more closely related antigen(s), which are used as reference points. Additionally, "specific binding" may relate to the ability of an antibody to discriminate between different parts of its target antigen, e.g. different domains, subdomains or regions of PRLR, such as epitopes in the N-terminal or in the C-terminal region of the ECD of PRLR, or between one or more key amino acid residues or stretches of amino acid residues of the ECD of PRLR.

"Affinity" or "binding affinity" $K_D$ are often determined by measurement of the equilibrium association constant (ka) and equilibrium dissociation constant (kd) and calculating the quotient of kd to ka ($K_D$=kd/ka). The term "immunospecific" or "specifically binding" means that the antibody binds to PRLR or its ECD with an affinity $K_D$ of lower than or equal to $10^{-6}$M (monovalent affinity). The term "high affinity" means that the $K_D$ that the antibody binds to PRLR or its ECD with an affinity $K_D$ of lower than or equal to $10^{-7}$M (monovalent affinity). The antibody may have substantially greater affinity for the target antigen compared to other unrelated molecules. The antibody may also have substantially greater affinity for the target antigen compared to homologs, e.g. at least 1.5-fold, 2-fold, 5-fold 10-fold, 100-fold, $10^{-3}$-fold, $10^{-4}$-fold, $10^{-5}$-fold, $10^{-6}$-fold or greater relative affinity for the target antigen. Such affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51: 660 (1949).

As used herein the phrase "antibodies antagonize prolactin mediated signaling" is meant to refer to a blockade of prolactin receptor activation by the antibodies of the present invention which leads to a complete inhibition of prolactin receptor mediated signaling.

As used herein the phrase "antibodies compete for binding" is meant to refer to a competition between one antibody and a second antibody or more antibodies for binding to the prolactin receptor.

The term "antibody" is used in the broadest sense and includes fully assembled antibodies, monoclonal antibodies, polyclonal antibodies, multispecific antibodies (e.g., bispecific antibodies), antibody fragments that can bind the antigen (e.g., Fab', F'(ab)$_2$, Fv, single chain antibodies, diabodies), camel bodies and recombinant peptides comprising the forgoing as long as they exhibit the desired biological activity. Antibodies may carry different constant domains (Fc domains) on their heavy chain preferably derived from IgG1, IgG2, or IgG4 isotypes (see below). Mutations for modification of effector functions may be introduced. Amino acid residues in the Fc-domain that play a dominant role in the interactions with the complement protein C1q and the Fc receptors have been identified and mutations influencing effector functions have been described (for a review see Labrijn et al., Current opinion in Immunology 20: 479-485, 2008). Particularly, aglycosylation of IgG1 may be achieved by mutating asparagine to alanine or asparagine to glutamine at amino acid position 297, which has been reported to abolish antibody-derived cell-mediated cytotoxicity (ADCC) (Sazinsky et al., Proc. Nat. Acad. Sci. 105 (51): 20169, 2008; Simmons et al., J. of Immunological Methods 263: 133-147, 2002). Replacement of lysine by alanine at position 322 leads to reduction of ADCC and removal of complement-derived cytotoxicity (CDC), while simultaneous replacement of the two leucines at position 234 and 235 by alanines leads to avoidance of ADCC and CDC [Hezareh et al., J. of Virology, 75 (24): 12161-12168, 2001]. In order to apply IgG4 isotypes as bivalent therapeutics in vivo which retain avidity, a modification such as the serine-to-proline exchange in the 'core hinge region' (Schuurman, J. et al. Immunology 97: 693-698, 1999) may be introduced. The tendency of human IgG2 molecules to form heterogeneous covalent dimers may be circumvented by exchanging one of the cysteines at position 127, 232 and 233 to serine (Allen et al., Biochemistry, 2009, 48 (17), pp 3755-3766). An alternative format with reduced effector function may be the IgG2 m4 format, derived from IgG2 carrying four IgG4-specific amino acid residue changes (An et al., mAbs 1(6), 2009). Antibody fragments may be produced by recombinant DNA techniques or by enzymatic or chemical cleavage of intact antibodies and are described further below. Nonlimiting examples of monoclonal antibodies include murine, chimeric, humanized, human, and Human Engineered™ immunoglobulins, antibodies, chimeric fusion proteins having sequences derived from immunoglobulins, or muteins or derivatives thereof, each described further below. Multimers or aggregates of intact molecules and/or fragments, including chemically derivatized antibodies, are contemplated.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the homogeneous culture, uncontaminated by other immunoglobulins with different specificities and characteristics.

The modifier "monoclonal" indicates the character of the antibody as being obtained from a substantially homogeneous population of antibodies, and is not to be construed as requiring production of the antibody by any particular method. For example, the monoclonal antibodies to be used may be made by the hybridoma method first described by Kohler et al., Nature, 256: 495 [1975, or may be made by recombinant DNA methods (see, e.g., U.S. Pat. No. 4,816, 567). The "monoclonal antibodies" may also be recombinant, chimeric, humanized, human, Human Engineered™, or antibody fragments, for example.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes often have ADCC activity. Human light chains are classified as kappa (K) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains [amino acid positions 1 to 109 of VL and 1 to 113 of VH, while numbering of amino acid positions occurs according to the Kabat database (Johnson and Wu, Nucleic Acids Res., 2000, 28, 214-218)]. A preferred class of immunoglobulins for use in the present invention is IgG.

The term "hypervariable" region refers to the amino acid residues of the variable domains VH and VL of an antibody or functional fragment which are responsible for antigen-binding. The hypervariable region comprises amino acid residues from a "complementarity determining region" or CDR [i.e., residues 24-34 (LCDR1), 50-56 (LCDR2) and 88-97 (LCDR3) in the light chain variable domain and 29-36 (HCDR1), 48-66 (HCDR2) and 93-102 (HCDR3) in the heavy chain variable domain as described in FIG. 12] and/or those residues from a hypervariable loop [i.e., residues 26-32 (within LCDR1), 50-52 (within LCDR2) and 91-96 (within LCDR3) in the light chain variable domain and 26-32 (within HCDR1), 53-55 (within HCDR2) and 96-101 (within HCDR3) in the heavy chain variable domain as described by Chothia et al., J. Mol. Biol. 196: 901-917 (1987)].

Nonlimiting examples of antibody fragments include Fab, Fab', F(ab')2, Fv, domain antibody (dAb), complementarity determining region (CDR) fragments, single-chain antibodies (scFv), single chain antibody fragments, diabodies, triabodies, tetrabodies, minibodies, linear antibodies (Zapata et al., Protein Eng., 8 (10): 1057-1062 (1995)); chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity; and multispecific antibodies formed from antibody fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). An antibody other than a "bispecific" or "bifunctional" antibody is understood to have each of its binding sites identical. The F(ab')$_2$ or Fab may be engineered to minimize or completely remove the intermolecular disulphide interactions that occur between the $C_{H1}$ and $C_L$ domains. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two "Fv" fragments. An "Fv" fragment is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen.

"Single-chain Fv" or "sFv" or "scFv" antibody fragments comprise the VH and VL domains of antibody, wherein these domains are present in a single polypeptide chain.

Preferably, the Fv polypeptide further comprises a polypeptide linker between the VH and VL domains that enables the Fv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them.

"Framework" or FR residues are those variable domain residues other than the hypervariable region residues.

The phrase "constant region" refers to the portion of the antibody molecule that confers effector functions.

The term "mutein" or "variant" can be used interchangeably and refers to the polypeptide sequence of an antibody that contains at least one amino acid substitution, deletion, or insertion in the variable region or the portion equivalent to the variable region, provided that the mutein or variant retains the desired binding affinity or biological activity.

Muteins may be substantially homologous or substantially identical to the parent antibody.

The term "derivative" refers to antibodies covalently modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids.

A "human" antibody or functional human antibody fragment is hereby defined as one that is not chimeric or "humanized" and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source). Examples of human antibodies include n-CoDeR-based antibodies as described by Carlsson and Söderlind Exp. Rev. Mol. Diagn. 1 (1), 102-108 (2001), Söderlin et al. Nat. Biotech. 18, 852-856 (2000) and U.S. Pat. No. 6,989,250.

A "humanized antibody" or functional humanized antibody fragment is defined herein as one that is (i) derived from a non-human source (e.g., a transgenic mouse which bears a heterologous immune system), which antibody is based on a human germline sequence; or (ii) CDR-grafted, wherein the CDRs of the variable domain are from a non-human origin, while one or more frameworks of the variable domain are of human origin and the constant domain (if any) is of human origin.

The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

"Human Engineered™" antibodies generated by altering the parent sequence according to the methods set forth in Studnicka et al., U.S. Pat. No. 5,766,886 such as the antibody represented by SEQ ID NOs 58, 61, 64, 67 and described in patent application WO08/022,295.

An antibody of the invention may be derived from a recombinant antibody gene library. The development of technologies for making repertoires of recombinant human antibody genes, and the display of the encoded antibody fragments on the surface of filamentous bacteriophage, has provided a recombinant means for directly making and selecting human antibodies, which also can be applied to humanized, chimeric, murine or mutein antibodies. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function. Typically, the Fd fragment (VH-CH1) and light chain (VL-CL) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and re-amplification, a procedure termed panning, Fab specific for the antigen are enriched and finally isolated.

A variety of procedures have been described for deriving human antibodies from phage-display libraries. Such libraries may be built on a single master framework, into which diverse in vivo-formed (i.e. human-derived) CDRs are allowed to recombine as described by Carlsson and Söderlind Exp. Rev. Mol. Diagn. 1 (1), 102-108 (2001), Söderlin et al. Nat. Biotech. 18, 852-856 (2000) and U.S. Pat. No. 6,989, 250. Alternatively, such an antibody library may be based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064. For a review of phage display techniques, see WO08/022,295 (Novartis).

Alternatively, an antibody of this invention may come from animals. Such an antibody may be humanized or Human Engineered summarized in WO08/022,295 (Novartis); such an antibody may come from transgenic animals [see also WO08/022,295 (Novartis)].

As used herein, different 'forms' of antigen, e.g. PRLR, are hereby defined as different protein molecules resulting from different translational and posttranslational modifications, such as, but not limited to, differences in splicing of the primary prolactin receptor transcript, differences in glycosylation, and differences in posttranslational proteolytic cleavage.

As used herein, the term 'epitope' includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. Two antibodies are said to 'bind the same epitope' if one antibody is shown to compete with the second antibody in a competitive binding assay, by any of the methods well known to those of skill in the art, and if preferably all amino acids of the epitope are bound by the two antibodies.

The term 'maturated antibodies' or 'maturated antigen-binding fragments' such as maturated Fab variants includes derivatives of an antibody or antibody fragment exhibiting stronger binding—i.e. binding with increased affinity- to a given antigen such as the extracellular domain of the PRLR. Maturation is the process of identifying a small number of mutations within the six CDRs of an antibody or antibody fragment leading to this affinity increase. The maturation process is the combination of molecular biology methods for introduction of mutations into the antibody and screening for identifying the improved binders.

Therapeutic Methods

Therapeutic methods involve administering to a subject in need of treatment a therapeutically effective amount of an antibody contemplated by the invention. A "therapeutically effective" amount hereby is defined as the amount of an antibody that is of sufficient quantity to block proliferation of PRLR-positive cells in a treated area of a subject either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, monkey or other lower-order primate).

An antibody of the invention might be co-administered with known medicaments, and in some instances the antibody might itself be modified. For example, an antibody could be conjugated to an immunotoxin or radioisotope to potentially further increase efficacy. The inventive antibodies can be used as a therapeutic or a diagnostic tool in a variety of situations where PRLR is undesirably highly expressed. Disorders and conditions particularly suitable for treatment with an antibody of the inventions are endometriosis, adenomyosis, non-hormonal female fertility contraception, benign breast disease and mastalgia, lactation inhibition, benign prostate hyperplasia, fibroids, hyper- and normoprolactinemic hair loss, and cotreatment in combined hormone therapy to inhibit mammary epithelial cell proliferation.

To treat any of the foregoing disorders, pharmaceutical compositions for use in accordance with the present invention may be formulated in a conventional manner using one or more physiologically acceptable carriers or excipients. An antibody of the invention can be administered by any suitable means, which can vary, depending on the type of disorder being treated. Possible administration routes include parenteral (e.g., intramuscular, intravenous, intraarterial, intraperitoneal, or subcutaneous), intrapulmonary and intranasal, and, if desired for local immunosuppressive treatment, intralesional administration. In addition, an antibody of the invention might be administered by pulse infusion, with, e.g., declining doses of the antibody. Preferably, the dosing is given by injections, most preferably intravenous or subcutaneous injections, depending in part on whether the administration is brief or chronic. The amount to be administered will depend on a variety of factors such as the clinical symptoms, weight of the individual, whether other drugs are administered. The skilled artisan will recognize that the route of administration will vary depending on the disorder or condition to be treated.

Determining a therapeutically effective amount of the novel polypeptide, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

Pharmaceutical Compositions and Administration

The present invention also relates to pharmaceutical compositions which may comprise PRLR antibodies, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

The present invention also relates to the administration of pharmaceutical compositions. Such administration is accomplished parenterally. Methods of parenteral delivery include topical, intra-arterial (directly to the tumor), intramuscular, subcutaneous, intramedullary, intrathecal, intraventricular, intravenous, intraperitoneal, intrauterine or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Ed. Maack Publishing Co, Easton, Pa.).

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The parenteral administration also comprises methods of parenteral delivery which also include intra-arterial, intramuscular, subcutaneous, intramedullary, intrathecal, and intraventricular, intravenous, intraperitoneal, intrauterine, vaginal, or intranasal administration.

Kits

The invention further relates to pharmaceutical packs and kits comprising one or more containers filled with one or more of the ingredients of the afore mentioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

In another embodiment, the kits may contain DNA sequences encoding the antibodies of the invention. Preferably the DNA sequences encoding these antibodies are provided in a plasmid suitable for transfection into and expression by a host cell. The plasmid may contain a promoter (often an inducible promoter) to regulate expression of the DNA in the host cell. The plasmid may also contain appropriate restriction sites to facilitate the insertion of other DNA sequences into the plasmid to produce various antibodies. The plasmids may also contain numerous other elements to facilitate cloning and expression of the encoded proteins. Such elements are well known to those of skill in the art and include, for example, selectable markers, initiation codons, termination codons, and the like.

Manufacture and Storage

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of PRLR antibodies, such labeling would include amount, frequency and method of administration.

Therapeutically Effective Dose

Pharmaceutical compositions suitable for use in the present invention include compositions wherein the active ingredients are contained in an effective amount to achieve the intended purpose, i.e. treatment of a particular disease state characterized by PRLR expression. The determination of an effective dose is well within the capability of those skilled in the art.

For any compound, the therapeutically effective dose can be estimated initially either in cell culture assays, e.g., lymphoma cells, or in animal models, usually mice, rats, rabbits, dogs, pigs or monkeys. The animal model is also used to achieve a desirable concentration range and route of administration. Such information can then be used to determine useful doses and routes for administration in humans.

A therapeutically effective dose refers to that amount of protein or its antibodies, antagonists, or inhibitors that ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations what include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, eg, size and location of endometriotic lesions; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks, or once within a month depending on half-life and clearance rate of the particular formulation.

Normal dosage amounts may vary from 0.1 to 100,000 micrograms, up to a total dose of about 2 g, depending upon the route of administration. Guidance as to particular dosages and methods of delivery is provided in the literature. See U.S. Pat. No. 4,657,760; U.S. Pat. No. 5,206,344; or U.S. Pat. No. 5,225,212. Those skilled in the art will employ different formulations for polynucleotides than for proteins or their inhibitors. Similarly, delivery of polynucleotides or polypeptides will be specific to particular cells, conditions, locations, etc. Preferred specific activities for a radiolabeled antibody may range from 0.1 to 10 mCi/mg of protein (Riva et al., Clin. Cancer Res. 5: 3275s-3280s, 1999; Wong et al., Clin. Cancer Res. 6: 3855-3863, 2000; Wagner et al., J. Nuclear Med. 43: 267-272, 2002).

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., Molecular Cloning: A Laboratory Manual, 2nd Ed.; Cold Spring Harbor Laboratory Press, Cold Spring Harbor, N.Y., 1989.

DESCRIPTION OF THE FIGURES

FIG. 1: Expression of prolactin-mRNA (PRL-mRNA) (analyzed by real-time TaqMan PCR analysis) in human endometrium and lesions (ectopic tissue) from healthy women and women suffering from endometriosis.

FIG. 2: Expression of prolactin receptor-mRNA (PRLR-mRNA) (analyzed by real-time TaqMan PCR analysis) in human endometrium and lesions (ectopic tissue) from healthy women and women suffering from endometriosis.

FIG. 3: Northern blot analysis of PRLR gene expression in rat tissues. Gene expression of the PRLR revealed high expression in placenta and prostate.

FIG. 4: Western blot analysis of PRLR expression in rat prostates treated with different hormones. Estradiol treatment of intact rats and castration lead to an upregulation of PRLR protein in rat prostates whereas dihydrotestosterone treatment of intact rats had no impact on PRLR expression in the prostate compared to vehicle treatment of intact animals.

FIG. 5: Inhibition of prolactin-activated Ba/F (=Baf) cell proliferation (stably expressing the human PRLR) by neutralizing PRLR antibodies and unspecific control antibodies. The $IC_{50}$ values were determined for the following antibodies in IgG1 format: 005-C04 (closed circles): 1.29 µg/ml=8.6 nM; 006-H08 (open circles): 0.15 µg/ml=1 nM; HE06.642 (closed triangles): 0.34 µg/ml=2.2 nM; 002-H06 (open triangles): 0.54 µg/ml=3.6 nM; 002-H08 (closed squares): 0.72 µg/ml=4.8 nM; unspecific control antibody (open squares): no inhibition of cell proliferation FIG. 6: Inhibition of prolactin-induced rat lymphoma cell proliferation (NB2 cells) by neutralizing PRLR antibodies and unspecific control antibodies. The following $IC_{50}$ values were determined: XHA06.642 (closed circles): 10 µg/ml=67 nM; XHA06.983 (open circles): no effect on rat lymphoma cell proliferation; unspecific control antibody (closed triangle): no effect at 10 µg/ml.

FIG. 7: Inhibition of prolactin-stimulated STAT5 phosphorylation in T47D cells by neutralizing PRLR antibodies and unspecific control antibody.

Figure 13:
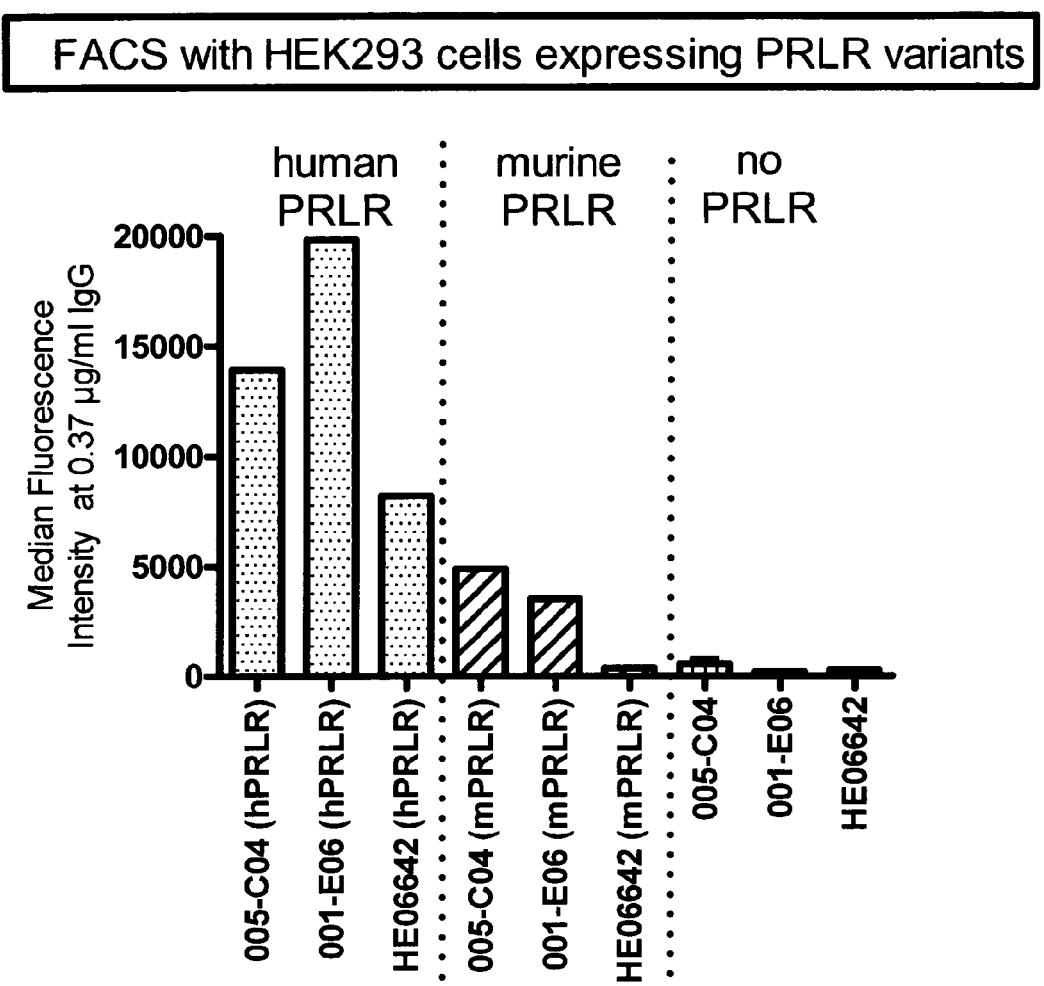

The unspecific control antibody (FITC) does not inhibit STAT5 phosphorylation in T47D cells. In contrast the antibodies XHA06.642, 005-C04 (=IgG1 005-C04), and 006-H08 (=IgG1 006-H08) inhibit in a dose-dependent manner phosphorylation of STAT5 in T47D cells.

FIG. 8: Effects of neutralizing PRLR antibodies and unspecific controls on prolactin-activated luciferase reporter gene activity using HEK293 cells stably transfected with the human prolactin receptor (hPRLR) and transiently expressing the luciferase gene under the control of lactogenic hormone response elements (LHREs). The $IC_{50}$ values were determined for the following antibodies in IgG1 format: 006-H08 (closed circles): 0.83 µg/ml=5.5 nM; HE06.642 (open circles): 0.63 µg/ml=4.2 nM; unspecific control antibody (closed triangle): no inhibition of luciferase activity.

FIG. 9: Effects of neutralizing PRLR antibodies and unspecific controls on prolactin-activated luciferase reporter gene activity using HEK293 cells stably transfected with the murine prolactin receptor (mPRLR) and transiently expressing the luciferase gene under the control of lactogenic hormone response elements (LHREs). The $IC_{50}$ values were determined for the following antibodies in IgG1 format: 005-C04 (closed triangles): 0.45 µg/ml=3 nM; XHA06.642

(closed circles): >>50 μg/ml>>333 nM, unspecific control antibody (open circles): no inhibition of luciferase activity.

FIG. 10: Inhibition of prolactin-activated Ba/F (=Baf) cell proliferation (stably expressing the murine prolactin receptor) by neutralizing prolactin receptor antibodies and unspecific control antibodies. The $IC_{50}$ values were determined for the following antibodies in IgG1 format: unspecific FITC antibody (closed squares): no inhibition of cell proliferation; HE06.642 (closed circles): >>>30 μg/ml>>>200 nM; 001-E06 (open circles): 43.7 μg/ml=291 nM; 001-D07 (closed triangles): 16.5 μg/ml=110 nM; 005-C04 (open triangles): 0.74 μg/ml=4.9 nM.

FIG. 11: Pregnancy rates and mean litter size in female mice treated with phosphate-buffered saline (=vehicle), unspecific control antibody (FITC IgG1) or neutralizing antibody IgG1 005-C04 (=005-C04). Pregnancy rates were 87.5% (vehicle treated females), 75% (females treated with 10 mg/kg unspecific antibody), 100% (females treated with 10 mg/kg IgG1 005-C04), and 0% (females treated with 30 mg/kg IgG1 005-C04). Mean litter size was 10.9 animals (vehicle treated females), 12.3 animals (females treated with 10 mg/kg unspecific antibody), 13 animals (females treated with 10 mg/kg IgG1 005-C04) and 0 animals (females treated with 30 mg/kg IgG1 005-C04).

FIG. 12: Kabat Numbering of framework amino acid positions according to Johnson and Wu (Nucleic Acids Res. 2000, 28, 214-218).

FIG. 13: FACS analysis results with selected anti-PRLR antibodies (005-C04, 001-E06, HE06642). Binding of the antibodies was determined at a fixed concentration on HEK293 cells expressing the human and mouse PRLR in comparison to the parental cell line not expressing PRLR.

FIG. 14A: Litter weight gain for each postpartal day expressed as percentage of litter weight obtained on postpartal day 1. Weight gain of litters from untreated mothers (closed circles), from mothers treated with 10 mg/kg unspecific murine IgG2a antibody (open circles), and from mothers treated with the neutralizing antibody 005-C04 containing murine IgG2a constant domains (=IgG2a 005-C04) at 10 mg/kg (closed triangles) and at 30 mg/kg (open triangles) is shown. Arrows indicate days on which antibody injection was performed. There is a significant reduction in weight gain from litters of mothers treated with 30 mg/kg IgG2a 005-C04 from postpartal day 8 onwards.

FIG. 14B: Incremental litter weight gain from day to day expressed as percentage of litter weight on postpartal day 1. Results from litters of untreated mothers (closed circles), mothers treated with 10 mg/kg unspecific murine IgG2a antibody (open circles), mothers treated with the neutralizing antibody 005-C04 containing murine IgG2a constant domains (=IgG2a 005-C04) at 10 mg/kg (closed triangles) and at 30 mg/kg (open triangles) are shown. Basically FIG. 14A presents the slope of the graphs shown in FIG. 14A. Daily weight gain in litters from untreated mothers and mothers treated with 10 mg/kg unspecific antibody oscillates around 30% of the litter weight on postpartal day 1. In contrast, treatment of mothers with 30 mg/kg IgG2a 005-C04 leads to a significant reduction in weight gain from day 7 onwards (*p<0.05;***p<0.005 vs. litters from mothers treated with unspecific antibody) whereas treatment with 10 mg/kg IgG2a 005-C04 leads to a significant reduction in daily weight gain from day 11 onwards (p<0.05 vs. litters from mothers treated with unspecific antibody). Arrows indicate days of antibody application.

FIG. 14C: Histological sections from mammary glands of lactating mothers. Mammary glands from untreated mothers or mothers treated with unspecific antibody are filled with ducts producing milk. In contrast mammary gland involution, evidenced by the appearance of fatty islands (black arrows), is induced dose-dependently by the neutralizing IgG2a 005-C04 antibody.

FIG. 14D: Milk protein expression in mammary glands from lactating mothers. Expression of the milk proteins beta casein (Csn-2), whey acidic protein (WAP), and IGF-1 is reduced in a dose-dependent manner in mothers treated with neutralizing PRLR antibody IgG2a 005-C04, but not with unspecific antibodies. Gene expression was normalized to the expression of TATA box binding protein (TBP).

FIG. 15A: Formation of side branches and alveolar like structures in a hyperprolactinemic mouse model of benign breast disease. The neutralizing PRLR antibody IgG1 005-C04 (=005-C04) inhibits side branching and the formation of alveolar like structures at 10 and 30 mg/kg in mice that received a pituitary isograft.

FIG. 15B: Extent of epithelial hyperplasia and epithelial cell proliferation in a hyperprolactinemic mouse model of benign breast disease. Some BrdU-positive cells are marked by white arrows. The neutralizing PRLR antibody IgG1 005-C04 (=005-C04) blocks epithelial hyperplasia and epithelial cell proliferation in the mammary gland.

FIG. 15C: Extent of STAT5 phosphorylation in a hyperprolactinemic mouse model of benign breast disease. Some phospho-STAT5-positive cells are indicated by white arrows. The neutralizing PRLR antibody IgG1 005-C04 (=005-C04) completely blocks STAT5 phosphorylation when applied at a dosage of 30 mg/kg.

FIG. 16: Inhibition of prostate growth by the neutralizing PRLR antibody 005-C04 containing murine IgG2a constant domains (=IgG2a 005-C04). Pituitary isografting stimulates prostate growth in comparison to untreated sham-operated mice. Treatment with neutralizing PRLR antibodies at doses of 10 mg/kg and at doses of 30 mg/kg inhibits prostate growth (***p<0.005 vs. untreated, sham-operated mice).

FIG. 17: Neutralizing PRLR antibodies stimulate hair growth in the presence of hyperprolactinemia. Photographs were taken three weeks after pituitary isografting (and shaving) from male mice used in the experiments described in Example 17 and in FIG. 16. Hyperprolactinemia inhibits hair regrowth in the shaved areas. Neutralizing PRLR antibodies, but not unspecific antibodies stimulate hair regrowth under hyperprolactinemic conditions at doses of 10 and 30 mg/kg of 005-C04 (=IgG2a 005-C04).

FIG. 18: Neutralizing PRLR antibodies but not unspecific antibodies stimulate hair regrowth in shaved areas in hyper- and normoprolactinemic male and female mice (Example 18). Neutralizing PRLR antibodies are therefore suitable for the treatment of hair loss under normo- and hyperprolactinemic conditions in men (FIG. 18 B) and women (FIG. 18A).

FIG. 19: Neutralizing PRLR antibodies but not unspecific control antibodies inhibit enhanced epithelial cell proliferation in the mammary gland after combined hormone therapy, i.e. combined estrogen plus progestin therapy.

The absolute number of proliferating ductal epithelial cells within 4 cross-sections of the mammary gland was evaluated and the medians are depicted as horizontal bars within the figure. Epithelial cell proliferation in ovariectomized, vehicle treated mice is rather low (median=0). Estradiol treatment leads to some stimulation of epithelial cell proliferation (median=9), maximal mammary epithelial cell proliferation is observed under estrogen plus progesterone treatment (median=144). Treatment with neutralising prolactin receptor antibody 005-C04 (median=84 after treatment with 10 mg/kg 005-C04; median=27 after treatment with 30 mg/kg 005-C04) but not with unspecific control antibody (median=154)

leads to a dose-dependent decrease in mammary epithelial cell proliferation almost back to estradiol-only levels.

Neutralising PRLR antibodies are therefore suitable to treat enhanced mammary epithelial cell proliferation under combined hormone therapy, i.e. estradiol plus progesterone treatment.

FIG. 20: Neutralizing PRLR antibodies but not unspecific control antibodies inhibit endometriosis interna in mice. The results are depicted as disease scores as described in Example 20. The median disease score for each experimental group is indicated as a horizontal bar. Normoprolactinemic mice develop endometriosis interna to some degree (median disease score=0.25). Hyperprolactinemia due to pituitary isografting enhances the disease score and more animals suffer from the disease (median disease score=2.5). Whereas treatment with 30 mg/kg unspecific antibody once (median score=2.5) or twice (median score=2) weekly had no influence on the disease, treatment with specific neutralizing antibodies shows a dose-dependent decrease in the amount of sick animals; the median disease score in all cases in which specific antibody was used was zero. Notably, all animals receiving either 10 or 30 mg/kg specific antibody twice weekly were completely cured and their disease score was significantly lower than the disease score of normoprolactinemic mice. Neutralising PRLR antibodies are therefore suitable to treat endometriosis interna (=adenomyosis uteri) and endometriosis externa in women.

FIG. 21: ELISA-based binding tests of maturated 005-C04 Fab variants:

Fab-containing *E coli* supernatants were tested for binding to the immobilized extracellular domain of the human PRLR. The figure illustrates the binding of the Fab variants as a bar diagram. The signal intensities (extinction) are given on the y-axes, the names of the Fab variants on the x-axes. In each diagram elevated signal intensities of the maturated Fab variants compared to the non-maturated Fab of the antibody 005-C04 (see bars named 005-C04 or C0$_4$ on the x-axes) demonstrate better PRLR-binding compared to 005-C04. The "variant" pET28 in diagram Part 1 represents a supernatant of an *E. coli* strain carrying the Fab-expression plasmid pET28a (Novagen, EMD Chemicals Group, Merck, Darmstadt, Germany) which does not express any Fab.

Seq ID NO:1 represents amino acid sequence of HCDR1, 006-H08

Seq ID NO:2 represents amino acid sequence of HCDR1, 002-H06

Seq ID NO:3 represents amino acid sequence of HCDR1, 002-H08

Seq ID NO:4 represents amino acid sequence of HCDR1, 006-H07

Seq ID NO:5 represents amino acid sequence of HCDR1, 001-E06

Seq ID NO:6 represents amino acid sequence of HCDR1, 005-C04

Seq ID NO:7 represents amino acid sequence of HCDR2, 006-H08

Seq ID NO:8 represents amino acid sequence of HCDR2, 002-H06

Seq ID NO:9 represents amino acid sequence of HCDR2, 002-H08

Seq ID NO:10 represents amino acid sequence of HCDR2, 006-H07

Seq ID NO:11 represents amino acid sequence of HCDR2, 001-E06

Seq ID NO:12 represents amino acid sequence of HCDR2, 005-C04

Seq ID NO:13 represents amino acid sequence of HCDR3, 006-H08, 002-H06

Seq ID NO:14 represents amino acid sequence of HCDR3, 002-H08

Seq ID NO:15 represents amino acid sequence of HCDR3, 006-H07

Seq ID NO:16 represents amino acid sequence of HCDR3, 001-E06

Seq ID NO:17 represents amino acid sequence of HCDR3, 005-C04

Seq ID NO:18 represents amino acid sequence of LCDR1, 006-H08

Seq ID NO:19 represents amino acid sequence of LCDR1, 002-H06

Seq ID NO:20 represents amino acid sequence of LCDR1, 002-H08

Seq ID NO:21 represents amino acid sequence of LCDR1, 006-H07

Seq ID NO:22 represents amino acid sequence of LCDR1, 001-E06

Seq ID NO:23 represents amino acid sequence of LCDR1, 005-C04

Seq ID NO:24 represents amino acid sequence of LCDR2, 006-H08, 002-H08

Seq ID NO:25 represents amino acid sequence of LCDR2, 002-H06

Seq ID NO:26 represents amino acid sequence of LCDR2, 006-H07

Seq ID NO:27 represents amino acid sequence of LCDR2, 001-E06

Seq ID NO:28 represents amino acid sequence of LCDR2, 005-C04

Seq ID NO:29 represents amino acid sequence of LCDR3, 006-H08

Seq ID NO:30 represents amino acid sequence of LCDR3, 002-H06, 001-E06

Seq ID NO:31 represents amino acid sequence of LCDR3, 002-H08

Seq ID NO:32 represents amino acid sequence of LCDR3, 006-H07

Seq ID NO:33 represents amino acid sequence of LCDR3, 005-C04

Seq ID NO:34 represents amino acid sequence of VH, 006-H08

Seq ID NO:35 represents amino acid sequence of VH, 002-H06

Seq ID NO:36 represents amino acid sequence of VH, 002-H08

Seq ID NO:37 represents amino acid sequence of VH, 006-H07

Seq ID NO:38 represents amino acid sequence of VH, 001-E06

Seq ID NO:39 represents amino acid sequence of VH, 005-C04

Seq ID NO:40 represents amino acid sequence of VL, 006-H08

Seq ID NO:41 represents amino acid sequence of VL, 002-H06

Seq ID NO:42 represents amino acid sequence of VL, 002-H08

Seq ID NO:43 represents amino acid sequence of VL, 006-H07

Seq ID NO:44 represents amino acid sequence of VL, 001-E06

Seq ID NO:45 represents amino acid sequence of VL, 005-C04

Seq ID NO:46 represents nucleic acid sequence VH, 006-H08
Seq ID NO:47 represents nucleic acid sequence VH, 002-H06
Seq ID NO:48 represents nucleic acid sequence VH, 002-H08
Seq ID NO:49 represents nucleic acid sequence VH, 006-H07
Seq ID NO:50 represents nucleic acid sequence VH, 001-E06
Seq ID NO:51 represents nucleic acid sequence VH, 005-C04
Seq ID NO:52 represents nucleic acid sequence VL, 006-H08
Seq ID NO:53 represents nucleic acid sequence VL, 002-H06
Seq ID NO:54 represents nucleic acid sequence VL, 002-H08
Seq ID NO:55 represents nucleic acid sequence VL, 006-H07
Seq ID NO:56 represents nucleic acid sequence VL, 001-E06
Seq ID NO:57 represents nucleic acid sequence VL, 005-C04
Seq ID NO:58 represents amino acid sequence of VH, HE06642, Novartis (WO2008/22295)
Seq ID NO:59 represents amino acid sequence of VH, XHA06642, Novartis (WO2008/22295)
Seq ID NO:60 represents amino acid sequence of VH, XHA06983, Novartis (WO2008/22295)
Seq ID NO:61 represents amino acid sequence of VL, HE06642
Seq ID NO:62 represents amino acid sequence of VL, XHA06642 Novartis (WO2008/22295)
Seq ID NO:63 represents amino acid sequence of VL, XHA06983 Novartis (WO2008/22295)
Seq ID NO:64 represents nucleic acid sequence VH, HE06642
Seq ID NO:65 represents nucleic acid sequence VH, XHA06642 Novartis (WO2008/22295)
Seq ID NO:66 represents nucleic acid sequence VH, XHA06983 Novartis (WO2008/22295)
Seq ID NO:67 represents nucleic acid sequence VL, HE06642
Seq ID NO:68 represents nucleic acid sequence VL, XHA06642, Novartis (WO2008/22295)
Seq ID NO:69 represents nucleic acid sequence VL, XHA06983, Novartis (WO2008/22295)
Seq ID NO:70 represents human ECD_PRLR, amino acid position 1-210, S1 domain 1-100 (S1 domain construct 1-102), S2 domain 101-210
Seq ID NO:71 represents CDS human ECD_PRLR, nucleotide position 1-630
Seq ID NO:72 represents murine ECD_PRLR, amino acid position 1-210
Seq ID NO:73 represents CDS murine ECD_PRLR, nucleotide position 1-630
SEQ ID NO:102 represents HCDR1, maturated 005-C04 variants, amino acid sequence
SEQ ID NO:103 represents HCDR1, maturated 005-C04 variants, amino acid sequence
SEQ ID NO:104 represents HCDR2, maturated 005-C04 variants, amino acid sequence
SEQ ID NO:105 represents HCDR2, maturated 005-C04 variants, amino acid sequence
SEQ ID NO:106 represents HCDR2, maturated 005-C04 variants, amino acid sequence
SEQ ID NO:107 represents HCDR2, maturated 005-C04 variants, amino acid sequence
SEQ ID NO:108 represents HCDR2, maturated 005-C04 variants, amino acid sequence
SEQ ID NO:109 represents HCDR2, maturated 005-C04 variants, amino acid sequence
SEQ ID NO:110 represents HCDR2, maturated 005-C04 variants, amino acid sequence
SEQ ID NO:111 represents HCDR2, maturated 005-C04 variants, amino acid sequence
SEQ ID NO:112 represents HCDR2, maturated 005-C04 variants, amino acid sequence
SEQ ID NO:113 represents HCDR2, maturated 005-C04 variants, amino acid sequence
SEQ ID NO:114 represents HCDR2, maturated 005-C04 variants, amino acid sequence
SEQ ID NO:115 represents HCDR2, maturated 005-C04 variants, amino acid sequence
SEQ ID NO:116 represents HCDR2, maturated 005-C04 variants, amino acid sequence
SEQ ID NO:117 represents HCDR2, maturated 005-C04 variants, amino acid sequence
SEQ ID NO:118 represents HCDR2, maturated 005-C04 variants, amino acid sequence
SEQ ID NO:119 represents HCDR2, maturated 005-C04 variants, amino acid sequence
SEQ ID NO:120 represents HCDR2, maturated 005-C04 variants, amino acid sequence
SEQ ID NO:121 represents HCDR2, maturated 005-C04 variants, amino acid sequence
SEQ ID NO:122 represents HCDR2, maturated 005-C04 variants, amino acid sequence
SEQ ID NO:123 represents HCDR2, maturated 005-C04 variants, amino acid sequence
SEQ ID NO:124 represents HCDR2, maturated 005-C04 variants, amino acid sequence
SEQ ID NO:125 represents HCDR2, maturated 005-C04 variants, amino acid sequence
SEQ ID NO:126 represents HCDR2, maturated 005-C04 variants, amino acid sequence
SEQ ID NO:127 represents HCDR2, maturated 005-C04 variants, amino acid sequence
SEQ ID NO:128 represents HCDR2, maturated 005-C04 variants, amino acid sequence
SEQ ID NO:129 represents HCDR2, maturated 005-C04 variants, amino acid sequence
SEQ ID NO:130 represents HCDR2, maturated 005-C04 variants, amino acid sequence
SEQ ID NO:131 represents HCDR2, maturated 005-C04 variants, amino acid sequence
SEQ ID NO:132 represents HCDR2, maturated 005-C04 variants, amino acid sequence
SEQ ID NO:133 represents HCDR2, maturated 005-C04 variants, amino acid sequence
SEQ ID NO:134 represents HCDR2, maturated 005-C04 variants, amino acid sequence
SEQ ID NO:135 represents LCDR1, maturated 005-C04 variants, amino acid sequence
SEQ ID NO:136 represents LCDR1, maturated 005-C04 variants, amino acid sequence
SEQ ID NO:137 represents LCDR2, maturated 005-C04 variants, amino acid sequence
SEQ ID NO:138 represents LCDR2, maturated 005-C04 variants, amino acid sequence
SEQ ID NO:139 represents LCDR2, maturated 005-C04 variants, amino acid sequence SEQ ID NO:140 represents LCDR2, maturated 005-C04 variants, amino acid sequence SEQ ID NO:141 represents LCDR2, maturated 005-C04 variants, amino acid sequence SEQ ID NO:142 represents LCDR2, maturated 005-C04 variants, amino acid sequence SEQ ID NO:187 represents VH, 005-C04-10-3, amino acid sequence SEQ ID NO:188 represents VH, 005-C04-11-5, amino acid sequence SEQ ID NO:189 represents VH, 005-C04-18-10-2, amino acid sequence SEQ ID NO:190 represents VH, 005-C04-18-10-4, amino acid sequence SEQ ID NO:191 represents VH, 005-C04-19-2, amino acid sequence SEQ ID NO:192 represents VH, 005-C04-2-2, amino acid sequence SEQ ID NO:193 represents VH, 005-C04-2-7, amino acid sequence SEQ ID NO:194 represents VH, 005-C04-20-12-7, amino acid sequence SEQ ID NO:195 represents VH, 005-C04-20-2, amino acid sequence SEQ ID NO:196 represents VH, 005-C04-21-1, amino acid sequence SEQ ID NO:197 represents VH, 005-C04-21-2, amino acid sequence SEQ ID NO:198 represents VH, 005-C04-25-6, amino acid sequence SEQ ID NO:199 represents VH, 005-C04-29-0, amino acid sequence SEQ ID NO:200 represents VH, 005-C04-29-17-0, amino acid sequence SEQ ID NO:201 represents VH, 005-C04-29-17-2, amino acid sequence SEQ ID NO:202 represents VH, 005-C04-29-17-3, amino acid sequence SEQ ID NO:203 represents VH, 005-C04-29-17-7, amino acid sequence SEQ ID NO:204 represents VH, 005-C04-35-3, amino acid sequence SEQ ID NO:205 represents VH, 005-C04-36-0, amino acid sequence SEQ ID NO:206 represents VH, 005-C04-37-2, amino acid sequence SEQ ID NO:207 represents VH, 005-C04-37-7, amino acid sequence SEQ ID NO:208 represents VH, 005-C04-4-3-7, amino acid sequence SEQ ID NO:209 represents VH, 005-C04-40-4, amino acid sequence SEQ ID NO:210 represents VH, 005-C04-41-2, amino acid sequence SEQ ID NO:211 represents VH, 005-C04-42-1, amino acid sequence SEQ ID NO:212 represents VH, 005-C04-44-25-1, amino acid sequence SEQ ID NO:213 represents VH, 005-C04-45-1, amino acid sequence SEQ ID NO:214 represents VH, 005-C04-46-0, amino acid sequence SEQ ID NO:215 represents VH, 005-C04-46-1, amino acid sequence SEQ ID NO:216 represents VH, 005-C04-47-3, amino acid sequence SEQ ID NO:217 represents VH, 005-C04-48-1, amino acid sequence SEQ ID NO:218 represents VH, 005-C04-5-5, amino acid sequence SEQ ID NO:219 represents VH, 005-C04-50-28-3, amino acid sequence SEQ ID NO:220 represents VH, 005-C04-50-28-7, amino acid sequence SEQ ID NO:221 represents VH, 005-C04-51-29-0, amino acid sequence SEQ ID NO:222 represents VH, 005-C04-52-29-0, amino acid sequence SEQ ID NO:223 represents VH, 005-C04-52-29-7, amino acid sequence SEQ ID NO:224 represents VH, 005-C04-53-31-7, amino acid sequence SEQ ID NO:225 represents VH, 005-C04-55-32-0, amino acid sequence SEQ ID NO:226 represents VH, 005-C04-58-33-1, amino acid sequence SEQ ID NO:227 represents VH, 005-C04-8-2, amino acid sequence SEQ ID NO:228 represents VH, 005-C04-8-6, amino acid sequence SEQ ID NO:229 represents VH, 005-C04-9-2, amino acid sequence SEQ ID NO:230 represents VH, 005-C04-L2-1-11-0, amino acid sequence SEQ ID NO:231 represents VH, 005-C04-L2-1-11-3, amino acid sequence SEQ ID NO:232 represents VH, 005-C04-L2-1-12-2, amino acid sequence SEQ ID NO:233 represents VH, 005-C04-L2-1-12-4, amino acid sequence SEQ ID NO:234 represents VH, 005-C04-L2-1-16-4, amino acid sequence SEQ ID NO:235 represents VH, 005-C04-L2-1-16-5, amino acid sequence SEQ ID NO:236 represents VH, 005-C04-L2-1-2-3, amino acid sequence SEQ ID NO:237 represents VH, 005-C04-L2-1-20-0, amino acid sequence SEQ ID NO:238 represents VH, 005-C04-L2-1-20-1, amino acid sequence SEQ ID NO:239 represents VH, 005-C04-L2-1-21-7, amino acid sequence SEQ ID NO:240 represents VH, 005-C04-L2-1-23-7, amino acid sequence SEQ ID NO:241 represents VH, 005-C04-L2-1-25-0, amino acid sequence SEQ ID NO:242 represents VH, 005-C04-L2-1-25-4, amino acid sequence SEQ ID NO:243 represents VH, 005-C04-L2-1-25-5, amino acid sequence SEQ ID NO:244 represents VH, 005-C04-L2-1-25-7, amino acid sequence SEQ ID NO:245 represents VH, 005-C04-L2-1-28-7, amino acid sequence SEQ ID NO:246 represents VH, 005-C04-L2-1-3-2, amino acid sequence SEQ ID NO:247 represents VH, 005-C04-L2-1-31-4, amino acid sequence SEQ ID NO:248 represents VH, 005-C04-L2-1-31-7, amino acid sequence SEQ ID NO:249 represents VH, 005-C04-L2-1-32-4, amino acid sequence SEQ ID NO:250 represents VH, 005-C04-L2-1-33-7, amino acid sequence
SEQ ID NO:251 represents VH, 005-C04-L2-1-36-6, amino acid sequence
SEQ ID NO:252 represents VH, 005-C04-L2-1-38-3, amino acid sequence
SEQ ID NO:253 represents VH, 005-C04-L2-1-4-5, amino acid sequence
SEQ ID NO:254 represents VH, 005-C04-L2-1-40-2, amino acid sequence
SEQ ID NO:255 represents VH, 005-C04-L2-1-40-7, amino acid sequence
SEQ ID NO:256 represents VH, 005-C04-L2-1-42-0, amino acid sequence
SEQ ID NO:257 represents VH, 005-C04-L2-1-47-0, amino acid sequence
SEQ ID NO:258 represents VH, 005-C04-L2-1-48-3, amino acid sequence
SEQ ID NO:259 represents VL, 005-C04-10-3, amino acid sequence
SEQ ID NO:260 represents VL, 005-C04-11-5, amino acid sequence
SEQ ID NO:261 represents VL, 005-C04-18-10-2, amino acid sequence
SEQ ID NO:262 represents VL, 005-C04-18-10-4, amino acid sequence
SEQ ID NO:263 represents VL, 005-C04-19-2, amino acid sequence
SEQ ID NO:264 represents VL, 005-C04-2-2, amino acid sequence
SEQ ID NO:265 represents VL, 005-C04-2-7, amino acid sequence
SEQ ID NO:266 represents VL, 005-C04-20-12-7, amino acid sequence
SEQ ID NO:267 represents VL, 005-C04-20-2, amino acid sequence
SEQ ID NO:268 represents VL, 005-C04-21-1, amino acid sequence
SEQ ID NO:269 represents VL, 005-C04-21-2, amino acid sequence
SEQ ID NO:270 represents VL, 005-C04-25-6, amino acid sequence
SEQ ID NO:271 represents VL, 005-C04-29-0, amino acid sequence
SEQ ID NO:272 represents VL, 005-C04-29-17-0, amino acid sequence
SEQ ID NO:273 represents VL, 005-C04-29-17-2, amino acid sequence
SEQ ID NO:274 represents VL, 005-C04-29-17-3, amino acid sequence
SEQ ID NO:275 represents VL, 005-C04-29-17-7, amino acid sequence
SEQ ID NO:276 represents VL, 005-C04-35-3, amino acid sequence
SEQ ID NO:277 represents VL, 005-C04-36-0, amino acid sequence
SEQ ID NO:278 represents VL, 005-C04-37-2, amino acid sequence
SEQ ID NO:279 represents VL, 005-C04-37-7, amino acid sequence
SEQ ID NO:280 represents VL, 005-C04-4-3-7, amino acid sequence
SEQ ID NO:281 represents VL, 005-C04-40-4, amino acid sequence
SEQ ID NO:282 represents VL, 005-C04-41-2, amino acid sequence
SEQ ID NO:283 represents VL, 005-C04-42-1, amino acid sequence
SEQ ID NO:284 represents VL, 005-C04-44-25-1, amino acid sequence
SEQ ID NO:285 represents VL, 005-C04-45-1, amino acid sequence
SEQ ID NO:286 represents VL, 005-C04-46-0, amino acid sequence
SEQ ID NO:287 represents VL, 005-C04-46-1, amino acid sequence
SEQ ID NO:288 represents VL, 005-C04-47-3, amino acid sequence
SEQ ID NO:289 represents VL, 005-C04-48-1, amino acid sequence
SEQ ID NO:290 represents VL, 005-C04-5-5, amino acid sequence
SEQ ID NO:291 represents VL, 005-C04-50-28-3, amino acid sequence
SEQ ID NO:292 represents VL, 005-C04-50-28-7, amino acid sequence
SEQ ID NO:293 represents VL, 005-C04-51-29-0, amino acid sequence
SEQ ID NO:294 represents VL, 005-C04-52-29-0, amino acid sequence
SEQ ID NO:295 represents VL, 005-C04-52-29-7, amino acid sequence
SEQ ID NO:296 represents VL, 005-C04-53-31-7, amino acid sequence
SEQ ID NO:297 represents VL, 005-C04-55-32-0, amino acid sequence
SEQ ID NO:298 represents VL, 005-C04-58-33-1, amino acid sequence
SEQ ID NO:299 represents VL, 005-C04-8-2, amino acid sequence
SEQ ID NO:300 represents VL, 005-C04-8-6, amino acid sequence
SEQ ID NO:301 represents VL, 005-C04-9-2, amino acid sequence
SEQ ID NO:302 represents VL, 005-C04-L2-1-11-0, amino acid sequence
SEQ ID NO:303 represents VL, 005-C04-L2-1-11-3, amino acid sequence
SEQ ID NO:304 represents VL, 005-C04-L2-1-12-2, amino acid sequence
SEQ ID NO:305 represents VL, 005-C04-L2-1-12-4, amino acid sequence
SEQ ID NO:306 represents VL, 005-C04-L2-1-16-4, amino acid sequence
SEQ ID NO:307 represents VL, 005-C04-L2-1-16-5, amino acid sequence
SEQ ID NO:308 represents VL, 005-C04-L2-1-2-3, amino acid sequence
SEQ ID NO:309 represents VL, 005-C04-L2-1-20-0, amino acid sequence
SEQ ID NO:310 represents VL, 005-C04-L2-1-20-1, amino acid sequence
SEQ ID NO:311 represents VL, 005-C04-L2-1-21-7, amino acid sequence
SEQ ID NO:312 represents VL, 005-C04-L2-1-23-7, amino acid sequence
SEQ ID NO:313 represents VL, 005-C04-L2-1-25-0, amino acid sequence
SEQ ID NO:314 represents VL, 005-C04-L2-1-25-4, amino acid sequence
SEQ ID NO:315 represents VL, 005-C04-L2-1-25-5, amino acid sequence SEQ ID NO:316 represents VL, 005-C04-L2-1-25-7, amino acid sequence
SEQ ID NO:317 represents VL, 005-C04-L2-1-28-7, amino acid sequence
SEQ ID NO:318 represents VL, 005-C04-L2-1-3-2, amino acid sequence
SEQ ID NO:319 represents VL, 005-C04-L2-1-31-4, amino acid sequence
SEQ ID NO:320 represents VL, 005-C04-L2-1-31-7, amino acid sequence
SEQ ID NO:321 represents VL, 005-C04-L2-1-32-4, amino acid sequence
SEQ ID NO:322 represents VL, 005-C04-L2-1-33-7, amino acid sequence
SEQ ID NO:323 represents VL, 005-C04-L2-1-36-6, amino acid sequence
SEQ ID NO:324 represents VL, 005-C04-L2-1-38-3, amino acid sequence
SEQ ID NO:325 represents VL, 005-C04-L2-1-4-5, amino acid sequence
SEQ ID NO:326 represents VL, 005-C04-L2-1-40-2, amino acid sequence
SEQ ID NO:327 represents VL, 005-C04-L2-1-40-7, amino acid sequence
SEQ ID NO:328 represents VL, 005-C04-L2-1-42-0, amino acid sequence
SEQ ID NO:329 represents VL, 005-C04-L2-1-47-0, amino acid sequence
SEQ ID NO:330 represents VL, 005-C04-L2-1-48-3, amino acid sequence
SEQ ID NO:375 represents VH, 005-C04-10-3, nucleic acid sequence
SEQ ID NO:376 represents VH, 005-C04-11-5, nucleic acid sequence
SEQ ID NO:377 represents VH, 005-C04-18-10-2, nucleic acid sequence
SEQ ID NO:378 represents VH, 005-C04-18-10-4, nucleic acid sequence
SEQ ID NO:379 represents VH, 005-C04-19-2, nucleic acid sequence
SEQ ID NO:380 represents VH, 005-C04-2-2, nucleic acid sequence
SEQ ID NO:381 represents VH, 005-C04-2-7, nucleic acid sequence
SEQ ID NO:382 represents VH, 005-C04-20-12-7, nucleic acid sequence
SEQ ID NO:383 represents VH, 005-C04-20-2, nucleic acid sequence
SEQ ID NO:384 represents VH, 005-C04-21-1, nucleic acid sequence
SEQ ID NO:385 represents VH, 005-C04-21-2, nucleic acid sequence
SEQ ID NO:386 represents VH, 005-C04-25-6, nucleic acid sequence
SEQ ID NO:387 represents VH, 005-C04-29-0, nucleic acid sequence
SEQ ID NO:388 represents VH, 005-C04-29-17-0, nucleic acid sequence
SEQ ID NO:389 represents VH, 005-C04-29-17-2, nucleic acid sequence
SEQ ID NO:390 represents VH, 005-C04-29-17-3, nucleic acid sequence
SEQ ID NO:391 represents VH, 005-C04-29-17-7, nucleic acid sequence
SEQ ID NO:392 represents VH, 005-C04-35-3, nucleic acid sequence
SEQ ID NO:393 represents VH, 005-C04-36-0, nucleic acid sequence
SEQ ID NO:394 represents VH, 005-C04-37-2, nucleic acid sequence
SEQ ID NO:395 represents VH, 005-C04-37-7, nucleic acid sequence
SEQ ID NO:396 represents VH, 005-C04-4-3-7, nucleic acid sequence
SEQ ID NO:397 represents VH, 005-C04-40-4, nucleic acid sequence
SEQ ID NO:398 represents VH, 005-C04-41-2, nucleic acid sequence
SEQ ID NO:399 represents VH, 005-C04-42-1, nucleic acid sequence
SEQ ID NO:400 represents VH, 005-C04-44-25-1, nucleic acid sequence
SEQ ID NO:401 represents VH, 005-C04-45-1, nucleic acid sequence
SEQ ID NO:402 represents VH, 005-C04-46-0, nucleic acid sequence
SEQ ID NO:403 represents VH, 005-C04-46-1, nucleic acid sequence
SEQ ID NO:404 represents VH, 005-C04-47-3, nucleic acid sequence
SEQ ID NO:405 represents VH, 005-C04-48-1, nucleic acid sequence
SEQ ID NO:406 represents VH, 005-C04-5-5, nucleic acid sequence
SEQ ID NO:407 represents VH, 005-C04-50-28-3, nucleic acid sequence
SEQ ID NO:408 represents VH, 005-C04-50-28-7, nucleic acid sequence
SEQ ID NO:409 represents VH, 005-C04-51-29-0, nucleic acid sequence
SEQ ID NO:410 represents VH, 005-C04-52-29-0, nucleic acid sequence
SEQ ID NO:411 represents VH, 005-C04-52-29-7, nucleic acid sequence
SEQ ID NO:412 represents VH, 005-C04-53-31-7, nucleic acid sequence
SEQ ID NO:413 represents VH, 005-C04-55-32-0, nucleic acid sequence
SEQ ID NO:414 represents VH, 005-C04-58-33-1, nucleic acid sequence
SEQ ID NO:415 represents VH, 005-C04-8-2, nucleic acid sequence
SEQ ID NO:416 represents VH, 005-C04-8-6, nucleic acid sequence
SEQ ID NO:417 represents VH, 005-C04-9-2, nucleic acid sequence
SEQ ID NO:418 represents VH, 005-C04-L2-1-11-0, nucleic acid sequence
SEQ ID NO:419 represents VH, 005-C04-L2-1-11-3, nucleic acid sequence
SEQ ID NO:420 represents VH, 005-C04-L2-1-12-2, nucleic acid sequence
SEQ ID NO:421 represents VH, 005-C04-L2-1-12-4, nucleic acid sequence
SEQ ID NO:422 represents VH, 005-C04-L2-1-16-4, nucleic acid sequence
SEQ ID NO:423 represents VH, 005-C04-L2-1-16-5, nucleic acid sequence
SEQ ID NO:424 represents VH, 005-C04-L2-1-2-3, nucleic acid sequence
SEQ ID NO:425 represents VH, 005-C04-L2-1-20-0, nucleic acid sequence SEQ ID NO:426 represents VH, 005-C04-L2-1-20-1, nucleic acid sequence
SEQ ID NO:427 represents VH, 005-C04-L2-1-21-7, nucleic acid sequence
SEQ ID NO:428 represents VH, 005-C04-L2-1-23-7, nucleic acid sequence
SEQ ID NO:429 represents VH, 005-C04-L2-1-25-0, nucleic acid sequence
SEQ ID NO:430 represents VH, 005-C04-L2-1-25-4, nucleic acid sequence
SEQ ID NO:431 represents VH, 005-C04-L2-1-25-5, nucleic acid sequence
SEQ ID NO:432 represents VH, 005-C04-L2-1-25-7, nucleic acid sequence
SEQ ID NO:433 represents VH, 005-C04-L2-1-28-7, nucleic acid sequence
SEQ ID NO:434 represents VH, 005-C04-L2-1-3-2, nucleic acid sequence
SEQ ID NO:435 represents VH, 005-C04-L2-1-31-4, nucleic acid sequence
SEQ ID NO:436 represents VH, 005-C04-L2-1-31-7, nucleic acid sequence
SEQ ID NO:437 represents VH, 005-C04-L2-1-32-4, nucleic acid sequence
SEQ ID NO:438 represents VH, 005-C04-L2-1-33-7, nucleic acid sequence
SEQ ID NO:439 represents VH, 005-C04-L2-1-36-6, nucleic acid sequence
SEQ ID NO:440 represents VH, 005-C04-L2-1-38-3, nucleic acid sequence
SEQ ID NO:441 represents VH, 005-C04-L2-1-4-5, nucleic acid sequence
SEQ ID NO:442 represents VH, 005-C04-L2-1-40-2, nucleic acid sequence
SEQ ID NO:443 represents VH, 005-C04-L2-1-40-7, nucleic acid sequence
SEQ ID NO:444 represents VH, 005-C04-L2-1-42-0, nucleic acid sequence
SEQ ID NO:445 represents VH, 005-C04-L2-1-47-0, nucleic acid sequence
SEQ ID NO:446 represents VH, 005-C04-L2-1-48-3, nucleic acid sequence
SEQ ID NO:447 represents VL, 005-C04-10-3, nucleic acid sequence
SEQ ID NO:448 represents VL, 005-C04-11-5, nucleic acid sequence
SEQ ID NO:449 represents VL, 005-C04-18-10-2, nucleic acid sequence
SEQ ID NO:450 represents VL, 005-C04-18-10-4, nucleic acid sequence
SEQ ID NO:451 represents VL, 005-C04-19-2, nucleic acid sequence
SEQ ID NO:452 represents VL, 005-C04-2-2, nucleic acid sequence
SEQ ID NO:453 represents VL, 005-C04-2-7, nucleic acid sequence
SEQ ID NO:454 represents VL, 005-C04-20-12-7, nucleic acid sequence
SEQ ID NO:455 represents VL, 005-C04-20-2, nucleic acid sequence
SEQ ID NO:456 represents VL, 005-C04-21-1, nucleic acid sequence
SEQ ID NO:457 represents VL, 005-C04-21-2, nucleic acid sequence
SEQ ID NO:458 represents VL, 005-C04-25-6, nucleic acid sequence
SEQ ID NO:459 represents VL, 005-C04-29-0, nucleic acid sequence
SEQ ID NO:460 represents VL, 005-C04-29-17-0, nucleic acid sequence
SEQ ID NO:461 represents VL, 005-C04-29-17-2, nucleic acid sequence
SEQ ID NO:462 represents VL, 005-C04-29-17-3, nucleic acid sequence
SEQ ID NO:463 represents VL, 005-C04-29-17-7, nucleic acid sequence
SEQ ID NO:464 represents VL, 005-C04-35-3, nucleic acid sequence
SEQ ID NO:465 represents VL, 005-C04-36-0, nucleic acid sequence
SEQ ID NO:466 represents VL, 005-C04-37-2, nucleic acid sequence
SEQ ID NO:467 represents VL, 005-C04-37-7, nucleic acid sequence
SEQ ID NO:468 represents VL, 005-C04-4-3-7, nucleic acid sequence
SEQ ID NO:469 represents VL, 005-C04-40-4, nucleic acid sequence
SEQ ID NO:470 represents VL, 005-C04-41-2, nucleic acid sequence
SEQ ID NO:471 represents VL, 005-C04-42-1, nucleic acid sequence
SEQ ID NO:472 represents VL, 005-C04-44-25-1, nucleic acid sequence
SEQ ID NO:473 represents VL, 005-C04-45-1, nucleic acid sequence
SEQ ID NO:474 represents VL, 005-C04-46-0, nucleic acid sequence
SEQ ID NO:475 represents VL, 005-C04-46-1, nucleic acid sequence
SEQ ID NO:476 represents VL, 005-C04-47-3, nucleic acid sequence
SEQ ID NO:477 represents VL, 005-C04-48-1, nucleic acid sequence
SEQ ID NO:478 represents VL, 005-C04-5-5, nucleic acid sequence
SEQ ID NO:479 represents VL, 005-C04-50-28-3, nucleic acid sequence
SEQ ID NO:480 represents VL, 005-C04-50-28-7, nucleic acid sequence
SEQ ID NO:481 represents VL, 005-C04-51-29-0, nucleic acid sequence
SEQ ID NO:482 represents VL, 005-C04-52-29-0, nucleic acid sequence
SEQ ID NO:483 represents VL, 005-C04-52-29-7, nucleic acid sequence
SEQ ID NO:484 represents VL, 005-C04-53-31-7, nucleic acid sequence
SEQ ID NO:485 represents VL, 005-C04-55-32-0, nucleic acid sequence
SEQ ID NO:486 represents VL, 005-C04-58-33-1, nucleic acid sequence
SEQ ID NO:487 represents VL, 005-C04-8-2, nucleic acid sequence
SEQ ID NO:488 represents VL, 005-C04-8-6, nucleic acid sequence
SEQ ID NO:489 represents VL, 005-C04-9-2, nucleic acid sequence
SEQ ID NO:490 represents VL, 005-C04-L2-1-11-0, nucleic acid sequence
SEQ ID NO:491 represents VL, 005-C04-L2-1-11-3, nucleic acid sequence SEQ ID NO:492 represents VL, 005-C04-L2-1-12-2, nucleic acid sequence
SEQ ID NO:493 represents VL, 005-C04-L2-1-12-4, nucleic acid sequence
SEQ ID NO:494 represents VL, 005-C04-L2-1-16-4, nucleic acid sequence
SEQ ID NO:495 represents VL, 005-C04-L2-1-16-5, nucleic acid sequence
SEQ ID NO:496 represents VL, 005-C04-L2-1-2-3, nucleic acid sequence
SEQ ID NO:497 represents VL, 005-C04-L2-1-20-0, nucleic acid sequence
SEQ ID NO:498 represents VL, 005-C04-L2-1-20-1, nucleic acid sequence
SEQ ID NO:499 represents VL, 005-C04-L2-1-21-7, nucleic acid sequence
SEQ ID NO:500 represents VL, 005-C04-L2-1-23-7, nucleic acid sequence
SEQ ID NO:501 represents VL, 005-C04-L2-1-25-0, nucleic acid sequence
SEQ ID NO:502 represents VL, 005-C04-L2-1-25-4, nucleic acid sequence
SEQ ID NO:503 represents VL, 005-C04-L2-1-25-5, nucleic acid sequence
SEQ ID NO:504 represents VL, 005-C04-L2-1-25-7, nucleic acid sequence
SEQ ID NO:505 represents VL, 005-C04-L2-1-28-7, nucleic acid sequence
SEQ ID NO:506 represents VL, 005-C04-L2-1-3-2, nucleic acid sequence
SEQ ID NO:507 represents VL, 005-C04-L2-1-31-4, nucleic acid sequence
SEQ ID NO:508 represents VL, 005-C04-L2-1-31-7, nucleic acid sequence
SEQ ID NO:509 represents VL, 005-C04-L2-1-32-4, nucleic acid sequence
SEQ ID NO:510 represents VL, 005-C04-L2-1-33-7, nucleic acid sequence
SEQ ID NO:511 represents VL, 005-C04-L2-1-36-6, nucleic acid sequence
SEQ ID NO:512 represents VL, 005-C04-L2-1-38-3, nucleic acid sequence
SEQ ID NO:513 represents VL, 005-C04-L2-1-4-5, nucleic acid sequence
SEQ ID NO:514 represents VL, 005-C04-L2-1-40-2, nucleic acid sequence
SEQ ID NO:515 represents VL, 005-C04-L2-1-40-7, nucleic acid sequence
SEQ ID NO:516 represents VL, 005-C04-L2-1-42-0, nucleic acid sequence
SEQ ID NO:517 represents VL, 005-C04-L2-1-47-0, nucleic acid sequence
SEQ ID NO:518 represents VL, 005-C04-L2-1-48-3, nucleic acid sequence

EXAMPLES

Example 1

Isolation of Target-Specific Antibodies from Human Antibody Phage Display Libraries To isolate a panel of antibodies able to neutralize the activity of human PRLR, three human antibody phage display libraries, expressing Fab and scFv fragments, were investigated in parallel. The target used for the library panning was the soluble extracellular domain (ECD) of the prolactin receptor represents human prolactin receptor amino acids 25-234, prepared as described above in WO08/022,295 represents (Novartis). Alternative targets were the ECD of PRLR C-terminally linked to six histidines or to a human IgG1-Fc domain via the linker with the amino acid sequence "isoleucine-glutamate-glycine-arginine-methionine-aspartate".

Selection of target-specific antibodies from phage display was carried out according to methods described by Marks et al. (Methods Mol. Biol. 248:161-76, 2004). Briefly, the phage display library was incubated with 50 pmols of the biotinylated ECD at room temperature for 1 hr and the complex formed was then captured using 100 µl of Streptavidin beads suspension (Dynabeads® M-280 Streptavidin, Invitrogen). Non specific phages were removed by washing the beads with wash buffer (PBS+5% Milk). Bound phages were eluted with 0.5 ml of 100 nM Triethylamine (TEA) and immediately neutralized by addition of an equal volume of IM TRIS-CI pH 7.4. Eluted phage pool was used to infect TG1 *E coli* cells growing in logarithmic phase, and phagemid was rescued as described (Methods Mol Biol. 248:161-76, 2004). Selection was repeated for a total of three rounds. Single colonies obtained from TG1 cells infected with eluted phage from the third round of panning were screened for binding activity in an ELISA assay. Briefly, single colonies obtained from the TG1 cell infected with eluted phage were used to inoculate media in 96-well plates.

Microcultures were grown to an $OD_{600}$=O.6 at which point expression of soluble antibody fragment was induced by addition of 1 mM IPTG following overnight culture in a shaker incubator at 30° C. Bacteria were spun down and periplasmic extract was prepared and used to detect antibody binding activity to ECD immobilized on 96-well microplates (96-well flat bottom Immunosorb plates, Nunc) following standard ELISA protocol provided by the microplate manufacturer.

The affinities of the anti-Prolactin Receptor (PRLR) antibodies for binding to the recombinant extracellular domain (ECD) were estimated using the Biacore® 2000 and used for affinity ranking of antibodies.

Example 2

Quantitative Analysis of Prolactin and Prolactin Receptor Gene Expression by Real-Time Taqman PCR Analysis in Eu- and Ectopic Endometrium and Endometriotic Lesions from Patients and Healthy Controls Real-timeTaqman PCR analysis was performed using the ABI Prism 7700 Sequence Detector System according to the manufacturer's instructions (PE Applied Biosystems) and as described Endocrinolgy 2008, 149 (8): 3952-3959) and known by the expert in the field. Relative expression levels of PRL and the PRLR were normalized to the expression of cyclophyllin. We analyzed the expression of PRL and the PRLR in the endometrium from healthy women and in endometrium and endometriotic lesions from patients by using quantitative real-time Taqman PCR analysis. The expression of prolactin and its receptor was clearly upregulated in endometriotic lesions compared to healthy endometrium or endometrium derived from patients.

Results are shown in FIGS. 1 and 2.

These findings imply that autocrine prolactin signaling plays a role in the development and maintenance of endometriosis and adenomyosis uteri (endometriosis interna, a form of endometriosis restricted to the uterus.

Example 3

Analysis of Prolactin Receptor Expression in Human Tissues by Northern Blot

RNA was isolated from different rat tissues and transferred to a nylon membrane after gel electrophoresis. The membranes were successively hybridized with radioactive labelled cDNAs for the rat prolactin receptor or β-actin (as loading control), washed, and exposed to film. The bands correspond to the mRNAs for the rat prolactin receptor and –β-actin. The results shown in FIG. 3 indicate a strong expression of the prolactin receptor in the placenta, the prostate, the ovary and the adrenal gland.

Example 4

Regulation of Prolactin Receptor Protein Expression in Rat Prostate—Influence of Castration and Hormonal Treatments Rats were either castrated or remained intact. Intact animals were treated daily for 14 days with vehicle (intact), DHT (3 mg/kg), or E2 (0.4 mg/kg). Afterwards prostates were isolated from animals of all treatment groups and protein extracts were prepared. Protein extracts were separated by gel electrophoresis and transferred to a membrane. The prolactin receptor was detected using the commercially available antibody MA610 (Santa Cruz Biotechnology). The results are shown in FIG. 4 and indicate the hormonal regulation of the prolactin receptor in the rat prostate.

Example 5

Inhibition of Prolactin-Induced Proliferation of BaF3 Cells (Stably Transfected with Human Prolactin Receptor) by Neutralizing Prolactin Receptor Antibodies and Unspecific Control Antibodies To analyze the in vitro efficacy of the neutralizing PRLR antibodies, the inhibition of prolactin-activated cellular proliferation of BaF3 cells was used. The cells were stably transfected with human PRLR and were routinely cultured in RPMI containing 2 mM glutamine in the presence of 10% FCS and 10 ng/ml of human prolactin. After six hours of starvation in prolactin-free medium containing 1% FCS, cells were seeded into 96-well plates at a density of 10000 cells per well. Cells were stimulated with 20 ng/ml prolactin and coincubated with increasing doses of neutralizing PRLR antibodies for two days. Cellular proliferation was analyzed using a CellTiter-Glo Luminescent Cell Viability Assay (Promega). Dose-response curves for the inhibition of prolactin-stimulated cellular growth were generated and $IC_{50}$ values calculated. As negative control, stimulation with an unspecific control antibody was used.

The dose-response curves and $IC_{50}$ values are depicted in FIG. 5. The unspecific antibody did not inhibit the proliferation of BaF cells stably expressing the human PRLR, whereas the specific antibodies blocked cell proliferation and exhibited different potencies. Neutralizing antibody 006-H08 showed the highest potency in this readout paradigm.

Example 6

Inhibition of Prolactin-Induced Rat Lymphoma Cell Proliferation by Specific and Unspecific Antibodies The in vitro efficacy of the neutralizing PRLR antibodies was also tested using inhibition of prolactin-dependent rat lymphoma cell (Nb2-11 cells) proliferation. Nb2-11 cells were routinely grown in RPMI containing 10% FCS and 10% horse serum. Before starting cellular growth assays, cells were grown for 24 hours in the same medium containing 1% FCS instead of 10% FCS. Afterwards, cells were seeded in 96-well plates in FCS-free medium at a density of 10000 cells per well. Cells were stimulated with 10 ng/ml human prolactin in the presence or absence of increasing doses of neutralizing PRLR antibodies or control antibodies for 2 days. Afterwards cellular proliferation was assessed using a CellTiter-Glo Luminescent Cell Viability Assay (Promega). Dose-response curves and $IC_{50}$ values are depicted in FIG. 6. The unspecific antibody and antibody XHA06.983, that does not bind the rat PRLR, did not block Nb2-11 cell proliferation. XHA06.642 which binds the rat PRLR blocked Nb2-11 cell proliferation.

Example 7

Inhibition of Prolactin-Induced STAT5 Phosphorylation in T47D Cells by Neutralizing Prolactin Receptor Antibodies To analyze the in vitro efficacy of the neutralizing PRLR antibodies in an additional readout, the inhibition of STAT5 phosphorylation in human T47D cells treated with prolactin was used. T47D cells were grown in RPMI containing 10% FCS and 2 mM glutamine. Cells were seeded on 24-well plates at a density of $0.5 \times 10^5$ cells per well. The next day, cells were starved for 1 h in serum free RPMI. Afterwards cells were incubated with or without different doses of neutralizing PRLR antibodies or unspecific control antibody in the absence or presence of 20 ng/ml human prolactin for 30 min. Afterwards cells were rinsed and lysed in 70 µl of lysisbuffer. Lysates were centrifuged and the supernatant was frozen at −80° C. Extracts were analyzed using Western blot (anti-pSTAT5A/B antibody from upstate 07-586, 1:1000 diluted). As loading control the stripped blots were incubated with anti-beta tubulin antibody (ab7287, 1:500 diluted). Results are shown in FIG. 7. With the exception of the unspecific FITC antibody, all neutralizing PRLR antibodies blocked STAT5 phosphorylation in human T47D cells dose-dependently. All tested antibodies bound to the human PRLR with high affinity.

Example 8

Inhibition of Luciferase Reporter Gene Activity in Hek293 Cells Stably Transfected with the Human PRLR—Analysis of Neutralizing Prolactin Receptor Antibodies and Unspecific Control Antibodies To further analyze the in vitro efficacy of the neutralizing PRLR antibodies, a reporter gene assay was used. HEK293HEK293 cells stably transfected with the human PRLR were transiently transfected with a luciferase reporter gene under the control of LHREs (lactogenic hormone response elements) for 7 hours. Afterwards, cells were seeded at a density of 20000 cells per well on a 96-well plate (0.5% charcoal stripped serum, DMEM). The next day 300 ng/ml human prolactin with and without increasing doses of neutralizing PRLR antibodies or control antibodies was added. 24 hours later, luciferase activity was determined. Results are depicted in FIG. 8. In contrast to the unspecific antibody, 006-H08 and HE06.642 inhibited luciferase activity in HEK293 cells stably transfected with the human PRLR.

Example 9

Inhibition of Luciferase Reporter Gene Activity in Hek293 Cells Stably Transfected with the Murine PRLR—Analysis of Neutralizing Prolactin Receptor Antibodies and Unspecific Control Antibodies To further analyze the in vitro efficacy of the neutralizing PRLR antibodies on the murine prolactin receptor, a reporter gene assay was used. HEK293 cells stably transfected with the murine PRLR were transiently transfected with a luciferase reporter gene under the control of LHREs (lactogenic hormone response elements) for 7 hours. Afterwards, cells were seeded at a density of 20000 cells per well on a 96-well plate (0.5% charcoal stripped serum, DMEM). The next day 200 ng/ml human prolactin with and without increasing doses of neutralizing PRLR antibodies or control antibodies was added. 24 hours later, luciferase activity was determined. Results are depicted in FIG. 9. Whereas the antibody 005-C04 (closed triangles) exhibits high activity (IC$_{50}$ value=3 nM), the antibody HE06.642 (closed circles) does not show activity up to 330 nM. The unspecific control antibody (open circles) is completely inactive. In contrast to the Novartis antibody HE06.642, the antibody 005-C04 is able to block murine PRLR-mediated signaling.

Example 10

Inhibition of Prolactin-Induced Proliferation of BaF3 Cells (Stably Transfected with the Murine Prolactin Receptor) by Neutralizing Prolactin Receptor Antibodies and Unspecific Control Antibodies To analyze the in vitro efficacy of the neutralizing PRLR antibodies, the inhibition of prolactin-activated cellular proliferation of Ba/F3 cells was used. The cells were stably transfected with the murine PRLR and were routinely cultured in RPMI containing 2 mM glutamine in the presence of 10% FCS and 10 ng/ml of human prolactin. After six hours of starvation in prolactin-free medium containing 1% FCS, cells were seeded into 96-well plates at a density of 10000 cells per well. Cells were stimulated with 40 ng/ml prolactin and coincubated with increasing doses of neutralizing PRLR antibodies for two days. Cellular proliferation was analyzed using a CellTiter-Glo Luminescent Cell Viability Assay (Promega). Dose-response curves for the inhibition of prolactin-stimulated cellular growth were generated and IC$_{50}$ values calculated. As negative control, stimulation with an unspecific control antibody was used.

The dose-response curves and IC$_{50}$ values are depicted in FIG. 10. The unspecific control antibody (closed squares) was inactive at the murine PRLR. There was only limited inhibition of murine PRLR activation by the antibodies HE06.642, 001-E06, and 001-D07. Only antibody 005-C04 completely blocked murine PRLR activation.

Example 11

Contraceptive Effect of Neutralizing Prolactin Receptor Antibody IgG1 005-C04 in Mice To test the influence of neutralizing prolactin receptor antibodies on fertility in mice, 12 week old female and male NMRI mice were mated for 7 days (day 0-day 7). Female mice were treated on days −3, 0, 3, and 6 with an intraperitoneal injection of either phosphate-buffered saline, unspecific IgG1 control antibody (anti-FITC, 10 mg/kg), or the neutralizing IgG1 antibody 005-C04 (=IgG1 005-C04) at concentrations of 10 or 30 mg per kg body weight dissolved in phosphate buffered saline. 10 females were used in each experimental group. Each male was mated with two females, one of the females was from a negative control group treated with either phosphate-buffered saline or unspecific antibody, the other female was treated with specific neutralizing antibody. Matings, in which the male did not produce at least one pregnant female, were excluded from data evaluation. Readout parameters were mean litter size and pregnancy rates (measured in %) calculated as litter number per experimental group divided by the number of theoretical possible litters within this group. Results are depicted in FIG. 11.

FIG. 11A shows the obtained pregnancy rates. Pregnancy rates were as follows:
  87.5% in the group of mice treated with phosphate buffered saline,
  75% in the group of mice treated with the unspecific control antibody (10 mg/kg),
  100% in the group of mice treated with the neutralizing PRLR antibody IgG1 005-C04 (10 mg/kg), and
  0% in the group of mice treated with the neutralizing PRLR antibody IgG1 005-C04 (30 mg/kg).

FIG. 11B shows the observed litter sizes for the different experimental groups. Litter sizes were as follows:
  10.9 mice per litter in the group of mice treated with phosphate buffered saline,
  12.3 mice per litter in the group of mice treated with the unspecific control antibody (10 mg/kg),
  13 mice per litter in the group of mice treated with the neutralizing PRLR antibody IgG1 005-C04 (10 mg/kg), and
  0 mice per litter in the group of mice treated with the neutralizing PRLR antibody IgG1 005-C04 (30 mg/kg).

The results from this mating study demonstrate that the neutralizing prolactin receptor antibody IgG1-005-C04 completely prevented pregnancy in mice when tested at 30 mg/kg body weight.

Example 12

Epitope Grouping

Epitope grouping experiments were performed using Biacore by monitoring simultaneous binding of pairs of anti-PRLR antibodies to ECD-PRLR (SEQ ID NO: 70). Briefly, the first antibody was covalently immobilized to the sensor chip through primary amine coupling using n-hydroxysuccinamide (NHC) and N-ethyl-N'-dimethylaminopropyl carbodiimide (EDC). Unoccupied binding sites on the surface were then blocked with ethanolamide. Soluble ECD-PRLR (SEQ ID NO: 70) was captured on the surface via the immobilized antibody, therefore, the epitope of the capture antibody is blocked for all bound ECD-PRLR molecules. A second antibody was immediately passed over the surface to bind to the immobilized ECD-PRLR. Two antibodies recognizing the same or overlapping epitopes cannot bind to the ECD-PRLR, whereas antibodies with distinct epitopes are able to bind. The antibody surface was regenerated with glycine, pH 2.8, to remove bound proteins and then the process was repeated with other antibodies. All combinations of antibodies were tested. Representative results are shown in Table 7. The antibodies 006-H08, 002-H06, 002-H08, 006-H07 and XHA06983 competitively bound to each other on ECD-PRLR, indicating that they target overlapping epitopes (epitope group 1, table 6). In addition, the antibodies competitively bound to PRL, which is also the case for 001-E06 (epitope group 2, table 6). This antibody targets a different site of ECD-PRLR than the aforementioned ones. Finally, the antibody 005-C04 competitively bound to HE06.642 and XHA06.642 without being competitive to PRL (epitope group 3, table 6).

TABLE 7

Groups of antibodies which target overlapping epitopes on the extracellular domain (ECD) of the human prolactin receptor (PRLR)

| Antibody | Epitope group | Competition to prolactin |
| --- | --- | --- |
| 006-H08 | 1 | Yes |
| 002-H06 | 1 | Yes |
| 002-H08 | 1 | Yes |
| 006-H07 | 1 | Yes |
| 001-E06 | 2 | Yes |
| 005-C04 | 3 | No |
| HE06.642 | 3 | No |
| XHA06.642 | 3 | No |
| XHA06.983 | 1 | Yes |

Example 13

Cross-Reactivity of Antibodies on Mouse and Human PRLR Expressed on Cell Surfaces In order to determine the binding characteristics of the anti-PRLR antibodies on mouse and human PRLR expressed on cells, binding was tested by flow cytometry on HEK293 cells stably expressing the human and murine PRLR, respectively. The cells as well as the parental HEK293 cell line without PRLR were harvested, centrifuged and resuspended at approximately $5 \times 10^6$ cells/ml in 1×PBS containing 2% FBS and 0.1% sodium azide (FACS buffer). The antibodies 005-C04, 001-E06 and HE06.642 were diluted to 2-fold final concentration in FACS buffer and added to appropriate sample wells (50 µl/well). For secondary antibody and autofluorescence controls, 50 µl FACS buffer was added to appropriate wells. 50 µl of cell suspension was added to each sample well. Samples were incubated at 4° C. for one hour, washed twice with cold FACS buffer and resuspended in FACS buffer containing PE-conjugated goat anti-human IgG at a 1:100 dilution. Following a 30 min incubation at 4° C., cells were washed twice with cold FACS buffer, resuspended in FACS buffer containing 1 mg/ml propidium iodide (Invitrogen, San Diego, Calif.) and analyzed by flow cytometry. As shown in FIG. 13, the antibodies 005-C04 and 001-E06 bound to human and murine PRLR on these cells, while HE06.642 only bound to the human PRLR. This observation is consistent with the finding reported in example 9 about the missing efficacy of HE06.642 in the murine PRLR-dependent luciferase reporter gene assay. Although 005-C04 and HE06.642 competitively bound to human PRLR, the different binding properties of both antibodies with respect to the murine PRLR indicate differences in their epitope specificity.

Example 14

Inhibitory Activity of Fab and scFv Antibodies on Cellular Signaling Cascades

To functionally characterize the activity of the Fab and scFv screening hits on the PRLR-triggered signaling cascade, the inhibition of phosphorylation on PRLR itself, and on the transcriptional regulators ERK1/2 and STAT5 in human T47D cells treated with prolactin was measured. T47D cells were grown in RPMI containing 2 mM L-glutamine, 10% charcoal stripped FBS and insulin-transferrin-selenium-A (Gibco). Cells were seeded on 6 well plates or 96-well plates at a density of $1.5 \times 10^6$ cells per well. The next day, growth medium was renewed. On the third day cells were starved for 1 hour in serumfree RPMI. Afterwards cells were incubated with or without different doses of neutralizing PRLR antibodies or unspecific control antibody in the presence of 500 ng/ml human prolactin for 5 min. Afterwards cells were rinsed and lysed in lysis buffer. Lysates were centrifuged and the supernatants were frozen at −80° C. Samples were tested by ELISA according to the DuoSet IC "Human Phospho-Prolactin R" kit (R&D Systems) for measurement of PRLR phosphorylation, according to the PathScan Phospho-STAT5 (Tyr694) Sandwich ELISA kit (Cell Signaling Technology; #7113) for measurement of STAT5 phosphorylation and according to the Phospho-ERK1/ERK2 kit (R&D Systems) for measurement of ERK1/2 phosphorylation. Table 8 provides an overview about the antagonistic activity of a selection of screening hits in Fab or scFv format at a fixed dose of 7.5 µg per ml.

TABLE 8

Antagonistic activity of a selection of screening hits on the phosphorylation of PRLR, ERK½ and STAT5 as determined by ELISAs on cell lysates of the human breast cancer cell line T47D

| | Inhibition of phosphorylation in % at a fixed antibody dose (7.5 µg/ml) | | |
| --- | --- | --- | --- |
| Antibody | PRLR | ERK½ | STAT5 |
| 006-H08* | 100 | 100 | 100 |
| 002-H06° | 92 | 86 | 72 |
| 002-H08° | 100 | 100 | 98 |
| 006-H07* | 88 | 85 | 73 |
| 001-E06° | 63 | 45 | 36 |
| Negative control | 2 | 9 | 0 |

*scFv format,
°Fab format

Example 15

Neutralizing PRLR antibodies inhibit lactation in mice Adult NMRI females were mated with NMRI males. On postpartal day 1, litter size was adjusted to 8 mice per lactating mother. The weight of the offspring was determined daily in the morning starting on postpartal day 1. Lactating mothers remained either untreated (closed circles in FIG. 14A,B) or were treated intraperitoneally with either unspecific antibody (10 mg/kg body weight; open circles in FIG. 14A,B), or with neutralizing PRLR antibody 005-C04 containing murine IgG2a constant domains (=IgG2a 005-C04; 10 mg/kg, closed triangles in FIG. 14A, B) or with neutralizing PRLR antibody IgG2a 005-C04 (30 mg/kg, open triangles in FIG. 14A, B). Group size was 5-6 lactating mothers per experimental group. Mothers were treated with specific or unspecific control antibodies on postpartal day 1, 3, 6, 9, 10, and 12 (indicated with arrows in FIG. 14A, B). The results are depicted in FIG. 14. FIG. 14A shows for each postpartal day the daily litter weight gain expressed as percentage of the respective litter weight on day 1. From postpartal day 8 onwards there is a significant difference in litter weight gain between offspring from mothers treated with neutralizing PRLR antibodies and offspring from mothers that remained untreated or received unspecific control antibodies. Due to ethical reasons several litters had to be killed on postpartal day 10 in the experimental group of mothers receiving the highest dose of the neutralizing PRLR antibody. In FIG. 14B the results are depicted in a different way. The differential litter weight gain from day to day is depicted and expressed as percentage of the litter weight on postpartal day 1. Basically FIG. 14B shows the slope of the graphs depicted in FIG. 14A. The differential daily increase in litter weight oscillates around 30% of the starting litter weight on postpartal day 1 for litters from untreated mothers or mothers treated with the unspecific antibody. There is a significant severe reduction in daily litter weight increase in litters from mothers treated with the neutralizing PRLR antibody at 30 mg/kg body weight from day 7 onwards (*$p<0.05$; ***$p<0.005$ vs. litters from mothers treated with unspecific antibody). From postpartal day 11 onwards, daily litter weight increase is significantly diminished also in litters from mothers treated with the neutralizing PRLR antibody at 10 mg/kg if compared to litters from mothers treated with unspecific control antibodies ($p<0.05$ vs. litters from mothers treated with unspecific antibody). In conclusion, there are dose-dependent effects of the neutralizing PRLR antibody IgG2a 005-C04 on lactation inhibition. FIG. 14C shows histological sections of the mammary glands from lactating mothers of the different experimental groups. Mammary glands of untreated mothers and mothers treated with unspecific control antibodies are filled with ducts producing milk. In contrast, there are signs of mammary gland involution in mothers treated with the neutralizing PRLR antibody IgG2a 005-C04. Black arrows in FIG. 14C point to fatty islands in the mammary gland tissue (see dose-dependent effect of the specific antibody IgG2a 005-C04 on the extent of mammary gland involution (FIG. 14C)). In addition, the expression of the major milk proteins beta-casein (Csn-2), whey acidic protein (WAP), and IGF-1 in the mammary glands of mothers from the different experimental groups were analyzed (FIG. 14D). Gene expression was normalized to the expression of TATA-box binding protein (TBP). The neutralizing PRLR antibody IgG2a 005-C04 dose-dependently decreased milk protein expression whereas the unspecific antibody (10 mg/kg) was without any significant effect.

The neutralizing PRLR antibody IgG2a 005-C04 dose-dependently blocked lactation and lead to mammary gland involution in lactating mice demonstrating its usefullness for lactation inhibition.

Example 16

Neutralizing PRLR Antibodies are Suitable for the Treatment of Benign Breast Disease An activating PRLR mutation or local or systemic hyperprolactinemia can provoke benign breast disease. Therefore, a hyperprolactinemic mouse model to induce enhanced proliferation in the mammary gland (hallmark of the most severe forms of benign breast disease) was employed. On day 0, 12 week old female Balb/c mice received a pituitary isograft under the kidney capsule or remained unoperated. Pituitary isografted mice remained untreated or were treated intraperitoneally with either unspecific antibody (10 mg/kg), neutralizing PRLR antibody 005-C04 in IgG1 format (=IgG1 005-C04; 10 mg/kg), or neutralizing PRLR antibody IgG1 005-C04 (30 mg/kg) on day 0, 3, 7, 11, and 15. Experimental group size was 8-10 animals. On day 17 after pituitary transplantation mice were sacrificed. Two hours before death, animals received an intraperitoneal injection of BrdU to monitor epithelial cell proliferation. The left inguinal mammary gland was fixed in Carnoy's solution and mammary gland whole mounts were prepared and stained with Carmine alaune (FIG. 15A). The right inguinal mammary gland was fixed in 4% phosphate-buffered formaline overnight. Mammary glands were subsequently embedded in paraffin and BrdU immunostainings were performed as described previously (Endocrinology 149 (8): 3952-3959; 2009). In addition, a pSTAT5 immunostaining was performed (anti pSTAT5 antibody from abcam, ab32364, diluted 1:60) to monitor the inhibition of PRLR-mediated signaling in response to treatment with neutralizing PRLR antibodies. FIG. 15A shows magnifications of mammary gland whole mounts from the different experimental groups. Mammary glands of adult mice that did not receive a pituitary show ducts and endbuds, whereas there is extreme side branching and formation of alveolar structures in mice receiving a pituitary isograft. Treatment with the unspecific antibody (10 mg/kg) did not inhibit side branching and formation of alveolar structures. In contrast, treatment with the neutralizing antibody IgG1 005-C04 at 10 mg/kg body weight leads to complete inhibition of side branching in 8 out of 10 animals receiving a pituitary isograft and treatment with IgG1 005-C04 at 30 mg/kg completely inhibits side branching in 9 out of 9 animals receiving a pituitary isograft. Histological analysis and BrdU immunostaining are depicted in FIG. 15B. Pituitary isografting leads to epithelial hyperplasia that is not inhibited by treatment with the unspecific antibody, whereas there is no epithelial hyperplasia in mice harbouring a pituitary isograft and treated with the neutralizing PRLR antibody at a dose of 10 or 30 mg/kg body weight. Some of the BrdU-positive cells, reflecting cells in the S-phase of the cell cycle which are going to divide, are indicated by white arrows in FIG. 15B. Mice treated with the neutralizing antibody IgG1 005-C04 (30 mg/kg body weight) showed almost complete inhibition of epithelial cell proliferation in mammary glands. Some of the cells positive for phospho-STAT5 are indicated by white arrows in FIG. 15C. Treatment with 30 mg/kg IgG1 005-C04 lead to complete inhibition of STAT5 phosphorylation, indicating complete blockade of PRLR-mediated signaling.

The results from FIGS. 15A, B, and C demonstrated that neutralizing PRLR antibodies are suitable for the treatment of mastopathia, a benign proliferative disease of the mammary gland. Neutralizing PRLR antibodies inhibit mammary epithelial cell proliferation and activation of phospho-STAT5.

Example 17

Treatment of Benign Prostate Hyperplasia with Neutralizing PRLR Antibodies

Benign prostate hyperplasia was established in male Balb/c mice by grafting of two pituitaries under the kidney capsule at the age of 8 weeks. A control group remained unoperated. Mice receiving pituitary isografts remained untreated or received intraperitoneal injections of either an unspecific antibody (10 mg/kg), or the neutralizing PRLR antibody 005-C04 containing murine IgG2a constant domains (=IgG2a 005-C04) at doses of 10 and 30 mg/kg body weight. Antibody injections were performed starting on the day of pituitary transplantation (=day 0), and on day 3, day 7, day 11, day 15, day 18, day 22, and day 25 after pituitary transplantation. Mice were sacrificed on day 28. The relative weight of the ventral prostate was determined. Results are depicted in FIG. 16. Pituitary isografting resulted in an increase in relative prostate weight. Treatment with 10 mg/kg and 30 mg/kg neutralizing PRLR antibody IgG2a 005-C04 reduced prostate weight whereas treatment with unspecific control antibody was without any effect. Neutralizing PRLR antibodies are therefore suitable for the treatment of benign prostate hyperplasia.

On day 18 after pituitary isografting it became evident that hair growth was diminished in animals receiving pituitary isografts. Neutralizing PRLR antibodies stimulated hair growth under hyperprolactinemic conditions. Representative photographs are shown in FIG. 17. Therefore neutralizing PRLR antibodies can be used for the treatment of hyperprolactinemic hair loss.

Example 18

Effect of Neutralizing PRLR Antibodies on Hair Growth

The dorsal hair of 8 weeks old male and female C57BL/6 mice was removed using electric shawers as described previously (British Journal of Dermatology 2008; 159:300-305). Hyperprolactinemia was induced in some groups by pituitary isografting under the kidney capsule, animals in the remaining groups were normoprolactinemic. Animals were treated with specific PRLR antibodies (IgG2a 005-C04) or unspecific control antibodies (30 mg/kg, intraperitoneally) once weekly (starting on day 0 which is the day of pituitary isografting). Subsequent antibody injections were performed on days 7 and 14. After three weeks, the regrown hair was visible as dark on the pinkish-white shaved skin, and the percentage of the shaved area that became dark was measured. Female mice were killed 15 days after shaving and male mice were sacrificed 18 days after shaving.

The following experimental groups were used (group size was 6 mice):
1. shaved females
2. shaved females with pituitary isograft
3. shaved females with pituitary isograft+30 mg/kg unspecific antibody IgG2a 005-C04 once weekly
4. shaved females with pituitary isograft+30 mg/kg specific antibody once weekly
5. shaved females+30 mg/kg unspecific antibody once weekly
6. shaved females+30 mg/kg specific antibody once weekly
7. shaved males
8. shaved males with pituitary isograft
9. shaved males with pituitary isograft+30 mg/kg unspecific antibody once weekly
10. shaved males with pituitary isograft+30 mg/kg specific antibody IgG2a 005-C04 once weekly
11. shaved males+30 mg/kg unspecific antibody once weekly
12. shaved males+30 mg/kg specific antibody once weekly Representative pictures from animals of the different groups are depicted in FIG. 18, the percentage of the area regrown with hair is indicated in FIG. 18.

Neutralising PRLR antibodies, but not unspecific antibodies, stimulate hair regrowth under hyper- and normoprolactinemic conditions in male and female mice. Neutralising PRLR antibodies are therefore suitable to treat hair loss in women and men under hyper- and normoprolactinemic conditions.

Example 19

Inhibition of Enhanced Mammary Epithelial Cell Proliferation by Neutralizing PRLR Antibodies To test the effect of neutralizing PRLR antibodies on enhanced mammary epithelial cell proliferation activated by combined hormone therapy (i.e. estrogen plus progestin therapy) a previously described mouse model that allowed for the quantification of proliferative effects in the uterus and the mammary gland was employed (Endocrinology 149:3952-3959, 2008). 6 week old C57BL/6 female mice were ovariectomized. 2 weeks after ovariectomy, animals were treated subcutaneously with daily injections of either vehicle (ethanol/arachisoil 10%/90%) or 100 ng estradiol plus 100 mg/kg progesterone for two weeks. Animals were treated once weekly with intraperitoneal injections of neutralizing PRLR antibodies (10 mg/kg and 30 mg/kg) in the murine IgG2a format or unspecific antibody (30 mg/kg) for three weeks. Autopsy was performed on day 36 after ovariectomy. Two hours before death animals received an intraperitoneal injection of BrdU dissolved in phosphate buffered saline (70 mg/kg body weight). The proximal ⅔ of the right inguinal mammary gland was analyzed for mammary epithelial cell proliferation (BrdU immunostaining) described previously (Endocrinology 149:3952-3959, 2008).

The experiment comprised the following groups:
1. ovariectomized animals treated with vehicle
2. ovariectomized animals treated with 100 ng estradiol
3. ovariectomized animals treated with 100 ng estradiol (E) and 100 mg/kg progesterone (P)
4. ovariectomized animals treated with E+P and 10 mg/kg specific antibody 005-C04
5. ovariectomized animals treated with E+P and 30 mg/kg specific antibody 005-C04
6. ovariectomized animals treated with E2+P and 30 mg/kg unspecific control antibody The results are shown in FIG. 19. The absolute number of proliferating ductal epithelial cells within 4 cross-sections of the mammary gland was evaluated. The medians are depicted as horizontal bars. Epithelial cell proliferation in ovariectomized, vehicle treated mice is rather low. Estradiol treatment leads to some stimulation of epithelial cell proliferation, maximal mammary epithelial cell proliferation is observed under estrogen plus progesterone treatment (FIG. 19). Treatment with neutralising prolactin receptor antibody 005-C04 but not with unspecific control antibody leads to a dose-dependent decrease in mammary epithelial cell proliferation almost back to estradiol-only levels.

Neutralising PRLR antibodies are therefore suitable to treat enhanced mammary epithelial cell proliferation under combined hormone therapy, i.e. estradiol plus progesterone treatment.

Example 20

Treatment of Adenomyosis Uteri (=Endometriosis Interna) in SHN Mice with Neutralizing PRLR Antibodies To test the efficacy of neutralizing PRLR antibodies in endometriosis, the adenomyosis uteri model in SHN mice relying on systemic hyperprolactinemia was employed (Acta anat. 116:46-54, 1983). Hyperprolactinemia in SHN mice was induced by pituitary isografting under the kidney capsule of 7 weeks old female mice (Acta anat. 116:46-54, 1983). Neutralizing PRLR antibodies (10 mg/kg or 30 mg/kg) or unspecific antibodies (30 mg/kg) were administered intraperitoneally starting one week after pituitary isografting. The infiltration of the uterine muscular layer by glandular tissue was assessed as described previously (Laboratory Animal Science 1998, 48:64-68). Treatment with the antibodies was performed for 9 weeks once and twice weekly by intraperitoneal injections. At autopsy (day 70 after pituitary transplantation), uteri were fixed overnight in buffered 4% formalin and embedded in paraffin. The degree of adenomyosis (=endometriosis interna) was assessed as follows:

Grade 0=no adenomyosis
Grade 0.5=the inner layer of the myometrium looses its concentric orientation
Grade 1=endometrial glands invading the inner layer of the myometrium
Grade 2=endometrial glands between the inner and outer layer of the uterine myometrium
Grade 3=endometrial glands invading the outer layer of the uterine myometrium
Grade 4=endometrial glands outside of the outer layer of the uterine myometrium The experiment comprised the following experimental groups:
1. Animals without pituitary transplantation, i.e. normoprolactinemic mice
2. Animals with pituitary transplantation, i.e. hyperprolactinemic mice
3. Animals with pituitary transplantation, treated with unspecific control antibody once weekly at a dose of 30 mg/kg
4. Animals with pituitary transplantation, treated with unspecific control antibody twice weekly at a dose of 30 mg/kg
5. Animals with pituitary transplantation, treated with the neutralizing prolactin receptor antibody 005-C04 in the murine IgG2a format once weekly at a dose of 10 mg/kg
6. Animals with pituitary transplantation, treated with the neutralizing prolactin receptor antibody 005-C04 in the murine IgG2a format twice weekly at a dose of 10 mg/kg
7. Animals with pituitary transplantation, treated with the neutralizing prolactin receptor antibody 005-C04 in the murine IgG2a format once weekly at a dose of 30 mg/kg
8. Animals with pituitary transplantation, treated with the neutralizing prolactin receptor antibody 005-C04 in the murine IgG2a format twice weekly at a dose of 30 mg/kg The results are depicted in FIG. 20. The scores for each animal in each treatment group are given individually and the medians for each treatment group are shown as horizontal bars. Normoprolactinemic mice develop endometriosis interna to some degree (median disease score=0.25). Hyperprolactinemia due to pituitary isografting enhances the disease score and more animals suffer from the disease (median disease score=2.5). Whereas treatment with 30 mg/kg unspecific antibody once or twice weekly had no influence on the disease, treatment with specific neutralizing antibodies shows a dose-dependent decrease in the disease score. Notably, all animals receiving either 10 or 30 mg/kg specific antibody twice weekly were completely cured and their disease score was significantly lower than the disease score of normoprolactinemic mice (FIG. 20). Neutralising PRLR antibodies are therefore suitable to treat endometriosis interna (=adenomyosis uteri) and endometriosis externa in women.

Example 21

Maturation of Antibody Variants

Antibody affinity maturation is a two step process where saturation mutagenesis and well-based high throughput screening are combined to identify a small number of mutations resulting in affinity increases. In the first round of affinity maturation positional diversification of wild-type antibody is introduced by site-directed mutagenesis using NNK-trinucleotide cassettes (whereby N represents a 25% mix each of adenine, thymine, guanine, and cytosine nucleotides and K represents a 50% mix each of thymine and guanine nucleotides) according to BMC Biotechnology 7: 65, 2007. This way, all 20 amino acids are introduced at an individual amino acid position. This positional randomization is restricted to the six complementarity determining regions (CDRs). In the second round of affinity maturation beneficial substitutions were recombined and screened for further improvements.

Screening of Maturated 005-C04 Fab Variants by ELISA Tests:

96 well microtiter plates were coated with 1 µg per milliliter of human PRLR. Plates were incubated over night at 4° C. After blocking with PBS buffer containing 3% bovine serum albumin, normalized E. coli-derived supernatants containing the Fab variants were added. Detection of formed complexes occurred via the addition of an anti-flag antibody (Sigma, A8592) labeled with horseradish peroxidase.

Amplex Red as fluorogenic substrate for horseradish peroxidase was added and incubated for 30 minutes at room temperature. Absorption at 570 nm and extinction at 585 nm was measured using the Tecan Infinite F500 reader. The obtained results are shown in FIG. 21.

The invention claimed is:

1. Antibody 005-C04, 005-C04-10-3, 005-C04-11-5, 005-C04-18-10-2, 005-C04-18-10-4, 005-C04-19-2, 005-C04-2-2, 005-C04-2-7, 005-C04-20-12-7, 005-C04-20-2, 005-C04-21-1, 005-C04-21-2, 005-C04-25-6, 005-C04-29-0, 005-C04-29-17-0, 005-C04-29-17-2, 005-C04-29-17-3, 005-C04-29-17-7, 005-C04-35-3, 005-C04-36-0, 005-C04-37-2, 005-C04-37-7, 005-C04-4-3-7, 005-C04-40-4, 005-C04-41-2, 005-C04-42-1, 005-C04-44-25-1, 005-C04-45-1, 005-C04-46-0, 005-C04-46-1, 005-C04-47-3, 005-C04-48-1, 005-C04-5-5, 005-C04-50-28-3, 005-C04-50-28-7, 005-C04-51-29-0, 005-C04-52-29-0, 005-C04-52-29-7, 005-C04-53-31-7, 005-C04-55-32-0, 005-C04-58-33-1, 005-C04-8-2, 005-C04-8-6, 005-C04-9-2, 005-C04-L2-1-11-0, 005-C04-L2-1-11-3, 005-C04-L2-1-12-2, 005-C04-L2-1-12-4, 005-C04-L2-1-16-4, 005-C04-L2-1-16-5, 005-C04-L2-1-2-3, 005-C04-L2-1-20-0, 005-C04-L2-1-20-1, 005-C04-L2-1-21-7, 005-C04-L2-1-23-7, 005-C04-L2-1-25-0, 005-C04-L2-1-25-4, 005-C04-L2-1-25-5, 005-C04-L2-1-25-7, 005-C04-L2-1-28-7, 005-C04-L2-1-3-2, 005-C04-L2-1-31-4, 005-C04-L2-1-31-7, 005-C04-L2-1-32-4, 005-C04-L2-1-33-7, 005-C04-L2-1-36-6, 005-C04-L2-1-38-3, 005-C04-L2-1-4-5, 005-C04-L2-1-40-2, 005-C04-L2-1-40-7, 005-C04-L2-1-42-0, 005-C04-L2-1-47-0, or 005-C04-L2-1-48-3 or antigen-binding fragments thereof.

2. Antibody or antigen-binding fragments according to claim 1 whereby the antibodies antagonize prolactin receptor-mediate signaling in human and mouse.

3. Antibody or antigen-binding fragment wherein a. the variable heavy chain contains the CDR sequences corresponding to SEQ ID NO: 6, 12 and 17 and the variable light chain contains the CDR sequences corresponding to SEQ ID NO: 23, 28, and 33, or b. the variable heavy chain contains the CDR sequences corresponding to SEQ ID NO: 103, 104, 17, and the variable light chain contains the CDR sequences corresponding to SEQ ID NO: 136, 140, 33; or c. the variable heavy chain contains the CDR sequences corresponding to SEQ ID NO: 103, 105, 17, and the variable light chain contains the CDR sequences corresponding to SEQ ID NO: 136, 139, 33; or d. the variable heavy chain contains the CDR sequences corresponding to SEQ ID NO: 6, 12, 17, and the variable light chain contains the CDR sequences corresponding to SEQ ID NO: 23, 139, 33; or e. the variable heavy chain contains the CDR sequences corresponding to SEQ ID NO: 6, 12, 17, and the variable light chain contains the CDR sequences corresponding to SEQ ID NO: 23, 141, 33; or f. the variable heavy chain contains the CDR sequences corresponding to SEQ ID NO: 102, 106, 17, and the variable light chain contains the CDR sequences corresponding to SEQ ID NO: 136, 138, 33; or g. the variable heavy chain contains the CDR sequences corresponding to SEQ ID NO: 102, 106, 17, and the variable light chain contains the CDR sequences corresponding to SEQ ID NO: 136, 140, 33; or h. the variable heavy chain contains the CDR sequences corresponding to SEQ ID NO: 103, 108, 17, and the variable light chain contains the CDR sequences corresponding to SEQ ID NO: 137, 28, 33; or i. the variable heavy chain contains the CDR sequences corresponding to SEQ ID NO: 6, 12, 17, and the variable light chain contains the CDR sequences corresponding to SEQ ID NO: 23, 138, 33; or j. the variable heavy chain contains the CDR sequences corresponding to SEQ ID NO: 102, 114, 17, and the variable light chain contains the CDR sequences corresponding to SEQ ID NO: 136, 28, 33; or k. the variable heavy chain contains the CDR sequences corresponding to SEQ ID NO: 102, 104, 17, and the variable light chain contains the CDR sequences corresponding to SEQ ID NO: 136, 140, 33; or l. the variable heavy chain contains the CDR sequences corresponding to SEQ ID NO: 102, 111, 17, and the variable light chain contains the CDR sequences corresponding to SEQ ID NO: 136, 139, 33; or m. the variable heavy chain contains the CDR sequences corresponding to SEQ ID NO: 103, 116, 17, and the variable light chain contains the CDR sequences corresponding to SEQ ID NO: 136, 140, 33; or n. the variable heavy chain contains the CDR sequences corresponding to SEQ ID NO: 102, 118, 17, and the variable light chain contains the CDR sequences corresponding to SEQ ID NO: 136, 138, 33; or o. the variable heavy chain contains the CDR sequences corresponding to SEQ ID NO: 6, 12, 17, and the variable light chain contains the CDR sequences corresponding to SEQ ID NO: 23, 28, 143; or p. the variable heavy chain contains the CDR sequences corresponding to SEQ ID NO: 6, 12, 17, and the variable light chain contains the CDR sequences corresponding to SEQ ID NO: 23, 28, 145; or
q. the variable heavy chain contains the CDR sequences corresponding to SEQ ID NO: 6, 12, 17, and the variable light chain contains the CDR sequences corresponding to SEQ ID NO: 23, 28, 144; or
r. the variable heavy chain contains the CDR sequences corresponding to SEQ ID NO: 6, 12, 17, and the variable light chain contains the CDR sequences corresponding to SEQ ID NO: 23, 28, 146; or
s. the variable heavy chain contains the CDR sequences corresponding to SEQ ID NO: 103, 110, 17, and the variable light chain contains the CDR sequences corresponding to SEQ ID NO: 136, 140, 33; or
t. the variable heavy chain contains the CDR sequences corresponding to SEQ ID NO: 103, 110, 17, and the variable light chain contains the CDR sequences corresponding to SEQ ID NO: 136, 139, 33; or
u. the variable heavy chain contains the CDR sequences corresponding to SEQ ID NO: 103, 127, 17, and the variable light chain contains the CDR sequences corresponding to SEQ ID NO: 136, 141, 33; or
v. the variable heavy chain contains the CDR sequences corresponding to SEQ ID NO: 103, 127, 17, and the variable light chain contains the CDR sequences corresponding to SEQ ID NO: 136, 141, 33; or
w. the variable heavy chain contains the CDR sequences corresponding to SEQ ID NO: 6, 12, 17, and the variable light chain contains the CDR sequences corresponding to SEQ ID NO: 136, 28, 33; or
x. the variable heavy chain contains the CDR sequences corresponding to SEQ ID NO: 102, 117, 17, and the variable light chain contains the CDR sequences corresponding to SEQ ID NO: 136, 140, 33; or
y. the variable heavy chain contains the CDR sequences corresponding to SEQ ID NO: 102, 119, 17, and the variable light chain contains the CDR sequences corresponding to SEQ ID NO: 136, 28, 33; or
z. the variable heavy chain contains the CDR sequences corresponding to SEQ ID NO: 102, 115, 17, and the variable light chain contains the CDR sequences corresponding to SEQ ID NO: 136, 138, 33; or
aa. the variable heavy chain contains the CDR sequences corresponding to SEQ ID NO: 102, 12, 17, and the variable light chain contains the CDR sequences corresponding to SEQ ID NO: 23, 28, 33; or
bb. the variable heavy chain contains the CDR sequences corresponding to SEQ ID NO: 102, 119, 17, and the variable light chain contains the CDR sequences corresponding to SEQ ID NO: 136, 139, 33; or
cc. the variable heavy chain contains the CDR sequences corresponding to SEQ ID NO: 102, 116, 17, and the variable light chain contains the CDR sequences corresponding to SEQ ID NO: 136, 140, 33; or
dd. the variable heavy chain contains the CDR sequences corresponding to SEQ ID NO: 102, 107, 17, and the variable light chain contains the CDR sequences corresponding to SEQ ID NO: 136, 140, 33; or
ee. the variable heavy chain contains the CDR sequences corresponding to SEQ ID NO: 103, 108, 17, and the variable light chain contains the CDR sequences corresponding to SEQ ID NO: 136, 28, 33; or
ff. the variable heavy chain contains the CDR sequences corresponding to SEQ ID NO: 102, 119, 17, and the variable light chain contains the CDR sequences corresponding to SEQ ID NO: 136, 28, 33; or
gg. the variable heavy chain contains the CDR sequences corresponding to SEQ ID NO: 102, 133, 17, and the variable light chain contains the CDR sequences corresponding to SEQ ID NO: 136, 138, 33; or
hh. the variable heavy chain contains the CDR sequences corresponding to SEQ ID NO: 6, 123, 17, and the variable light chain contains the CDR sequences corresponding to SEQ ID NO: 23, 28, 33; or
ii. the variable heavy chain contains the CDR sequences corresponding to SEQ ID NO: 6, 120, 17, and the variable light chain contains the CDR sequences corresponding to SEQ ID NO: 23, 28, 33; or
jj. the variable heavy chain contains the CDR sequences corresponding to SEQ ID NO: 6, 125, 17, and the variable light chain contains the CDR sequences corresponding to SEQ ID NO: 23, 28, 33; or
kk. the variable heavy chain contains the CDR sequences corresponding to SEQ ID NO: 6, 134, 17, and the variable light chain contains the CDR sequences corresponding to SEQ ID NO: 23, 28, 33; or
ll. the variable heavy chain contains the CDR sequences corresponding to SEQ ID NO: 6, 119, 17, and the variable light chain contains the CDR sequences corresponding to SEQ ID NO: 23, 28, 33; or
mm. the variable heavy chain contains the CDR sequences corresponding to SEQ ID NO: 6, 128, 17, and the variable light chain contains the CDR sequences corresponding to SEQ ID NO: 23, 28, 33; or
nn. the variable heavy chain contains the CDR sequences corresponding to SEQ ID NO: 6, 122, 17, and the variable light chain contains the CDR sequences corresponding to SEQ ID NO: 23, 28, 33; or
oo. the variable heavy chain contains the CDR sequences corresponding to SEQ ID NO: 6, 124, 17, and the variable light chain contains the CDR sequences corresponding to SEQ ID NO: 23, 28, 33; or
pp. the variable heavy chain contains the CDR sequences corresponding to SEQ ID NO: 102, 106, 17, and the variable light chain contains the CDR sequences corresponding to SEQ ID NO: 136, 28, 33; or
qq. the variable heavy chain contains the CDR sequences corresponding to SEQ ID NO: 103, 118, 17, and the variable light chain contains the CDR sequences corresponding to SEQ ID NO: 135, 28, 33; or
rr. the variable heavy chain contains the CDR sequences corresponding to SEQ ID NO: 103, 120, 17, and the variable light chain contains the CDR sequences corresponding to SEQ ID NO: 136, 142, 33; or
ss. the variable heavy chain contains the CDR sequences corresponding to SEQ ID NO: 103, 117, 17, and the variable light chain contains the CDR sequences corresponding to SEQ ID NO: 23, 140, 33; or
tt. the variable heavy chain contains the CDR sequences corresponding to SEQ ID NO: 102, 130, 17, and the variable light chain contains the CDR sequences corresponding to SEQ ID NO: 23, 139, 33; or
uu. the variable heavy chain contains the CDR sequences corresponding to SEQ ID NO: 102, 111, 17, and the variable light chain contains the CDR sequences corresponding to SEQ ID NO: 23, 140, 33; or
vv. the variable heavy chain contains the CDR sequences corresponding to SEQ ID NO: 102, 114, 17, and the variable light chain contains the CDR sequences corresponding to SEQ ID NO: 23, 141, 33; or
ww. the variable heavy chain contains the CDR sequences corresponding to SEQ ID NO: 102, 116, 17, and the variable light chain contains the CDR sequences corresponding to SEQ ID NO: 23, 141, 33; or
xx. the variable heavy chain contains the CDR sequences corresponding to SEQ ID NO: 103, 119, 17, and the variable light chain contains the CDR sequences corresponding to SEQ ID NO: 23, 140, 33; or
yy. the variable heavy chain contains the CDR sequences corresponding to SEQ ID NO: 102, 112, 17, and the variable light chain contains the CDR sequences corresponding to SEQ ID NO: 23, 141, 33; or
zz. the variable heavy chain contains the CDR sequences corresponding to SEQ ID NO: 103, 116, 17, and the variable light chain contains the CDR sequences corresponding to SEQ ID NO: 23, 140, 33; or
aaa. the variable heavy chain contains the CDR sequences corresponding to SEQ ID NO: 103, 120, 17, and the variable light chain contains the CDR sequences corresponding to SEQ ID NO: 136, 141, 33; or
bbb. the variable heavy chain contains the CDR sequences corresponding to SEQ ID NO: 103, 116, 17, and the variable light chain contains the CDR sequences corresponding to SEQ ID NO: 23, 138, 33; or
ccc. the variable heavy chain contains the CDR sequences corresponding to SEQ ID NO: 102, 109, 17, and the variable light chain contains the CDR sequences corresponding to SEQ ID NO: 23, 141, 33; or
ddd. the variable heavy chain contains the CDR sequences corresponding to SEQ ID NO: 103, 120, 17, and the variable light chain contains the CDR sequences corresponding to SEQ ID NO: 23, 141, 33; or
eee. the variable heavy chain contains the CDR sequences corresponding to SEQ ID NO: 102, 105, 17, and the variable light chain contains the CDR sequences corresponding to SEQ ID NO: 23, 138, 33; or
fff. the variable heavy chain contains the CDR sequences corresponding to SEQ ID NO: 102, 132, 17, and the variable light chain contains the CDR sequences corresponding to SEQ ID NO: 23, 138, 33; or
ggg. the variable heavy chain contains the CDR sequences corresponding to SEQ ID NO: 103, 120, 17, and the variable light chain contains the CDR sequences corresponding to SEQ ID NO: 136, 141, 33; or
hhh. the variable heavy chain contains the CDR sequences corresponding to SEQ ID NO: 102, 129, 17, and the variable light chain contains the CDR sequences corresponding to SEQ ID NO: 23, 140, 33; or
iii. the variable heavy chain contains the CDR sequences corresponding to SEQ ID NO: 102, 117, 17, and the variable light chain contains the CDR sequences corresponding to SEQ ID NO: 23, 140, 33; or
jjj. the variable heavy chain contains the CDR sequences corresponding to SEQ ID NO: 102, 129, 17, and the variable light chain contains the CDR sequences corresponding to SEQ ID NO: 23, 142, 33; or
kkk. the variable heavy chain contains the CDR sequences corresponding to SEQ ID NO: 103, 104, 17, and the variable light chain contains the CDR sequences corresponding to SEQ ID NO: 23, 142, 33; or
lll. the variable heavy chain contains the CDR sequences corresponding to SEQ ID NO: 102, 107, 17, and the variable light chain contains the CDR sequences corresponding to SEQ ID NO: 23, 142, 33; or
mmm. the variable heavy chain contains the CDR sequences corresponding to SEQ ID NO: 102, 113, 17, and the variable light chain contains the CDR sequences corresponding to SEQ ID NO: 23, 140, 33; or
nnn. the variable heavy chain contains the CDR sequences corresponding to SEQ ID NO: 102, 131, 17, and the variable light chain contains the CDR sequences corresponding to SEQ ID NO: 23, 142, 33; or
ooo. the variable heavy chain contains the CDR sequences corresponding to SEQ ID NO: 102, 115, 17, and the variable light chain contains the CDR sequences corresponding to SEQ ID NO: 136, 141, 33; or
ppp. the variable heavy chain contains the CDR sequences corresponding to SEQ ID NO: 103, 119, 17, and the variable light chain contains the CDR sequences corresponding to SEQ ID NO: 136, 141, 33; or
qqq. the variable heavy chain contains the CDR sequences corresponding to SEQ ID NO: 102, 109, 17, and the variable light chain contains the CDR sequences corresponding to SEQ ID NO: 23, 138, 33; or
rrr. the variable heavy chain contains the CDR sequences corresponding to SEQ ID NO: 102, 121, 17, and the variable light chain contains the CDR sequences corresponding to SEQ ID NO: 23, 142, 33; or
sss. the variable heavy chain contains the CDR sequences corresponding to SEQ ID NO: 102, 126, 17, and the variable light chain contains the CDR sequences corresponding to SEQ ID NO: 23, 142, 33; or
ttt. the variable heavy chain contains the CDR sequences corresponding to SEQ ID NO: 102, 105, 17, and the variable light chain contains the CDR sequences corresponding to SEQ ID NO: 23, 141, 33; or
uuu. the variable heavy chain contains the CDR sequences corresponding to SEQ ID NO: 102, 108, 17, and the variable light chain contains the CDR sequences corresponding to SEQ ID NO: 23, 138, 33.

4. Antibody or antigen-binding fragment comprising
a. a variable heavy chain domain corresponding to an amino acid sequence according to SEQ ID NO: 39, and a variable light chain domain with an amino acid sequence according to SEQ ID NO: 45,
b. a variable heavy chain domain corresponding to an amino acid sequence according to SEQ ID NO: 187, and a variable light chain domain with an amino acid sequence according to SEQ ID NO: 259,
c. a variable heavy chain domain corresponding to an amino acid sequence according to SEQ ID NO: 188, and a variable light chain domain with an amino acid sequence according to SEQ ID NO: 260,
d. a variable heavy chain domain corresponding to an amino acid sequence according to SEQ ID NO: 189, and a variable light chain domain with an amino acid sequence according to SEQ ID NO: 261,
e. a variable heavy chain domain corresponding to an amino acid sequence according to SEQ ID NO: 190, and a variable light chain domain with an amino acid sequence according to SEQ ID NO: 262,
f. a variable heavy chain domain corresponding to an amino acid sequence according to SEQ ID NO: 191, and a variable light chain domain with an amino acid sequence according to SEQ ID NO: 263,
g. a variable heavy chain domain corresponding to an amino acid sequence according to SEQ ID NO: 192, and a variable light chain domain with an amino acid sequence according to SEQ ID NO: 264,
h. a variable heavy chain domain corresponding to an amino acid sequence according to SEQ ID NO: 193, and a variable light chain domain with an amino acid sequence according to SEQ ID NO: 265,
i. a variable heavy chain domain corresponding to an amino acid sequence according to SEQ ID NO: 194, and a variable light chain domain with an amino acid sequence according to SEQ ID NO: 266,
j. a variable heavy chain domain corresponding to an amino acid sequence according to SEQ ID NO: 195, and a variable light chain domain with an amino acid sequence according to SEQ ID NO: 267,
k. a variable heavy chain domain corresponding to an amino acid sequence according to SEQ ID NO: 196, and a variable light chain domain with an amino acid sequence according to SEQ ID NO: 268,
l. a variable heavy chain domain corresponding to an amino acid sequence according to SEQ ID NO: 197, and a variable light chain domain with an amino acid sequence according to SEQ ID NO: 269,
m. a variable heavy chain domain corresponding to an amino acid sequence according to SEQ ID NO: 198, and a variable light chain domain with an amino acid sequence according to SEQ ID NO: 270,
n. a variable heavy chain domain corresponding to an amino acid sequence according to SEQ ID NO: 199, and a variable light chain domain with an amino acid sequence according to SEQ ID NO: 271,
o. a variable heavy chain domain corresponding to an amino acid sequence according to SEQ ID NO: 200, and a variable light chain domain with an amino acid sequence according to SEQ ID NO: 272,
p. a variable heavy chain domain corresponding to an amino acid sequence according to SEQ ID NO: 201, and a variable light chain domain with an amino acid sequence according to SEQ ID NO: 273,
q. a variable heavy chain domain corresponding to an amino acid sequence according to SEQ ID NO: 202, and a variable light chain domain with an amino acid sequence according to SEQ ID NO: 274,
r. a variable heavy chain domain corresponding to an amino acid sequence according to SEQ ID NO: 203, and a variable light chain domain with an amino acid sequence according to SEQ ID NO: 275,
s. a variable heavy chain domain corresponding an amino acid sequence according to SEQ ID NO: 204, and a variable light chain domain with an amino acid sequence according to SEQ ID NO: 276,
t. a variable heavy chain domain corresponding to an amino acid sequence according to SEQ ID NO: 205, and a variable light chain domain with an amino acid sequence according to SEQ ID NO: 277,
u. a variable heavy chain domain corresponding to an amino acid sequence according to SEQ ID NO: 206, and a variable light chain domain with an amino acid sequence according to SEQ ID NO: 278,
v. a variable heavy chain domain corresponding to an amino acid sequence according to SEQ ID NO: 207, and a variable light chain domain with an amino acid sequence according to SEQ ID NO: 279,
w. a variable heavy chain domain corresponding to an amino acid sequence according to SEQ ID NO: 208, and a variable light chain domain with an amino acid sequence according to SEQ ID NO: 280,
x. a variable heavy chain domain corresponding to an amino acid sequence according to SEQ ID NO: 209, and a variable light chain domain with an amino acid sequence according to SEQ ID NO: 281,
y. a variable heavy chain domain corresponding to an amino acid sequence according to SEQ ID NO: 210, and a variable light chain domain with an amino acid sequence according to SEQ ID NO: 282,
z. a variable heavy chain domain corresponding to an amino acid sequence according to SEQ ID NO: 211, and a variable light chain domain with an amino acid sequence according to SEQ ID NO: 283,
aa. a variable heavy chain domain corresponding to an amino acid sequence according to SEQ ID NO: 212, and a variable light chain domain with an amino acid sequence according to SEQ ID NO: 284,
bb. a variable heavy chain domain corresponding to an amino acid sequence according to SEQ ID NO: 213, and a variable light chain domain with an amino acid sequence according to SEQ ID NO: 285,
cc. a variable heavy chain domain corresponding to an amino acid sequence according to SEQ ID NO: 214, and a variable light chain domain with an amino acid sequence according to SEQ ID NO: 286,
dd. a variable heavy chain domain corresponding to an amino acid sequence according to SEQ ID NO: 215, and a variable light chain domain with an amino acid sequence according to SEQ ID NO: 287,
ee. a variable heavy chain domain corresponding to an amino acid sequence according to SEQ ID NO: 216, and a variable light chain domain with an amino acid sequence according to SEQ ID NO: 288,
ff. a variable heavy chain domain corresponding to an amino acid sequence according to SEQ ID NO: 217, and a variable light chain domain with an amino acid sequence according to SEQ ID NO: 289,
gg. a variable heavy chain domain corresponding to an amino acid sequence according to SEQ ID NO: 218, and a variable light chain domain with an amino acid sequence according to SEQ ID NO: 290,
hh. a variable heavy chain domain corresponding to an amino acid sequence according to SEQ ID NO: 219, and a variable light chain domain with an amino acid sequence according to SEQ ID NO: 291,
ii. a variable heavy chain domain corresponding to an amino acid sequence according to SEQ ID NO: 220, and a variable light chain domain with an amino acid sequence according to SEQ ID NO: 292,
jj. a variable heavy chain domain corresponding to an amino acid sequence according to SEQ ID NO: 221, and a variable light chain domain with an amino acid sequence according to SEQ ID NO: 293,
kk. a variable heavy chain domain corresponding an amino acid sequence according to SEQ ID NO: 222, and a variable light chain domain with an amino acid sequence according to SEQ ID NO: 294,
ll. a variable heavy chain domain corresponding to an amino acid sequence according to SEQ ID NO: 223, and a variable light chain domain with an amino acid sequence according to SEQ ID NO: 295,
mm. a variable heavy chain domain corresponding to an amino acid sequence according to SEQ ID NO: 224, and a variable light chain domain with an amino acid sequence according to SEQ ID NO: 296,
nn. a variable heavy chain domain corresponding an amino acid sequence according to SEQ ID NO: 225, and a variable light chain domain with an amino acid sequence according to SEQ ID NO: 297,
oo. a variable heavy chain domain corresponding to an amino acid sequence according to SEQ ID NO: 226, and a variable light chain domain with an amino acid sequence according to SEQ ID NO: 298,
pp. a variable heavy chain domain corresponding to an amino acid sequence according to SEQ ID NO: 227, and a variable light chain domain with an amino acid sequence according to SEQ ID NO: 299,
qq. a variable heavy chain domain corresponding to an amino acid sequence according to SEQ ID NO: 228, and a variable light chain domain with an amino acid sequence according to SEQ ID NO: 300,
rr. a variable heavy chain domain corresponding to an amino acid sequence according to SEQ ID NO: 229, and a variable light chain domain with an amino acid sequence according to SEQ ID NO: 301,
ss. a variable heavy chain domain corresponding to an amino acid sequence according to SEQ ID NO: 230, and a variable light chain domain with an amino acid sequence according to SEQ ID NO: 302,
tt. a variable heavy chain domain corresponding to an amino acid sequence according to SEQ ID NO: 231, and a variable light chain domain with an amino acid sequence according to SEQ ID NO: 303,
uu. a variable heavy chain domain corresponding to an amino acid sequence according to SEQ ID NO: 232, and a variable light chain domain with an amino acid sequence according to SEQ ID NO: 304,
vv. a variable heavy chain domain corresponding to an amino acid sequence according to SEQ ID NO: 233, and a variable light chain domain with an amino acid sequence according to SEQ ID NO: 305,
ww. a variable heavy chain domain corresponding to an amino acid sequence according to SEQ ID NO: 234, and a variable light chain domain with an amino acid sequence according to SEQ ID NO: 306,
xx. a variable heavy chain domain corresponding to an amino acid sequence according to SEQ ID NO: 235, and a variable light chain domain with an amino acid sequence according to SEQ ID NO: 307,
yy. a variable heavy chain domain corresponding to an amino acid sequence according to SEQ ID NO: 236, and a variable light chain domain with an amino acid sequence according to SEQ ID NO: 308,
zz. a variable heavy chain domain corresponding to an amino acid sequence according to SEQ ID NO: 237, and a variable light chain domain with an amino acid sequence according to SEQ ID NO: 309,
aaa. a variable heavy chain domain corresponding to an amino acid sequence according to SEQ ID NO: 238, and a variable light chain domain with an amino acid sequence according to SEQ ID NO: 310,
bbb. a variable heavy chain domain corresponding to an amino acid sequence according to SEQ ID NO: 239, and a variable light chain domain with an amino acid sequence according to SEQ ID NO: 311,
ccc. a variable heavy chain domain corresponding to an amino acid sequence according to SEQ ID NO: 240, and a variable light chain domain with an amino acid sequence according to SEQ ID NO: 312,
ddd. a variable heavy chain domain corresponding to an amino acid sequence according to SEQ ID NO: 241, and a variable light chain domain with an amino acid sequence according to SEQ ID NO: 313,
eee. a variable heavy chain domain corresponding to an amino acid sequence according to SEQ ID NO: 242, and a variable light chain domain with an amino acid sequence according to SEQ ID NO: 314,
fff. a variable heavy chain domain corresponding to an amino acid sequence according to SEQ ID NO: 243, and a variable light chain domain with an amino acid sequence according to SEQ ID NO: 315,
ggg. a variable heavy chain domain corresponding to an amino acid sequence according to SEQ ID NO: 244, and a variable light chain domain with an amino acid sequence according to SEQ ID NO: 316,
hhh. a variable heavy chain domain corresponding to an amino acid sequence according to SEQ ID NO: 245, and a variable light chain domain with an amino acid sequence according to SEQ ID NO: 317,
iii. a variable heavy chain domain corresponding to an amino acid sequence according to SEQ ID NO: 246, and a variable light chain domain with an amino acid sequence according to SEQ ID NO: 318,
jjj. a variable heavy chain domain corresponding to an amino acid sequence according to SEQ ID NO: 247, and a variable light chain domain with an amino acid sequence according to SEQ ID NO: 319,
kkk. a variable heavy chain domain corresponding to an amino acid sequence according to SEQ ID NO: 248, and a variable light chain domain with an amino acid sequence according to SEQ ID NO: 320,
lll. a variable heavy chain domain corresponding to an amino acid sequence according to SEQ ID NO: 249, and a variable light chain domain with an amino acid sequence according to SEQ ID NO: 321
mmm. a variable heavy chain domain corresponding to an amino acid sequence according to SEQ ID NO: 250, and a variable light chain domain with an amino acid sequence according to SEQ ID NO: 322,
nnn. a variable heavy chain domain corresponding to an amino acid sequence according to SEQ ID NO: 251, and a variable light chain domain with an amino acid sequence according to SEQ ID NO: 323,
ooo. a variable heavy chain domain corresponding to an amino acid sequence according to SEQ ID NO: 252, and a variable light chain domain with an amino acid sequence according to SEQ ID NO: 324,
ppp. a variable heavy chain domain corresponding to an amino acid sequence according to SEQ ID NO: 253, and a variable light chain domain with an amino acid sequence according to SEQ ID NO: 325,
qqq. a variable heavy chain domain corresponding to an amino acid sequence according to SEQ ID NO: 254, and a variable light chain domain with an amino acid sequence according to SEQ ID NO: 326,
rrr. a variable heavy chain domain corresponding to an amino acid sequence according to SEQ ID NO: 255, and a variable light chain domain with an amino acid sequence according to SEQ ID NO: 327,
sss. a variable heavy chain domain corresponding to an amino acid sequence according to SEQ ID NO: 256, and a variable light chain domain with an amino acid sequence according to SEQ ID NO: 328,
ttt. a variable heavy chain domain corresponding to an amino acid sequence according to SEQ ID NO: 257, and a variable light chain domain with an amino acid sequence according to SEQ ID NO: 329,
uuu. a variable heavy chain domain corresponding to an amino acid sequence according to SEQ ID NO: 258, and a variable light chain domain with an amino acid sequence according to SEQ ID NO: 330.

5. Antibody and antigen-binding fragment according to claim 1, whereby the antibody consists of an antigen-binding region that binds specifically to or has a high affinity of for one or more regions of PRLR, whose amino acid sequence is depicted by SEQ ID NO: 70 and human polymorphic variants of SEQ ID NO: 70, amino acid position 1 to 210, whereby the affinity is at least 30 nM, more preferred with an affinity of less than about 10 nM, or even more preferred with an affinity of less than 1 nM.

6. Antibody of claim 1 wherein the heavy constant is a modified or unmodified IgG1, IgG2, IgG3 or IgG4.

7. An isolated nucleic acid sequence encoding an antibody or antigen-binding fragment according to claim 1.

8. An isolated nucleic acid sequence according to claim 7, whereby the nucleic acid sequences are according to table 5.

9. Expression vector comprising a nucleic acid sequence of claim 7.

10. Host cell comprising the vector of claim 9.

11. A method of producing an antibody or antigen-binding fragment, comprising culturing the host cell of claim 10 under suitable conditions and recovering said antibody.

12. A method for treating endometriosis, adenomyosis (endometriosis interna), hot flashes, benign breast disease, mastalgia, benign prostate hyperplasia, hyper- and normoprolactinemic hair loss comprising the step of administering to a patient in need thereof an antibody according to claim 1.

13. A method of contraception or for preventing pregnancy comprising the step of administering to a patient in need thereof an antibody according to claim 1.

14. A method for inhibition of lactation comprising the step of administering to a patient in need thereof an antibody according to claim 1.

15. Antibody 005-C04-10-3, 005-C04-11-5, 005-C04-18-10-2, 005-C04-18-10-4, 005-C04-19-2, 005-C04-2-2, 005-C04-2-7, 005-C04-20-12-7, 005-C04-20-2, 005-C04-21-1, 005-C04-21-2, 005-C04-25-6, 005-C04-29-0, 005-C04-29-17-0, 005-C04-29-17-2, 005-C04-29-17-3, 005-C04-29-17-7, 005-C04-35-3, 005-C 04-36-0, 005-C04-37-2, 005-C04-37-7, 005-C04-4-3-7, 005-C04-40-4, 005-C04-41-2, 005-C04-42-1, 005-C04-44-25-1, 005-C04-45-1, 005-C04-46-0, 005-C04-46-1, 005-C04-47-3, 005-C04-48-1, 005-C04-5-5, 005-C04-50-28-3, 005-C04-50-28-7, 005-C04-51-29-0, 005-C04-52-29-0, 005-C04-52-29-7, 005-C04-53-31-7, 005-C04-55-32-0, 005-C04-58-33-1, 005-C04-8-2, 005-C04-8-6, 005-C04-9-2, 005-C04-L2-1-11-0, 005-C04-L2-1-11-3, 005-C04-L2-1-12-2, 005-C04-L2-1-12-4, 005-C04-L2-1-16-4, 005-C04-L2-1-16-5, 005-C04-L2-1-2-3, 005-C04-L2-1-20-0, 005-C04-L2-1-20-1, 005-C04-L2-1-21-7, 005-C04-L2-1-23-7, 005-C04-L2-1-25-0, 005-C04-L2-1-25-4, 005-C04-L2-1-25-5, 005-C04-L2-1-25-7, 005-C04-L2-1-28-7, 005-C04-L2-1-3-2, 005-C04-L2-1-31-4, 005-C04-L2-1-31-7, 005-C04-L2-1-32-4, 005-C04-L2-1-33-7, 005-C04-L2-1-36-6, 005-C04-L2-1-38-3, 005-C04-L2-1-4-5, 005-C04-L2-1-40-2, 005-C04-L2-1-40-7, 005-C04-L2-1-42-0, 005-C04-L2-1-47-0, or 005-C04-L2-1-48-3, or antigen-binding fragments thereof which antagonize prolactin receptor-mediated signalling.

16. Antibody 005-C04 or an antigen-binding fragment thereof.

* * * * *

SEQUENCE LISTING

<160> NUMBER OF SEQ ID NOS: 518

<210> SEQ ID NO 1
<211> LENGTH: 8
<212> TYPE: PRT
<213> ORGANISM: Homo sapiens

<400> SEQUENCE: 1

Phe Asp Asp Tyr Gly Met Ser Trp
1               5

<210> SEQ ID NO 2
<211> LENGTH: 8
<212> TYPE: PRT
<213> ORGANISM: Homo sapiens

<400> SEQUENCE: 2

Phe Ala Asn Tyr Gly Leu Thr Trp

```
1               5
```

<210> SEQ ID NO 3
<211> LENGTH: 8
<212> TYPE: PRT
<213> ORGANISM: Homo sapiens

<400> SEQUENCE: 3

```
Phe Ser Ser Tyr Gly Met His Trp
1               5
```

<210> SEQ ID NO 4
<211> LENGTH: 8
<212> TYPE: PRT
<213> ORGANISM: Homo sapiens

<400> SEQUENCE: 4

```
Phe Glu Asp His Gly Met Ser Trp
1               5
```

<210> SEQ ID NO 5
<211> LENGTH: 8
<212> TYPE: PRT
<213> ORGANISM: Homo sapiens

<400> SEQUENCE: 5

```
Phe Ser Ser Tyr Trp Met Ser Trp
1               5
```

<210> SEQ ID NO 6
<211> LENGTH: 8
<212> TYPE: PRT
<213> ORGANISM: Homo sapiens

<400> SEQUENCE: 6

```
Phe Ser Ser Tyr Trp Met His Trp
1               5
```

<210> SEQ ID NO 7
<211> LENGTH: 19
<212> TYPE: PRT
<213> ORGANISM: Homo sapiens

<400> SEQUENCE: 7

```
Ala Val Ile Ser Tyr Asp Gly Ser Asn Lys Tyr Tyr Ala Asp Ser Val
1               5                   10                  15

Lys Gly Arg
```

<210> SEQ ID NO 8
<211> LENGTH: 19
<212> TYPE: PRT
<213> ORGANISM: Homo sapiens

<400> SEQUENCE: 8

```
Ala Val Ile Ser Phe Asn Gly Asp Lys Lys Tyr Tyr Ala Asp Ser Val
1               5                   10                  15

Lys Gly Arg
```

<210> SEQ ID NO 9
<211> LENGTH: 19
<212> TYPE: PRT
<213> ORGANISM: Homo sapiens

<400> SEQUENCE: 9

```
Ser Gly Val Ser Trp Asn Gly Ser Arg Thr His Tyr Ala Asp Ser Val
1               5                   10                  15

Lys Gly Arg

<210> SEQ ID NO 10
<211> LENGTH: 20
<212> TYPE: PRT
<213> ORGANISM: Homo sapiens

<400> SEQUENCE: 10

Ser Leu Ile Ser Trp Asp Asp Gly Ser Asn Tyr Tyr Ala Asp Ser
1               5                   10                  15

Val Lys Gly Arg
            20

<210> SEQ ID NO 11
<211> LENGTH: 19
<212> TYPE: PRT
<213> ORGANISM: Homo sapiens

<400> SEQUENCE: 11

Ser Ser Val Ser Asp Thr Gly Thr Asp Thr His Tyr Ala Asp Ser Val
1               5                   10                  15

Lys Gly Arg

<210> SEQ ID NO 12
<211> LENGTH: 19
<212> TYPE: PRT
<213> ORGANISM: Homo sapiens

<400> SEQUENCE: 12

Ser Asp Ile Ser Ser Ala Ser Ser Tyr Thr Asn Tyr Ala Asp Ser Val
1               5                   10                  15

Lys Gly Arg

<210> SEQ ID NO 13
<211> LENGTH: 12
<212> TYPE: PRT
<213> ORGANISM: Homo sapiens

<400> SEQUENCE: 13

Ala Ser Pro Leu Glu Ser Pro Val Ala Phe Asp Ile
1               5                   10

<210> SEQ ID NO 14
<211> LENGTH: 9
<212> TYPE: PRT
<213> ORGANISM: Homo sapiens

<400> SEQUENCE: 14

Cys Ala Arg Gly Gly Asp Phe Asp Tyr
1               5

<210> SEQ ID NO 15
<211> LENGTH: 11
<212> TYPE: PRT
<213> ORGANISM: Homo sapiens

<400> SEQUENCE: 15

Ala Thr Ser Leu Arg Ala Thr Ala Phe Asp Thr
1               5                   10
```

```
<210> SEQ ID NO 16
<211> LENGTH: 16
<212> TYPE: PRT
<213> ORGANISM: Homo sapiens

<400> SEQUENCE: 16

Ala Lys Thr Pro Leu Ala Tyr Ser Ser Gly Trp Tyr Tyr Phe Asp Tyr
1               5                   10                  15

<210> SEQ ID NO 17
<211> LENGTH: 11
<212> TYPE: PRT
<213> ORGANISM: Homo sapiens

<400> SEQUENCE: 17

Ala Arg Gly Leu Asp Ala Arg Arg Met Asp Tyr
1               5                   10

<210> SEQ ID NO 18
<211> LENGTH: 13
<212> TYPE: PRT
<213> ORGANISM: Homo sapiens

<400> SEQUENCE: 18

Ser Gly Ser Asn Ser Asn Ile Gly Ser Asn Pro Val Asn
1               5                   10

<210> SEQ ID NO 19
<211> LENGTH: 13
<212> TYPE: PRT
<213> ORGANISM: Homo sapiens

<400> SEQUENCE: 19

Ser Gly Ser Tyr Ser Asn Ile Gly Gly Asn Pro Val Asn
1               5                   10

<210> SEQ ID NO 20
<211> LENGTH: 13
<212> TYPE: PRT
<213> ORGANISM: Homo sapiens

<400> SEQUENCE: 20

Ser Gly Ser Ser Ser Asn Ile Gly Ser Asn Asp Val Tyr
1               5                   10

<210> SEQ ID NO 21
<211> LENGTH: 13
<212> TYPE: PRT
<213> ORGANISM: Homo sapiens

<400> SEQUENCE: 21

Ser Gly Ser Ser Ser Asn Ile Gly Asn Asn Ala Val Asn
1               5                   10

<210> SEQ ID NO 22
<211> LENGTH: 13
<212> TYPE: PRT
<213> ORGANISM: Homo sapiens

<400> SEQUENCE: 22

Ser Gly Ser Ser Ser Asn Ile Gly Ser Asn Thr Val Asn
1               5                   10

<210> SEQ ID NO 23
```

```
<211> LENGTH: 14
<212> TYPE: PRT
<213> ORGANISM: Homo sapiens

<400> SEQUENCE: 23

Thr Gly Ser Ser Ser Asn Ile Gly Ala Gly Tyr Val Val His
1               5                   10

<210> SEQ ID NO 24
<211> LENGTH: 7
<212> TYPE: PRT
<213> ORGANISM: Homo sapiens

<400> SEQUENCE: 24

Asp Asn Asn Lys Arg Pro Ser
1               5

<210> SEQ ID NO 25
<211> LENGTH: 7
<212> TYPE: PRT
<213> ORGANISM: Homo sapiens

<400> SEQUENCE: 25

Gly Asn Ser Asn Arg Pro Ser
1               5

<210> SEQ ID NO 26
<211> LENGTH: 7
<212> TYPE: PRT
<213> ORGANISM: Homo sapiens

<400> SEQUENCE: 26

Ser Asn Asn Gln Arg Pro Ser
1               5

<210> SEQ ID NO 27
<211> LENGTH: 7
<212> TYPE: PRT
<213> ORGANISM: Homo sapiens

<400> SEQUENCE: 27

Arg Asn Tyr Gln Arg Pro Ser
1               5

<210> SEQ ID NO 28
<211> LENGTH: 7
<212> TYPE: PRT
<213> ORGANISM: Homo sapiens

<400> SEQUENCE: 28

Arg Asn Asn Gln Arg Pro Ser
1               5

<210> SEQ ID NO 29
<211> LENGTH: 12
<212> TYPE: PRT
<213> ORGANISM: Homo sapiens

<400> SEQUENCE: 29

Cys Gln Ser Tyr Asp Thr Gly Leu Ser Gly Trp Val
1               5                   10

<210> SEQ ID NO 30
<211> LENGTH: 12
<212> TYPE: PRT
```

```
<213> ORGANISM: Homo sapiens

<400> SEQUENCE: 30

Cys Gln Ser Tyr Asp Ser Ser Leu Ser Gly Ser Val
1               5                   10

<210> SEQ ID NO 31
<211> LENGTH: 13
<212> TYPE: PRT
<213> ORGANISM: Homo sapiens

<400> SEQUENCE: 31

Cys Gln Ser Tyr Asp Ser Ser Leu Ser Gly Ser Trp Val
1               5                   10

<210> SEQ ID NO 32
<211> LENGTH: 12
<212> TYPE: PRT
<213> ORGANISM: Homo sapiens

<400> SEQUENCE: 32

Cys Ala Ala Trp Asp Asp Ser Leu Ser Gly Trp Leu
1               5                   10

<210> SEQ ID NO 33
<211> LENGTH: 12
<212> TYPE: PRT
<213> ORGANISM: Homo sapiens

<400> SEQUENCE: 33

Cys Ala Ala Trp Asp Asp Ser Leu Asn Gly Trp Leu
1               5                   10

<210> SEQ ID NO 34
<211> LENGTH: 119
<212> TYPE: PRT
<213> ORGANISM: Homo sapiens

<400> SEQUENCE: 34

Gln Val Glu Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Met Val Ile Val Ser Ser
        115

<210> SEQ ID NO 35
<211> LENGTH: 119
<212> TYPE: PRT
<213> ORGANISM: Homo sapiens

<400> SEQUENCE: 35
```

Gln Val Glu Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asn Tyr
            20                  25                  30

Gly Leu Thr Trp Val Arg Gln Ala Pro Gly Lys Gly Leu Glu Trp Val
            35                  40                  45

Ala Val Ile Ser Phe Asn Gly Asp Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
            115

<210> SEQ ID NO 36
<211> LENGTH: 115
<212> TYPE: PRT
<213> ORGANISM: Homo sapiens

<400> SEQUENCE: 36

Gln Val Glu Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Gly Val Ser Trp Asn Gly Ser Arg Thr His Tyr Ala Asp Ser Val
        50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Phe Asp Tyr Trp Gly Gln Gly Thr Leu Val Thr
            100                 105                 110

Val Ser Ser
        115

<210> SEQ ID NO 37
<211> LENGTH: 119
<212> TYPE: PRT
<213> ORGANISM: Homo sapiens

<400> SEQUENCE: 37

Gln Val Glu Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Asp His
            20                  25                  30

Gly Met Ser Trp Val Arg Gln Ala Pro Gly Lys Gly Leu Glu Trp Val
            35                  40                  45

Ser Leu Ile Ser Trp Asp Asp Gly Ser Asn Lys Tyr Tyr Ala Asp Ser
        50                  55                  60

Val Lys Gly Arg Phe Thr Ile Ser Arg Asp Asn Ser Lys Asn Thr Leu
65                  70                  75                  80

-continued

Tyr Leu Gln Met Asn Ser Leu Arg Ala Glu Asp Thr Ala Val Tyr Tyr
                 85                  90                  95

Cys Ala Thr Ser Leu Arg Ala Thr Ala Phe Asp Thr Trp Gly Gln Gly
            100                 105                 110

Thr Leu Val Thr Val Ser Ser
        115

<210> SEQ ID NO 38
<211> LENGTH: 123
<212> TYPE: PRT
<213> ORGANISM: Homo sapiens

<400> SEQUENCE: 38

Gln Val Glu Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Ser Val Ser Asp Thr Gly Thr Asp Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Pro Leu Ala Tyr Ser Ser Gly Tyr Tyr Phe Asp Tyr
            100                 105                 110

Trp Gly Gln Gly Thr Leu Val Thr Val Ser Ser
        115                 120

<210> SEQ ID NO 39
<211> LENGTH: 118
<212> TYPE: PRT
<213> ORGANISM: Homo sapiens

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Ser Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Ser Ser
        115

<210> SEQ ID NO 40
<211> LENGTH: 112
<212> TYPE: PRT
<213> ORGANISM: Homo sapiens

<400> SEQUENCE: 40

Asp Ile Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Thr Gly Leu
                85                  90                  95

Ser Gly Trp Val Phe Gly Gly Gly Thr Lys Leu Thr Val Leu Gly Gln
            100                 105                 110

<210> SEQ ID NO 41
<211> LENGTH: 112
<212> TYPE: PRT
<213> ORGANISM: Homo sapiens

<400> SEQUENCE: 41

Gln Ser Val Leu Thr Gln Pro Pro Ser Ala Ser Gly Thr Pro Gly Gln
1               5                   10                  15

Arg Val Thr Ile Ser Cys Ser Gly Ser Tyr Ser Asn Ile Gly Gly Asn
            20                  25                  30

Pro Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Thr Lys Leu Thr Val Leu Gly Gln
            100                 105                 110

<210> SEQ ID NO 42
<211> LENGTH: 113
<212> TYPE: PRT
<213> ORGANISM: Homo sapiens

<400> SEQUENCE: 42

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asp Val Tyr Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

-continued

Ser Gly Ser Trp Val Phe Gly Gly Thr Lys Leu Thr Val Leu Gly
                100                 105                 110

Gln

<210> SEQ ID NO 43
<211> LENGTH: 112
<212> TYPE: PRT
<213> ORGANISM: Homo sapiens

<400> SEQUENCE: 43

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Thr Lys Leu Thr Val Leu Gly Gln
            100                 105                 110

<210> SEQ ID NO 44
<211> LENGTH: 112
<212> TYPE: PRT
<213> ORGANISM: Homo sapiens

<400> SEQUENCE: 44

Asp Ile Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Tyr Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Thr Lys Leu Thr Val Leu Gly Gln
            100                 105                 110

<210> SEQ ID NO 45
<211> LENGTH: 113
<212> TYPE: PRT
<213> ORGANISM: Homo sapiens

<400> SEQUENCE: 45

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
            50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln

<210> SEQ ID NO 46
<211> LENGTH: 357
<212> TYPE: DNA
<213> ORGANISM: Homo sapiens

<400> SEQUENCE: 46
caggtggaat tgttggagtc tgggggaggc ttggtacagc ctgggggtc cctgagactc      60 tcctgtgcag cctctggatt cacctttgat gattatggca tgagctgggt ccgccaagct    120
ccagggaagg ggctggagtg ggtggcagtt atatcatatg atggaagtaa taaatactat    180
gcagactccg tgaagggccg attcaccatc tccagagaca attcccagaa cacgctgtat    240
ctgcaaatga acagcctgag agccgaggac actgccgtgt attactgtgc gagtcccctt    300
gaaagtcccg tcgcttttga tatctggggc caagggacaa tggtcatcgt gagctca      357

<210> SEQ ID NO 47
<211> LENGTH: 357
<212> TYPE: DNA
<213> ORGANISM: Homo sapiens

<400> SEQUENCE: 47
caggtggaat tgttggagtc tgggggaggc ttggtacagc ctgggggtc cctgagactc      60 tcctgtgcag cctctggatt caccttcgct aactacggcc tgacctgggt ccgccaggct    120
ccagggaagg ggctggagtg ggtggcagtt atatcattta tggagacaa aaaatattac    180 gcagactccg tgaagggccg gttcaccatc tccagagaca attccaagaa cacgctgtat    240
ctgcaaatga acagcctgag agccgaggac actgccgtgt attactgtgc gagtcccctt    300
gaaagtcccg tcgcttttga tatctggggc caaggtaccc tggtcaccgt gagctca      357

<210> SEQ ID NO 48
<211> LENGTH: 345
<212> TYPE: DNA
<213> ORGANISM: Homo sapiens

<400> SEQUENCE: 48
caggtggaat tgttggagtc tgggggaggc ttggtacagc ctgggggtc cctgagactc      60 tcctgtgcag cctctggatt caccttcagt agctatggca tgcactgggt ccgccaggct    120
ccagggaagg ggctggagtg ggtatcgggt gttagttgga tggcagtag gacgcactat    180 gcagactctg tgaagggccg actcaccatc tccagagaca attccaagaa cacgctgtat    240
ctgcaaatga acagcctgag agccgaggac actgccgtgt attactgtgc gagaggaggg    300
gactttgact actggggcca aggtaccctg gtcaccgtga gctca                    345

<210> SEQ ID NO 49
<211> LENGTH: 357
<212> TYPE: DNA

<213> ORGANISM: Homo sapiens

<400> SEQUENCE: 49

| caggtggaat | tgttggagtc | tgggggaggc | ttggtacagc | ctgggggtc | cctgagactc | 60 |
| tcctgtgcag | cctctggatt | cacctttgag | gatcatggca | tgagctgggt | ccgccaagct | 120 |
| ccagggaagg | ggctggagtg | ggtctctctt | attagttggg | atgatggaag | taataaatac | 180 |
| tacgcagact | ccgtgaaggg | ccgattcacc | atctccagag | acaattccaa | gaacacgctg | 240 |
| tatctgcaaa | tgaacagcct | gagagccgag | gacactgccg | tgtattactg | tgcgacttcc | 300 |
| ctacgggcca | cggcttttga | tacgtggggc | caaggtacac | tggtcaccgt | gagctca | 357 |

<210> SEQ ID NO 50
<211> LENGTH: 369
<212> TYPE: DNA
<213> ORGANISM: Homo sapiens

<400> SEQUENCE: 50

| caggtggaat | tgttggagtc | tgggggaggc | ttggtacagc | ctgggggtc | cctgagactc | 60 |
| tcctgtgcag | cctctggatt | caccttagt | agctattgga | tgagctgggt | ccgccaggct | 120 |
| ccagggaagg | ggctggagtg | gtctcaagt | gttagcgata | ctggtactga | tactcattac | 180 |
| gcagactccg | tgaagggccg | cttcaccatc | tccagagaca | attccaagaa | cacgctgtat | 240 |
| ctgcaaatga | acagcctgag | agccgaggac | actgccgtgt | attactgtgc | aaaaacccct | 300 |
| ctcgcatata | gcagtggctg | gtactacttt | gactactggg | gccaaggtac | cctggtcacc | 360 |
| gtgagctca | | | | | | 369 |

<210> SEQ ID NO 51
<211> LENGTH: 354
<212> TYPE: DNA
<213> ORGANISM: Homo sapiens

<400> SEQUENCE: 51

| gaggtgcagc | tgttggagtc | tgggggaggc | ttggtacagc | ctgggggtc | cctgagactc | 60 |
| tcctgtgcag | cctctggatt | cacctcagt | agctactgga | tgcactgggt | ccgccaagct | 120 |
| ccagggaagg | ggctggagtg | ggtttcagac | attagcagtg | ctagtagtta | cacaaactac | 180 |
| gcagactcag | tgaagggccg | attcaccatc | tccagagaca | attccaagaa | cacgctgtat | 240 |
| ctgcaaatga | acagcctgag | agccgaggac | actgccgtgt | attactgtgc | gaggggttg | 300 |
| gatgcgcgac | ggatggacta | ctggggccaa | ggtaccctgg | tcaccgtgag | ctca | 354 |

<210> SEQ ID NO 52
<211> LENGTH: 336
<212> TYPE: DNA
<213> ORGANISM: Homo sapiens

<400> SEQUENCE: 52

| gatatcgtgc | tgactcagcc | accctcagcg | tctgggaccc | ctgggcagag | ggtcaccatc | 60 |
| tcttgttctg | gaagcaactc | caacatcgga | agtaatcctg | taaactggta | tcagcagctc | 120 |
| ccaggaacgg | cccccaaact | cctcatctat | gacaataata | agcgaccctc | agggtccct | 180 |
| gaccgattct | ctggctccaa | gtctggcacc | tcagcctccc | tggccatcag | tgggctccgg | 240 |
| tccgaggatg | aggctgatta | ttactgccag | tcctatgaca | ccggcctgag | tggttgggtg | 300 |
| ttcggcggag | gaaccaagtt | aaccgtccta | ggtcag | | | 336 |

```
<210> SEQ ID NO 53
<211> LENGTH: 336
<212> TYPE: DNA
<213> ORGANISM: Homo sapiens

<400> SEQUENCE: 53
cagtctgtgc tgactcagcc accctcagcg tctgggaccc ccgggcagag ggtcaccatc      60
tcttgttccg gaagctactc caacatcggg ggtaatcctg taaactggta tcagcagctc     120
ccaggaacgg cccccaaact cctcatctat ggtaacagca atcggccctc agggtccct      180 gaccgattct ctggctccaa gtctggcacc tcagcctccc tggccatcag tgggctccgg     240
tccgaggatg aggctgatta ttactgccag tcctatgaca gcagcctgag tggttcggta     300
ttcggcggag gaaccaagct gacggtccta ggtcag                               336

<210> SEQ ID NO 54
<211> LENGTH: 339
<212> TYPE: DNA
<213> ORGANISM: Homo sapiens

<400> SEQUENCE: 54
cagtctgtgc tgactcagcc accctcagcg tctgggaccc ccgggcagag ggtcaccatc      60
tcttgttctg gaagcagctc caatatcgga agtaatgatg tatattggta tcagcagctc     120
ccaggaacgg cccccaaact cctcatctat gacaataata agcgaccctc agggtccct      180 gaccgattct ctggctccaa gtctggcacc tcagcctccc tggccatcag tgggctccgg     240
tccgaggatg aggctgatta ttactgccag tcctatgaca gcagcctgag tggttcttgg     300
gtgttcggcg gaggaaccaa gctgacggtc ctaggtcag                             339

<210> SEQ ID NO 55
<211> LENGTH: 336
<212> TYPE: DNA
<213> ORGANISM: Homo sapiens

<400> SEQUENCE: 55
cagtctgtgc tgactcagcc accctcagcg tctgggaccc ccgggcagag ggtcaccatc      60
tcctgttctg gaagcagctc caacatcgga aataatgctg taaactggta tcagcagctc     120
ccaggaacgg cccccaaact cctcatctat agtaataatc agcggccctc agggtccct      180 gaccgattct ctggctccaa gtctggcacc tcagcctccc tggccatcag tgggctccgg     240
tccgaggatg aggctgatta ttactgtgca gcatgggatg acagcctgag tggttgggtg     300
ttcggcggag gaaccaagtt aaccgtccta ggtcag                               336

<210> SEQ ID NO 56
<211> LENGTH: 336
<212> TYPE: DNA
<213> ORGANISM: Homo sapiens

<400> SEQUENCE: 56
gatatcgtgc tgactcagcc accctcagcg tctgggaccc ccgggcagag ggtcaccatc      60
tcttgttctg gaagcagctc caacatcgga agtaatactg taaactggta tcagcagctc     120
ccaggaacgg cccccaaact cctcatctat agaaattatc agcgaccctc agggtccct      180 gaccgattct ctggctccaa gtctggcacc tcagcctccc tggccatcag tgggctccgg     240
tccgaggatg aggctgatta ttactgccag tcctatgaca gcagcctgag tggttcggtg     300
ttcggcggag gaaccaagtt aaccgtccta ggtcag                               336
```

<210> SEQ ID NO 57
<211> LENGTH: 339
<212> TYPE: DNA
<213> ORGANISM: Homo sapiens

<400> SEQUENCE: 57

```
cagtctgtgc tgactcagcc accctcagcg tctgggaccc ccgggcagag ggtcaccatc      60
tcctgcactg ggagcagctc aacattggg gcgggttatg ttgtacattg gtatcagcag     120
ctcccaggaa cggcccccaa actcctcatc tataggaata atcagcggcc ctcaggggtc     180
cctgaccgat tctctggctc caagtctggc acctcagcct ccctggccat cagtgggctc     240
cggtccgagg atgaggctga ttattactgt gcagcatggg atgacagcct gaatggttgg     300
ctgttcggcg gaggaaccaa gttaaccgtc ctaggtcag                            339
```

<210> SEQ ID NO 58
<211> LENGTH: 124
<212> TYPE: PRT
<213> ORGANISM: Homo sapiens

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Val Ser Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Tyr Tyr Ala Thr Tyr Tyr Tyr Ala Met Asp
            100                 105                 110

Tyr Trp Gly Gln Gly Thr Leu Val Thr Val Ser Ser
        115                 120

<210> SEQ ID NO 59
<211> LENGTH: 124
<212> TYPE: PRT
<213> ORGANISM: Artificial Sequence
<220> FEATURE:
<223> OTHER INFORMATION: maturated PRLR antibody

<400> SEQUENCE: 59

Glu Val Gln Leu Val Glu Ser Gly Gly Asp Leu Val Lys Pro Gly Gly
1               5                   10                  15

Ser Leu Lys Leu Ser Cys Ala Val Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Val Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Ser Ala Met Tyr Tyr Cys
                85                  90                  95

Ala Arg His Arg Gly Asn Tyr Tyr Ala Thr Tyr Tyr Ala Met Asp
            100                 105                 110

Tyr Trp Gly Gln Gly Thr Ser Val Thr Val Ser Ser
        115                 120

<210> SEQ ID NO 60
<211> LENGTH: 114
<212> TYPE: PRT
<213> ORGANISM: Artificial Sequence
<220> FEATURE:
<223> OTHER INFORMATION: maturated PRLR antibody

<400> SEQUENCE: 60

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Ala Phe Ser Ser Phe
            20                  25                  30

Gly Met Gln Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Val Arg Ser Gly Arg Asp Tyr Trp Gly Gln Gly Thr Ser Val Thr Val
            100                 105                 110

Ser Ser

<210> SEQ ID NO 61
<211> LENGTH: 113
<212> TYPE: PRT
<213> ORGANISM: Homo sapiens

<400> SEQUENCE: 61

Asp Ile Val Leu Thr Gln Ser Pro Asp Ser Leu Ala Val Ser Leu Gly
1               5                   10                  15

Glu Arg Ala Thr Ile Asn Cys Lys Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Pro Val Gln Ala Glu Asp Val Ala Thr Tyr Tyr Cys Gln His Ser Gly
                85                  90                  95

Glu Leu Pro Pro Ser Phe Gly Gln Gly Thr Lys Leu Glu Ile Lys Arg
            100                 105                 110

Ala

<210> SEQ ID NO 62
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 62

Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Pro Ser Phe Gly Gly Gly Thr Lys Leu Glu Ile Lys Arg
            100                 105                 110

Ala

<210> SEQ ID NO 63
<211> LENGTH: 108
<212> TYPE: PRT
<213> ORGANISM: Homo sapiens

<400> SEQUENCE: 63

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Gly Val Ser Asn Asp
            20                  25                  30

Val Ala Trp Phe Gln Gln Lys Pro Gly Gln Ser Pro Lys Leu Leu Ile
        35                  40                  45

Tyr Ser Ala Ser Thr Arg Tyr Thr Gly Val Pro Asp Arg Leu Thr Gly
    50                  55                  60

Ser Gly Tyr Gly Thr Asp Phe Thr Phe Thr Ile Asn Thr Val Gln Ala
65                  70                  75                  80

Glu Asp Leu Ala Val Tyr Phe Cys Gln Gln Asp Tyr Thr Ser Pro Thr
                85                  90                  95

Phe Gly Gly Gly Thr Lys Leu Glu Ile Lys Arg Ala
            100                 105

<210> SEQ ID NO 64
<211> LENGTH: 372
<212> TYPE: DNA
<213> ORGANISM: Homo sapiens

<400> SEQUENCE: 64
gaggtgcagc tcgtggagtc tggcggcgga ctggtgcagc tggcggcag cctgagactg        60 agctgcgccg tgagcggctt caccttcagc agctacggca tgagctgggt gcgccaggct      120
cctggcaagg gactggaatg ggtggccacc gtgtccagcg gcggcaccta cacctactac      180
cccgacagcg tgaagggccg gttcaccatc agccgggaca acagcaagaa caccctgtac      240
ctgcagatga acagcctgcg ggccgaggac accgccgtgt actactgcgc cagacaccgg      300
ggcaactact acgccaccta ctactatgcc atggactact ggggccaggg caccctggtg      360
accgtgagct ca                                                          372

<210> SEQ ID NO 65
<211> LENGTH: 372

```
<212> TYPE: DNA
<213> ORGANISM: Artificial Sequence
<220> FEATURE:
<223> OTHER INFORMATION: maturated PRLR antibody

<400> SEQUENCE: 65
gaggtgcagc tcgtggagtc tggcggcgac ctggtgaagc tggcggcag cctgaagctg      60 tcctgcgccg tgagcggctt caccttcagc agctacggca tgagctgggt gcgccagacc    120
cccgacaaga gactggaatg ggtggcaacc gtgtctagcg gcggcaccta cacctactac    180
cccgacagcg tgaagggccg gttcaccatc agccgggaca cgccaagaa caccctgtac    240 ctgcagatgt ccagcctgaa gtccgaggac agcgccatgt actattgcgc cagacatcgg    300
ggcaactact acgccaccta ctactatgcc atggactact ggggccaggg caccagcgtg    360
accgtgagct ca                                                         372

<210> SEQ ID NO 66
<211> LENGTH: 342
<212> TYPE: DNA
<213> ORGANISM: Artificial Sequence
<220> FEATURE:
<223> OTHER INFORMATION: maturated PRLR antibody

<400> SEQUENCE: 66
gacgtgcagc tcgtggagtc tggcggcgga ctggtgcagc tggcggaag ccggaaactg      60 tcctgcgctg ccagcggctt cgccttcagc agcttcggca tgcagtgggt gcgccaggcc    120
cccgagaagg gcctggaatg ggtggcctac atcagcagcg gcagcagcac catctactac    180
gccgacaccg tgaagggccg gttcaccatc agcagagaca ccccaagaa tacctgttc      240 ctgcagatga ccagcctgcg gagcgaggac accgccatgt actctgcgt gcggagcggc    300 agagactact ggggccaggg caccagcgtg accgtgagct ca                       342

<210> SEQ ID NO 67
<211> LENGTH: 339
<212> TYPE: DNA
<213> ORGANISM: Homo sapiens

<400> SEQUENCE: 67
gatatcgtgc tgacccagag cccccgacagc ctggccgtga gcctgggcga gcgggccacc    60
atcaactgca aggccagcaa gtccgtgagc cagcggct acacctacat gcactggtat      120
cagcagaagc ccggccagcc ccccaagctg ctgatctacc tggccagcaa ccgggagagc    180
ggcgtgcccg accggtttag cggcagcggc tccggcaccg acttcaccct gaccatcagc    240
cccgtgcagg ccgaggacgt ggccacctac tactgccagc acagcggcga gctgcccccc    300
agcttcggcc agggcaccaa gctggaaatc aagcgggcc                           339

<210> SEQ ID NO 68
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 68
gatatcgtgc tgacccagag ccccgccagc ctggctgtgt ctctgggcca gcgccacc        60 atcagctgcc gggccagcaa gtccgtgagc cagcggct acacctacat gcactggtat      120
cagcagaagc ccggccagcc ccccaagctg ctgatctacc tggccagcaa cctggaaagc    180
```

```
ggcgtgcccg ccagattcag cggcagcggc tccggcaccg acttcaccct gaacatccac    240
cccgtggagg aagaggacgc cgccacctac tactgccagc acagcggcga gctgcccct     300 agctttggcg gcggaacaaa gctggaaatc aagcgggcc                           339
```

<210> SEQ ID NO 69
<211> LENGTH: 324
<212> TYPE: DNA
<213> ORGANISM: Artificial Sequence
<220> FEATURE:
<223> OTHER INFORMATION: maturated PRLR antibody

<400> SEQUENCE: 69

```
agcatcgtga tgacccagac ccccaagttc ctgctggtgt ctgccggcga cagagtgacc     60
atcacctgca aggccagcca gggcgtgagc aacgacgtgg cctggttcca gcagaagccc    120
ggccagagcc ccaagctgct gatctacagc gccagcaccc ggtacaccgg cgtgcccgac    180
agactgaccg gctccggcta cggcaccgat tcaccttca ccatcaacac cgtgcaggcc     240
gaggacctgg ccgtgtactt ctgccagcag gactacacca gccccacctt tggcggcgga   300
acaaagctgg aaatcaagcg ggcc                                           324
```

<210> SEQ ID NO 70
<211> LENGTH: 222
<212> TYPE: PRT
<213> ORGANISM: Homo sapiens

<400> SEQUENCE: 70

```
Gln Leu Pro Pro Gly Lys Pro Glu Ile Phe Lys Cys Arg Ser Pro Asn
1               5                   10                  15

Lys Glu Thr Phe Thr Cys Trp Trp Arg Pro Gly Thr Asp Gly Gly Leu
            20                  25                  30

Pro Thr Asn Tyr Ser Leu Thr Tyr His Arg Glu Gly Glu Thr Leu Met
        35                  40                  45

His Glu Cys Pro Asp Tyr Ile Thr Gly Gly Pro Asn Ser Cys His Phe
    50                  55                  60

Gly Lys Gln Tyr Thr Ser Met Trp Arg Thr Tyr Ile Met Met Val Asn
65                  70                  75                  80

Ala Thr Asn Gln Met Gly Ser Ser Phe Ser Asp Glu Leu Tyr Val Asp
                85                  90                  95

Val Thr Tyr Ile Val Gln Pro Asp Pro Pro Leu Glu Leu Ala Val Glu
            100                 105                 110

Val Lys Gln Pro Glu Asp Arg Lys Pro Tyr Leu Trp Ile Lys Trp Ser
        115                 120                 125

Pro Pro Thr Leu Ile Asp Leu Lys Thr Gly Trp Phe Thr Leu Leu Tyr
    130                 135                 140

Glu Ile Arg Leu Lys Pro Glu Lys Ala Ala Glu Trp Glu Ile His Phe
145                 150                 155                 160

Ala Gly Gln Gln Thr Glu Phe Lys Ile Leu Ser Leu His Pro Gly Gln
                165                 170                 175

Lys Tyr Leu Val Gln Val Arg Cys Lys Pro Asp His Gly Tyr Trp Ser
            180                 185                 190

Ala Trp Ser Pro Ala Thr Phe Ile Gln Ile Pro Ser Asp Phe Thr Met
        195                 200                 205

Asn Asp Ile Glu Gly Arg Met Asp His His His His His
    210                 215                 220
```

<210> SEQ ID NO 71
<211> LENGTH: 666
<212> TYPE: DNA
<213> ORGANISM: Homo sapiens

<400> SEQUENCE: 71

```
cagttacctc ctggaaaacc tgagatcttt aaatgtcgtt ctcccaataa ggaaacattc      60
acctgctggt ggaggcctgg gacagatgga ggacttccta ccaattattc actgacttac     120
cacagggaag agagacact catgcatgaa tgtccagact acataaccgg tggccccaac      180
tcctgccact ttggcaagca gtacacctcc atgtggagga catacatcat gatggtcaat     240
gccactaacc agatgggaag cagtttctcg gatgaacttt atgtggacgt gacttacata     300
gttcagccag accctccttt ggagctggct gtggaagtaa acagccaga agacagaaaa      360
ccctacctgt ggattaaatg gtctccacct accctgattg acttaaaaac tggttggttc     420
acgctcctgt atgaaattcg attaaaaccc gagaaagcag ctgagtggga gatccatttt     480
gctgggcagc aaacagagtt taagattctc agcctacatc aggacagaa ataccttgtc      540
caggttcgct gcaaaccaga ccatggatac tggagtgcat ggagtccagc gaccttcatt     600
cagataccta gtgacttcac catgaatgat atcgagggcc gcatggacca ccaccaccac     660
caccac                                                                666
```

<210> SEQ ID NO 72
<211> LENGTH: 222
<212> TYPE: PRT
<213> ORGANISM: Mus musculus

<400> SEQUENCE: 72

```
Gln Ser Pro Pro Gly Lys Pro Glu Ile His Lys Cys Arg Ser Pro Asp
1               5                   10                  15

Lys Glu Thr Phe Thr Cys Trp Trp Asn Pro Gly Ser Asp Gly Gly Leu
            20                  25                  30

Pro Thr Asn Tyr Ser Leu Thr Tyr Ser Lys Glu Gly Glu Lys Asn Thr
        35                  40                  45

Tyr Glu Cys Pro Asp Tyr Lys Thr Ser Gly Pro Asn Ser Cys Phe Phe
50                  55                  60

Ser Lys Gln Tyr Thr Ser Ile Trp Lys Ile Tyr Ile Ile Thr Val Asn
65                  70                  75                  80

Ala Thr Asn Glu Met Gly Ser Ser Thr Ser Asp Pro Leu Tyr Val Asp
                85                  90                  95

Val Thr Tyr Ile Val Glu Pro Glu Pro Pro Arg Asn Leu Thr Leu Glu
            100                 105                 110

Val Lys Gln Leu Lys Asp Lys Lys Thr Tyr Leu Trp Val Lys Trp Leu
        115                 120                 125

Pro Pro Thr Ile Thr Asp Val Lys Thr Gly Trp Phe Thr Met Glu Tyr
130                 135                 140

Glu Ile Arg Leu Lys Ser Glu Glu Ala Asp Trp Glu Ile His Phe
145                 150                 155                 160

Thr Gly His Gln Thr Gln Phe Lys Val Phe Asp Leu Tyr Pro Gly Gln
                165                 170                 175

Lys Tyr Leu Val Gln Thr Arg Cys Lys Pro Asp His Gly Tyr Trp Ser
            180                 185                 190

Arg Trp Gly Gln Glu Lys Ser Ile Glu Ile Pro Asn Asp Phe Thr Leu
        195                 200                 205

Lys Asp Ile Glu Gly Arg Met Asp His His His His His His
```

<210> SEQ ID NO 73
<211> LENGTH: 666
<212> TYPE: DNA
<213> ORGANISM: Mus musculus

<400> SEQUENCE: 73

```
cagtcaccac ctggaaaacc tgaaatccac aaatgtcgtt ccctgacaa ggaaacattc     60
acctgctggt ggaatcctgg gtcagatgga ggactcccca ccaattattc attgacatac   120
agcaaagaag gagagaaaaa cacctatgaa tgtccagact acaaaaccag tggccccaat   180
tcctgtttct ttagcaagca gtacacttcc atatggaaaa tatacatcat cacagtaaat   240
gccacgaacg aaatgggaag cagtacctcg gatccacttt atgtggatgt gacttacatt   300
gttgaaccag agcctcctcg gaacctgact ttagaagtga acaactaaa agacaaaaaa    360
acatatctgt gggtaaaatg gttgccacct accataactg atgtaaaaac tggttggttt   420
acaatggaat atgaaattcg attaaagtct gaagaagcag atgagtggga gatccacttc   480
acaggtcatc aaacacaatt taaggttttt gacttatatc aggacaaaa gtatcttgtc    540
cagactcgct gcaagccaga ccatggatac tggagtagat ggggccagga gaaatctatt   600
gaaataccaa atgacttcac cttgaaagac atcgagggcc gcatggacca ccaccaccac   660
caccac                                                              666
```

<210> SEQ ID NO 74
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 74

Ala Val Ile Ser Phe Asp Gly Ser Asn Lys Tyr Tyr Ala Asp Ser Val
1               5                   10                  15

Lys Gly Arg

<210> SEQ ID NO 75
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 75

Ala Val Ile Ser Tyr Asp Gly Ser Asn Lys Tyr Tyr Ala Asp Ser Val
1               5                   10                  15

Lys Gly Arg

<210> SEQ ID NO 76
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 76

Ala Val Ile Ser Phe Asp Gly Thr Asn Lys Tyr Tyr Ala Asp Ser Val
1               5                   10                  15

Lys Gly Arg

```
<210> SEQ ID NO 77
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 77

Ala Val Ile Ser Phe Asp Gly Ser Asn Lys Tyr Tyr Ala Asp Ser Val
1               5                   10                  15

Lys Gly Arg

<210> SEQ ID NO 78
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 78

Ser Gly Leu Asn Ser Asn Val Gly Ser Ser Pro Val Asn
1               5                   10

<210> SEQ ID NO 79
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 79

Ser Gly Leu Asn Ser Asn Val Gly Ser Asn Pro Val Asn
1               5                   10

<210> SEQ ID NO 80
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 80

Ser Gly Leu Asn Ser Asn Ile Gly Ser Asn Pro Val Asn
1               5                   10

<210> SEQ ID NO 81
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 81

Ser Gly Leu Asn Asp Asn Val Gly Ser Asn Pro Val Asn
1               5                   10

<210> SEQ ID NO 82
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 82

Ser Gly Ser Asn Ser Asn Ile Gly Gly Asn Pro Val Asn
1               5                   10
```

<210> SEQ ID NO 83
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 83

Ser Gly Ser Asn Ser Asn Val Gly Gly Asn Pro Val Asn
1               5                   10

<210> SEQ ID NO 84
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 84

Ser Gly Ser Asn Ser Asn Val Gly Ser Asn Pro Val Asn
1               5                   10

<210> SEQ ID NO 85
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 85

Ser Gly Ser Asn Asp Asn Ile Gly Ser Asn Pro Val Asn
1               5                   10

<210> SEQ ID NO 86
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 86

Ser Gly Ser Asn Ser Asn Ile Gly Ser Ser Pro Val Asn
1               5                   10

<210> SEQ ID NO 87
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 87

Ser Gly Leu Asn Ser Asn Ile Gly Gly Ser Pro Val Asn
1               5                   10

<210> SEQ ID NO 88
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 88

Ser Gly Leu Asn Ser Asn Val Gly Gly Ser Pro Val Asn
1               5                   10

```
<210> SEQ ID NO 89
<211> LENGTH: 13
<212> TYPE: PRT
<213> ORGANISM: Artificial Sequence
<220> FEATURE:
<223> OTHER INFORMATION: maturated PRLR antibody

<400> SEQUENCE: 89

Ser Gly Leu Asn Asp Asn Val Gly Gly Ser Pro Val Asn
1               5                   10

<210> SEQ ID NO 90
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 90

Cys Gln Ser Tyr Asp Glu Gly Ser Gly Met Trp Val
1               5                   10

<210> SEQ ID NO 91
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 91

Cys Gln Ser Tyr Asp Glu Gly Ser Ser Met Trp Val
1               5                   10

<210> SEQ ID NO 92
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 92

Cys Gln Ser Tyr Asp Glu Gly Ala Ser Met Trp Val
1               5                   10

<210> SEQ ID NO 93
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 93

Cys Gln Ser Tyr Asp Thr Gly Ala Gly Met Trp Val
1               5                   10

<210> SEQ ID NO 94
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 94

Cys Gln Ser Tyr Asp Thr Gly Leu Ser Met Trp Val
1               5                   10
```

```
<210> SEQ ID NO 95
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 95

Cys Gln Ser Tyr Asp Thr Gly Ser Ser Met Trp Val
 1               5                  10

<210> SEQ ID NO 96
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 96

Cys Gln Ser Tyr Asp Thr Gly Leu Gly Gly Trp Val
 1               5                  10

<210> SEQ ID NO 97
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 97

Cys Gln Ser Tyr Asp Thr Gly Ala Ser Gly Trp Val
 1               5                  10

<210> SEQ ID NO 98
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 98

Cys Gln Ser Tyr Asp Thr Gly Ser Ser Gly Trp Val
 1               5                  10

<210> SEQ ID NO 99
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 99

Cys Gln Ser Tyr Asp Thr Gly Ser Gly Gly Trp Val
 1               5                  10

<210> SEQ ID NO 100
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 100

Cys Gln Ser Tyr Asp Glu Gly Leu Ser Gly Trp Val
 1               5                  10

<210> SEQ ID NO 101
```

```
<211> LENGTH: 12
<212> TYPE: PRT
<213> ORGANISM: Artificial Sequence
<220> FEATURE:
<223> OTHER INFORMATION: maturated PRLR antibody

<400> SEQUENCE: 101

Cys Gln Ser Tyr Asp Glu Gly Leu Gly Gly Trp Val
1               5                   10

<210> SEQ ID NO 102
<211> LENGTH: 8
<212> TYPE: PRT
<213> ORGANISM: Artificial Sequence
<220> FEATURE:
<223> OTHER INFORMATION: maturated PRLR antibody

<400> SEQUENCE: 102

Phe Ser Ser Tyr Trp Asn His Trp
1               5

<210> SEQ ID NO 103
<211> LENGTH: 8
<212> TYPE: PRT
<213> ORGANISM: Artificial Sequence
<220> FEATURE:
<223> OTHER INFORMATION: maturated PRLR antibody

<400> SEQUENCE: 103

Phe Ser Ser Tyr Trp Trp His Trp
1               5

<210> SEQ ID NO 104
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 104

Ser Asp Ile Ala Arg Leu Ser Pro Tyr Thr Asn Tyr Ala Asp Ser Val
1               5                   10                  15

Lys Gly Arg

<210> SEQ ID NO 105
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 105

Ser Asp Ile Ser Arg Leu Ser Pro Tyr Thr Asn Tyr Ala Asp Ser Val
1               5                   10                  15

Lys Gly Arg

<210> SEQ ID NO 106
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 106

Ser Asp Met Ala Arg Leu Ser Pro Tyr Thr Asn Tyr Ala Asp Ser Val
1               5                   10                  15
```

Lys Gly Arg

<210> SEQ ID NO 107
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 107

Ser Asp Met Ser Arg Leu Ser Pro Tyr Thr Asn Tyr Ala Asp Ser Val
1               5                   10                  15

Lys Gly Arg

<210> SEQ ID NO 108
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 108

Ser Asp Ile Ser Arg Ala Ser Pro Tyr Thr Asn Tyr Ala Asp Ser Val
1               5                   10                  15

Lys Gly Arg

<210> SEQ ID NO 109
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 109

Ser Asp Ile Ser Arg Ala Ser Pro Tyr Thr Gly Tyr Ala Asp Ser Val
1               5                   10                  15

Lys Gly Arg

<210> SEQ ID NO 110
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 110

Ser Asp Ile Ala Arg Ala Ser Pro Tyr Thr Asn Tyr Ala Asp Ser Val
1               5                   10                  15

Lys Gly Arg

<210> SEQ ID NO 111
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 111

Ser Asp Met Ala Arg Ala Ser Pro Tyr Thr Asn Tyr Ala Asp Ser Val
1               5                   10                  15

Lys Gly Arg

```
<210> SEQ ID NO 112
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 112

Ser Asp Met Ala Arg Ala Ser Pro Tyr Thr Gly Tyr Ala Asp Ser Val
1               5                   10                  15

Lys Gly Arg

<210> SEQ ID NO 113
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 113

Ser Asp Ile Ala Arg Leu Ser Pro Tyr Thr Gly Tyr Ala Asp Ser Val
1               5                   10                  15

Lys Gly Arg

<210> SEQ ID NO 114
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 114

Ser Asp Ile Ala Arg Leu Ser Ser Tyr Thr Asn Tyr Ala Asp Ser Val
1               5                   10                  15

Lys Gly Arg

<210> SEQ ID NO 115
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 115

Ser Asp Ile Ser Arg Leu Ser Ser Tyr Thr Asn Tyr Ala Asp Ser Val
1               5                   10                  15

Lys Gly Arg

<210> SEQ ID NO 116
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 116

Ser Asp Met Ser Arg Leu Ser Ser Tyr Thr Asn Tyr Ala Asp Ser Val
1               5                   10                  15

Lys Gly Arg

<210> SEQ ID NO 117
<211> LENGTH: 19
<212> TYPE: PRT
<213> ORGANISM: Artificial Sequence
```

```
<220> FEATURE:
<223> OTHER INFORMATION: maturated PRLR antibody

<400> SEQUENCE: 117

Ser Asp Met Ala Arg Leu Ser Ser Tyr Thr Asn Tyr Ala Asp Ser Val
1               5                   10                  15

Lys Gly Arg

<210> SEQ ID NO 118
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 118

Ser Asp Met Ser Arg Ala Ser Ser Tyr Thr Asn Tyr Ala Asp Ser Val
1               5                   10                  15

Lys Gly Arg

<210> SEQ ID NO 119
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 119

Ser Asp Ile Ser Arg Ala Ser Ser Tyr Thr Asn Tyr Ala Asp Ser Val
1               5                   10                  15

Lys Gly Arg

<210> SEQ ID NO 120
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 120

Ser Asp Met Ser Ser Ala Ser Ser Tyr Thr Asn Tyr Ala Asp Ser Val
1               5                   10                  15

Lys Gly Arg

<210> SEQ ID NO 121
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 121

Ser Asp Ile Ala Ser Ala Ser Ser Tyr Thr Gly Tyr Ala Asp Ser Val
1               5                   10                  15

Lys Gly Arg

<210> SEQ ID NO 122
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 122
```

```
Ser Asp Ile Ser Ser Ala Ser Pro Tyr Thr Asn Tyr Ala Asp Ser Val
1               5                   10                  15

Lys Gly Arg

<210> SEQ ID NO 123
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 123

Ser Asp Arg Ser Ser Ala Ser Ser Tyr Thr Asn Tyr Ala Asp Ser Val
1               5                   10                  15

Lys Gly Arg

<210> SEQ ID NO 124
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 124

Ser Asp Ile Ser Ser Ala Ser Ser Tyr Thr Gly Tyr Ala Asp Ser Val
1               5                   10                  15

Lys Gly Arg

<210> SEQ ID NO 125
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 125

Ser Asp Ile Ala Ser Ala Ser Ser Tyr Thr Asn Tyr Ala Asp Ser Val
1               5                   10                  15

Lys Gly Arg

<210> SEQ ID NO 126
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 126

Ser Asp Ile Ala Arg Ala Ser Ser Tyr Thr Gly Tyr Ala Asp Ser Val
1               5                   10                  15

Lys Gly Arg

<210> SEQ ID NO 127
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 127

Ser Asp Ile Ser Ser Leu Ser Ser Tyr Thr Gly Tyr Ala Asp Ser Val
1               5                   10                  15
```

Lys Gly Arg

<210> SEQ ID NO 128
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 128

Ser Asp Ile Ser Ser Leu Ser Ser Tyr Thr Asn Tyr Ala Asp Ser Val
1               5                   10                  15

Lys Gly Arg

<210> SEQ ID NO 129
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 129

Ser Asp Met Ser Ser Leu Ser Ser Tyr Thr Gly Tyr Ala Asp Ser Val
1               5                   10                  15

Lys Gly Arg

<210> SEQ ID NO 130
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 130

Ser Asp Met Ser Ser Leu Ser Ser Tyr Thr Asn Tyr Ala Asp Ser Val
1               5                   10                  15

Lys Gly Arg

<210> SEQ ID NO 131
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 131

Ser Asp Met Ala Ser Leu Ser Ser Tyr Thr Asn Tyr Ala Asp Ser Val
1               5                   10                  15

Lys Gly Arg

<210> SEQ ID NO 132
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 132

Ser Asp Met Ala Ser Leu Ser Pro Tyr Thr Gly Tyr Ala Asp Ser Val
1               5                   10                  15

Lys Gly Arg

<210> SEQ ID NO 133

```
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 133

Ser Asp Met Ser Trp Leu Ser Ser Tyr Thr Asn Tyr Ala Asp Ser Val
1               5                   10                  15

Lys Gly Arg

<210> SEQ ID NO 134
<211> LENGTH: 19
<212> TYPE: PRT
<213> ORGANISM: Artificial Sequence
<220> FEATURE:
<223> OTHER INFORMATION: maturated PRLR antibody

<400> SEQUENCE: 134

Ser Asp Ile Ser Trp Ala Ser Ser Tyr Thr Asn Tyr Ala Asp Ser Val
1               5                   10                  15

Lys Gly Arg

<210> SEQ ID NO 135
<211> LENGTH: 14
<212> TYPE: PRT
<213> ORGANISM: Artificial Sequence
<220> FEATURE:
<223> OTHER INFORMATION: maturated PRLR antibody

<400> SEQUENCE: 135

Thr Gly Gln Ser Ser Asn Ile Gly Ala Gly Tyr Val Val His
1               5                   10

<210> SEQ ID NO 136
<211> LENGTH: 14
<212> TYPE: PRT
<213> ORGANISM: Artificial Sequence
<220> FEATURE:
<223> OTHER INFORMATION: maturated PRLR antibody

<400> SEQUENCE: 136

Thr Gly Ser Ser Ser Asn Ile Gly Tyr Gly Tyr Val Val His
1               5                   10

<210> SEQ ID NO 137
<211> LENGTH: 14
<212> TYPE: PRT
<213> ORGANISM: Artificial Sequence
<220> FEATURE:
<223> OTHER INFORMATION: maturated PRLR antibody

<400> SEQUENCE: 137

Thr Gly Val Ser Ser Asn Ile Gly Ala Gly Tyr Val Val His
1               5                   10

<210> SEQ ID NO 138
<211> LENGTH: 7
<212> TYPE: PRT
<213> ORGANISM: Artificial Sequence
<220> FEATURE:
<223> OTHER INFORMATION: maturated PRLR antibody

<400> SEQUENCE: 138

Arg Asn Asn Gln Arg Gln Ser
1               5
```

```
<210> SEQ ID NO 139
<211> LENGTH: 7
<212> TYPE: PRT
<213> ORGANISM: Artificial Sequence
<220> FEATURE:
<223> OTHER INFORMATION: maturated PRLR antibody

<400> SEQUENCE: 139

Arg Asn Asn Val Arg Pro Ser
1               5

<210> SEQ ID NO 140
<211> LENGTH: 7
<212> TYPE: PRT
<213> ORGANISM: Artificial Sequence
<220> FEATURE:
<223> OTHER INFORMATION: maturated PRLR antibody

<400> SEQUENCE: 140

Arg Asn Asn Val Arg Gln Ser
1               5

<210> SEQ ID NO 141
<211> LENGTH: 7
<212> TYPE: PRT
<213> ORGANISM: Artificial Sequence
<220> FEATURE:
<223> OTHER INFORMATION: maturated PRLR antibody

<400> SEQUENCE: 141

Arg Asn Asn Trp Arg Pro Ser
1               5

<210> SEQ ID NO 142
<211> LENGTH: 7
<212> TYPE: PRT
<213> ORGANISM: Artificial Sequence
<220> FEATURE:
<223> OTHER INFORMATION: maturated PRLR antibody

<400> SEQUENCE: 142

Arg Asn Asn Trp Arg Gln Ser
1               5

<210> SEQ ID NO 143
<211> LENGTH: 12
<212> TYPE: PRT
<213> ORGANISM: Homo sapiens

<400> SEQUENCE: 143

Cys Ala Ala Trp Asp Asp Ser Leu Ser Gly Trp Leu
1               5                   10

<210> SEQ ID NO 144
<211> LENGTH: 12
<212> TYPE: PRT
<213> ORGANISM: Homo sapiens

<400> SEQUENCE: 144

Cys Ala Ala Trp Asp Asp Ser Leu Phe Gly Trp Leu
1               5                   10

<210> SEQ ID NO 145
<211> LENGTH: 12
<212> TYPE: PRT
```

```
<213> ORGANISM: Homo sapiens

<400> SEQUENCE: 145

Cys Ala Ala Trp Asp Asp Ser Leu Gly Gly Trp Leu
1               5                   10

<210> SEQ ID NO 146
<211> LENGTH: 12
<212> TYPE: PRT
<213> ORGANISM: Homo sapiens

<400> SEQUENCE: 146

Cys Ala Ala Trp Asp Asp Ser Leu Leu Gly Trp Leu
1               5                   10

<210> SEQ ID NO 147
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Met Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 148
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Met Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Ser Pro Leu Glu Ser Pro Val Ala Phe Asp Ile Trp Gly Gln Gly
            100                 105                 110

Thr Leu Val Thr Val Ser Ser
        115
```

<210> SEQ ID NO 149
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 149

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Met Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115
```

<210> SEQ ID NO 150
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 150

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Met Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115
```

<210> SEQ ID NO 151
<211> LENGTH: 119
<212> TYPE: PRT

<213> ORGANISM: Artificial Sequence
<220> FEATURE:
<223> OTHER INFORMATION: maturated PRLR antibody

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Met Val
        35                  40                  45

Ala Val Ile Ser Phe Asp Gly Thr Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 152
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 153
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 153

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

```
Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 154
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 155
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 155

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Met Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
```

```
                85                  90                  95
Ala Ser Pro Leu Glu Ser Pro Val Ala Phe Asp Ile Trp Gly Gln Gly
        100                 105                 110

Thr Leu Val Thr Val Ser Ser
        115

<210> SEQ ID NO 156
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
        100                 105                 110

Thr Leu Val Thr Val Ser Ser
        115

<210> SEQ ID NO 157
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
        100                 105                 110

Thr Leu Val Thr Val Ser Ser
        115

<210> SEQ ID NO 158
<211> LENGTH: 119
```

```
<212> TYPE: PRT
<213> ORGANISM: Artificial Sequence
<220> FEATURE:
<223> OTHER INFORMATION: maturated PRLR antibody

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Met Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 159
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Met Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 160
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
```

```
                  20                  25                  30
Gly Met Ser Trp Val Arg Gln Ala Pro Gly Lys Gly Leu Glu Met Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                 85                  90                  95

Ala Ser Pro Leu Glu Ser Pro Val Ala Phe Asp Ile Trp Gly Gln Gly
            100                 105                 110

Thr Leu Val Thr Val Ser Ser
            115

<210> SEQ ID NO 161
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 161

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Asp Asp Tyr
             20                  25                  30

Gly Met Ser Trp Val Arg Gln Ala Pro Gly Lys Gly Leu Glu Trp Val
             35                  40                  45

Ala Val Ile Ser Phe Asp Gly Ser Asn Lys Tyr Tyr Ala Asp Ser Val
         50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                 85                  90                  95

Ala Ser Pro Leu Glu Ser Pro Val Ala Phe Asp Ile Trp Gly Gln Gly
            100                 105                 110

Thr Leu Val Thr Val Ser Ser
            115

<210> SEQ ID NO 162
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 162

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Asp Asp Tyr
             20                  25                  30

Gly Met Ser Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Gln Asn Thr Leu Tyr
65                  70                  75                  80
```

-continued

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 163
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 164
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Leu Glu Ser Pro Val Ala Phe Asp Ile Trp Gly Gln Gly
            100                 105                 110

Thr Leu Val Thr Val Ser Ser
        115

<210> SEQ ID NO 165

```
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 165

Gln Ser Val Leu Thr Gln Pro Pro Ser Ala Ser Gly Thr Pro Gly Gln
1               5                   10                  15

Arg Val Thr Ile Ser Cys Ser Gly Leu Asn Ser Asn Val Gly Ser Ser
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Glu Gly Ser
                85                  90                  95

Gly Met Trp Val Phe Gly Gly Gly Thr Lys Leu Thr Val Leu Gly Gln
            100                 105                 110

<210> SEQ ID NO 166
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 166

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Gly Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Glu Gly Ser
                85                  90                  95

Ser Met Trp Val Phe Gly Gly Gly Thr Lys Leu Thr Val Leu Gly Gln
            100                 105                 110

<210> SEQ ID NO 167
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 167

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Gly Asn
            20                  25                  30

Pro Val Asn Trp Tyr Gln Gln Leu Pro Gly Thr Ala Pro Lys Leu Leu
        35                  40                  45
```

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ser Tyr Asp Thr Gly Leu
                85                  90                  95

Ser Gly Trp Val Phe Gly Gly Gly Thr Lys Leu Thr Val Leu Gly Gln
            100                 105                 110

<210> SEQ ID NO 168
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 168

Gln Ser Val Leu Thr Gln Pro Pro Ser Ala Ser Gly Thr Pro Gly Gln
 1               5                  10                  15

Arg Val Thr Ile Ser Cys Ser Gly Ser Asn Ser Asn Ile Gly Ser Ser
                20                  25                  30

Pro Val Asn Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ser Tyr Asp Thr Gly Leu
                85                  90                  95

Ser Gly Trp Val Phe Gly Gly Gly Thr Lys Leu Thr Val Leu Gly Gln
            100                 105                 110

<210> SEQ ID NO 169
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 169

Gln Ser Val Leu Thr Gln Pro Pro Ser Ala Ser Gly Thr Pro Gly Gln
 1               5                  10                  15

Arg Val Thr Ile Ser Cys Ser Gly Leu Asn Ser Asn Ile Gly Gly Ser
                20                  25                  30

Pro Val Asn Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ser Tyr Asp Glu Gly Leu
                85                  90                  95

Ser Gly Trp Val Phe Gly Gly Gly Thr Lys Leu Thr Val Leu Gly Gln
            100                 105                 110

<210> SEQ ID NO 170
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 170

Gln Ser Val Leu Thr Gln Pro Pro Ser Ala Ser Gly Thr Pro Gly Gln
1               5                   10                  15

Arg Val Thr Ile Ser Cys Ser Gly Leu Asn Ser Asn Ile Gly Gly Ser
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Glu Gly Ala
                85                  90                  95

Ser Met Trp Val Phe Gly Gly Gly Thr Lys Leu Thr Val Leu Gly Gln
            100                 105                 110

<210> SEQ ID NO 171
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 171

Gln Ser Val Leu Thr Gln Pro Pro Ser Ala Ser Gly Thr Pro Gly Gln
1               5                   10                  15

Arg Val Thr Ile Ser Cys Ser Gly Leu Asn Asp Asn Val Gly Gly Ser
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Thr Gly Ala
                85                  90                  95

Gly Met Trp Val Phe Gly Gly Gly Thr Lys Leu Thr Val Leu Gly Gln
            100                 105                 110

<210> SEQ ID NO 172
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 172

Gln Ser Val Leu Thr Gln Pro Pro Ser Ala Ser Gly Thr Pro Gly Gln
1               5                   10                  15

Arg Val Thr Ile Ser Cys Ser Gly Leu Asn Ser Asn Val Gly Ser Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Glu Gly Leu
                85                  90                  95

Gly Gly Trp Val Phe Gly Gly Gly Thr Lys Leu Thr Val Leu Gly Gln
            100                 105                 110

<210> SEQ ID NO 173
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 173

Gln Ser Val Leu Thr Gln Pro Pro Ser Ala Ser Gly Thr Pro Gly Gln
1               5                   10                  15

Arg Val Thr Ile Ser Cys Ser Gly Leu Asn Asp Asn Val Gly Gly Ser
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Glu Gly Ser
                85                  90                  95

Gly Met Trp Val Phe Gly Gly Gly Thr Lys Leu Thr Val Leu Gly Gln
            100                 105                 110

<210> SEQ ID NO 174
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 174

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Glu Gly Leu
                85                  90                  95

Ser Gly Trp Val Phe Gly Gly Gly Thr Lys Leu Thr Val Leu Gly Gln
            100                 105                 110

<210> SEQ ID NO 175
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 175

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Thr Gly Ala
                85                  90                  95

Ser Gly Trp Val Phe Gly Gly Gly Thr Lys Leu Thr Val Leu Gly Gln
            100                 105                 110

<210> SEQ ID NO 176
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 176

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Thr Gly Ser
                85                  90                  95

Ser Gly Trp Val Phe Gly Gly Gly Thr Lys Leu Thr Val Leu Gly Gln
            100                 105                 110

<210> SEQ ID NO 177
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 177

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Val Gly Gly Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

```
Ser Glu Asp Glu Ala Asp Tyr Tyr Cys Gln Ser Tyr Asp Thr Gly Ser
                85                  90                  95

Gly Gly Trp Val Phe Gly Gly Gly Thr Lys Leu Thr Val Leu Gly Gln
            100                 105                 110
```

<210> SEQ ID NO 178
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 178

```
Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Thr Gly Leu
                85                  90                  95

Gly Gly Trp Val Phe Gly Gly Gly Thr Lys Leu Thr Val Leu Gly Gln
            100                 105                 110
```

<210> SEQ ID NO 179
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 179

```
Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Thr Gly Leu
                85                  90                  95

Ser Met Trp Val Phe Gly Gly Gly Thr Lys Leu Thr Val Leu Gly Gln
            100                 105                 110
```

<210> SEQ ID NO 180
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 180

```
Gln Ser Val Leu Thr Gln Pro Pro Ser Ala Ser Gly Thr Pro Gly Gln
1               5                   10                  15
Arg Val Thr Ile Ser Cys Ser Gly Leu Asn Ser Asn Val Gly Gly Ser
                20                  25                  30
Pro Val Asn Trp Tyr Gln Gln Leu Pro Gly Thr Ala Pro Lys Leu Leu
            35                  40                  45
Ile Tyr Asp Asn Asn Lys Arg Pro Ser Gly Val Pro Asp Arg Phe Ser
        50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Gln Ser Tyr Asp Glu Gly Ser
                85                  90                  95
Gly Met Trp Val Phe Gly Gly Gly Thr Lys Leu Thr Val Leu Gly Gln
            100                 105                 110
```

<210> SEQ ID NO 181
<211> LENGTH: 80
<212> TYPE: PRT
<213> ORGANISM: Artificial Sequence
<220> FEATURE:
<223> OTHER INFORMATION: maturated PRLR antibody

<400> SEQUENCE: 181

```
Gln Ser Val Leu Thr Gln Pro Pro Ser Ala Ser Gly Thr Pro Gly Gln
1               5                   10                  15
Arg Val Thr Ile Ser Cys Ser Gly Leu Asn Asp Asn Val Gly Ser Asn
                20                  25                  30
Pro Val Asn Trp Tyr Gln Gln Leu Pro Gly Thr Ala Pro Lys Leu Leu
            35                  40                  45
Ile Tyr Asp Asn Asn Lys Arg Pro Ser Gly Val Pro Asp Arg Phe Ser
        50                  55                  60
Gly Ser Lys Ser Gly Thr Ser Ala Ser Leu Ala Ile Ser Gly Leu Arg
65                  70                  75                  80
```

<210> SEQ ID NO 182
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 182

```
Gln Ser Val Leu Thr Gln Pro Pro Ser Ala Ser Gly Thr Pro Gly Gln
1               5                   10                  15
Arg Val Thr Ile Ser Cys Ser Gly Ser Asn Ser Asn Ile Gly Ser Asn
                20                  25                  30
Pro Val Asn Trp Tyr Gln Gln Leu Pro Gly Thr Ala Pro Lys Leu Leu
            35                  40                  45
Ile Tyr Asp Asn Asn Lys Arg Pro Ser Gly Val Pro Asp Arg Phe Ser
        50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Gln Ser Tyr Asp Thr Gly Leu
                85                  90                  95
Ser Gly Trp Val Phe Gly Gly Gly Thr Lys Leu Thr Val Leu Gly Gln
            100                 105                 110
```

<210> SEQ ID NO 183

```
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 183

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Thr Gly Leu
                85                  90                  95

Ser Gly Trp Val Phe Gly Gly Gly Thr Lys Leu Thr Val Leu Gly Gln
            100                 105                 110

<210> SEQ ID NO 184
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 184

Gln Ser Val Leu Thr Gln Pro Pro Ser Ala Ser Gly Thr Pro Gly Gln
1               5                   10                  15

Arg Val Thr Ile Ser Cys Ser Gly Leu Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Thr Gly Leu
                85                  90                  95

Ser Gly Trp Val Phe Gly Gly Gly Thr Lys Leu Thr Val Leu Gly Gln
            100                 105                 110

<210> SEQ ID NO 185
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 185

Gln Ser Val Leu Thr Gln Pro Pro Ser Ala Ser Gly Thr Pro Gly Gln
1               5                   10                  15

Arg Val Thr Ile Ser Cys Ser Gly Ser Asn Asp Asn Ile Gly Ser Asn
            20                  25                  30

Pro Val Asn Trp Tyr Gln Gln Leu Pro Gly Thr Ala Pro Lys Leu Leu
        35                  40                  45
```

```
Ile Tyr Asp Asn Asn Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ser Tyr Asp Thr Gly Leu
                 85                  90                  95

Ser Gly Trp Val Phe Gly Gly Gly Thr Lys Leu Thr Val Leu Gly Gln
            100                 105                 110
```

<210> SEQ ID NO 186
<211> LENGTH: 112
<212> TYPE: PRT
<213> ORGANISM: Artificial Sequence
<220> FEATURE:
<223> OTHER INFORMATION: maturated PRLR antibody

<400> SEQUENCE: 186

```
Gln Ser Val Leu Thr Gln Pro Pro Ser Ala Ser Gly Thr Pro Gly Gln
 1               5                  10                  15

Arg Val Thr Ile Ser Cys Ser Gly Ser Asn Ser Asn Val Gly Ser Asn
                20                  25                  30

Pro Val Asn Trp Tyr Gln Gln Leu Pro Gly Thr Ala Pro Lys Leu Leu
             35                  40                  45

Ile Tyr Asp Asn Asn Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ser Tyr Asp Thr Gly Leu
                 85                  90                  95

Ser Gly Trp Val Phe Gly Gly Gly Thr Lys Leu Thr Val Leu Gly Gln
            100                 105                 110
```

<210> SEQ ID NO 187
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 187

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Trp His Trp Val Arg Gln Ala Pro Gly Lys Gly Leu Glu Trp Val
             35                  40                  45

Ser Asp Ile Ala Arg Leu Ser Pro Tyr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
            100                 105                 110

Leu Val Thr Val Thr Ser Ser
        115
```

<210> SEQ ID NO 188

```
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
        35                  40                  45

Ser Asp Ile Ser Arg Leu Ser Pro Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 189
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Ser Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 190
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 190

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Ser Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 191
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ala Arg Leu Ser Pro Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 192
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ala Arg Leu Ser Pro Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 193
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 193

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
        35                  40                  45

Ser Asp Ile Ser Arg Ala Ser Pro Tyr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 194
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 194

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Ser Ala Ser Ser Tyr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

```
<210> SEQ ID NO 195
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ala Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 196
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ala Arg Leu Ser Pro Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 197
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 197

Glu Val Gln Leu Leu Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ser Ser Tyr
        20                  25                  30

Trp Asn His Trp Val Arg Gln Ala Pro Gly Lys Gly Leu Glu Trp Val
        35                  40                  45

Ser Asp Met Ala Arg Ala Ser Pro Tyr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 198
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 198

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
        20                  25                  30

Trp Trp His Trp Val Arg Gln Ala Pro Gly Lys Gly Leu Glu Trp Val
        35                  40                  45

Ser Asp Met Ser Arg Leu Ser Ser Tyr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 199
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 199

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
        20                  25                  30

Trp Asn His Trp Val Arg Gln Ala Pro Gly Lys Gly Leu Glu Trp Val
        35                  40                  45

Ser Asp Met Ser Arg Ala Ser Ser Tyr Thr Asn Tyr Ala Asp Ser Val
 50                  55                  60

Lys Gly Arg Phe Thr Ile Ser Arg Asp Asn Ser Lys Asn Thr Leu Tyr

```
              65                  70                  75                  80
Leu Gln Met Asn Ser Leu Arg Ala Glu Asp Thr Ala Val Tyr Tyr Cys
                    85                  90                  95

Ala Arg Gly Leu Asp Ala Arg Arg Met Asp Tyr Trp Gly Gln Gly Thr
                100                 105                 110

Leu Val Thr Val Thr Ser Ser
            115

<210> SEQ ID NO 200
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 200

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met His Trp Val Arg Gln Ala Pro Gly Lys Gly Leu Glu Trp Val
            35                  40                  45

Ser Asp Ile Ser Ser Ala Ser Ser Tyr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
                100                 105                 110

Leu Val Thr Val Thr Ser Ser
            115

<210> SEQ ID NO 201
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met His Trp Val Arg Gln Ala Pro Gly Lys Gly Leu Glu Trp Val
            35                  40                  45

Ser Asp Ile Ser Ser Ala Ser Ser Tyr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
                100                 105                 110

Leu Val Thr Val Thr Ser Ser
            115
```

```
<210> SEQ ID NO 202
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Ser Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 203
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Ser Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 204
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 204

Glu Val Gln Leu Leu Glu Ser Gly Gly Gly Leu Val Gln Pro Gly Gly
```

-continued

```
                1               5                  10                  15
        Ser Leu Arg Leu Ser Cys Ala Ala Ser Gly Phe Thr Phe Ser Ser Tyr
                    20                  25                  30

Trp Trp His Trp Val Arg Gln Ala Pro Gly Lys Gly Leu Glu Trp Val
                    35                  40                  45

Ser Asp Ile Ala Arg Ala Ser Pro Tyr Thr Asn Tyr Ala Asp Ser Val
                    50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                    85                  90                  95

Ala Arg Gly Leu Asp Ala Arg Arg Met Asp Tyr Trp Gly Gln Gly Thr
                    100                 105                 110

Leu Val Thr Val Thr Ser Ser
                    115

<210> SEQ ID NO 205
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 205

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
            35                  40                  45

Ser Asp Ile Ala Arg Ala Ser Pro Tyr Thr Asn Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 206
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 206

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
            35                  40                  45

Ser Asp Ile Ser Ser Leu Ser Tyr Thr Gly Tyr Ala Asp Ser Val
            50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 207
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 207

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Trp His Trp Val Arg Gln Ala Pro Gly Lys Gly Leu Glu Trp Val
             35                  40                  45

Ser Asp Ile Ser Ser Leu Ser Ser Tyr Thr Gly Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 208
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 208

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Met His Trp Val Arg Gln Ala Pro Gly Lys Gly Leu Glu Trp Val
             35                  40                  45

Ser Asp Ile Ser Ser Ala Ser Ser Tyr Thr Asn Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
            100                 105                 110

Leu Val Thr Val Thr Ser Ser
            115
```

<210> SEQ ID NO 209
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 209

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ala Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 210
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ser Arg Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 211
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 211

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ser Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 212
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 212

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ser Ser Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 213
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ser Arg Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 214
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 214

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ser Arg Leu Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 215
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 215

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ser Arg Leu Ser Pro Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser

<210> SEQ ID NO 216
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 216

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
        35                  40                  45

Ser Asp Ile Ser Arg Ala Ser Pro Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115
```

<210> SEQ ID NO 217
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 217

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ser Arg Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115
```

<210> SEQ ID NO 218
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 218

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ser Trp Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115
```

<210> SEQ ID NO 219
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 219

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Arg Ser Ser Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115
```

<210> SEQ ID NO 220
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 220

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Met Ser Ser Ala Ser Ser Tyr Thr Asn Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
                100                 105                 110

Leu Val Thr Val Thr Ser Ser
            115

<210> SEQ ID NO 221
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 221

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met His Trp Val Arg Gln Ala Pro Gly Lys Gly Leu Glu Trp Val
            35                  40                  45

Ser Asp Ile Ala Ser Ala Ser Ser Tyr Thr Asn Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
                100                 105                 110

Leu Val Thr Val Thr Ser Ser
            115

<210> SEQ ID NO 222
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 222

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met His Trp Val Arg Gln Ala Pro Gly Lys Gly Leu Glu Trp Val
            35                  40                  45

Ser Asp Ile Ser Trp Ala Ser Ser Tyr Thr Asn Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
                100                 105                 110
```

```
Leu Val Thr Val Thr Ser Ser
        115

<210> SEQ ID NO 223
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 223

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Arg Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 224
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Ser Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 225
<211> LENGTH: 119
<212> TYPE: PRT
<213> ORGANISM: Artificial Sequence
<220> FEATURE:
<223> OTHER INFORMATION: maturated PRLR antibody
```

```
<400> SEQUENCE: 225

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Ser Ala Ser Pro Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 226
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ser Ser Ala Ser Ser Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 227
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 227

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45
```

Ser Asp Met Ala Arg Leu Ser Pro Tyr Thr Asn Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
                100                 105                 110

Leu Val Thr Val Thr Ser Ser
                115

<210> SEQ ID NO 228
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 228

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Trp His Trp Val Arg Gln Ala Pro Gly Lys Gly Leu Glu Trp Val
                35                  40                  45

Ser Asp Met Ser Arg Ala Ser Ser Tyr Thr Asn Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
                100                 105                 110

Leu Val Thr Val Thr Ser Ser
                115

<210> SEQ ID NO 229
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 229

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Trp His Trp Val Arg Gln Ala Pro Gly Lys Gly Leu Glu Trp Val
                35                  40                  45

Ser Asp Ile Ala Arg Ala Ser Ser Tyr Thr Asn Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
                100                 105                 110

Leu Val Thr Val Thr Ser Ser
        115

<210> SEQ ID NO 230
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 230

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
        35                  40                  45

Ser Asp Met Ala Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 231
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 231

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ser Ser Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 232
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 232

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ala Arg Ala Ser Pro Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 233
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 233

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ala Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
            115

<210> SEQ ID NO 234
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 234

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ser Arg Leu Ser Ser Tyr Thr Asn Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 235
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 235

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Ser Tyr
                20                  25                  30

Trp Trp His Trp Val Arg Gln Ala Pro Gly Lys Gly Leu Glu Trp Val
            35                  40                  45

Ser Asp Met Ala Arg Ala Ser Ser Tyr Thr Asn Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 236
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 236

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Ser Tyr
                20                  25                  30

Trp Asn His Trp Val Arg Gln Ala Pro Gly Lys Gly Leu Glu Trp Val
            35                  40                  45

Ser Asp Met Ala Arg Ala Ser Pro Tyr Thr Gly Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr

Leu Val Thr Val Thr Ser Ser
        115

<210> SEQ ID NO 237
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 237

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
        35                  40                  45

Ser Asp Met Ser Arg Leu Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 238
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 238

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
        35                  40                  45

Ser Asp Ile Ala Arg Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 239
<211> LENGTH: 119
<212> TYPE: PRT
<213> ORGANISM: Artificial Sequence
<220> FEATURE:

<223> OTHER INFORMATION: maturated PRLR antibody

<400> SEQUENCE: 239

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
        35                  40                  45

Ser Asp Met Ser Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 240
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 240

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ser Arg Ala Ser Pro Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 241
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 241

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val

```
                35                  40                  45

Ser Asp Ile Ala Arg Ala Ser Ser Tyr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
                100                 105                 110

Leu Val Thr Val Thr Ser Ser
                115

<210> SEQ ID NO 242
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 242

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Asn His Trp Val Arg Gln Ala Pro Gly Lys Gly Leu Glu Trp Val
                 35                  40                  45

Ser Asp Ile Ser Arg Leu Ser Pro Tyr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
                100                 105                 110

Leu Val Thr Val Thr Ser Ser
                115

<210> SEQ ID NO 243
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 243

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Asn His Trp Val Arg Gln Ala Pro Gly Lys Gly Leu Glu Trp Val
                 35                  40                  45

Ser Asp Met Ala Ser Leu Ser Pro Tyr Thr Gly Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 244
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 244

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
        35                  40                  45

Ser Asp Ile Ala Arg Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 245
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 245

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ser Ser Leu Ser Ser Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 246
<211> LENGTH: 119
<212> TYPE: PRT
<213> ORGANISM: Artificial Sequence

```
<220> FEATURE:
<223> OTHER INFORMATION: maturated PRLR antibody

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ala Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 247
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 247

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ser Ser Leu Ser Ser Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 248
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 248

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Trp Trp His Trp Val Arg Gln Ala Pro Gly Lys Gly Leu Glu Trp Val
        35                  40                  45

Ser Asp Ile Ala Arg Leu Ser Pro Tyr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
                100                 105                 110

Leu Val Thr Val Thr Ser Ser
            115
```

<210> SEQ ID NO 249
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 249

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Asn His Trp Val Arg Gln Ala Pro Gly Lys Gly Leu Glu Trp Val
        35                  40                  45

Ser Asp Met Ser Arg Leu Ser Pro Tyr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Ala Arg Arg Met Asp Tyr Trp Gly Gln Gly Thr
                100                 105                 110

Leu Val Thr Val Thr Ser Ser
            115
```

<210> SEQ ID NO 250
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 250

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Asn His Trp Val Arg Gln Ala Pro Gly Lys Gly Leu Glu Trp Val
        35                  40                  45

Ser Asp Ile Ala Arg Leu Ser Pro Tyr Thr Gly Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 251
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 251

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Met Ala Ser Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 252
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 252

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ser Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 253
<211> LENGTH: 119
<212> TYPE: PRT
```

<213> ORGANISM: Artificial Sequence
<220> FEATURE:
<223> OTHER INFORMATION: maturated PRLR antibody

<400> SEQUENCE: 253

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Trp His Trp Val Arg Gln Ala Pro Gly Lys Gly Leu Glu Trp Val
        35                  40                  45

Ser Asp Ile Ser Arg Ala Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 254
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 254

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Asn His Trp Val Arg Gln Ala Pro Gly Lys Gly Leu Glu Trp Val
        35                  40                  45

Ser Asp Ile Ser Arg Ala Ser Pro Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Thr Ser Ser
        115

<210> SEQ ID NO 255
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Trp Asn His Trp Val Arg Gln Ala Pro Gly Lys Gly Leu Glu Trp Val
            35                  40                  45

Ser Asp Ile Ala Ser Ala Ser Ser Tyr Thr Gly Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
               100                 105                 110

Leu Val Thr Val Thr Ser Ser
               115
```

<210> SEQ ID NO 256
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 256

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Asn His Trp Val Arg Gln Ala Pro Gly Lys Gly Leu Glu Trp Val
            35                  40                  45

Ser Asp Ile Ala Arg Ala Ser Ser Tyr Thr Gly Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
               100                 105                 110

Leu Val Thr Val Thr Ser Ser
               115
```

<210> SEQ ID NO 257
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 257

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Asn His Trp Val Arg Gln Ala Pro Gly Lys Gly Leu Glu Trp Val
            35                  40                  45

Ser Asp Ile Ser Arg Leu Ser Pro Tyr Thr Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                    85                  90                  95

Ala Arg Gly Leu Asp Ala Arg Arg Met Asp Tyr Trp Gly Gln Gly Thr
                100                 105                 110

Leu Val Thr Val Thr Ser Ser
            115

<210> SEQ ID NO 258
<211> LENGTH: 119
<212> TYPE: PRT
<213> ORGANISM: Artificial Sequence
<220> FEATURE:
<223> OTHER INFORMATION: maturated PRLR antibody

<400> SEQUENCE: 258

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Asn His Trp Val Arg Gln Ala Pro Gly Lys Gly Leu Glu Trp Val
                35                  40                  45

Ser Asp Ile Ser Arg Ala Ser Pro Tyr Thr Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
                100                 105                 110

Leu Val Thr Val Thr Ser Ser
            115

<210> SEQ ID NO 259
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 259

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
                35                  40                  45

Leu Ile Tyr Arg Asn Asn Val Arg Gln Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
                100                 105                 110

Gln

<210> SEQ ID NO 260
<211> LENGTH: 113
<212> TYPE: PRT
```

```
<213> ORGANISM: Artificial Sequence
<220> FEATURE:
<223> OTHER INFORMATION: maturated PRLR antibody

<400> SEQUENCE: 260

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val His Trp Tyr Gln Gln Leu Pro Gly Thr Ala Pro Lys Leu
            35                  40                  45

Leu Ile Tyr Arg Asn Asn Val Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 261
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 261

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Arg Asn Asn Val Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 262
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 262

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
```

```
                35                  40                  45
Leu Ile Tyr Arg Asn Asn Trp Arg Pro Ser Gly Val Pro Asp Arg Phe
 50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
                100                 105                 110

Gln

<210> SEQ ID NO 263
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 263

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
                35                  40                  45

Leu Ile Tyr Arg Asn Asn Gln Arg Gln Ser Gly Val Pro Asp Arg Phe
 50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
                100                 105                 110

Gln

<210> SEQ ID NO 264
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 264

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
                35                  40                  45

Leu Ile Tyr Arg Asn Asn Val Arg Gln Ser Gly Val Pro Asp Arg Phe
 50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
                100                 105                 110
```

Gln

```
<210> SEQ ID NO 265
<211> LENGTH: 113
<212> TYPE: PRT
<213> ORGANISM: Artificial Sequence
<220> FEATURE:
<223> OTHER INFORMATION: maturated PRLR antibody
```

<400> SEQUENCE: 265

| Gln | Ser | Val | Leu | Thr | Gln | Pro | Pro | Ser | Ala | Ser | Gly | Thr | Pro | Gly | Gln |
|---|---|---|---|---|---|---|---|---|---|---|---|---|---|---|---|
| 1 | | | | 5 | | | | | 10 | | | | | 15 | |

| Arg | Val | Thr | Ile | Ser | Cys | Thr | Gly | Val | Ser | Ser | Asn | Ile | Gly | Ala | Gly |
| | | | 20 | | | | | 25 | | | | | 30 | | |

| Tyr | Val | Val | His | Trp | Tyr | Gln | Gln | Leu | Pro | Gly | Thr | Ala | Pro | Lys | Leu |
| | | 35 | | | | | 40 | | | | | 45 | | | |

| Leu | Ile | Tyr | Arg | Asn | Asn | Gln | Arg | Pro | Ser | Gly | Val | Pro | Asp | Arg | Phe |
| | 50 | | | | | 55 | | | | | 60 | | | | |

| Ser | Gly | Ser | Lys | Ser | Gly | Thr | Ser | Ala | Ser | Leu | Ala | Ile | Ser | Gly | Leu |
| 65 | | | | | 70 | | | | | 75 | | | | | 80 |

| Arg | Ser | Glu | Asp | Glu | Ala | Asp | Tyr | Tyr | Cys | Ala | Ala | Trp | Asp | Asp | Ser |
| | | | | 85 | | | | | 90 | | | | | 95 | |

| Leu | Asn | Gly | Trp | Leu | Phe | Gly | Gly | Gly | Thr | Lys | Leu | Thr | Val | Leu | Gly |
| | | | 100 | | | | | 105 | | | | | 110 | | |

Gln

```
<210> SEQ ID NO 266
<211> LENGTH: 113
<212> TYPE: PRT
<213> ORGANISM: Artificial Sequence
<220> FEATURE:
<223> OTHER INFORMATION: maturated PRLR antibody
```

<400> SEQUENCE: 266

| Gln | Ser | Val | Leu | Thr | Gln | Pro | Pro | Ser | Ala | Ser | Gly | Thr | Pro | Gly | Gln |
|---|---|---|---|---|---|---|---|---|---|---|---|---|---|---|---|
| 1 | | | | 5 | | | | | 10 | | | | | 15 | |

| Arg | Val | Thr | Ile | Ser | Cys | Thr | Gly | Ser | Ser | Ser | Asn | Ile | Gly | Ala | Gly |
| | | | 20 | | | | | 25 | | | | | 30 | | |

| Tyr | Val | Val | His | Trp | Tyr | Gln | Gln | Leu | Pro | Gly | Thr | Ala | Pro | Lys | Leu |
| | | 35 | | | | | 40 | | | | | 45 | | | |

| Leu | Ile | Tyr | Arg | Asn | Asn | Gln | Gln | Ser | Gly | Val | Pro | Asp | Arg | Phe |
| | 50 | | | | | 55 | | | | | 60 | | | |

| Ser | Gly | Ser | Lys | Ser | Gly | Thr | Ser | Ala | Ser | Leu | Ala | Ile | Ser | Gly | Leu |
| 65 | | | | | 70 | | | | | 75 | | | | | 80 |

| Arg | Ser | Glu | Asp | Glu | Ala | Asp | Tyr | Tyr | Cys | Ala | Ala | Trp | Asp | Asp | Ser |
| | | | | 85 | | | | | 90 | | | | | 95 | |

| Leu | Asn | Gly | Trp | Leu | Phe | Gly | Gly | Gly | Thr | Lys | Leu | Thr | Val | Leu | Gly |
| | | | 100 | | | | | 105 | | | | | 110 | | |

Gln

```
<210> SEQ ID NO 267
<211> LENGTH: 113
<212> TYPE: PRT
<213> ORGANISM: Artificial Sequence
<220> FEATURE:
<223> OTHER INFORMATION: maturated PRLR antibody
```

<400> SEQUENCE: 267

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 268
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 268

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Val Arg Gln Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 269
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 269

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Leu Pro Gly Thr Ala Pro Lys Leu
            35                  40                  45

Leu Ile Tyr Arg Asn Asn Val Arg Pro Ser Gly Val Pro Asp Arg Phe
        50                  55                  60

Ser Gly Ser Lys Ser Gly Thr Ser Ala Ser Leu Ala Ile Ser Gly Leu 65                  70                  75                  80
Arg Ser Glu Asp Glu Ala Asp Tyr Tyr Cys Ala Ala Trp Asp Asp Ser
                     85                  90                  95

Leu Asn Gly Trp Leu Phe Gly Gly Gly Thr Lys Leu Thr Val Leu Gly
                100                 105                 110

Gln

<210> SEQ ID NO 270
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 270

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Val Arg Gln Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                    85                  90                  95

Leu Asn Gly Trp Leu Phe Gly Gly Gly Thr Lys Leu Thr Val Leu Gly
                100                 105                 110

Gln

<210> SEQ ID NO 271
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 271

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Gln Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                    85                  90                  95

Leu Asn Gly Trp Leu Phe Gly Gly Gly Thr Lys Leu Thr Val Leu Gly
                100                 105                 110

Gln

<210> SEQ ID NO 272
<211> LENGTH: 113

```
<212> TYPE: PRT
<213> ORGANISM: Artificial Sequence
<220> FEATURE:
<223> OTHER INFORMATION: maturated PRLR antibody

<400> SEQUENCE: 272

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Trp Leu Phe Gly Gly Gly Thr Lys Leu Thr Val Leu Gly
            100                 105                 110

Gln

<210> SEQ ID NO 273
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 273

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Gly Gly Trp Leu Phe Gly Gly Gly Thr Lys Leu Thr Val Leu Gly
            100                 105                 110

Gln

<210> SEQ ID NO 274
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 274

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30
```

```
Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
 50                      55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Phe Gly Trp Leu Phe Gly Gly Gly Thr Lys Leu Thr Val Leu Gly
            100                 105                 110

Gln

<210> SEQ ID NO 275
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 275

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ala Gly
             20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
 50                      55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Leu Gly Trp Leu Phe Gly Gly Gly Thr Lys Leu Thr Val Leu Gly
            100                 105                 110

Gln

<210> SEQ ID NO 276
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 276

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Tyr Gly
             20                  25                  30

Tyr Val Val His Trp Tyr Gln Gln Leu Pro Gly Thr Ala Pro Lys Leu
            35                  40                  45

Leu Ile Tyr Arg Asn Asn Val Arg Gln Ser Gly Val Pro Asp Arg Phe
 50                      55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
```

<210> SEQ ID NO 277
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 277

```
Gln Ser Val Leu Thr Gln Pro Pro Ser Ala Ser Gly Thr Pro Gly Gln
1               5                   10                  15
Arg Val Thr Ile Ser Cys Thr Gly Ser Ser Asn Ile Gly Tyr Gly
            20                  25                  30
Tyr Val Val His Trp Tyr Gln Gln Leu Pro Gly Thr Ala Pro Lys Leu
        35                  40                  45
Leu Ile Tyr Arg Asn Asn Val Arg Pro Ser Gly Val Pro Asp Arg Phe
    50                  55                  60
Ser Gly Ser Lys Ser Gly Thr Ser Ala Ser Leu Ala Ile Ser Gly Leu
65                  70                  75                  80
Arg Ser Glu Asp Glu Ala Asp Tyr Tyr Cys Ala Ala Trp Asp Asp Ser
                85                  90                  95
Leu Asn Gly Trp Leu Phe Gly Gly Gly Thr Lys Leu Thr Val Leu Gly
            100                 105                 110
Gln
```

<210> SEQ ID NO 278
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 278

```
Gln Ser Val Leu Thr Gln Pro Pro Ser Ala Ser Gly Thr Pro Gly Gln
1               5                   10                  15
Arg Val Thr Ile Ser Cys Thr Gly Ser Ser Asn Ile Gly Tyr Gly
            20                  25                  30
Tyr Val Val His Trp Tyr Gln Gln Leu Pro Gly Thr Ala Pro Lys Leu
        35                  40                  45
Leu Ile Tyr Arg Asn Asn Trp Arg Pro Ser Gly Val Pro Asp Arg Phe
    50                  55                  60
Ser Gly Ser Lys Ser Gly Thr Ser Ala Ser Leu Ala Ile Ser Gly Leu
65                  70                  75                  80
Arg Ser Glu Asp Glu Ala Asp Tyr Tyr Cys Ala Ala Trp Asp Asp Ser
                85                  90                  95
Leu Asn Gly Trp Leu Phe Gly Gly Gly Thr Lys Leu Thr Val Leu Gly
            100                 105                 110
Gln
```

<210> SEQ ID NO 279
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 279

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Trp Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln
```

<210> SEQ ID NO 280
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 280

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln
```

<210> SEQ ID NO 281
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 281

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Val Arg Gln Ser Gly Val Pro Asp Arg Phe
        50                  55                  60
```

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 282
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 282

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 283
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 283

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Gln Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 284

```
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 284

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 285
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 285

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
            20                  25                  30

Tyr Val Val His Trp Tyr Gln Gln Leu Pro Gly Thr Ala Pro Lys Leu
        35                  40                  45

Leu Ile Tyr Arg Asn Asn Val Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 286
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 286

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
            20                  25                  30
```

```
Tyr Val Val His Trp Tyr Gln Gln Leu Pro Gly Thr Ala Pro Lys Leu
            35                  40                  45

Leu Ile Tyr Arg Asn Asn Val Arg Gln Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
            85                  90                  95

Leu Asn Gly Trp Leu Phe Gly Gly Gly Thr Lys Leu Thr Val Leu Gly
            100                 105                 110

Gln

<210> SEQ ID NO 287
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 287

Gln Ser Val Leu Thr Gln Pro Pro Ser Ala Ser Gly Thr Pro Gly Gln
 1               5                   10                  15

Arg Val Thr Ile Ser Cys Thr Gly Ser Ser Ser Asn Ile Gly Tyr Gly
            20                  25                  30

Tyr Val Val His Trp Tyr Gln Gln Leu Pro Gly Thr Ala Pro Lys Leu
            35                  40                  45

Leu Ile Tyr Arg Asn Asn Val Arg Gln Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
            85                  90                  95

Leu Asn Gly Trp Leu Phe Gly Gly Gly Thr Lys Leu Thr Val Leu Gly
            100                 105                 110

Gln

<210> SEQ ID NO 288
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 288

Gln Ser Val Leu Thr Gln Pro Pro Ser Ala Ser Gly Thr Pro Gly Gln
 1               5                   10                  15

Arg Val Thr Ile Ser Cys Thr Gly Ser Ser Ser Asn Ile Gly Tyr Gly
            20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
            85                  90                  95
```

-continued

Leu Asn Gly Trp Leu Phe Gly Gly Gly Thr Lys Leu Thr Val Leu Gly
            100                 105                 110

Gln

<210> SEQ ID NO 289
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 289

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
            20                  25                  30

Tyr Val Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 290
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 290

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
            20                  25                  30

Tyr Val Val His Trp Tyr Gln Gln Leu Pro Gly Thr Ala Pro Lys Leu
        35                  40                  45

Leu Ile Tyr Arg Asn Asn Gln Arg Gln Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 291
<211> LENGTH: 113
<212> TYPE: PRT
<213> ORGANISM: Artificial Sequence
<220> FEATURE:
<223> OTHER INFORMATION: maturated PRLR antibody -continued

```
<400> SEQUENCE: 291

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 292
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 292

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 293
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 293

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60
```

```
Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln
```

<210> SEQ ID NO 294
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 294

```
Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ala Gly
                 20                  25                  30

Tyr Val Val His Trp Tyr Gln Gln Leu Pro Gly Thr Ala Pro Lys Leu
             35                  40                  45

Leu Ile Tyr Arg Asn Asn Gln Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln
```

<210> SEQ ID NO 295
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 295

```
Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ala Gly
                 20                  25                  30

Tyr Val Val His Trp Tyr Gln Gln Leu Pro Gly Thr Ala Pro Lys Leu
             35                  40                  45

Leu Ile Tyr Arg Asn Asn Gln Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln
```

```
<210> SEQ ID NO 296
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 296
```

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

```
<210> SEQ ID NO 297
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 297
```

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

```
<210> SEQ ID NO 298
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 298
```

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly

```
                    20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 299
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 299

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 300
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 300

Gln Ser Val Leu Thr Gln Pro Pro Ser Ala Ser Gly Thr Pro Gly Gln
1               5                   10                  15

Arg Val Thr Ile Ser Cys Thr Gly Gln Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95
```

-continued

Leu Asn Gly Trp Leu Phe Gly Gly Gly Thr Lys Leu Thr Val Leu Gly
              100                 105                 110

Gln

<210> SEQ ID NO 301
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 301

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
            20                  25                  30

Tyr Val Val His Trp Tyr Gln Gln Leu Pro Gly Thr Ala Pro Lys Leu
        35                  40                  45

Leu Ile Tyr Arg Asn Asn Trp Arg Gln Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
              100                 105                 110

Gln

<210> SEQ ID NO 302
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 302

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Val Arg Gln Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
              100                 105                 110

Gln

<210> SEQ ID NO 303
<211> LENGTH: 113
<212> TYPE: PRT
<213> ORGANISM: Artificial Sequence
<220> FEATURE:
<223> OTHER INFORMATION: maturated PRLR antibody -continued

<400> SEQUENCE: 303

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Val Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 304
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 304

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Val Arg Gln Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 305
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 305

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Trp Arg Pro Ser Gly Val Pro Asp Arg Phe

```
                    50                  55                  60
Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln

<210> SEQ ID NO 306
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 306

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ala Gly
             20                  25                  30

Tyr Val Val His Trp Tyr Gln Gln Leu Pro Gly Thr Ala Pro Lys Leu
         35                  40                  45

Leu Ile Tyr Arg Asn Asn Trp Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln

<210> SEQ ID NO 307
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 307

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ala Gly
             20                  25                  30

Tyr Val Val His Trp Tyr Gln Gln Leu Pro Gly Thr Ala Thr Lys Leu
         35                  40                  45

Leu Ile Tyr Arg Asn Asn Val Arg Gln Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln
```

<210> SEQ ID NO 308
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 308

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
            35                  40                  45

Leu Ile Tyr Arg Asn Asn Trp Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln
```

<210> SEQ ID NO 309
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 309

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
            35                  40                  45

Leu Ile Tyr Arg Asn Asn Val Arg Gln Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln
```

<210> SEQ ID NO 310
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 310

```
Gln Ser Val Leu Thr Gln Pro Pro Ser Ala Ser Gly Thr Pro Gly Gln
1               5                   10                  15
```

Arg Val Thr Ile Ser Cys Thr Gly Ser Ser Asn Ile Gly Tyr Gly
                20                  25                  30

Tyr Val Val His Trp Tyr Gln Gln Leu Pro Gly Thr Ala Pro Lys Leu
            35                  40                  45

Leu Ile Tyr Arg Asn Asn Trp Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
                100                 105                 110

Gln

<210> SEQ ID NO 311
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 311

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Gln Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
                100                 105                 110

Gln

<210> SEQ ID NO 312
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 312

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Arg Asn Asn Trp Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser 85                  90                  95

Leu Asn Gly Trp Leu Phe Gly Gly Gly Thr Lys Leu Thr Val Leu Gly
                100                 105                 110

Gln

<210> SEQ ID NO 313
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 313

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Arg Asn Asn Trp Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
                100                 105                 110

Gln

<210> SEQ ID NO 314
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 314

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Gln Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
                100                 105                 110

Gln

<210> SEQ ID NO 315
<211> LENGTH: 113
<212> TYPE: PRT
<213> ORGANISM: Artificial Sequence
<220> FEATURE:

<223> OTHER INFORMATION: maturated PRLR antibody

<400> SEQUENCE: 315

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Gln Arg Gln Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 316
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 316

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
            20                  25                  30

Tyr Val Val His Trp Tyr Gln Gln Leu Pro Gly Thr Ala Pro Lys Leu
        35                  40                  45

Leu Ile Tyr Arg Asn Asn Trp Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 317
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 317

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

```
Leu Ile Tyr Arg Asn Asn Val Arg Gln Ser Gly Val Pro Asp Arg Phe
    50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln

<210> SEQ ID NO 318
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 318

Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Ala Gly
                 20                  25                  30

Tyr Val Val His Trp Tyr Gln Gln Leu Pro Gly Thr Ala Pro Lys Leu
             35                  40                  45

Leu Ile Tyr Arg Asn Asn Val Arg Gln Ser Gly Val Pro Asp Arg Phe
    50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln

<210> SEQ ID NO 319
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 319

Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Ala Gly
                 20                  25                  30

Tyr Val Val His Trp Tyr Gln Gln Leu Pro Gly Thr Ala Pro Lys Leu
             35                  40                  45

Leu Ile Tyr Arg Asn Asn Trp Arg Gln Ser Gly Val Pro Asp Arg Phe
    50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
            100                 105                 110

Gln
```

<210> SEQ ID NO 320
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 320

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Trp Arg Gln Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 321
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 321

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Trp Arg Gln Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 322
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 322

Gln Ser Val Leu Thr Gln Pro Pro Ser Ala Ser Gly Thr Pro Gly Gln
1               5                   10                  15

```
Arg Val Thr Ile Ser Cys Thr Gly Ser Ser Asn Ile Gly Ala Gly
            20                  25                  30

Tyr Val His Trp Tyr Gln Gln Leu Pro Gly Thr Ala Pro Lys Leu
        35                  40                  45

Leu Ile Tyr Arg Asn Asn Val Arg Gln Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 323
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 323

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val His Trp Tyr Gln Gln Leu Pro Gly Thr Ala Pro Lys Leu
        35                  40                  45

Leu Ile Tyr Arg Asn Asn Trp Arg Gln Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 324
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 324

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Tyr Gly
            20                  25                  30

Tyr Val Val His Trp Tyr Gln Gln Leu Pro Gly Thr Ala Pro Lys Leu
        35                  40                  45

Leu Ile Tyr Arg Asn Asn Trp Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80
```

```
Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 325
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 325

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Tyr Gly
            20                  25                  30

Tyr Val Val His Trp Tyr Gln Gln Leu Pro Gly Thr Ala Pro Lys Leu
        35                  40                  45

Leu Ile Tyr Arg Asn Asn Trp Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 326
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 326

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Gln Arg Gln Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 327
<211> LENGTH: 113
<212> TYPE: PRT
<213> ORGANISM: Artificial Sequence
```

```
<220> FEATURE:
<223> OTHER INFORMATION: maturated PRLR antibody

<400> SEQUENCE: 327

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Trp Arg Gln Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
            85                  90                  95

Leu Asn Gly Trp Leu Phe Gly Gly Gly Thr Lys Leu Thr Val Leu Gly
            100                 105                 110

Gln

<210> SEQ ID NO 328
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 328

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Trp Arg Gln Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
            85                  90                  95

Leu Asn Gly Trp Leu Phe Gly Gly Gly Thr Lys Leu Thr Val Leu Gly
            100                 105                 110

Gln

<210> SEQ ID NO 329
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 329

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45
```

```
Leu Ile Tyr Arg Asn Asn Trp Arg Pro Ser Gly Val Pro Asp Arg Phe
        50                  55                  60
Ser Gly Ser Lys Ser Gly Thr Ser Ala Ser Leu Ala Ile Ser Gly Leu
 65                  70                  75                  80
Arg Ser Glu Asp Glu Ala Asp Tyr Tyr Cys Ala Ala Trp Asp Asp Ser
                85                  90                  95
Leu Asn Gly Trp Leu Phe Gly Gly Gly Thr Lys Leu Thr Val Leu Gly
               100                 105                 110
Gln
```

<210> SEQ ID NO 330
<211> LENGTH: 113
<212> TYPE: PRT
<213> ORGANISM: Artificial Sequence
<220> FEATURE:
<223> OTHER INFORMATION: maturated PRLR antibody

<400> SEQUENCE: 330

```
Gln Ser Val Leu Thr Gln Pro Pro Ser Ala Ser Gly Thr Pro Gly Gln
 1               5                  10                  15
Arg Val Thr Ile Ser Cys Thr Gly Ser Ser Ser Asn Ile Gly Ala Gly
                20                  25                  30
Tyr Val Val His Trp Tyr Gln Gln Leu Pro Gly Thr Ala Pro Lys Leu
            35                  40                  45
Leu Ile Tyr Arg Asn Asn Gln Arg Gln Ser Gly Val Pro Asp Arg Phe
        50                  55                  60
Ser Gly Ser Lys Ser Gly Thr Ser Ala Ser Leu Ala Ile Ser Gly Leu
 65                  70                  75                  80
Arg Ser Glu Asp Glu Ala Asp Tyr Tyr Cys Ala Ala Trp Asp Asp Ser
                85                  90                  95
Leu Asn Gly Trp Leu Phe Gly Gly Gly Thr Lys Leu Thr Val Leu Gly
               100                 105                 110
Gln
```

<210> SEQ ID NO 331
<211> LENGTH: 357
<212> TYPE: DNA
<213> ORGANISM: Artificial Sequence
<220> FEATURE:
<223> OTHER INFORMATION: maturated PRLR antibody

<400> SEQUENCE: 331

```
gaagttcagc tgctggaaag cggtggtggt ctggttcagc ctggtggtag cctgcgtctg    60
agctgtgcag caagcggttt tacctttgat gattatggta tgagctgggt tcgtcaggca   120
ccgggtaaag gtctggaaat ggttgcagtt attagctttg atggcagcaa taaatattat   180
gccgatagcg tgaaaggtcg ctttaccatt agccgtgata tagccagaa taccctgtat    240 ctgcagatga atagcctgcg tgcagaagat accgcagttt attattgtgc aagtccgctg   300
gaaagtccgg ttgcatttga tatttggggt cagggcaccc tggttaccgt tagcagc     357
```

<210> SEQ ID NO 332
<211> LENGTH: 357
<212> TYPE: DNA
<213> ORGANISM: Artificial Sequence
<220> FEATURE:
<223> OTHER INFORMATION: maturated PRLR antibody

<400> SEQUENCE: 332

```
gaagttcagc tgctggaaag cggtggtggt ctggttcagc ctggtggtag cctgcgtctg    60
agctgtgcag caagcggttt tacctttgat gattatggta tgagctgggt tcgtcaggca   120
ccgggtaaag gtctggaaat ggttgcagtt attagctatg atggcagcaa taaatattat   180
gccgatagcg tgaaaggtcg ctttaccatt agccgtgata atagccagaa tacccctgtat   240 ctgcagatga atagcctgcg tgcagaagat accgcagttt attattgtgc aagtccgctg   300
gaaagtccgg ttgcatttga tatttggggt cagggcaccc tggttaccgt tagcagc      357
```

<210> SEQ ID NO 333
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 333

```
gaagttcagc tgctggaaag cggtggtggt ctggttcagc ctggtggtag cctgcgtctg    60
agctgtgcag caagcggttt tacctttgat gattatggta tgagctgggt tcgtcaggca   120
ccgggtaaag gtctggaatg ggttgcagtt attagctatg atggcagcaa taaatattat   180
gccgatagcg tgaaaggtcg ctttaccatt agccgtgata atagccagaa tacccctgtat   240 ctgcagatga atagcctgcg tgcagaagat accgcagttt attattgtgc aagtccgctg   300
gaaagtccgg ttgcatttga tatttggggt cagggcaccc tggttaccgt tagctcagca   360
tatatgcagc                                                          370
```

<210> SEQ ID NO 334
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 334

```
gaagttcagc tgctggaaag cggtggtggt ctggttcagc ctggtggtag cctgcgtctg    60
agctgtgcag caagcggttt tacctttgat gattatggta tgagctgggt tcgtcaggca   120
ccgggtaaag gtctggaatg ggttgcagtt attagctatg atggcagcaa taaatattat   180
gccgatagcg tgaaaggtcg ctttaccatt agccgtgata atagccagaa tacccctgtat   240 ctgcagatga atagcctgcg tgcagaagat accgcagttt attattgtgc aagtccgctg   300
gaaagtccgg ttgcatttga tatttggggt cagggcaccc tggttaccgt tagctcagca   360
tatatgcagc                                                          370
```

<210> SEQ ID NO 335
<211> LENGTH: 357
<212> TYPE: DNA
<213> ORGANISM: Artificial Sequence
<220> FEATURE:
<223> OTHER INFORMATION: maturated PRLR antibody

<400> SEQUENCE: 335

```
gaagttcagc tgctggaaag cggtggtggt ctggttcagc ctggtggtag cctgcgtctg    60
agctgtgcag caagcggttt tacctttgat gattatggta tgagctgggt tcgtcaggca   120
ccgggtaaag gtctggaaat ggttgcagtt attagctttg atggcagcaa taaatattat   180
gccgatagcg tgaaaggtcg ctttaccatt agccgtgata atagccagaa tacccctgtat   240
```

```
ctgcagatga atagcctgcg tgcagaagat accgcagttt attattgtgc aagtccgctg    300
gaaagtccgg ttgcatttga tatttggggt cagggcaccc tggttaccgt tagcagc      357
```

<210> SEQ ID NO 336
<211> LENGTH: 357
<212> TYPE: DNA
<213> ORGANISM: Artificial Sequence
<220> FEATURE:
<223> OTHER INFORMATION: maturated PRLR antibody

<400> SEQUENCE: 336

```
gaagttcagc tgctggaaag cggtggtggt ctggttcagc ctggtggtag cctgcgtctg    60
agctgtgcag caagcggttt tacctttgat gattatggta tgagctgggt tcgtcaggca    120
ccgggtaaag gtctggaaat ggttgcagtt attagctttg atggcagcaa taaatattat    180
gccgatagcg tgaaaggtcg ctttaccatt agccgtgata tagccagaa taccctgtat     240 ctgcagatga atagcctgcg tgcagaagat accgcagttt attattgtgc aagtccgctg    300
gaaagtccgg ttgcatttga tatttggggt cagggcaccc tggttaccgt tagcagc      357
```

<210> SEQ ID NO 337
<211> LENGTH: 357
<212> TYPE: DNA
<213> ORGANISM: Artificial Sequence
<220> FEATURE:
<223> OTHER INFORMATION: maturated PRLR antibody

<400> SEQUENCE: 337

```
gaagttcagc tgctggaaag cggtggtggt ctggttcagc ctggtggtag cctgcgtctg    60
agctgtgcag caagcggttt tacctttgat gattatggta tgagctgggt tcgtcaggca    120
ccgggtaaag gtctggaaat ggttgcagtt attagctttg atggcagcaa taaatattat    180
gccgatagcg tgaaaggtcg ctttaccatt agccgtgata tagccagaa taccctgtat     240 ctgcagatga atagcctgcg tgcagaagat accgcagttt attattgtgc aagtccgctg    300
gaaagtccgg ttgcatttga tatttggggt cagggcaccc tggttaccgt tagcagc      357
```

<210> SEQ ID NO 338
<211> LENGTH: 357
<212> TYPE: DNA
<213> ORGANISM: Artificial Sequence
<220> FEATURE:
<223> OTHER INFORMATION: maturated PRLR antibody

<400> SEQUENCE: 338

```
gaagttcagc tgctggaaag cggtggtggt ctggttcagc ctggtggtag cctgcgtctg    60
agctgtgcag caagcggttt tacctttgat gattatggta tgagctgggt tcgtcaggca    120
ccgggtaaag gtctggaaat ggttgcagtt attagctttg atggcagcaa taaatattat    180
gccgatagcg tgaaaggtcg ctttaccatt agccgtgata tagccagaa taccctgtat     240 ctgcagatga atagcctgcg tgcagaagat accgcagttt attattgtgc aagtccgctg    300
gaaagtccgg ttgcatttga tatttggggt cagggcaccc tggttaccgt tagcagc      357
```

<210> SEQ ID NO 339
<211> LENGTH: 357
<212> TYPE: DNA
<213> ORGANISM: Artificial Sequence
<220> FEATURE:
<223> OTHER INFORMATION: maturated PRLR antibody

<400> SEQUENCE: 339

```
gaagttcagc tgctggaaag cggtggtggt ctggttcagc ctggtggtag cctgcgtctg      60
agctgtgcag caagcggttt tacctttgat gattatggta tgagctgggt tcgtcaggca     120
ccgggtaaag gtctggaaat ggttgcagtt attagctttg atggcaccaa taaatattat     180
gccgatagcg tgaaaggtcg ctttaccatt agccgtgata atagccagaa taccctgtat     240
ctgcagatga atagcctgcg tgcagaagat accgcagttt attattgtgc aagtccgctg     300
gaaagtccgg ttgcatttga tatttggggt cagggcaccc tggttaccgt tagcagc        357
```

<210> SEQ ID NO 340
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 340

```
gaagttcagc tgctggaaag cggtggtggt ctggttcagc ctggtggtag cctgcgtctg      60
agctgtgcag caagcggttt tacctttgat gattatggta tgagctgggt tcgtcaggca     120
ccgggtaaag gtctggaatg ggttgcagtt attagctatg atggcagcaa taaatattat     180
gccgatagcg tgaaaggtcg ctttaccatt agccgtgata atagccagaa taccctgtat     240
ctgcagatga atagcctgcg tgcagaagat accgcagttt attattgtgc aagtccgctg     300
gaaagtccgg ttgcatttga tatttggggt cagggcaccc tggttaccgt tagctcagca     360
tatatgcagc                                                            370
```

<210> SEQ ID NO 341
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 341

```
gaagttcagc tgctggaaag cggtggtggt ctggttcagc ctggtggtag cctgcgtctg      60
agctgtgcag caagcggttt tacctttgat gattatggta tgagctgggt tcgtcaggca     120
ccgggtaaag gtctggaatg ggttgcagtt attagctatg atggcagcaa taaatattat     180
gccgatagcg tgaaaggtcg ctttaccatt agccgtgata atagccagaa taccctgtat     240
ctgcagatga atagcctgcg tgcagaagat accgcagttt attattgtgc aagtccgctg     300
gaaagtccgg ttgcatttga tatttggggt cagggcaccc tggttaccgt tagctcagca     360
tatatgcagc                                                            370
```

<210> SEQ ID NO 342
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 342

```
gaagttcagc tgctggaaag cggtggtggt ctggttcagc ctggtggtag cctgcgtctg      60
agctgtgcag caagcggttt tacctttgat gattatggta tgagctgggt tcgtcaggca     120
ccgggtaaag gtctggaatg ggttgcagtt attagctatg atggcagcaa taaatattat     180
gccgatagcg tgaaaggtcg ctttaccatt agccgtgata atagccagaa taccctgtat     240
```

```
ctgcagatga atagcctgcg tgcagaagat accgcagttt attattgtgc aagtccgctg    300
gaaagtccgg ttgcatttga tatttggggt cagggcaccc tggttaccgt tagctcagca    360
tatatgcagc                                                           370
```

<210> SEQ ID NO 343
<211> LENGTH: 357
<212> TYPE: DNA
<213> ORGANISM: Artificial Sequence
<220> FEATURE:
<223> OTHER INFORMATION: maturated PRLR antibody

<400> SEQUENCE: 343

```
gaagttcagc tgctggaaag cggtggtggt ctggttcagc ctggtggtag cctgcgtctg     60
agctgtgcag caagcggttt tacctttgat gattatggta tgagctgggt tcgtcaggca    120
ccgggtaaag gtctggaaat ggttgcagtt attagctttg atggcagcaa taaatattat    180
gccgatagcg tgaaaggtcg ctttaccatt agccgtgata atagccagaa taccctgtat    240
ctgcagatga atagcctgcg tgcagaagat accgcagttt attattgtgc aagtccgctg    300
gaaagtccgg ttgcatttga tatttggggt cagggcaccc tggttaccgt tagcagc      357
```

<210> SEQ ID NO 344
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 344

```
gaagttcagc tgctggaaag cggtggtggt ctggttcagc ctggtggtag cctgcgtctg     60
agctgtgcag caagcggttt tacctttgat gattatggta tgagctgggt tcgtcaggca    120
ccgggtaaag gtctggaatg ggttgcagtt attagctatg atggcagcaa taaatattat    180
gccgatagcg tgaaaggtcg ctttaccatt agccgtgata atagccagaa taccctgtat    240
ctgcagatga atagcctgcg tgcagaagat accgcagttt attattgtgc aagtccgctg    300
gaaagtccgg ttgcatttga tatttggggt cagggcaccc tggttaccgt tagctcagca    360
tatatgcagc                                                           370
```

<210> SEQ ID NO 345
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 345

```
gaagttcagc tgctggaaag cggtggtggt ctggttcagc ctggtggtag cctgcgtctg     60
agctgtgcag caagcggttt tacctttgat gattatggta tgagctgggt tcgtcaggca    120
ccgggtaaag gtctggaatg ggttgcagtt attagctatg atggcagcaa taaatattat    180
gccgatagcg tgaaaggtcg ctttaccatt agccgtgata atagccagaa taccctgtat    240
ctgcagatga atagcctgcg tgcagaagat accgcagttt attattgtgc aagtccgctg    300
gaaagtccgg ttgcatttga tatttggggt cagggcaccc tggttaccgt tagctcagca    360
tatatgcagc                                                           370
```

<210> SEQ ID NO 346
<211> LENGTH: 357

```
<212> TYPE: DNA
<213> ORGANISM: Artificial Sequence
<220> FEATURE:
<223> OTHER INFORMATION: maturated PRLR antibody

<400> SEQUENCE: 346
gaagttcagc tgctggaaag cggtggtggt ctggttcagc ctggtggtag cctgcgtctg      60
agctgtgcag caagcggttt tacctttgat gattatggta tgagctgggt tcgtcaggca     120
ccgggtaaag gtctggaaat ggttgcagtt attagctttg atggcagcaa taaatattat     180
gccgatagcg tgaaaggtcg ctttaccatt agccgtgata tagccagaa taccctgtat      240 ctgcagatga atagcctgcg tgcagaagat accgcagttt attattgtgc aagtccgctg     300
gaaagtccgg ttgcatttga tatttggggt cagggcaccc tggttaccgt tagcagc        357

<210> SEQ ID NO 347
<211> LENGTH: 357
<212> TYPE: DNA
<213> ORGANISM: Artificial Sequence
<220> FEATURE:
<223> OTHER INFORMATION: maturated PRLR antibody

<400> SEQUENCE: 347
gaagttcagc tgctggaaag cggtggtggt ctggttcagc ctggtggtag cctgcgtctg      60
agctgtgcag caagcggttt tacctttgat gattatggta tgagctgggt tcgtcaggca     120
ccgggtaaag gtctggaaat ggttgcagtt attagctttg atggcagcaa taaatattat     180
gccgatagcg tgaaaggtcg ctttaccatt agccgtgata tagccagaa taccctgtat      240 ctgcagatga atagcctgcg tgcagaagat accgcagttt attattgtgc aagtccgctg     300
gaaagtccgg ttgcatttga tatttggggt cagggcaccc tggttaccgt tagcagc        357

<210> SEQ ID NO 348
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 348
gaagttcagc tgctggaaag cggtggtggt ctggttcagc ctggtggtag cctgcgtctg      60
agctgtgcag caagcggttt tacctttgat gattatggta tgagctgggt tcgtcaggca     120
ccgggtaaag gtctggaaat ggttgcagtt attagctatg atggcagcaa taaatattat     180
gccgatagcg tgaaaggtcg ctttaccatt agccgtgata tagccagaa taccctgtat      240 ctgcagatga atagcctgcg tgcagaagat accgcagttt attattgtgc aagtccgctg     300
gaaagtccgg ttgcatttga tatttggggt cagggcaccc tggttaccgt tagctcagca    360
tatatgcagc                                                            370

<210> SEQ ID NO 349
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 349
gaagttcagc tgctggaaag cggtggtggt ctggttcagc ctggtggtag cctgcgtctg      60
agctgtgcag caagcggttt tacctttgat gattatggta tgagctgggt tcgtcaggca     120
```

```
ccgggtaaag gtctggaatg ggttgcagtt attagctttg atggcagcaa taaatattat      180
gccgatagcg tgaaaggtcg ctttaccatt agccgtgata atagccagaa tacccctgtat     240 ctgcagatga atagcctgcg tgcagaagat accgcagttt attattgtgc aagtccgctg      300
gaaagtccgg ttgcatttga tatttggggt cagggcaccc tggttaccgt tagctcagca     360
tatatgcagc                                                            370

<210> SEQ ID NO 350
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 350
gaagttcagc tgctggaaag cggtggtggt ctggttcagc ctggtggtag cctgcgtctg     60
agctgtgcag caagcggttt tacctttgat gattatggta tgagctgggt tcgtcaggca    120
ccgggtaaag gtctggaatg ggttgcagtt attagctatg atggcagcaa taaatattat   180
gccgatagcg tgaaaggtcg ctttaccatt agccgtgata atagccagaa tacccctgtat   240 ctgcagatga atagcctgcg tgcagaagat accgcagttt attattgtgc aagtccgctg   300
gaaagtccgg ttgcatttga tatttggggt cagggcaccc tggttaccgt tagctcagca   360
tatatgcagc                                                          370

<210> SEQ ID NO 351
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 351
gaagttcagc tgctggaaag cggtggtggt ctggttcagc ctggtggtag cctgcgtctg     60
agctgtgcag caagcggttt tacctttgat gattatggta tgagctgggt tcgtcaggca    120
ccgggtaaag gtctggaatg ggttgcagtt attagctatg atggcagcaa taaatattat   180
gccgatagcg tgaaaggtcg ctttaccatt agccgtgata atagccagaa tacccctgtat   240 ctgcagatga atagcctgcg tgcagaagat accgcagttt attattgtgc aagtccgctg   300
gaaagtccgg ttgcatttga tatttggggt cagggcaccc tggttaccgt tagctcagca   360
tatatgcagc                                                          370

<210> SEQ ID NO 352
<211> LENGTH: 370
<212> TYPE: DNA
<213> ORGANISM: Artificial Sequence
<220> FEATURE:
<223> OTHER INFORMATION: maturated PRLR antibody

<400> SEQUENCE: 352
gaagttcagc tgctggaaag cggtggtggt ctggttcagc ctggtggtag cctgcgtctg     60
agctgtgcag caagcggttt tacctttgat gattatggta tgagctgggt tcgtcaggca    120
ccgggtaaag gtctggaatg ggttgcagtt attagctatg atggcagcaa taaatattat   180
gccgatagcg tgaaaggtcg ctttaccatt agccgtgata atagccagaa tacccctgtat   240 ctgcagatga atagcctgcg tgcagaagat accgcagttt attattgtgc aagtccgctg   300
gaaagtccgg ttgcatttga tatttggggt cagggcaccc tggttaccgt tagctcagca   360
```

<210> SEQ ID NO 353
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 353

```
cagagcgttc tgacccagcc tccgagcgca agcggtacac cgggtcagcg tgttaccatt      60
agctgtagcg gtctgaatag caatgttggt agcagcccgg tgaattggta tcagcagctg     120
cctggtacag caccgaaact gctgatttat gataataata acgtccgag cggtgttccg      180
gatcgtttta gcggtagtaa aagcggcacc agcgcaagcc tggcaattag cggtctgcgt     240
agcgaagatg aagcagatta ttattgccag agctatgatg aaggtagcgg catgtgggtt     300
tttggtggtg gcaccaaact gaccgttctg ggtcag                               336
```

<210> SEQ ID NO 354
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 354

```
cagagcgttc tgacccagcc tccgagcgca agcggtacac cgggtcagcg tgttaccatt      60
agctgtagcg gtagcaatag caatattggt ggcaacccgg tgaattggta tcagcagctg     120
cctggtacag caccgaaact gctgatttat gataataata acgtccgag cggtgttccg      180
gatcgtttta gcggtagtaa aagcggcacc agcgcaagcc tggcaattag cggtctgcgt     240
agcgaagatg aagcagatta ttattgccag agctatgatg aaggtagcag catgtgggtt     300
tttggtggtg gcaccaaact gaccgttctg ggtcag                               336
```

<210> SEQ ID NO 355
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 355

```
cagagcgttc tgacccagcc tccgagcgca agcggtacac cgggtcagcg tgttaccatt      60
agctgtagcg gtagcaatag caatattggt gggaatccgg tgaattggta tcagcagctg     120
cctggtacag caccgaaact gctgatttat gataataata acgtccgag cggtgttccg      180
gatcgtttta gcggtagtaa aagcggcacc agcgcaagcc tggcaattag cggtctgcgt     240
agcgaagatg aagcagatta ttattgccag agctatgata ccggtctgag cggttgggtt    300
tttggtggtg gcaccaaact gaccgttctg ggtcag                               336
```

<210> SEQ ID NO 356
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 356
cagagcgttc tgacccagcc tccgagcgca agcggtacac cgggtcagcg tgttaccatt     60
agctgtagcg gtagcaatag caatattggt agctcgccgg tgaattggta tcagcagctg    120
cctggtacag caccgaaact gctgatttat gataataata acgtccgag cggtgttccg    180 gatcgtttta gcggtagtaa aagcggcacc agcgcaagcc tggcaattag cggtctgcgt    240
agcgaagatg aagcagatta ttattgccag agctatgata ccggtctgag cggttgggtt    300
tttggtggtg gcaccaaact gaccgttctg ggtcag                              336

<210> SEQ ID NO 357
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 357
cagagcgttc tgacccagcc tccgagcgca agcggtacac cgggtcagcg tgttaccatt     60
agctgtagcg gtctgaatag caatattggt ggcagcccgg tgaattggta tcagcagctg    120
cctggtacag caccgaaact gctgatttat gataataata acgtccgag cggtgttccg    180 gatcgtttta gcggtagtaa aagcggcacc agcgcaagcc tggcaattag cggtctgcgt    240
agcgaagatg aagcagatta ttattgccag agctatgatg aaggtctgag cggttgggtt    300
tttggtggtg gcaccaaact gaccgttctg ggtcag                              336

<210> SEQ ID NO 358
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 358
cagagcgttc tgacccagcc tccgagcgca agcggtacac cgggtcagcg tgttaccatt     60
agctgtagcg gtctgaatag caatattggt ggcagcccgg tgaattggta tcagcagctg    120
cctggtacag caccgaaact gctgatttat gataataata acgtccgag cggtgttccg    180 gatcgtttta gcggtagtaa aagcggcacc agcgcaagcc tggcaattag cggtctgcgt    240
agcgaagatg aagcagatta ttattgccag agctatgatg aaggtgcgag catgtgggtt    300
tttggtggtg gcaccaaact gaccgttctg ggtcag                              336

<210> SEQ ID NO 359
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 359
cagagcgttc tgacccagcc tccgagcgca agcggtacac cgggtcagcg tgttaccatt     60
agctgtagcg gtctgaatga taatgttggt ggcagcccgg tgaattggta tcagcagctg    120
cctggtacag caccgaaact gctgatttat gataataata acgtccgag cggtgttccg    180 gatcgtttta gcggtagtaa aagcggcacc agcgcaagcc tggcaattag cggtctgcgt    240
agcgaagatg aagcagatta ttattgccag agctatgata ccggtgcggg catgtgggtt    300
tttggtggtg gcaccaaact gaccgttctg ggtcag                              336

<210> SEQ ID NO 360
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 360

```
cagagcgttc tgacccagcc tccgagcgca agcggtacac cgggtcagcg tgttaccatt      60
agctgtagcg gtctgaatag caatgttggt agcaacccgg tgaattggta tcagcagctg     120
cctggtacag caccgaaact gctgatttat gataataata acgtccgag cggtgttccg      180
gatcgtttta gcggtagtaa aagcggcacc agcgcaagcc tggcaattag cggtctgcgt     240
agcgaagatg aagcagatta ttattgccag agctatgatg aaggtctggg cggttgggtt     300
tttggtggtg gcaccaaact gaccgttctg ggtcag                               336
```

<210> SEQ ID NO 361
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 361

```
cagagcgttc tgacccagcc tccgagcgca agcggtacac cgggtcagcg tgttaccatt      60
agctgtagcg gtctgaatga taatgttggt ggcagcccgg tgaattggta tcagcagctg     120
cctggtacag caccgaaact gctgatttat gataataata acgtccgag cggtgttccg      180
gatcgtttta gcggtagtaa aagcggcacc agcgcaagcc tggcaattag cggtctgcgt     240
agcgaagatg aagcagatta ttattgccag agctatgatg aaggtagcgg catgtgggtt     300
tttggtggtg gcaccaaact gaccgttctg ggtcag                               336
```

<210> SEQ ID NO 362
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 362

```
cagagcgttc tgacccagcc tccgagcgca agcggtacac cgggtcagcg tgttaccatt      60
agctgtagcg gtagcaatag caatattggt agcaatccgg tgaattggta tcagcagctg     120
cctggtacag caccgaaact gctgatttat gataataata acgtccgag cggtgttccg      180
gatcgtttta gcggtagtaa aagcggcacc agcgcaagcc tggcaattag cggtctgcgt     240
agcgaagatg aagcagatta ttattgccag agctatgatg agggtctgag cggttgggtt     300
tttggtggtg gcaccaaact gaccgttctg ggtcag                               336
```

<210> SEQ ID NO 363
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 363

```
cagagcgttc tgacccagcc tccgagcgca agcggtacac cgggtcagcg tgttaccatt      60
agctgtagcg gtagcaatag caatattggt agcaatccgg tgaattggta tcagcagctg     120
```

```
cctggtacag caccgaaact gctgatttat gataataata aacgtccgag cggtgttccg      180
gatcgtttta gcggtagtaa aagcggcacc agcgcaagcc tggcaattag cggtctgcgt      240
agcgaagatg aagcagatta ttattgccag agctatgata ccggtgcgag cggttgggtt      300
tttggtggtg gcaccaaact gaccgttctg ggtcag                                336

<210> SEQ ID NO 364
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 364
cagagcgttc tgacccagcc tccgagcgca agcggtacac cgggtcagcg tgttaccatt       60
agctgtagcg gtagcaatag caatattggt agcaatccgg tgaattggta tcagcagctg      120
cctggtacag caccgaaact gctgatttat gataataata aacgtccgag cggtgttccg      180
gatcgtttta gcggtagtaa aagcggcacc agcgcaagcc tggcaattag cggtctgcgt      240
agcgaagatg aagcagatta ttattgccag agctatgata ccggttctag cggttgggtt      300
tttggtggtg gcaccaaact gaccgttctg ggtcag                                336

<210> SEQ ID NO 365
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 365
cagagcgttc tgacccagcc tccgagcgca agcggtacac cgggtcagcg tgttaccatt       60
agctgtagcg gtagcaatag caatgttggt ggcaacccgg tgaattggta tcagcagctg      120
cctggtacag caccgaaact gctgatttat gataataata aacgtccgag cggtgttccg      180
gatcgtttta gcggtagtaa aagcggcacc agcgcaagcc tggcaattag cggtctgcgt      240
agcgaagatg aagcagatta ttattgccag agctatgata ccggtagcgg cggttgggtt      300
tttggtggtg gcaccaaact gaccgttctg ggtcag                                336

<210> SEQ ID NO 366
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 366
cagagcgttc tgacccagcc tccgagcgca agcggtacac cgggtcagcg tgttaccatt       60
agctgtagcg gtagcaatag caatattggt agcaatccgg tgaattggta tcagcagctg      120
cctggtacag caccgaaact gctgatttat gataataata aacgtccgag cggtgttccg      180
gatcgtttta gcggtagtaa aagcggcacc agcgcaagcc tggcaattag cggtctgcgt      240
agcgaagatg aagcagatta ttattgccag agctatgata ccggtctggg gggttgggtt      300
tttggtggtg gcaccaaact gaccgttctg ggtcag                                336

<210> SEQ ID NO 367
<211> LENGTH: 336
<212> TYPE: DNA
<213> ORGANISM: Artificial Sequence
```

```
<220> FEATURE:
<223> OTHER INFORMATION: maturated PRLR antibody

<400> SEQUENCE: 367
cagagcgttc tgacccagcc tccgagcgca agcggtacac cgggtcagcg tgttaccatt      60
agctgtagcg gtagcaatag caatattggt agcaatccgg tgaattggta tcagcagctg     120
cctggtacag caccgaaact gctgatttat gataataata acgtccgag cggtgttccg      180 gatcgtttta gcggtagtaa aagcggcacc agcgcaagcc tggcaattag cggtctgcgt     240
agcgaagatg aagcagatta ttattgccag agctatgata ccggtctgag catgtgggtt    300
tttggtggtg gcaccaaact gaccgttctg ggtcag                               336

<210> SEQ ID NO 368
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 368
cagagcgttc tgacccagcc tccgagcgca agcggtacac cgggtcagcg tgttaccatt      60
agctgtagcg gtctgaatag caatgttggt ggcagcccgg tgaattggta tcagcagctg     120
cctggtacag caccgaaact gctgatttat gataataata acgtccgag cggtgttccg      180 gatcgtttta gcggtagtaa aagcggcacc agcgcaagcc tggcaattag cggtctgcgt     240
agcgaagatg aagcagatta ttattgccag agctatgatg aaggtagcgg catgtgggtt    300
tttggtggtg gcaccaaact gaccgttctg ggtcag                               336

<210> SEQ ID NO 369
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 369
cagagcgttc tgacccagcc tccgagcgca agcggtacac cgggtcagcg tgttaccatt      60
agctgtagcg gtctgaatga taatgttggt agcaacccgg tgaattggta tcagcagctg     120
cctggtacag caccgaaact gctgatttat gataataata acgtccgag cggtgttccg      180 gatcgtttta gcggtagtaa aagcggcacc agcgcaagcc tggcaattag cggtctgcgt     240
agcgaagatg aagcagatta ttattgccag agctatgata ccggtagcag catgtgggtt    300
tttggtggtg gcaccaaact gaccgttctg ggtcag                               336

<210> SEQ ID NO 370
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 370
cagagcgttc tgacccagcc tccgagcgca agcggtacac cgggtcagcg tgttaccatt      60
agctgtagcg gtagcaatag caatattggt agcaatccgg tgaattggta tcagcagctg     120
cctggtacag caccgaaact gctgatttat gataataata acgtccgag cggtgttccg      180 gatcgtttta gcggtagtaa aagcggcacc agcgcaagcc tggcaattag cggtctgcgt     240
```

```
agcgaagatg aagcagatta ttattgccag agctatgata ccggtctgag cggttgggtt      300
tttggtggtg gcaccaaact gaccgttctg ggtcag                                336
```

<210> SEQ ID NO 371
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 371

```
cagagcgttc tgacccagcc tccgagcgca agcggtacac cgggtcagcg tgttaccatt       60
agctgtagcg gtagcaatag caatattggt agcaatccgg tgaattggta tcagcagctg      120
cctggtacag caccgaaact gctgatttat gataataata acgtccgag cggtgttccg       180 gatcgtttta gcggtagtaa aagcggcacc agcgcaagcc tggcaattag cggtctgcgt      240
agcgaagatg aagcagatta ttattgccag agctatgata ccggtctgag cggttgggtt      300
tttggtggtg gcaccaaact gaccgttctg ggtcag                                336
```

<210> SEQ ID NO 372
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 372

```
cagagcgttc tgacccagcc tccgagcgca agcggtacac cgggtcagcg tgttaccatt       60
agctgtagcg gtcttaatag caatattggt agcaatccgg tgaattggta tcagcagctg      120
cctggtacag caccgaaact gctgatttat gataataata acgtccgag cggtgttccg       180 gatcgtttta gcggtagtaa aagcggcacc agcgcaagcc tggcaattag cggtctgcgt      240
agcgaagatg aagcagatta ttattgccag agctatgata ccggtctgag cggttgggtt      300
tttggtggtg gcaccaaact gaccgttctg ggtcag                                336
```

<210> SEQ ID NO 373
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 373

```
cagagcgttc tgacccagcc tccgagcgca agcggtacac cgggtcagcg tgttaccatt       60
agctgtagcg gtagcaatga taatattggt agcaatccgg tgaattggta tcagcagctg      120
cctggtacag caccgaaact gctgatttat gataataata acgtccgag cggtgttccg       180 gatcgtttta gcggtagtaa aagcggcacc agcgcaagcc tggcaattag cggtctgcgt      240
agcgaagatg aagcagatta ttattgccag agctatgata ccggtctgag cggttgggtt      300
tttggtggtg gcaccaaact gaccgttctg ggtcag                                336
```

<210> SEQ ID NO 374
<211> LENGTH: 336
<212> TYPE: DNA
<213> ORGANISM: Artificial Sequence
<220> FEATURE:
<223> OTHER INFORMATION: maturated PRLR antibody

<400> SEQUENCE: 374

```
cagagcgttc tgacccagcc tccgagcgca agcggtacac cgggtcagcg tgttaccatt      60
agctgtagcg gtagcaatag caatgtgggt agcaatccgg tgaattggta tcagcagctg     120
cctggtacag caccgaaact gctgatttat gataataata aacgtccgag cggtgttccg     180
gatcgtttta gcggtagtaa aagcggcacc agcgcaagcc tggcaattag cggtctgcgt     240
agcgaagatg aagcagatta ttattgccag agctatgata ccggtctgag cggttgggtt     300
tttggtggtg gcaccaaact gaccgttctg ggtcag                               336
```

```
<210> SEQ ID NO 375
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 375
gaagttcagc tgctggaaag cggtggtggt ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atcgcacggc tgagcccgta taccaattat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcacccctgg ttaccgttac cagc          354
```

```
<210> SEQ ID NO 376
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 376
gaagttcagc tgctggaaag cggtggtggt ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atcagccggc tgagcccgta taccaattat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcacccctgg ttaccgttac cagc          354
```

```
<210> SEQ ID NO 377
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 377
gaagttcagc tgctggaaag cggtggtggt ctggttcagc ctggtggtag cctgcgtctg      60
agctgtgcag caagcggttt tacctttagc agctattgga tgcattgggt tcgtcaggca     120
ccgggtaaag gtctggaatg ggttagcgat attagcagcg caagcagcta taccaattat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcacccctgg ttaccgttac cagc          354
```

<210> SEQ ID NO 378
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 378

```
gaagttcagc tgctggaaag cggtggtggt ctggttcagc ctggtggtag cctgcgtctg      60
agctgtgcag caagcggttt tacctttagc agctattgga tgcattgggt tcgtcaggca     120
ccgggtaaag gtctggaatg ggttagcgat attagcagcg caagcagcta taccaattat     180
gcagatagcg tgaaaggtcg ttttaccatt agccgtgata tagcaaaaa tacctgtat      240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 379
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 379

```
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atggcacggc tgagcccgta taccaattat     180
gcagatagcg tgaaaggtcg ttttaccatt agccgtgata tagcaaaaa tacctgtat      240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 380
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 380

```
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atggcaaggc tgagcccgta taccaattat     180
gcagatagcg tgaaaggtcg ttttaccatt agccgtgata tagcaaaaa tacctgtat      240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 381
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 381

```
gaagttcagc tgctggaaag cggtggtggt ctggttcagc ctggtggtag cctgcgtctg      60
agctgtgcag caagcggttt tacctttagc agctattggt ggcattgggt tcgtcaggca     120
```

```
ccgggtaaag gtctggaatg ggttagcgat atcagcaggg caagcccgta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 382
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 382

```
gaagttcagc tgctggaaag cggtggtggt ctggttcagc ctggtggtag cctgcgtctg     60
agctgtgcag caagcggttt tacctttagc agctattgga tgcattgggt tcgtcaggca    120
ccgggtaaag gtctggaatg ggttagcgat attagcagcg caagcagcta taccaattat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 383
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 383

```
gaagttcagc tgctggaaag cggtggtggt ctggttcagc ctggtggtag cctgcgtctg     60
agctgtgcag caagcggttt tacctttagc agctattgga tcattgggt tcgtcaggca    120 ccgggtaaag gtctggaatg ggttagcgat atcgcaaggc tgagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 384
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 384

```
gaagttcagc tgctggaaag cggtggtggt ctggttcagc ctggtggtag cctgcgtctg     60
agctgtgcag caagcggttt tacctttagc agctattgga tcattgggt tcgtcaggca    120 ccgggtaaag gtctggaatg ggttagcgat atcgcacggc tgagcccgta taccaattat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 385
<211> LENGTH: 354
<212> TYPE: DNA

<213> ORGANISM: Artificial Sequence
<220> FEATURE:
<223> OTHER INFORMATION: maturated PRLR antibody

<400> SEQUENCE: 385

```
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atggcacgcg caagcccgta taccaactat     180
gcagatagcg tgaaaggtcg tttaccatt agccgtgata atagcaaaaa taccctgtat      240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 386
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 386

```
gaagttcagc tgctggaaag cggtggtggt ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atgagccgcc tgagcagcta taccaactat     180
gcagatagcg tgaaaggtcg tttaccatt agccgtgata atagcaaaaa taccctgtat      240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 387
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 387

```
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atgagcaggg caagcagcta taccaactat     180
gcagatagcg tgaaaggtcg tttaccatt agccgtgata atagcaaaaa taccctgtat      240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 388
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 388

```
gaagttcagc tgctggaaag cggtggtggt ctggttcagc ctggtggtag cctgcgtctg      60
agctgtgcag caagcggttt tacctttagc agctattgga tgcattgggt tcgtcaggca     120
ccgggtaaag gtctggaatg ggttagcgat attagcagcg caagcagcta taccaattat     180
gcagatagcg tgaaaggtcg tttaccatt agccgtgata atagcaaaaa taccctgtat      240
```

```
ctgcagatga atagcctgcg tgcagaagat accgcagttt attattgcgc acgtggtctg      300
gatgcacgtc gtatggatta ttggggtcag ggcaccctgg ttaccgttac cagc            354
```

<210> SEQ ID NO 389
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 389

```
gaagttcagc tgctggaaag cggtggtggt ctggttcagc ctggtggtag cctgcgtctg      60
agctgtgcag caagcggttt tacctttagc agctattgga tgcattgggt tcgtcaggca      120
ccgggtaaag gtctggaatg ggttagcgat attagcagcg caagcagcta taccaattat      180
gcagatagcg tgaaaggtcg ttttaccatt agccgtgata atagcaaaaa taccctgtat      240
ctgcagatga atagcctgcg tgcagaagat accgcagttt attattgcgc acgtggtctg      300
gatgcacgtc gtatggatta ttggggtcag ggcaccctgg ttaccgttac cagc            354
```

<210> SEQ ID NO 390
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 390

```
gaagttcagc tgctggaaag cggtggtggt ctggttcagc ctggtggtag cctgcgtctg      60
agctgtgcag caagcggttt tacctttagc agctattgga tgcattgggt tcgtcaggca      120
ccgggtaaag gtctggaatg ggttagcgat attagcagcg caagcagcta taccaattat      180
gcagatagcg tgaaaggtcg ttttaccatt agccgtgata atagcaaaaa taccctgtat      240
ctgcagatga atagcctgcg tgcagaagat accgcagttt attattgcgc acgtggtctg      300
gatgcacgtc gtatggatta ttggggtcag ggcaccctgg ttaccgttac cagc            354
```

<210> SEQ ID NO 391
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 391

```
gaagttcagc tgctggaaag cggtggtggt ctggttcagc ctggtggtag cctgcgtctg      60
agctgtgcag caagcggttt tacctttagc agctattgga tgcattgggt tcgtcaggca      120
ccgggtaaag gtctggaatg ggttagcgat attagcagcg caagcagcta taccaattat      180
gcagatagcg tgaaaggtcg ttttaccatt agccgtgata atagcaaaaa taccctgtat      240
ctgcagatga atagcctgcg tgcagaagat accgcagttt attattgcgc acgtggtctg      300
gatgcacgtc gtatggatta ttggggtcag ggcaccctgg ttaccgttac cagc            354
```

<210> SEQ ID NO 392
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 392

```
gaagttcagc tgctggaaag cggtggtggt ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atcgcaaggg caagcccgta taccaactat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 393
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 393

```
gaagttcagc tgctggaaag cggtggtggt ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atcgcaaggg caagcccgta taccaactat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 394
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 394

```
gaagttcagc tgctggaaag cggtggtggc ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atcagcagcc tgagcagcta taccggctat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 395
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 395

```
gaagttcagc tgctggaaag cggtggtggc ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atcagcagcc tgagcagcta taccggctat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 396
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 396

```
gaagttcagc tgctggaaag cggtggtggt ctggttcagc ctggtggtag cctgcgtctg      60
agctgtgcag caagcggttt tacctttagc agctattgga tgcattgggt tcgtcaggca     120
ccgggtaaag gtctggaatg ggttagcgat attagcagcg caagcagcta taccaattat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 397
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 397

```
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atggcaaggc tgagcagcta taccaactat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 398
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 398

```
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atcagccgcg caagcagcta taccaactat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 399
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 399

```
gaagttcagc tgctggaaag cggtggtggt ctggttcagc ctggtggtag cctgcgtctg      60
```

```
agctgtgcag caagcggttt tacctttagc agctattgga atcattgggt tcgtcaggca    120
ccgggtaaag gtctggaatg ggttagcgat atcagcaggc tgagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 400
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 400

```
gaagttcagc tgctggaaag cggtggtggt ctggttcagc ctggtggtag cctgcgtctg     60
agctgtgcag caagcggttt tacctttagc agctattgga atcattgggt tcgtcaggca    120
ccgggtaaag gtctggaatg ggttagcgat attagcagcg caagcagcta taccaattat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 401
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 401

```
gaagttcagc tgctggaaag cggtggtggt ctggttcagc ctggtggtag cctgcgtctg     60
agctgtgcag caagcggttt tacctttagc agctattgga atcattgggt tcgtcaggca    120
ccgggtaaag gtctggaatg ggttagcgat atcagccgcg caagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 402
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 402

```
gaagttcagc tgctggaaag cggtggtggt ctggttcagc ctggtggtag cctgcgtctg     60
agctgtgcag caagcggttt tacctttagc agctattgga atcattgggt tcgtcaggca    120
ccgggtaaag gtctggaatg ggttagcgat atgagccggc tgagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 403
<211> LENGTH: 354

<212> TYPE: DNA
<213> ORGANISM: Artificial Sequence
<220> FEATURE:
<223> OTHER INFORMATION: maturated PRLR antibody

<400> SEQUENCE: 403

```
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atgagccggc tgagcccgta taccaattat     180
gcagatagcg tgaaaggtcg ttttaccatt agccgtgata tagcaaaaa taccctgtat      240
ctgcagatga atagcctgcg tgcagaagat accgcagttt attattgcgc acgtggtctg     300
gatgcacgtc gtatggatta ttggggtcag ggcaccctgg ttaccgttac cagc            354
```

<210> SEQ ID NO 404
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 404

```
gaagttcagc tgctggaaag cggtggtggt ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atcagcaggg caagcccgta taccaactat     180
gcagatagcg tgaaaggtcg ttttaccatt agccgtgata tagcaaaaa taccctgtat      240
ctgcagatga atagcctgcg tgcagaagat accgcagttt attattgcgc acgtggtctg     300
gatgcacgtc gtatggatta ttggggtcag ggcaccctgg ttaccgttac cagc            354
```

<210> SEQ ID NO 405
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 405

```
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atcagccgcg caagcagcta taccaactat     180
gcagatagcg tgaaaggtcg ttttaccatt agccgtgata tagcaaaaa taccctgtat      240
ctgcagatga atagcctgcg tgcagaagat accgcagttt attattgcgc acgtggtctg     300
gatgcacgtc gtatggatta ttggggtcag ggcaccctgg ttaccgttac cagc            354
```

<210> SEQ ID NO 406
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 406

```
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atgagctggc tgagcagcta taccaactat     180
```

```
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 407
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 407

```
gaagttcagc tgctggaaag cggtggtggt ctggttcagc ctggtggtag cctgcgtctg     60
agctgtgcag caagcggttt tacctttagc agctattgga tgcattgggt tcgtcaggca    120
ccgggtaaag gtctggaatg ggttagcgat cgtagcagcg caagcagcta taccaattat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 408
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 408

```
gaagttcagc tgctggaaag cggtggtggt ctggttcagc ctggtggtag cctgcgtctg     60
agctgtgcag caagcggttt tacctttagc agctattgga tgcattgggt tcgtcaggca    120
ccgggtaaag gtctggaatg ggttagcgat atgagcagcg caagcagcta taccaattat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 409
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 409

```
gaagttcagc tgctggaaag cggtggtggt ctggttcagc ctggtggtag cctgcgtctg     60
agctgtgcag caagcggttt tacctttagc agctattgga tgcattgggt tcgtcaggca    120
ccgggtaaag gtctggaatg ggttagcgat attgcgagcg caagcagcta taccaattat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 410
<211> LENGTH: 354
<212> TYPE: DNA
<213> ORGANISM: Artificial Sequence
<220> FEATURE:
<223> OTHER INFORMATION: maturated PRLR antibody

```
<400> SEQUENCE: 410
gaagttcagc tgctggaaag cggtggtggt ctggttcagc ctggtggtag cctgcgtctg      60
agctgtgcag caagcggttt tacctttagc agctattgga tgcattgggt tcgtcaggca     120
ccgggtaaag gtctggaatg ggttagcgat attagctggg caagcagcta taccaattat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354

<210> SEQ ID NO 411
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 411
gaagttcagc tgctggaaag cggtggtggt ctggttcagc ctggtggtag cctgcgtctg      60
agctgtgcag caagcggttt tacctttagc agctattgga tgcattgggt tcgtcaggca     120
ccgggtaaag gtctggaatg ggttagcgat attagccgtg caagcagcta taccaattat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354

<210> SEQ ID NO 412
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 412
gaagttcagc tgctggaaag cggtggtggt ctggttcagc ctggtggtag cctgcgtctg      60
agctgtgcag caagcggttt tacctttagc agctattgga tgcattgggt tcgtcaggca     120
ccgggtaaag gtctggaatg ggttagcgat attagcagcc tgagcagcta taccaattat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
gatgcacgtc gtatggatta ttggggtcag ggcaccctgg ttaccgttac cagc           354

<210> SEQ ID NO 413
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 413
gaagttcagc tgctggaaag cggtggtggt ctggttcagc ctggtggtag cctgcgtctg      60
agctgtgcag caagcggttt tacctttagc agctattgga tgcattgggt tcgtcaggca     120
ccgggtaaag gtctggaatg ggttagcgat attagcagcg caagcccgta taccaattat     180
gcagatagcg tgaaaggtcg ttttaccatt agccgtgata atagcaaaaa taccctgtat     240
ctgcagatga atagcctgcg tgcagaagat accgcagttt attattgcgc acgtggtctg     300
```

```
gatgcacgtc gtatggatta ttggggtcag ggcaccctgg ttaccgttac cagc      354
```

<210> SEQ ID NO 414
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 414

```
gaagttcagc tgctggaaag cggtggtggt ctggttcagc ctggtggtag cctgcgtctg      60
agctgtgcag caagcggttt tacctttagc agctattgga tgcattgggt tcgtcaggca     120
ccgggtaaag gtctggaatg ggttagcgat attagcagcg caagcagcta taccggttat     180
gcagatagcg tgaaaggtcg ttttaccatt agccgtgata tagcaaaaa taccctgtat      240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 415
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 415

```
gaagttcagc tgctggaaag cggtggtggt ctggttcagc ctggtggtag cctgcgtctg      60
agctgtgcag caagcggttt tacctttagc agctattgga tcattgggt tcgtcaggca     120
ccgggtaaag gtctggaatg ggttagcgat atggcaaggc tgagcccgta taccaattat     180
gcagatagcg tgaaaggtcg ttttaccatt agccgtgata tagcaaaaa taccctgtat      240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 416
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 416

```
gaagttcagc tgctggaaag cggtggtggt ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atgagccggg caagcagcta taccaactat     180
gcagatagcg tgaaaggtcg ttttaccatt agccgtgata tagcaaaaa taccctgtat      240
ctgcagatga atagcctgcg tgcagaagat accgcagttt attattgcgc acgtggtctg     300
gatgcacgtc gtatggatta ttggggtcag ggcaccctgg ttaccgttac cagc           354
```

<210> SEQ ID NO 417
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 417

```
gaagttcagc tgctggaaag cggtggtggt ctggttcagc ctggtggtag cctgcgtctg      60
```

```
agctgtgcag caagcggttt tacctttagc agctattggt ggcattgggt tcgtcaggca    120
ccgggtaaag gtctggaatg ggttagcgat atcgcacgcg caagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 418
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 418

```
gaagttcagc tgctggaaag cggtggtggt ctggttcagc ctggtggtag cctgcgtctg     60
agctgtgcag caagcggttt tacctttagc agctattggt ggcattgggt tcgtcaggca    120
ccgggtaaag gtctggaatg ggttagcgat atggcacggc tgagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 419
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 419

```
gaagttcagc tgctggaaag cggtggtggt ctggttcagc ctggtggtag cctgcgtctg     60
agctgtgcag caagcggttt tacctttagc agctattgga atcattgggt tcgtcaggca    120
ccgggtaaag gtctggaatg ggttagcgat atgagcagcc tgagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 420
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 420

```
gaagttcagc tgctggaaag cggtggtggt ctggttcagc ctggtggtag cctgcgtctg     60
agctgtgcag caagcggttt tacctttagt agctattgga atcattgggt tcgtcaggca    120
ccgggtaaag gtctggaatg ggttagcgat atggcacgcg caagcccgta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 421

```
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 421
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atcgcacgcc tgagcagcta taccaactat     180
gcagatagcg tgaaaggtcg ttttaccatt agccgtgata tagcaaaaa tacccctgtat     240 ctgcagatga atagcctgcg tgcagaagat accgcagttt attattgcgc acgtggtctg     300
gatgcacgtc gtatggatta ttggggtcag ggcaccctgg ttaccgttac cagc          354

<210> SEQ ID NO 422
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 422
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atgagcaggc tgagcagcta taccaactat     180
gcagatagcg tgaaaggtcg ttttaccatt agccgtgata tagcaaaaa tacccctgtat     240 ctgcagatga atagcctgcg tgcagaagat accgcagttt attattgcgc acgtggtctg     300
gatgcacgtc gtatggatta ttggggtcag ggcaccctgg ttaccgttac cagc          354

<210> SEQ ID NO 423
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 423
gaagttcagc tgctggaaag cggtggtggt ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atggcacggg caagcagcta taccaactat     180
gcagatagcg tgaaaggtcg ttttaccatt agccgtgata tagcaaaaa tacccctgtat     240 ctgcagatga atagcctgcg tgcagaagat accgcagttt attattgcgc acgtggtctg     300
gatgcacgtc gtatggatta ttggggtcag ggcaccctgg ttaccgttac cagc          354

<210> SEQ ID NO 424
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 424
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atggcacggg caagcccgta taccggctat     180
```

```
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 425
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 425

```
gaagttcagc tgctggaaag cggtggtggt ctggttcagc ctggtggtag cctgcgtctg     60
agctgtgcag caagcggttt tacctttagc agctattggt ggcattgggt tcgtcaggca    120
ccgggtaaag gtctggaatg ggttagcgat atgagccggc tgagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 426
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 426

```
gaagttcagc tgctggaaag cggtggtggt ctggttcagc ctggtggtag cctgcgtctg     60
agctgtgcag caagcggttt tacctttagc agctattggt ggcattgggt tcgtcaggca    120
ccgggtaaag gtctggaatg ggttagcgat atcgcacggg caagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 427
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 427

```
gaagttcagc tgctggaaag cggtggtggt ctggttcagc ctggtggtag cctgcgtctg     60
agctgtgcag caagcggttt tacctttagc agctattggt ggcattgggt tcgtcaggca    120
ccgggtaaag gtctggaatg ggttagcgat atgagcaggc tgagcagcta taccaactat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttggggtcag ggcaccctgg ttaccgttac cagc          354
```

<210> SEQ ID NO 428
<211> LENGTH: 354
<212> TYPE: DNA
<213> ORGANISM: Artificial Sequence
<220> FEATURE:

<223> OTHER INFORMATION: maturated PRLR antibody

<400> SEQUENCE: 428

```
gaagttcagc tgctggaaag cggtggtggt ctggttcagc ctggtggtag cctgcgtctg    60
agctgtgcag caagcggttt tacctttagc agctattgga atcattgggt tcgtcaggca   120
ccgggtaaag gtctggaatg ggttagcgat atcagccgcg caagcccgta taccggctat   180
gcagatagcg tgaaaggtcg ttttaccatt agccgtgata tagcaaaaaa taccctgtat   240
ctgcagatga atagcctgcg tgcagaagat accgcagttt attattgcgc acgtggtctg   300
gatgcacgtc gtatggatta ttggggtcag ggcaccctgg ttaccgttac cagc         354
```

<210> SEQ ID NO 429
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 429

```
gaagttcagc tgctggaaag cggtggtggt ctggttcagc ctggtggtag cctgcgtctg    60
agctgtgcag caagcggttt tacctttagc agctattggt ggcattgggt tcgtcaggca   120
ccgggtaaag gtctggaatg ggttagcgat atcgcacgcg caagcagcta taccaactat   180
gcagatagcg tgaaaggtcg ttttaccatt agccgtgata tagcaaaaaa taccctgtat   240
ctgcagatga atagcctgcg tgcagaagat accgcagttt attattgcgc acgtggtctg   300
gatgcacgtc gtatggatta ttggggtcag ggcaccctgg ttaccgttac cagc         354
```

<210> SEQ ID NO 430
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 430

```
gaagttcagc tgctggaaag cggtggtggt ctggttcagc ctggtggtag cctgcgtctg    60
agctgtgcag caagcggttt tacctttagc agctattgga atcattgggt tcgtcaggca   120
ccgggtaaag gtctggaatg ggttagcgat atcagccggc tgagcccgta taccaattat   180
gcagatagcg tgaaaggtcg ttttaccatt agccgtgata tagcaaaaaa taccctgtat   240
ctgcagatga atagcctgcg tgcagaagat accgcagttt attattgcgc acgtggtctg   300
gatgcacgtc gtatggatta ttggggtcag ggcaccctgg ttaccgttac cagc         354
```

<210> SEQ ID NO 431
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 431

```
gaagttcagc tgctggaaag cggtggtggt ctggttcagc ctggtggtag cctgcgtctg    60
agctgtgcag caagcggttt tacctttagc agctattgga atcattgggt tcgtcaggca   120
ccgggtaaag gtctggaatg ggttagcgat atggcaagcc tgagcccgta taccggctat   180
gcagatagcg tgaaaggtcg ttttaccatt agccgtgata tagcaaaaaa taccctgtat   240
ctgcagatga atagcctgcg tgcagaagat accgcagttt attattgcgc acgtggtctg   300
```

```
gatgcacgtc gtatggatta ttggggtcag ggcaccctgg ttaccgttac cagc         354
```

<210> SEQ ID NO 432
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 432

```
gaagttcagc tgctggaaag cggtggtggt ctggttcagc ctggtggtag cctgcgtctg    60
agctgtgcag caagcggttt tacctttagc agctattggt ggcattgggt tcgtcaggca   120
ccgggtaaag gtctggaatg ggttagcgat atcgcacggg caagcagcta taccaactat   180
gcagatagcg tgaaaggtcg ttttaccatt agccgtgata atagcaaaaa taccctgtat   240
ctgcagatga atagcctgcg tgcagaagat accgcagttt attattgcgc acgtggtctg   300
gatgcacgtc gtatggatta ttggggtcag ggcaccctgg ttaccgttac cagc         354
```

<210> SEQ ID NO 433
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 433

```
gaagttcagc tgctggaaag cggtggtggt ctggttcagc ctggtggtag cctgcgtctg    60
agctgtgcag caagcggttt tacctttagc agctattgga atcattgggt tcgtcaggca   120
ccgggtaaag gtctggaatg ggttagcgat atgagcagcc tgagcagcta taccggctat   180
gcagatagcg tgaaaggtcg ttttaccatt agccgtgata atagcaaaaa taccctgtat   240
ctgcagatga atagcctgcg tgcagaagat accgcagttt attattgcgc acgtggtctg   300
gatgcacgtc gtatggatta ttggggtcag ggcaccctgg ttaccgttac cagc         354
```

<210> SEQ ID NO 434
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 434

```
gaagttcagc tgctggaaag cggtggtggt ctggttcagc ctggtggtag cctgcgtctg    60
agctgtgcag caagcggttt tacctttagc agctattgga atcattgggt tcgtcaggca   120
ccgggtaaag gtctggaatg ggttagcgat atggcacggc tgagcagcta taccaactat   180
gcagatagcg tgaaaggtcg ttttaccatt agccgtgata atagcaaaaa taccctgtat   240
ctgcagatga atagcctgcg tgcagaagat accgcagttt attattgcgc acgtggtctg   300
gatgcacgtc gtatggatta ttggggtcag ggcaccctgg ttaccgttac cagc         354
```

<210> SEQ ID NO 435
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 435

```
gaagttcagc tgctggaaag cggtggtggt ctggttcagc tggtggtag cctgcgtctg      60 agctgtgcag caagcggttt tacctttagc agctattgga atcattgggt tcgtcaggca    120
ccgggtaaag gtctggaatg ggttagcgat atgagcagcc tgagcagcta taccggctat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttgggggtcag ggcaccctgg ttaccgttac cagc         354
```

<210> SEQ ID NO 436
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 436

```
gaagttcagc tgctggaaag cggtggtggt ctggttcagc tggtggtag cctgcgtctg      60 agctgtgcag caagcggttt tacctttagc agctattggt ggcattgggt tcgtcaggca    120
ccgggtaaag gtctggaatg ggttagcgat atcgcacggc tgagcccgta taccaattat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttgggggtcag ggcaccctgg ttaccgttac cagc         354
```

<210> SEQ ID NO 437
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 437

```
gaagttcagc tgctggaaag cggtggtggt ctggttcagc tggtggtag cctgcgtctg      60 agctgtgcag caagcggttt tacctttagc agctattgga atcattgggt tcgtcaggca    120
ccgggtaaag gtctggaatg ggttagcgat atgagccggc tgagcccgta taccaattat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttgggggtcag ggcaccctgg ttaccgttac cagc         354
```

<210> SEQ ID NO 438
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 438

```
gaagttcagc tgctggaaag cggtggtggt ctggttcagc tggtggtag cctgcgtctg      60 agctgtgcag caagcggttt tacctttagc agctattgga atcattgggt tcgtcaggca    120
ccgggtaaag gtctggaatg ggttagcgat atcgcacgcc tgagcccgta taccggctat    180
gcagatagcg tgaaaggtcg ttttaccatt agccgtgata atagcaaaaa taccctgtat    240
ctgcagatga atagcctgcg tgcagaagat accgcagttt attattgcgc acgtggtctg    300
gatgcacgtc gtatggatta ttgggggtcag ggcaccctgg ttaccgttac cagc         354
```

```
<210> SEQ ID NO 439
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 439
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atggcaagcc tgagcagcta taccaactat     180
gcagatagcg tgaaaggtcg ttttaccatt agccgtgata tagcaaaaa taccctgtat     240 ctgcagatga atagcctgcg tgcagaagat accgcagttt attattgcgc acgtggtctg     300
gatgcacgtc gtatggatta ttggggtcag ggcaccctgg ttaccgttac cagc           354

<210> SEQ ID NO 440
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 440
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atcagccgcc tgagcagcta taccaactat     180
gcagatagcg tgaaaggtcg ttttaccatt agccgtgata tagcaaaaa taccctgtat     240 ctgcagatga atagcctgcg tgcagaagat accgcagttt attattgcgc acgtggtctg     300
gatgcacgtc gtatggatta ttggggtcag ggcaccctgg ttaccgttac cagc           354

<210> SEQ ID NO 441
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 441
gaagttcagc tgctggaaag cggtggtggt ctggttcagc ctggtggtag cctgcgtctg      60
agctgtgcag caagcggttt tacctttagc agctattggt ggcattgggt tcgtcaggca     120
ccgggtaaag gtctggaatg ggttagcgat atcagccggg caagcagcta taccaactat     180
gcagatagcg tgaaaggtcg ttttaccatt agccgtgata tagcaaaaa taccctgtat     240 ctgcagatga atagcctgcg tgcagaagat accgcagttt attattgcgc acgtggtctg     300
gatgcacgtc gtatggatta ttggggtcag ggcaccctgg ttaccgttac cagc           354

<210> SEQ ID NO 442
<211> LENGTH: 354
<212> TYPE: DNA
<213> ORGANISM: Artificial Sequence
<220> FEATURE:
<223> OTHER INFORMATION: maturated PRLR antibody

<400> SEQUENCE: 442
gaagttcagc tgctggaaag cggtggtggt ctggttcagc ctggtggtag cctgcgtctg      60
agctgtgcag caagcggttt tacctttagc agctattgga atcattgggt tcgtcaggca     120
```

| | |
|---|---|
| ccgggtaaag gtctggaatg ggttagcgat atcagccggg caagcccgta taccggctat | 180 |
| gcagatagcg tgaaaggtcg ttttaccatt agccgtgata atagcaaaaa taccctgtat | 240 |
| ctgcagatga atagcctgcg tgcagaagat accgcagttt attattgcgc acgtggtctg | 300 |
| gatgcacgtc gtatggatta ttggggtcag ggcaccctgg ttaccgttac cagc | 354 |

<210> SEQ ID NO 443
<211> LENGTH: 354
<212> TYPE: DNA
<213> ORGANISM: Artificial Sequence
<220> FEATURE:
<223> OTHER INFORMATION: maturated PRLR antibody
<400> SEQUENCE: 443

| | |
|---|---|
| gaagttcagc tgctggaaag cggtggtggt ctggttcagc ctggtggtag cctgcgtctg | 60 |
| agctgtgcag caagcggttt tacctttagc agctattgga atcattgggt tcgtcaggca | 120 |
| ccgggtaaag gtctggaatg ggttagcgat atcgcaagcg caagcagcta taccggctat | 180 |
| gcagatagcg tgaaaggtcg ttttaccatt agccgtgata atagcaaaaa taccctgtat | 240 |
| ctgcagatga atagcctgcg tgcagaagat accgcagttt attattgcgc acgtggtctg | 300 |
| gatgcacgtc gtatggatta ttggggtcag ggcaccctgg ttaccgttac cagc | 354 |

<210> SEQ ID NO 444
<211> LENGTH: 354
<212> TYPE: DNA
<213> ORGANISM: Artificial Sequence
<220> FEATURE:
<223> OTHER INFORMATION: maturated PRLR antibody
<400> SEQUENCE: 444

| | |
|---|---|
| gaagttcagc tgctggaaag cggtggtggt ctggttcagc ctggtggtag cctgcgtctg | 60 |
| agctgtgcag caagcggttt tacctttagc agctattgga atcattgggt tcgtcaggca | 120 |
| ccgggtaaag gtctggaatg ggttagcgat atcgcacgcg caagcagcta taccggctat | 180 |
| gcagatagcg tgaaaggtcg ttttaccatt agccgtgata atagcaaaaa taccctgtat | 240 |
| ctgcagatga atagcctgcg tgcagaagat accgcagttt attattgcgc acgtggtctg | 300 |
| gatgcacgtc gtatggatta ttggggtcag ggcaccctgg ttaccgttac cagc | 354 |

<210> SEQ ID NO 445
<211> LENGTH: 354
<212> TYPE: DNA
<213> ORGANISM: Artificial Sequence
<220> FEATURE:
<223> OTHER INFORMATION: maturated PRLR antibody
<400> SEQUENCE: 445

| | |
|---|---|
| gaagttcagc tgctggaaag cggtggtggt ctggttcagc ctggtggtag cctgcgtctg | 60 |
| agctgtgcag caagcggttt tacctttagc agctattgga atcattgggt tcgtcaggca | 120 |
| ccgggtaaag gtctggaatg ggttagcgat atcagccggc tgagcccgta taccaattat | 180 |
| gcagatagcg tgaaaggtcg ttttaccatt agccgtgata atagcaaaaa taccctgtat | 240 |
| ctgcagatga atagcctgcg tgcagaagat accgcagttt attattgcgc acgtggtctg | 300 |
| gatgcacgtc gtatggatta ttggggtcag ggcaccctgg ttaccgttac cagc | 354 |

<210> SEQ ID NO 446
<211> LENGTH: 354
<212> TYPE: DNA
<213> ORGANISM: Artificial Sequence

```
<220> FEATURE:
<223> OTHER INFORMATION: maturated PRLR antibody

<400> SEQUENCE: 446
gaagttcagc tgctggaaag cggtggtggt ctggttcagc ctggtggtag cctgcgtctg      60
agctgtgcag caagcggttt tacctttagc agctattgga atcattgggt tcgtcaggca     120
ccgggtaaag gtctggaatg ggttagcgat atcagccggg caagcccgta taccaactat     180
gcagatagcg tgaaaggtcg ttttaccatt agccgtgata tagcaaaaa taccctgtat      240 ctgcagatga atagcctgcg tgcagaagat accgcagttt attattgcgc acgtggtctg     300
gatgcacgtc gtatggatta ttggggtcag ggcaccctgg ttaccgttac cagc           354

<210> SEQ ID NO 447
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 447
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata atgtgcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339

<210> SEQ ID NO 448
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 448
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata atgtgcgtcc gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339

<210> SEQ ID NO 449
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 449
cagagcgttc tgacccagcc tccgagcgca agcggtacac cgggtcagcg tgttaccatt      60
agctgtaccg gtagcagcag caatattggt gcaggttatg ttgttcattg gtatcagcag     120
ctgcctggta cagcaccgaa actgctgatt tatcgtaata atgtgcgtcc gagcggtgtt     180
ccggatcgtt ttagcggtag caaaagcggc accagcgcaa gcctggcaat tagcggtctg     240
```

```
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 450
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 450

```
cagagcgttc tgacccagcc tccgagcgca agcggtacac cgggtcagcg tgttaccatt    60
agctgtaccg gtagcagcag caatattggt gcaggttatg ttgttcattg gtatcagcag   120
ctgcctggta cagcaccgaa actgctgatt tatcgtaata attggcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 451
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 451

```
cagagcgttc tgacccagcc tccgagcgca agcggtacac cgggtcagcg tgttaccatt    60
agctgtaccg gtagcagcag caatattggt tatggttatg ttgttcattg gtatcagcag   120
ctgcctggta cagcaccgaa actgctgatt tatcgtaata atcagcgtca gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 452
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 452

```
cagagcgttc tgacccagcc tccgagcgca agcggtacac cgggtcagcg tgttaccatt    60
agctgtaccg gtagcagcag caatattggt tatggttatg ttgttcattg gtatcagcag   120
ctgcctggta cagcaccgaa actgctgatt tatcgtaata atgtgcgtca gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 453
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 453

```
cagagcgttc tgacccagcc tccgagcgca agcggtacac cgggtcagcg tgttaccatt    60
agctgtaccg gtgtgagcag caatattggt gcaggttatg ttgttcattg gtatcagcag   120
ctgcctggta cagcaccgaa actgctgatt tatcgtaata atcagcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 454
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 454

```
cagagcgttc tgacccagcc tccgagcgca agcggtacac cgggtcagcg tgttaccatt    60
agctgtaccg gtagcagcag caatattggt gcaggttatg ttgttcattg gtatcagcag   120
ctgcctggta cagcaccgaa actgctgatt tatcgtaata atcagcgtca gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 455
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 455

```
cagagcgttc tgacccagcc tccgagcgca agcggtacac cgggtcagcg tgttaccatt    60
agctgtaccg gtagcagcag caatattggt tatggttatg ttgttcattg gtatcagcag   120
ctgcctggta cagcaccgaa actgctgatt tatcgtaata atcagcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 456
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 456

```
cagagcgttc tgacccagcc tccgagcgca agcggtacac cgggtcagcg tgttaccatt    60
agctgtaccg gtagcagcag caatattggt tatggttatg ttgttcattg gtatcagcag   120
ctgcctggta cagcaccgaa actgctgatt tatcgtaata atgtgcgtca gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 457
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 457

```
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata atgtgcgtcc gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 458
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 458

```
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata atgtgcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 459
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 459

```
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata atcagcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 460
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 460

```
cagagcgttc tgacccagcc tccgagcgca agcggtacac cgggtcagcg tgttaccatt      60
agctgtaccg gtagcagcag caatattggt gcaggttatg ttgttcattg gtatcagcag     120
```

```
ctgcctggta cagcaccgaa actgctgatt tatcgtaata atcagcgtcc gagcggtgtt      180
ccggatcgtt ttagcggtag caaaagcggc accagcgcaa gcctggcaat tagcggtctg      240
cgtagcgaag atgaagcaga ttattattgt gcagcatggg atgatagcct gagtggttgg      300
ctgtttggtg gtggcaccaa actgaccgtt ctgggtcag                             339

<210> SEQ ID NO 461
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 461
cagagcgttc tgacccagcc tccgagcgca agcggtacac cgggtcagcg tgttaccatt       60
agctgtaccg gtagcagcag caatattggt gcaggttatg ttgttcattg gtatcagcag      120
ctgcctggta cagcaccgaa actgctgatt tatcgtaata atcagcgtcc gagcggtgtt      180
ccggatcgtt ttagcggtag caaaagcggc accagcgcaa gcctggcaat tagcggtctg      240
cgtagcgaag atgaagcaga ttattattgt gcagcatggg atgatagcct gggtggttgg      300
ctgtttggtg gtggcaccaa actgaccgtt ctgggtcag                             339

<210> SEQ ID NO 462
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 462
cagagcgttc tgacccagcc tccgagcgca agcggtacac cgggtcagcg tgttaccatt       60
agctgtaccg gtagcagcag caatattggt gcaggttatg ttgttcattg gtatcagcag      120
ctgcctggta cagcaccgaa actgctgatt tatcgtaata atcagcgtcc gagcggtgtt      180
ccggatcgtt ttagcggtag caaaagcggc accagcgcaa gcctggcaat tagcggtctg      240
cgtagcgaag atgaagcaga ttattattgt gcagcatggg atgatagcct gtttggttgg      300
ctgtttggtg gtggcaccaa actgaccgtt ctgggtcag                             339

<210> SEQ ID NO 463
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 463
cagagcgttc tgacccagcc tccgagcgca agcggtacac cgggtcagcg tgttaccatt       60
agctgtaccg gtagcagcag caatattggt gcaggttatg ttgttcattg gtatcagcag      120
ctgcctggta cagcaccgaa actgctgatt tatcgtaata atcagcgtcc gagcggtgtt      180
ccggatcgtt ttagcggtag caaaagcggc accagcgcaa gcctggcaat tagcggtctg      240
cgtagcgaag atgaagcaga ttattattgt gcagcatggg atgatagcct gttgggttgg      300
ctgtttggtg gtggcaccaa actgaccgtt ctgggtcag                             339

<210> SEQ ID NO 464
<211> LENGTH: 339
<212> TYPE: DNA
```

<213> ORGANISM: Artificial Sequence
<220> FEATURE:
<223> OTHER INFORMATION: maturated PRLR antibody

<400> SEQUENCE: 464

```
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata atgtgcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 465
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 465

```
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata atgtgcgtcc gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 466
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 466

```
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata attggcgtcc gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 467
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 467

```
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata attggcgtcc gagcggtgtt     180
ccggatcgtt ttagcggtag caaaagcggc accagcgcaa gcctggcaat tagcggtctg     240
```
cgtagcgaag atgaagcaga ttattattgt gcagcatggg atgatagcct gaatggttgg    300
ctgtttggtg gtggcaccaa actgaccgtt ctgggtcag                           339

<210> SEQ ID NO 468
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 468
cagagcgttc tgacccagcc tccgagcgca agcggtacac cgggtcagcg tgttaccatt    60
agctgtaccg gtagcagcag caatattggt tatggttatg ttgttcattg gtatcagcag    120
ctgcctggta cagcaccgaa actgctgatt tatcgtaata atcagcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339

<210> SEQ ID NO 469
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 469
cagagcgttc tgacccagcc tccgagcgca agcggtacac cgggtcagcg tgttaccatt    60
agctgtaccg gtagcagcag caatattggt tatggttatg ttgttcattg gtatcagcag    120
ctgcctggta cagcaccgaa actgctgatt tatcgtaata atgtgcgtca gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339

<210> SEQ ID NO 470
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 470
cagagcgttc tgacccagcc tccgagcgca agcggtacac cgggtcagcg tgttaccatt    60
agctgtaccg gtagcagcag caatattggt tatggttatg ttgttcattg gtatcagcag    120
ctgcctggta cagcaccgaa actgctgatt tatcgtaata atcagcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339

<210> SEQ ID NO 471
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 471

```
cagagcgttc tgacccagcc tccgagcgca agcggtacac cgggtcagcg tgttaccatt        60
agctgtaccg gtagcagcag caatattggt tatggttatg ttgttcattg gtatcagcag       120
ctgcctggta cagcaccgaa actgctgatt tatcgtaata atcagcgtca gagcggtgtt       180
ccggatcgtt ttagcggtag caaaagcggc accagcgcaa gcctggcaat tagcggtctg       240
cgtagcgaag atgaagcaga ttattattgt gcagcatggg atgatagcct gaatggttgg       300
ctgtttggtg gtggcaccaa actgaccgtt ctgggtcag                              339
```

<210> SEQ ID NO 472
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 472

```
cagagcgttc tgacccagcc tccgagcgca agcggtacac cgggtcagcg tgttaccatt        60
agctgtaccg gtagcagcag caatattggt gcaggttatg ttgttcattg gtatcagcag       120
ctgcctggta cagcaccgaa actgctgatt tatcgtaata atcagcgtcc gagcggtgtt       180
ccggatcgtt ttagcggtag caaaagcggc accagcgcaa gcctggcaat tagcggtctg       240
cgtagcgaag atgaagcaga ttattattgt gcagcatggg atgatagcct gaatggttgg       300
ctgtttggtg gtggcaccaa actgaccgtt ctgggtcag                              339
```

<210> SEQ ID NO 473
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 473

```
cagagcgttc tgacccagcc tccgagcgca agcggtacac cgggtcagcg tgttaccatt        60
agctgtaccg gtagcagcag caatattggt tatggttatg ttgttcattg gtatcagcag       120
ctgcctggta cagcaccgaa actgctgatt tatcgtaata atgtgcgtcc gagcggtgtt       180
ccggatcgtt ttagcggtag caaaagcggc accagcgcaa gcctggcaat tagcggtctg       240
cgtagcgaag atgaagcaga ttattattgt gcagcatggg atgatagcct gaatggttgg       300
ctgtttggtg gtggcaccaa actgaccgtt ctgggtcag                              339
```

<210> SEQ ID NO 474
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 474

```
cagagcgttc tgacccagcc tccgagcgca agcggtacac cgggtcagcg tgttaccatt        60
agctgtaccg gtagcagcag caatattggt tatggttatg ttgttcattg gtatcagcag       120
ctgcctggta cagcaccgaa actgctgatt tatcgtaata atgtgcgtca gagcggtgtt       180
ccggatcgtt ttagcggtag caaaagcggc accagcgcaa gcctggcaat tagcggtctg       240
cgtagcgaag atgaagcaga ttattattgt gcagcatggg atgatagcct gaatggttgg       300
ctgtttggtg gtggcaccaa actgaccgtt ctgggtcag                              339
```

<210> SEQ ID NO 475
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 475

```
cagagcgttc tgacccagcc tccgagcgca agcggtacac cgggtcagcg tgttaccatt    60
agctgtaccg gtagcagcag caatattggt tatggttatg ttgttcattg gtatcagcag   120
ctgcctggta cagcaccgaa actgctgatt tatcgtaata atgtgcgtca gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                           339
```

<210> SEQ ID NO 476
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 476

```
cagagcgttc tgacccagcc tccgagcgca agcggtacac cgggtcagcg tgttaccatt    60
agctgtaccg gtagcagcag caatattggt tatggttatg ttgttcattg gtatcagcag   120
ctgcctggta cagcaccgaa actgctgatt tatcgtaata atcagcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                           339
```

<210> SEQ ID NO 477
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 477

```
cagagcgttc tgacccagcc tccgagcgca agcggtacac cgggtcagcg tgttaccatt    60
agctgtaccg gtagcagcag caatattggt tatggttatg ttgttcattg gtatcagcag   120
ctgcctggta cagcaccgaa actgctgatt tatcgtaata atcagcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                           339
```

<210> SEQ ID NO 478
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 478

```
cagagcgttc tgacccagcc tccgagcgca agcggtacac cgggtcagcg tgttaccatt    60
```

| agctgtaccg gtagcagcag caatattggt tatggttatg ttgttcattg gtatcagcag | 120 |
| ctgcctggta cagcaccgaa actgctgatt tatcgtaata atcagcgtca gagcggtgtt | 180 |
| ccggatcgtt ttagcggtag caaaagcggc accagcgcaa gcctggcaat tagcggtctg | 240 |
| cgtagcgaag atgaagcaga ttattattgt gcagcatggg atgatagcct gaatggttgg | 300 |
| ctgtttggtg gtggcaccaa actgaccgtt ctgggtcag | 339 |

<210> SEQ ID NO 479
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 479

| cagagcgttc tgacccagcc tccgagcgca agcggtacac cgggtcagcg tgttaccatt | 60 |
| agctgtaccg gtagcagcag caatattggt gcaggttatg ttgttcattg gtatcagcag | 120 |
| ctgcctggta cagcaccgaa actgctgatt tatcgtaata atcagcgtcc gagcggtgtt | 180 |
| ccggatcgtt ttagcggtag caaaagcggc accagcgcaa gcctggcaat tagcggtctg | 240 |
| cgtagcgaag atgaagcaga ttattattgt gcagcatggg atgatagcct gaatggttgg | 300 |
| ctgtttggtg gtggcaccaa actgaccgtt ctgggtcag | 339 |

<210> SEQ ID NO 480
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 480

| cagagcgttc tgacccagcc tccgagcgca agcggtacac cgggtcagcg tgttaccatt | 60 |
| agctgtaccg gtagcagcag caatattggt gcaggttatg ttgttcattg gtatcagcag | 120 |
| ctgcctggta cagcaccgaa actgctgatt tatcgtaata atcagcgtcc gagcggtgtt | 180 |
| ccggatcgtt ttagcggtag caaaagcggc accagcgcaa gcctggcaat tagcggtctg | 240 |
| cgtagcgaag atgaagcaga ttattattgt gcagcatggg atgatagcct gaatggttgg | 300 |
| ctgtttggtg gtggcaccaa actgaccgtt ctgggtcag | 339 |

<210> SEQ ID NO 481
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 481

| cagagcgttc tgacccagcc tccgagcgca agcggtacac cgggtcagcg tgttaccatt | 60 |
| agctgtaccg gtagcagcag caatattggt gcaggttatg ttgttcattg gtatcagcag | 120 |
| ctgcctggta cagcaccgaa actgctgatt tatcgtaata atcagcgtcc gagcggtgtt | 180 |
| ccggatcgtt ttagcggtag caaaagcggc accagcgcaa gcctggcaat tagcggtctg | 240 |
| cgtagcgaag atgaagcaga ttattattgt gcagcatggg atgatagcct gaatggttgg | 300 |
| ctgtttggtg gtggcaccaa actgaccgtt ctgggtcag | 339 |

<210> SEQ ID NO 482
<211> LENGTH: 339

```
<212> TYPE: DNA
<213> ORGANISM: Artificial Sequence
<220> FEATURE:
<223> OTHER INFORMATION: maturated PRLR antibody

<400> SEQUENCE: 482
cagagcgttc tgacccagcc tccgagcgca agcggtacac cgggtcagcg tgttaccatt     60
agctgtaccg gtagcagcag caatattggt gcaggttatg ttgttcattg gtatcagcag    120
ctgcctggta cagcaccgaa actgctgatt tatcgtaata atcagcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339

<210> SEQ ID NO 483
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 483
cagagcgttc tgacccagcc tccgagcgca agcggtacac cgggtcagcg tgttaccatt     60
agctgtaccg gtagcagcag caatattggt gcaggttatg ttgttcattg gtatcagcag    120
ctgcctggta cagcaccgaa actgctgatt tatcgtaata atcagcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339

<210> SEQ ID NO 484
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 484
cagagcgttc tgacccagcc tccgagcgca agcggtacac cgggtcagcg tgttaccatt     60
agctgtaccg gtagcagcag caatattggt gcaggttatg ttgttcattg gtatcagcag    120
ctgcctggta cagcaccgaa actgctgatt tatcgtaata atcagcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339

<210> SEQ ID NO 485
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 485
cagagcgttc tgacccagcc tccgagcgca agcggtacac cgggtcagcg tgttaccatt     60
agctgtaccg gtagcagcag caatattggt gcaggttatg ttgttcattg gtatcagcag    120
ctgcctggta cagcaccgaa actgctgatt tatcgtaata atcagcgtcc gagcggtgtt    180
```

```
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 486
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 486

```
cagagcgttc tgacccagcc tccgagcgca agcggtacac cgggtcagcg tgttaccatt     60
agctgtaccg gtagcagcag caatattggt gcaggttatg ttgttcattg gtatcagcag    120
ctgcctggta cagcaccgaa actgctgatt tatcgtaata atcagcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 487
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 487

```
cagagcgttc tgacccagcc tccgagcgca agcggtacac cgggtcagcg tgttaccatt     60
agctgtaccg gtagcagcag caatattggt tatggttatg ttgttcattg gtatcagcag    120
ctgcctggta cagcaccgaa actgctgatt tatcgtaata atcagcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 488
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 488

```
cagagcgttc tgacccagcc tccgagcgca agcggtacac cgggtcagcg tgttaccatt     60
agctgtaccg gtcagagcag caatattggt gcaggttatg ttgttcattg gtatcagcag    120
ctgcctggta cagcaccgaa actgctgatt tatcgtaata atcagcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 489
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 489

```
cagagcgttc tgacccagcc tccgagcgca agcggtacac cgggtcagcg tgttaccatt      60
agctgtaccg gtagcagcag caatattggt tatggttatg ttgttcattg gtatcagcag     120
ctgcctggta cagcaccgaa actgctgatt tatcgtaata attggcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 490
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 490

```
cagagcgttc tgacccagcc tccgagcgca agcggtacac cgggtcagcg tgttaccatt      60
agctgtaccg gtagcagcag caatattggt gcaggttatg ttgttcattg gtatcagcag     120
ctgcctggta cagcaccgaa actgctgatt tatcgtaata atgtgcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 491
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 491

```
cagagcgttc tgacccagcc tccgagcgca agcggtacac cgggtcagcg tgttaccatt      60
agctgtaccg gtagcagcag caatattggt gcaggttatg ttgttcattg gtatcagcag     120
ctgcctggta cagcaccgaa actgctgatt tatcgtaata atgtgcgtcc gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 492
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 492

```
cagagcgttc tgacccagcc tccgagcgca agcggtacac cgggtcagcg tgttaccatt      60
agctgtaccg ggagcagcag caatattggt gcaggttatg ttgttcattg gtatcagcag     120
ctgcctggta cagcaccgaa actgctgatt tatcgtaata atgtgcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
```

```
ctgtttggtg gtggcaccaa actgaccgtt ctgggtcag         339
```

<210> SEQ ID NO 493
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 493

```
cagagcgttc tgacccagcc tccgagcgca agcggtacac cgggtcagcg tgttaccatt    60
agctgtaccg gtagcagcag caatattggt gcaggttatg ttgttcattg gtatcagcag   120
ctgcctggta cagcaccgaa actgctgatt tatcgtaata attggcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 494
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 494

```
cagagcgttc tgacccagcc tccgagcgca agcggtacac cgggtcagcg tgttaccatt    60
agctgtaccg gtagcagcag caatattggt gcaggttatg ttgttcattg gtatcagcag   120
ctgcctggta cagcaccgaa actgctgatt tatcgtaata attggcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 495
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 495

```
cagagcgttc tgacccagcc tccgagcgca agcggtacac cgggtcagcg tgttaccatt    60
agctgtaccg gtagcagcag caatattggt gcaggttatg ttgttcattg gtatcagcag   120
ctacctggta cagcaacgaa actgctgatt tatcgtaata atgtgcgtca gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339
```

<210> SEQ ID NO 496
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 496

```
cagagcgttc tgacccagcc tccgagcgca agcggtacac cgggtcagcg tgttaccatt    60
```

```
agctgtaccg gtagcagcag caatattggt gcaggttatg ttgttcattg gtatcagcag    120
ctgcctggta cagcaccgaa actgctgatt tatcgtaata attggcgtcc gagcggtgtt    180
ccggatcgtt ttagtggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 497
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 497

```
cagagcgttc tgacccagcc tccgagcgca agcggtacac cgggtcagcg tgttaccatt     60
agctgtaccg gtagcagcag caatattggt gcaggttatg ttgttcattg gtatcagcag    120
ctgcctggta cagcaccgaa actgctgatt tatcgtaata atgtgcgtca gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 498
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 498

```
cagagcgttc tgacccagcc tccgagcgca agcggtacac cgggtcagcg tgttaccatt     60
agctgtaccg gtagcagcag caatattggt tatggttatg ttgttcattg gtatcagcag    120
ctgcctggta cagcaccgaa actgctgatt tatcgtaata attggcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 499
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 499

```
cagagcgttc tgacccagcc tccgagcgca agcggtacac cgggtcagcg tgttaccatt     60
agctgtaccg gtagcagcag caatattggt gcaggttatg ttgttcattg gtatcagcag    120
ctgcctggta cagcaccgaa actgctgatt tatcgtaata atcagcgtca gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 500

```
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 500
cagagcgttc tgacccagcc tccgagcgca agcggtacac cgggtcagcg tgttaccatt    60
agctgtaccg gtagctcgag caatattggt gcaggttatg ttgttcattg gtatcagcag   120
ctgcctggta cagcaccgaa actgctgatt tatcgtaata attggcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339

<210> SEQ ID NO 501
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 501
cagagcgttc tgacccagcc tccgagcgca agcggtacac cgggtcagcg tgttaccatt    60
agctgtaccg gtagcagcag caatattggt gcaggttatg ttgttcattg gtatcagcag   120
ctgcctggta cagcaccgaa actgctgatt tatcgtaata attggcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339

<210> SEQ ID NO 502
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 502
cagagcgttc tgacccagcc tccgagcgca agcggtacac cgggtcagcg tgttaccatt    60
agctgtaccg gtagcagcag caatattggt gcaggttatg ttgttcattg gtatcagcag   120
ctgcctggta cagcaccgaa actgctgatt tatcgtaata atcagcgtca gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                          339

<210> SEQ ID NO 503
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 503
cagagcgttc tgacccagcc tccgagcgca agcggtacac cgggtcagcg tgttaccatt    60
agctgtaccg gtagcagcag caatattggt gcaggttatg ttgttcattg gtatcagcag   120
ctgcctggta cagcaccgaa actgctgatt tatcgtaata atcagcgtca gagcggtgtt   180
```

```
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 504
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 504

```
cagagcgttc tgacccagcc tccgagcgca agcggtacac cgggtcagcg tgttaccatt     60
agctgtaccg gtagcagcag caatattggt tatggttatg ttgttcattg gtatcagcag    120
ctgcctggta cagcaccgaa actgctgatt tatcgtaata attggcgtcc gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 505
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 505

```
cagagcgttc tgacccagcc tccgagcgca agcggtacac cgggtcagcg tgttaccatt     60
agctgtaccg gtagcagcag caatattggt gcaggttatg ttgttcattg gtatcagcag    120
ctgcctggta cagcaccgaa actgctgatt tatcgtaata atgtgcgtca gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 506
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 506

```
cagagcgttc tgacccagcc tccgagcgca agcggtacac cgggtcagcg tgttaccatt     60
agctgtaccg gtagcagcag caatattggt gcaggttatg ttgttcattg gtatcagcag    120
ctgcctggta cagcaccgaa actgctgatt tatcgtaata atgtgcgtca gagcggtgtt    180
ccggatcgtt ttagcggtag caaaagcggc accagcgcaa gcctggcaat tagcggtctg    240
cgtagcgaag atgaagcaga ttattattgt gcagcatggg atgatagcct gaatggttgg    300
ctgtttggtg gtggcaccaa actgaccgtt ctgggtcag                           339
```

<210> SEQ ID NO 507
<211> LENGTH: 339
<212> TYPE: DNA
<213> ORGANISM: Artificial Sequence
<220> FEATURE:

<223> OTHER INFORMATION: maturated PRLR antibody

<400> SEQUENCE: 507

```
cagagcgttc tgacccagcc tccgagcgca agcggtacac cgggtcagcg tgttaccatt      60
agctgtaccg gtagcagcag caatattggt gcaggttatg ttgttcattg gtatcagcag     120
ctgcctggta cagcaccgaa actgctgatt tatcgtaata attggcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 508
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 508

```
cagagcgttc tgacccagcc tccgagcgca agcggtacac cgggtcagcg tgttaccatt      60
agctgtaccg gtagcagcag caatattggt gcaggttatg ttgttcattg gtatcagcag     120
ctgcctggta cagcaccgaa actgctgatt tatcgtaata attggcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 509
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 509

```
cagagcgttc tgacccagcc tccgagcgca agcggtacac cgggtcagcg tgttaccatt      60
agctgtaccg gtagcagcag caatattggt gcaggttatg ttgttcattg gtatcagcag     120
ctgcctggta cagcaccgaa actgctgatt tatcgtaata attggcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```

<210> SEQ ID NO 510
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 510

```
cagagcgttc tgacccagcc tccgagcgca agcggtacac cgggtcagcg tgttaccatt      60
agctgtaccg gtagcagcag caatattggt gcaggttatg ttgttcattg gtatcagcag     120
ctgcctggta cagcaccgaa actgctgatt tatcgtaata atgtgcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
```
ctgtttggtg gtggcaccaa actgaccgtt ctgggtcag                           339

<210> SEQ ID NO 511
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 511
cagagcgttc tgacccagcc tccgagcgca agcggtacac cgggtcagcg tgttaccatt    60
agctgtaccg gtagcagcag caatattggt gcaggttatg ttgttcattg gtatcagcag   120
ctgcctggta cagcaccgaa actgctgatt tatcgtaata attggcgtca gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                           339

<210> SEQ ID NO 512
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 512
cagagcgttc tgacccagcc tccgagcgca agcggtacac cgggtcagcg tgttaccatt    60
agctgtaccg gtagcagcag caatattggt tatggttatg ttgttcattg gtatcagcag   120
ctgcctggta cagcaccgaa actgctgatt tatcgtaata attggcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                           339

<210> SEQ ID NO 513
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 513
cagagcgttc tgacccagcc tccgagcgca agcggtacac cgggtcagcg tgttaccatt    60
agctgtaccg gtagcagcag caatattggt tatggttatg ttgttcattg gtatcagcag   120
ctgcctggta cagcaccgaa actgctgatt tatcgtaata attggcgtcc gagcggtgtt   180
ccggatcgtt ttagcggtag caaaagcggc accagcgcaa gcctggcaat tagcggtctg   240
cgtagcgaag atgaagcaga ttattattgt gcagcatggg atgatagcct gaatggttgg   300
ctgtttggtg gtggcaccaa actgaccgtt ctgggtcag                           339

<210> SEQ ID NO 514
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 514

| cagagcgttc tgacccagcc tccgagcgca agcggtacac cgggtcagcg tgttaccatt | 60 |
| agctgtaccg gtagcagcag caatattggt gcaggttatg ttgttcattg gtatcagcag | 120 |
| ctgcctggta cagcaccgaa actgctgatt tatcgtaata atcagcgtca gagcggtgtt | 180 |
| ccggatcgtt ttagcggtag caaaagcggc accagcgcaa gcctggcaat tagcggtctg | 240 |
| cgtagcgaag atgaagcaga ttattattgt gcagcatggg atgatagcct gaatggttgg | 300 |
| ctgtttggtg gtggcaccaa actgaccgtt ctgggtcag | 339 |

```
<210> SEQ ID NO 515
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 515
```

| cagagcgttc tgacccagcc tccgagcgca agcggtacac cgggtcagcg tgttaccatt | 60 |
| agctgtaccg gtagcagcag caatattggt gcaggttatg ttgttcattg gtatcagcag | 120 |
| ctgcctggta cagcaccgaa actgctgatt tatcgtaata attggcgtca gagcggtgtt | 180 |
| ccggatcgtt ttagcggtag caaaagcggc accagcgcaa gcctggcaat tagcggtctg | 240 |
| cgtagcgaag atgaagcaga ttattattgt gcagcatggg atgatagcct gaatggttgg | 300 |
| ctgtttggtg gtggcaccaa actgaccgtt ctgggtcag | 339 |

```
<210> SEQ ID NO 516
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 516
```

| cagagcgttc tgacccagcc tccgagcgca agcggtacac cgggtcagcg tgttaccatt | 60 |
| agctgtaccg gtagcagcag caatattggt gcaggttatg ttgttcattg gtatcagcag | 120 |
| ctgcctggta cagcaccgaa actgctgatt tatcgtaata attggcgtca gagcggtgtt | 180 |
| ccggatcgtt ttagcggtag caaaagcggc accagcgcaa gcctggcaat tagcggtctg | 240 |
| cgtagcgaag atgaagcaga ttattattgt gcagcatggg atgatagcct gaatggttgg | 300 |
| ctgtttggtg gtggcaccaa actgaccgtt ctgggtcag | 339 |

```
<210> SEQ ID NO 517
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 517
```

| cagagcgttc tgacccagcc tccgagcgca agcggtacac cgggtcagcg tgttaccatt | 60 |
| agctgtaccg gtagcagcag caatattggt gcaggttatg ttgttcattg gtatcagcag | 120 |
| ctgcctggta cagcaccgaa actgctgatt tatcgtaata attggcgtcc gagcggtgtt | 180 |
| ccggatcgtt ttagcggtag caaaagcggc accagcgcaa gcctggcaat tagcggtctg | 240 |
| cgtagcgaag atgaagcaga ttattattgt gcagcatggg atgatagcct gaatggttgg | 300 |
| ctgtttggtg gtggcaccaa actgaccgtt ctgggtcag | 339 |

```
<210> SEQ ID NO 518
<211> LENGTH: 339
<212> TYPE: DNA
<213> ORGANISM: Artificial Sequence
<220> FEATURE:
<223> OTHER INFORMATION: maturated PRLR antibody

<400> SEQUENCE: 518
cagagcgttc tgacccagcc tccgagcgca agcggtacac cgggtcagcg tgttaccatt      60
agctgtaccg gtagcagcag caatattggt gcaggttatg ttgttcattg gtatcagcag     120
ctgcctggta cagcaccgaa actgctgatt tatcgtaata atcagcgtca gagcggtgtt     180
ccggatcgtt ttagcggtag caaaagcggc accagcgcaa gcctggcaat tagcggtctg     240
cgtagcgaag atgaagcaga ttattattgt gcagcatggg atgatagcct gaatggttgg     300
ctgtttggtg gtggcaccaa actgaccgtt ctgggtcag                            339
```